(12) United States Patent
Zavoronkovs et al.

(10) Patent No.: US 12,286,443 B2
(45) Date of Patent: Apr. 29, 2025

(54) BYCYCLIC JAK INHIBITORS AND USES THEREOF

(71) Applicant: Insilico Medicine IP Limited, Hong Kong (HK)

(72) Inventors: Aleksandrs Zavoronkovs, Pak Shek Kok (HK); Yan Ivanenkov, Moscow (RU); Aleksandr Aliper, Moscow (RU); Anton S. Vantskul, Moscow (RU)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 861 days.

(21) Appl. No.: 17/478,152

(22) Filed: Sep. 17, 2021

(65) Prior Publication Data

US 2022/0119419 A1   Apr. 21, 2022

Related U.S. Application Data

(63) Continuation of application No. PCT/US2020/025206, filed on Mar. 27, 2020.
(Continued)

(51) Int. Cl.
*C07D 519/00* (2006.01)

(52) U.S. Cl.
CPC .................. *C07D 519/00* (2013.01)

(58) Field of Classification Search
None
See application file for complete search history.

(56) References Cited

U.S. PATENT DOCUMENTS

| 3,794,652 A | 2/1974 | Naito |
| 5,376,645 A | 12/1994 | Stella et al. |

(Continued)

FOREIGN PATENT DOCUMENTS

| CN | 105732636 A | 7/2016 |
| CN | 107673978 A | 2/2018 |

(Continued)

OTHER PUBLICATIONS

Berge et al. Pharmaceutical Salts. Journal of Pharmaceutical Sciences 66(1):1-19 (Jan. 1977).
(Continued)

*Primary Examiner* — Jeffrey S Lundgren
*Assistant Examiner* — Anthony Joseph Seitz
(74) *Attorney, Agent, or Firm* — WILSON SONSINI GOODRICH & ROSATI

(57) ABSTRACT

Provided herein are compounds of Formulas (I), (II), (III), and (IV)

and subformulas thereof, wherein the variables are defined herein. Also provided herein are pharmaceutical compositions comprising a compound of Formula (I), (II), (III), or
(Continued)

(IV) and methods of using the compounds, e.g., in the treatment of immune disorders, inflammatory disorders, and cancer.

20 Claims, No Drawings

Related U.S. Application Data

(60) Provisional application No. 62/824,485, filed on Mar. 27, 2019.

(56) References Cited

U.S. PATENT DOCUMENTS

| | | |
|---|---|---|
| 6,635,762 B1 | 10/2003 | Blumenkopf et al. |
| 2001/0053782 A1 | 12/2001 | Blumenkopf et al. |
| 2012/0110702 A1 | 5/2012 | Yap et al. |
| 2015/0158864 A1 | 6/2015 | Thorarensen et al. |
| 2017/0360794 A1 | 12/2017 | Wu et al. |

FOREIGN PATENT DOCUMENTS

| | | | |
|---|---|---|---|
| EP | 3248980 A1 | 11/2017 | |
| WO | WO-9965908 A1 | 12/1999 | |
| WO | WO-9965909 A1 | 12/1999 | |
| WO | WO-0142246 A2 | 6/2001 | |
| WO | WO-0200661 A1 | 1/2002 | |
| WO | WO-02096909 A1 | 12/2002 | |
| WO | WO-2004046112 A2 | 6/2004 | |
| WO | WO-2004111003 A1 | 12/2004 | |
| WO | WO-2006028545 A2 | 3/2006 | |
| WO | WO-2006100208 A1 | 9/2006 | |
| WO | WO-2007012953 A2 | 2/2007 | |
| WO | WO-2007036727 A1 | 4/2007 | |
| WO | WO-2007098169 A1 | 8/2007 | |
| WO | WO-2008107444 A1 * | 9/2008 | ............ A61P 35/00 |
| WO | WO-2009124746 A1 | 10/2009 | |
| WO | WO-2010032200 A1 | 3/2010 | |
| WO | WO-2013134085 A1 | 9/2013 | |
| WO | WO-2013190123 A1 | 12/2013 | |
| WO | WO-2015083028 A1 | 6/2015 | |
| WO | WO-2020198583 A1 | 10/2020 | |

OTHER PUBLICATIONS

Davies, et al. Targeting conserved water molecules: design of 4-aryl-5-cyanopyrrolo[2,3-d]pyrimidine Hsp90 inhibitors using fragment-based screening and structure-based optimization. Bioorg Med Chem. Nov. 15, 2012;20(22):6770-89. doi: 10.1016/j.bmc. 2012.08.050. Epub Sep. 4, 2012.

Garcia, et al. Microwave-Enhanced Rhodium-Catalyzed [2+2+2] Cycloaddition Reactions To Afford Highly Functionalized Pyridines and Bipyridines. Eur. J. Org. Chem. 2010, Issue 18, pp. 3407-3415. https://doi.org/10.1002/ejoc.200901318.

Guo, et al. Oxa-Michael Addition to α,β-Unsaturated Nitriles: An Expedient Route to γ-Amino Alcohols and Derivatives. ChemCatChem. Jul. 9, 2018;10(13):2868-2872. doi: 10.1002/cctc.201800509. Epub May 8, 2018.

International search report with written opinion dated Jun. 17, 2020 for PCT/US2020/025206.

Kisseleva, et al. Signaling through the JAK/STAT pathway, recent advances and future challenges. Gene. Feb. 20, 2002;285(1-2):1-24. doi: 10.1016/s0378-1119(02)00398-0.

Lefoix, et al. Versatile and Convenient Methods for the Synthesis of C-2 and C-3 Functionalised 5-Azaindoles. Synthesis 2005(20): 3581-3588. DOI: 10.1055/s-2005-916028.

Li, et al. Synthesis and antiviral, insecticidal, and fungicidal activities of gossypol derivatives containing alkylimine, oxime or hydrazine moiety. Bioorg. Med. Chem., vol. 24, Issue 3, Feb. 1, 2016, pp. 474-483.

Ojima, et al. New and effective routes to fluoro analogs of aliphatic and aromatic amino acids. J. Org. Chem. 1989, 54, 19, 4511-4522. https://doi.org/10.1021/jo00280a014.

Shin, et al. Synthesis and biological properties of new 1 beta-methylcarbapenems. Bioorg Med Chem Lett. Jul. 7, 1998;8(13):1607-1612. doi: 10.1016/s0960-894x(98)00270-4.

Wilen et al., Tetrahedron Report No. 38. Strategies in Optical Resolutions. Tetrahedron. 33(21):2725-2736 (1977).

Wilen, Tables of Resolving Agents and Optical Resolutions (Ed. Eliel). Univ. of Notre Dame Press. 268-298 (1972).

Yamaoka, et al. The Janus kinases (Jaks). Genome Biol. 2004;5(12):253. doi: 10.1186/gb-2004-5-12-253. Epub Nov. 30, 2004.

* cited by examiner

BICYCLIC JAK INHIBITORS AND USES THEREOF

CROSS-REFERENCE TO RELATED APPLICATION

This application is a continuation application of International Application No. PCT/US2020/025206, filed on Mar. 27, 2020, which claims priority to and the benefit of U.S. Provisional Patent Application No. 62/824,485 titled "BICYCLIC JAK INHIBITORS AND USES THEREOF" and filed on Mar. 27, 2019, the entirety of which is incorporated herein by reference.

BACKGROUND OF THE INVENTION

Protein kinases are enzymes that catalyze the phosphorylation of specific residues in proteins. Inappropriate kinase activity, arising from mutation, over-expression, or inappropriate regulation, dys-regulation or de-regulation, as well as over- or underproduction of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases. For these reasons, protein kinases are important targets for drug design.

The JAK family of cellular protein tyrosine kinases (JAK1, JAK2, JAK3, and Tyk2) play a central role in cytokine signaling (Kisseleva, et al., *Gene*, 2002, 285, 1: Yamaoka, et al. *Genome Biology*, 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the IFN family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23, IL-27 and IL-35), gamma-common chain family (IL-2, IL-4, IL-7, IL-9, IL-15, IL-21), and IL-13, TLSP, IL-3 family (IL-3. IL-5, GM-CSF), single chain family (EPO, GH, PRL, TPO), receptor tyrosine kinases (EGF, PDGF, CSF-1, HGF), and G-protein coupled receptors (AT1).

There remains a need for new compounds that effectively and selectively inhibit specific JAK enzymes, and JAK3 in particular, which is expressed to various levels in all tissues. Many cytokine receptors signal through pairs of JAK kinases in the following combinations: JAK1/JAK2, JAK1/JAK3, JAK1/TYK2, JAK2/TYK2 or JAK2/JAK2 Animal studies have shown that JAK3 is implicated in the development, function and homeostasis of the immune system. Modulation of immune activity through inhibition of JAK3 kinase activity can prove useful in the treatment of various disorders, including immune disorders and organ transplant rejection.

SUMMARY OF THE INVENTION

Provided herein are bicyclic compounds which are modulators of JAK family kinases designed, for example, to treat a disease or disorder associated with JAK. In some embodiments, such compounds are envisioned to be useful as therapeutic agents for treating immune disorders, inflammatory disorders, and cancer.

In one aspect, provided herein is compound of formula I, formula II, formula III, or formula IV:

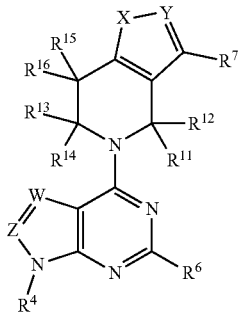

(I)

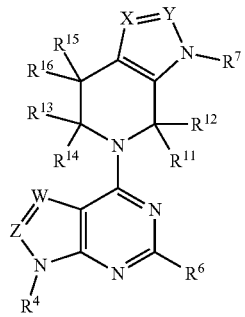

(II)

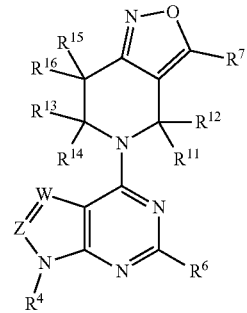

(III)

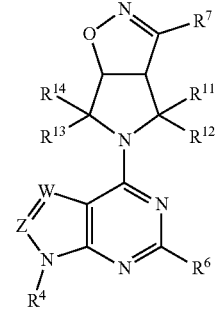

(IV)

or a pharmaceutically acceptable salt thereof, wherein
For formula I: X is $NR^1$, $C(R^8)R^1$, O, S, S(O), or $S(O)_2$;
For formula II: X is N or $CR^1$; and
For formula I, formula II, formula III, and formula IV:
W is N or $CR^1$;
Y is N or $CR^2$;
Z is N or $CR^3$;

wherein W and Z are not both N;

R$^1$ is selected from the group consisting of cyano, hydroxyl, NR$^a$R$^b$, C$_{1-6}$alkoxy, and -A-L$^1$-R$^9$;

R$^2$, R$^3$, R$^4$, and R$^6$ are each independently selected from the group consisting of hydrogen, deuterium, halogen, cyano, hydroxyl, —NR$^a$R$^b$, C$_{1-6}$alkyl, C$_{2-6}$alkenyl, C$_{2-6}$alkynyl, C$_{1-6}$haloalkyl, and C$_{1-6}$alkoxy;

R$^5$ is selected from the group consisting of hydrogen, C$_{1-6}$alkyl, C$_{2-6}$alkenyl, C$_{2-6}$alkynyl, C$_{1-6}$-haloalkyl, aryl, heteroaryl, cycloalkyl, heterocyclyl, -aryl-C$_{1-6}$alkyl, -heteroaryl-C$_{1-6}$alkyl, -heterocyclyl-C$_{1-6}$alkyl, halogen, cyano, hydroxyl, C$_{1-6}$alkoxy, C$_{1-6}$haloalkoxy, amino, carboxy, aminocarbonyl, —C$_{1-6}$alkyl-aminocarbonylamino, C$_{1-6}$alkyl-aminocarbonyl, —S(O)—R$^8$, —S(O)$_2$—R$^8$, —NR$^8$—S(O)$_2$—R$^8$, —S(O)$_2$—NR$^a$R$^b$, —NR$^8$—S(O)$_2$—NR$^a$R$^b$, —C$_{1-6}$alkyl-aryl, —C$_{1-6}$alkyl-heteroaryl, —C$_{1-6}$alkyl-heterocycle, and —C$_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, CF$_3$, aminocarbonyl, —C$_{1-6}$alkyl-aminocarbonylamino, and C$_{3-6}$cycloalkyl;

R$^7$ is B-L$^2$-R$^{10}$, or R$^7$ is aryl or heteroaryl, wherein the aryl or heteroaryl is optionally substituted with one to four R$^{17}$;

each R$^8$ is independently selected from the group consisting of hydrogen, C$_{1-6}$alkyl, C$_{1-6}$haloalkyl, hydroxy, C$_{1-6}$alkoxy, and —O—C$_{1-6}$haloalkyl;

R$^9$ is selected from the group consisting of hydrogen, cycloalkyl, heterocycloalkyl, aryl, and heteroaryl, wherein any non-hydrogen R$^9$ is optionally substituted with one to four R$^{17}$;

R$^{10}$ is selected from the group consisting of hydrogen, cyano, hydroxyl, C$_{1-6}$haloalkyl, C$_{1-6}$alkoxy, —O—C$_{1-6}$ haloalkyl, cycloalkyl, heterocycloalkyl, aryl, heteroaryl, —C(O)— heterocycloalkyl, and —S(O)$_2$-heterocycloalkyl, wherein any R$^{10}$ other than hydrogen, cyano, and hydroxyl is optionally substituted with one to four R$^{17}$;

R$^{11}$, R$^{12}$, R$^{13}$, R$^{14}$, R$^{15}$, and R$^{16}$ are each independently selected from the group consisting of hydrogen, C$_{1-6}$alkyl, C$_{2-6}$alkenyl, C$_{2-6}$alkynyl, C$_{1-6}$haloalkyl, aryl, heteroaryl, cycloalkyl, heterocyclyl, -aryl-C$_{1-6}$alkyl, -heteroaryl-C$_{1-6}$alkyl, halogen, cyano, hydroxyl, C$_{1-6}$alkoxy, amino, carboxy, aminocarbonyl, —C$_{1-6}$alkyl-aryl, —C$_{1-6}$alkyl-heteroaryl, —C$_{1-6}$alkyl-heterocycle, and C$_{1-6}$alkyl-cycloalkyl, wherein said alkyl is optionally substituted with one or more substituents independently selected from the group consisting of halo, hydroxyl, methoxy, alkylamino, dialkylamino, CF$_3$, and C$_{3-6}$cycloalkyl; or R$^{11}$ and R$^{12}$, R$^{13}$ and R$^{14}$, or R$^{15}$ and R$^{16}$ can betaken together including the atom to which they are attached to form a 3-6-membered spiro-fused ring optionally substituted by 1-3 substituents independently selected from the group consisting of halogen, C$_{1-6}$alkyl, and C$_{1-6}$haloalkyl;

R$^{17}$ is, independently for each occurrence, selected from the group consisting of halogen, cyano, hydroxyl, —NR$^a$R$^b$, C$_{1-6}$alkyl, C$_{2-6}$alkenyl, C$_{2-6}$alkynyl, C$_{1-6}$haloalkyl, C$_{1-6}$alkoxy, CF$_3$, —SH, —S—C$_{1-6}$alkyl, —COOH, —CO$_2$—C$_{1-6}$alkyl, —C$_{1-6}$alkyl-CN, —C(O)NR$^a$R$^b$, —C(O)—C$_{1-6}$alkyl-NR$^a$R$^b$, —C(O)—NR$^a$—S(O)$_2$—C$_{1-6}$alkyl, —S(O)$_2$—C$_{1-6}$alkyl, —S(O)$_2$—NR$^a$R$^b$, —S(O)$_2$—C$_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR$^8$—, —CH$_2$—NR$^8$—, and —C(O)NR$^8$—;

L$^2$ is selected from the group consisting of a bond, C$_{1-6}$alkylene, C$_{1-6}$ heteroalkylene, C$_{2-6}$alkenylene, and C$_{2-6}$alkynylene, wherein L$^1$ is optionally substituted with one to four R$^{17}$ groups;

L$^2$ is selected from the group consisting of a bond, C$_{1-6}$alkylene, C$_{2-6}$alkenylene, and C$_{2-6}$alkynylene, wherein any CH$_2$ group of C$_{1-6}$alkylene can be replaced with a moiety selected from the group consisting of —O—, —NR$^a$—, and —S(O)$_2$—, and one CH$_2$ group of C$_{1-6}$alkylene can be replaced with a moiety selected from the group consisting of cycloalkylene, heterocycloalkylene, arylene, and heteroarylene, and wherein L$^2$ is optionally substituted with one to four R$^{17}$ groups; or when B is —S(O)$_2$—NR$^8$—, —CH$_2$—NR$^8$—, or —C(O) NR$^8$—, R$^8$ and L$^2$ can be taken together including the nitrogen atom to which they are attached to form a 3-7-membered heterocycloalkyl optionally substituted with one to four R$^{17}$ groups; and each of R$^a$ and R$^b$ are, independently for each occurrence, selected from the group consisting of hydrogen, C$_{1-6}$alkyl, and C$_{1-6}$haloalkyl, or R$^a$ and R$^b$ are taken together, including the nitrogen to which they are attached, to form a heterocycloalkyl ring.

In another aspect, provided herein is a compound of formula I or formula II:

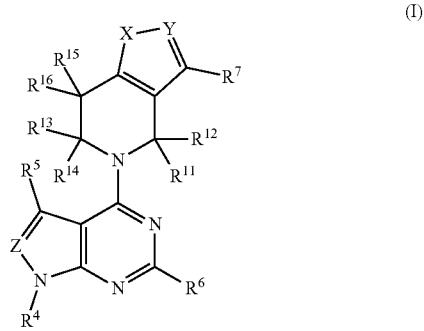

(I)

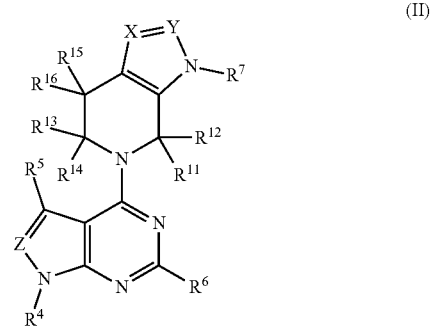

(II)

or a pharmaceutically acceptable salt thereof, wherein
For formula I: X is NR$^1$, C(R$^8$)R$^1$, O, S, S(O), or S(O)$_2$;
For formula II: X is N or CR$^1$; and
For both formula I and formula II:
Y is N or CR$^2$;
Z is N or CR$^3$;

R¹ is selected from the group consisting of cyano, hydroxyl, NR$^a$R$^b$, C$_{1-6}$alkoxy, and -A-L¹-R⁹;

R², R³, R⁴, and R⁶ are each independently selected from the group consisting of hydrogen, deuterium, halogen, cyano, hydroxyl, —NR$^a$R$^b$, C$_{1-4}$alkyl, C$_{2-6}$alkenyl, C$_{2-6}$alkynyl, C$_{1-6}$-haloalkyl, and C$_{1-6}$alkoxy;

R⁵ is selected from the group consisting of hydrogen, C$_{1-6}$alkyl, C$_{2-6}$alkenyl, C$_{2-6}$alkynyl, C$_{1-6}$haloalkyl, aryl, heteroaryl, cycloalkyl, heterocyclyl, -aryl-C$_{1-6}$alkyl, -heteroaryl-C$_{1-6}$alkyl, -heterocyclyl-C$_{1-6}$alkyl, halogen, cyano, hydroxyl, C$_{1-6}$alkoxy, C$_{1-6}$haloalkoxy, amino, carboxy, aminocarbonyl, —C$_{1-6}$alkyl-aminocarbonylamino, C$_{1-6}$alkyl-aminocarbonyl, —S(O)—R⁸, —S(O)$_2$—R⁸, —NR⁸—S(O)$_2$—R⁸, —S(O)$_2$—NR$^a$R$^b$, —NR⁸—S(O)$_2$—NR$^a$R$^b$, —C$_{1-6}$alkyl-aryl, —C$_{1-6}$alkyl-heteroaryl, —C$_{1-6}$alkyl-heterocycle, and —C$_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, CF$_3$, aminocarbonyl, —C$_{1-6}$alkyl-aminocarbonylamino, and C$_{3-6}$cycloalkyl;

R⁷ is B-L²-R¹⁰, or R⁷ is aryl or heteroaryl, wherein the aryl or heteroaryl is optionally substituted with one to four R¹⁷;

each R⁸ is independently selected from the group consisting of hydrogen, C$_{1-6}$alkyl, C$_{1-6}$haloalkyl, hydroxy, C$_{1-6}$alkoxy, and —O—C$_{1-6}$haloalkyl;

R⁹ is selected from the group consisting of hydrogen, cycloalkyl, heterocycloalkyl, aryl, and heteroaryl, wherein any non-hydrogen R⁹ is optionally substituted with one to four R¹⁷;

R¹⁰ is selected from the group consisting of hydrogen, cyano, hydroxyl, C$_{1-6}$haloalkyl, C$_{1-6}$alkoxy, —O—C$_{1-6}$ haloalkyl, cycloalkyl, heterocycloalkyl, aryl, heteroaryl, —C(O)— heterocycloalkyl, and —S(O)$_2$-heterocycloalkyl, wherein any R¹⁰ other than hydrogen, cyano, and hydroxyl is optionally substituted with one to four R¹⁷;

R¹¹, R¹², R¹³, R¹⁴, R¹⁵, and R¹⁶ are each independently selected from the group consisting of hydrogen, C$_{1-6}$alkyl, C$_{2-6}$alkenyl, C$_{2-6}$alkynyl, C$_{1-6}$haloalkyl, aryl, heteroaryl, cycloalkyl, heterocyclyl, -aryl-C$_{1-6}$alkyl, -heteroaryl-C$_{1-6}$alkyl, halogen, cyano, hydroxyl, C$_{1-6}$alkoxy, amino, carboxy, aminocarbonyl, —C$_{1-6}$alkyl-aryl, —C$_{1-6}$alkyl-heteroaryl, —C$_{1-6}$alkyl-heterocycle, and C$_{1-6}$alkyl-cycloalkyl, wherein said alkyl is optionally substituted with one or more substituents independently selected from the group consisting of halo, hydroxyl, methoxy, alkylamino, dialkylamino, CF$_3$, and C$_{3-6}$cycloalkyl;

R¹⁷ is, independently for each occurrence, selected from the group consisting of halogen, cyano, hydroxyl, —NR$^a$R$^b$, C$_{1-6}$alkyl, C$_{2-6}$alkenyl, C$_{2-6}$alkynyl, C$_{1-6}$haloalkyl, C$_{1-6}$alkoxy, CF$_3$, —SH, —S—C$_{1-6}$alkyl, —COOH, —CO$_2$—C$_{1-6}$alkyl, —C$_{1-6}$alkyl-CN, —C(O)NR$^a$R$^b$, —C(O)—C$_{1-6}$alkyl-NR$^a$R$^b$, —C(O)—NR$^a$—S(O)$_2$—C$_{1-6}$alkyl, —S(O)$_2$—C$_{1-6}$alkyl, —S(O)$_2$—NR$^a$R$^b$, —S(O)$_2$—C$_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR⁸—, —CH$_2$—NR⁸—, and —C(O)NR⁸—;

L¹ is selected from the group consisting of a bond, C$_{1-6}$alkylene, C$_{1-6}$heteroalkylene, C$_{2-6}$alkenylene, and C$_{2-6}$alkynylene, wherein L¹ is optionally substituted with one to four R¹⁷ groups;

L² is selected from the group consisting of a bond, C$_{1-6}$alkylene, C$_{2-6}$alkenylene, and C$_{2-6}$alkynylene, wherein any CH$_2$ group of C$_{1-6}$alkylene can be replaced with a moiety selected from the group consisting of —O—, —NR$^a$—, and —S(O)$_2$—, and one CH$_2$ group of C$_{1-6}$alkylene can be replaced with a moiety selected from the group consisting of cycloalkylene, heterocycloalkylene, arylene, and heteroarylene, and wherein L² is optionally substituted with one to four R¹⁷ groups; and each of R$^a$ and R$^b$ are, independently for each occurrence, selected from the group consisting of hydrogen, C$_{1-6}$alkyl, and C$_{1-6}$haloalkyl, or R$^a$ and R$^b$ are taken together, including the nitrogen to which they are attached, to form a heterocycloalkyl ring.

In another aspect, provided herein is compound of formula I:

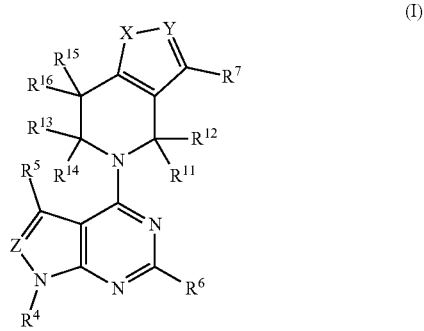

(I)

or a pharmaceutically acceptable salt thereof, wherein

X is NR¹, C(R⁸)R¹, O, S, S(O), or S(O)$_2$;

Y is N or CR²;

Z is N or CR³;

R¹ is selected from the group consisting of cyano, hydroxyl, NR$^a$R$^b$, C$_{1-6}$alkoxy, and -A-L¹-R⁹;

R², R³, R⁴, R⁵, and R⁶ are each independently selected from the group consisting of hydrogen, halogen, cyano, hydroxyl, —NR$^a$R$^b$, C$_{1-6}$alkyl, C$_{2-6}$alkenyl, C$_{2-6}$alkynyl, C$_{1-6}$haloalkyl, and C$_{1-6}$alkoxy;

R⁷ is B-L²-R¹⁰, or R⁷ is aryl or heteroaryl, wherein the aryl or heteroaryl is optionally substituted with one to four R¹⁷;

each R⁸ is independently selected from the group consisting of hydrogen, C$_{1-6}$alkyl, C$_{1-6}$haloalkyl, hydroxy, C$_{1-6}$alkoxy, and —O—C$_{1-6}$haloalkyl;

R⁹ is selected from the group consisting of hydrogen, cycloalkyl, heterocycloalkyl, aryl, and heteroaryl, wherein any non-hydrogen R⁹ is optionally substituted with one to four R¹⁷;

R¹⁰ is selected from the group consisting of hydrogen, cyano, hydroxyl, C$_{1-6}$haloalkyl, C$_{1-6}$alkoxy, —O—C$_{1-6}$ haloalkyl, cycloalkyl, heterocycloalkyl, aryl, heteroaryl, —C(O)— heterocycloalkyl, and —S(O)$_2$-heterocycloalkyl, wherein any R¹⁰ other than hydrogen, cyano, and hydroxyl is optionally substituted with one to four R¹⁷;

R¹¹, R¹², R¹³, R¹⁴, R¹⁵, and R¹⁶ are each independently selected from the group consisting of hydrogen, halogen, hydroxy, cyano, C$_{1-6}$alkyl, C$_{2-6}$alkenyl, C$_{2-6}$alkynyl, C$_{1-6}$haloalkyl, and C$_{1-6}$alkoxy;

R¹⁷ is, independently for each occurrence, selected from the group consisting of halogen, cyano, hydroxyl, —NR$^a$R$^b$, C$_{1-6}$alkyl, C$_{2-6}$alkenyl, C$_{2-6}$alkynyl, C$_{1-6}$haloalkyl, C$_{1-6}$alkoxy, CF$_3$, —SH, —S—C$_{1-6}$alkyl, —COOH, —CO$_2$—C$_{1-6}$alkyl, —C$_{1-6}$alkyl-CN, —C(O)NR$^a$R$^b$, —C(O)—C$_{1-6}$alkyl-NR$^a$R$^b$, —C(O)—NR$^a$—S(O)$_2$—C$_{1-6}$alkyl, —S(O)$_2$—C$_{1-6}$alkyl, —S(O)$_2$—NR$^a$R$^b$, —S(O)$_2$—C$_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR$^8$—, —CH$_2$—NR$^8$—, and —C(O)NR$^8$—;

L$^1$ is selected from the group consisting of a bond, C$_{1-6}$alkylene, C$_{1-6}$heteroalkylene, C$_{2-6}$alkenylene, and C$_{2-6}$alkynylene, wherein L$^1$ is optionally substituted with one to four R$^{17}$ groups;

L$^2$ is selected from the group consisting of a bond, C$_{1-6}$alkylene, C$_{2-6}$alkenylene, and C$_{2-6}$alkynylene, wherein any CH$_2$ group of C$_{1-6}$alkylene can be replaced with a moeity selected from the group consisting of —O—, —NR$^a$—, and —S(O)$_2$—, and one CH$_2$ group of C$_{1-6}$alkylene can be replaced with a moiety selected from the group consisting of cycloalkylene, heterocycloalkylene, arylene, and heteroarylene, and wherein L$^2$ is optionally substituted with one to four R$^{17}$ groups; and each of R$^a$ and R$^b$ are, independently for each occurrence, selected from the group consisting of hydrogen, C$_{1-6}$alkyl, and C$_{1-6}$haloalkyl, or R$^a$ and R$^b$ are taken together, including the nitrogen to which they are attached, to form a heterocycloalkyl ring.

In yet another aspect, provided herein is a pharmaceutical composition comprising a pharmaceutically acceptable carrier and a compound of formula I, formula II, formula III, or formula IV:

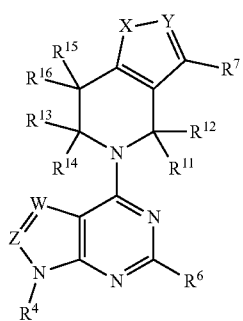

(I)

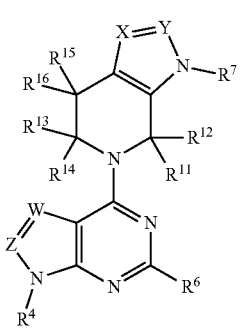

(II)

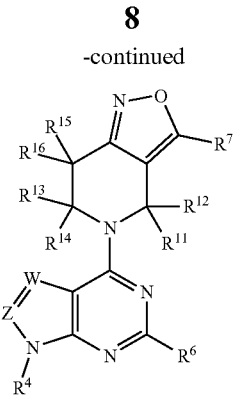

(III)

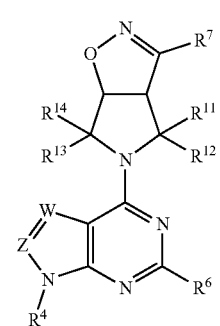

(IV)

or a pharmaceutically acceptable salt thereof, wherein
For formula I: X is NR$^1$, C(R$^8$)R$^1$, O, S, S(O), or S(O)$_2$;
For formula II: X is N or CR$^1$; and
For formula I, formula II, formula III, and formula IV:
W is N or CR$^1$;
Y is N or CR$^2$;
Z is N or CR$^3$;
wherein W and Z are not both N;
R$^1$ is selected from the group consisting of cyano, hydroxyl, NR$^a$R$^b$, C$_{1-6}$alkoxy, and -A-L$^1$-R$^9$;
R$^2$, R$^3$, R$^4$, and R$^6$ are each independently selected from the group consisting of hydrogen, deuterium, halogen, cyano, hydroxyl, —NR$^a$R$^b$, C$_{1-6}$alkyl, C$_{2-6}$alkenyl, C$_{2-6}$alkynyl, C$_{1-6}$haloalkyl, and C$_{1-6}$alkoxy;
R$^1$ is selected from the group consisting of hydrogen, C$_{1-6}$alkyl, C$_{2-6}$alkenyl, C$_{2-6}$alkynyl, C$_{1-6}$-haloalkyl, aryl, heteroaryl, cycloalkyl, heterocyclyl, -aryl-C$_{1-6}$alkyl, -heteroaryl-C$_{1-6}$alkyl, -heterocyclyl-C$_{1-6}$alkyl, halogen, cyano, hydroxyl, C$_{1-6}$alkoxy, C$_{1-6}$haloalkoxy, amino, carboxy, aminocarbonyl, —C$_{1-6}$alkyl-aminocarbonylamino, C$_{1-6}$alkyl-aminocarbonyl, —S(O)—R$^8$, —S(O)$_2$—R$^8$, —NR$^8$—S(O)$_2$—R$^8$, —S(O)$_2$—NR$^a$R$^b$, —NR$^8$—S(O)$_2$—NR$^a$R$^b$, —C$_{1-6}$alkyl-aryl, —C$_{1-6}$alkyl-heteroaryl, —C$_{1-6}$alkyl-heterocycle, and —C$_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, CF$_3$, aminocarbonyl, —C$_{1-6}$alkyl-aminocarbonylamino, and C$_{3-6}$cycloalkyl;
R$^7$ is B-L$^2$-R$^{10}$, or R$^7$ is aryl or heteroaryl, wherein the aryl or heteroaryl is optionally substituted with one to four R$^{17}$;
each R$^8$ is independently selected from the group consisting of hydrogen, C$_{1-6}$alkyl, C$_{1-6}$haloalkyl, hydroxy, C$_{1-6}$alkoxy, and —O—C$_{1-6}$haloalkyl;
R$^9$ is selected from the group consisting of hydrogen, cycloalkyl, heterocycloalkyl, aryl, and heteroaryl, wherein any non-hydrogen R$^9$ is optionally substituted with one to four R$^{17}$;

$R^{10}$ is selected from the group consisting of hydrogen, cyano, hydroxyl, $C_{1-6}$haloalkyl, $C_{1-6}$alkoxy, —O—$C_{1-6}$ haloalkyl, cycloalkyl, heterocycloalkyl, aryl, heteroaryl, —C(O)— heterocycloalkyl, and —S(O)$_2$-heterocycloalkyl, wherein any $R^{10}$ other than hydrogen, cyano, and hydroxyl is optionally substituted with one to four $R^{17}$;

$R^{11}$, $R^{12}$, $R^{13}$, $R^{14}$, $R^{15}$, and $R^{16}$ are each independently selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, halogen, cyano, hydroxyl, $C_{1-6}$alkoxy, amino, carboxy, aminocarbonyl, —$C_{1-6}$alkyl-aryl, —$C_{1-6}$alkyl-heteroaryl, —$C_{1-6}$alkyl-heterocycle, and $C_{1-6}$alkyl-cycloalkyl, wherein said alkyl is optionally substituted with one or more substituents independently selected from the group consisting of halo, hydroxyl, methoxy, alkylamino, dialkylamino, $CF_3$, and $C_{3-6}$cycloalkyl; or $R^{11}$ and $R^{12}$, $R^{13}$ and $R^{14}$, or $R^{15}$ and $R^{16}$ can betaken together including the atom to which they are attached to form a 3-6-membered spiro-fused ring optionally substituted by 1-3 substituents independently selected from the group consisting of halogen, $C_{1-6}$alkyl, and $C_{1-6}$haloalkyl;

$R^{17}$ is, independently for each occurrence, selected from the group consisting of halogen, cyano, hydroxyl, —NR$^a$R$^b$, $C_{1-6}$alkyl, $C_{2-6}$alkenyl, $C_{2-6}$alkynyl, $C_{1-6}$haloalkyl, $C_{1-6}$alkoxy, $CF_3$, —SH, —S—$C_{1-6}$alkyl, —COOH, —CO$_2$—$C_{1-6}$alkyl, —$C_{1-6}$alkyl-CN, —C(O)NR$^a$R$^b$, —C(O)—$C_{1-6}$alkyl-NR$^a$R$^b$, —C(O)—NR$^a$—S(O)$_2$—$C_{1-6}$alkyl, —S(O)$_2$—$C_{1-6}$alkyl, —S(O)$_2$—NR$^a$R$^b$, —S(O)$_2$—$C_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR$^8$—, —CH$_2$—NR$^8$—, and —C(O)NR$^8$—;

$L^1$ is selected from the group consisting of a bond, $C_{1-6}$alkylene, $C_{1-6}$heteroalkylene, $C_{2-6}$alkenylene, and $C_{2-6}$alkynylene, wherein $L^1$ is optionally substituted with one to four $R^{17}$ groups;

$L^2$ is selected from the group consisting of a bond, $C_{1-6}$alkylene, $C_{2-6}$alkenylene, and $C_{2-6}$alkynylene, wherein any CH$_2$ group of $C_{1-6}$alkylene can be replaced with a moeity selected from the group consisting of —O—, —NR$^a$—, and —S(O)$_2$—, and one CH$_2$ group of $C_{1-6}$alkylene can be replaced with a moiety selected from the group consisting of cycloalkylene, heterocycloalkylene, arylene, and heteroarylene, and wherein $L^2$ is optionally substituted with one to four $R^{17}$ groups; or when B is —S(O)$_2$—NR$^8$—, —CH$_2$—NR$^8$—, or —C(O)NR$^8$—, R$^8$ and $L^2$ can be taken together including the nitrogen atom to which they are attached to form a 3-7-membered heterocycloalkyl optionally substituted with one to four $R^{17}$ groups; and each of R$^a$ and R$^b$ are, independently for each occurrence, selected from the group consisting of hydrogen, $C_{1-6}$alkyl, and $C_{1-6}$haloalkyl, or R$^a$ and R$^b$ are taken together, including the nitrogen to which they are attached, to form a heterocycloalkyl ring.

In yet another aspect, provided herein is a pharmaceutical composition comprising a pharmaceutically acceptable carrier and a m und of formula I or formula II:

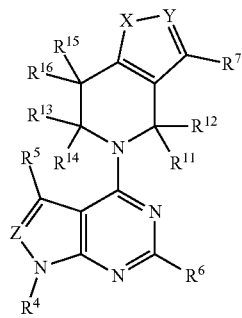

(I)

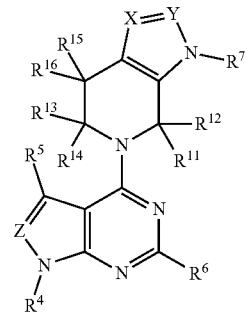

(II)

or a pharmaceutically acceptable salt thereof, wherein

For formula I: X is NR$^1$, C(R$^8$)R$^1$, O, S, S(O), or S(O)$_2$;

For formula II: X is N or CR$^1$; and

For both formula I and formula II:

Y is N or CR$^2$;

Z is N or CR$^3$;

$R^1$ is selected from the group consisting of cyano, hydroxyl, NR$^a$R$^b$, $C_{1-6}$alkoxy, and -A-$L^1$-R$^9$;

$R^2$, $R^3$, $R^4$, and $R^6$ are each independently selected from the group consisting of hydrogen, deuterium, halogen, cyano, hydroxyl, —NR$^a$R$^b$, $C_{1-6}$alkyl, $C_{2-6}$alkenyl, $C_{2-6}$alkynyl, $C_{1-6}$haloalkyl, and $C_{1-6}$alkoxy;

$R^5$ is selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, -heterocyclyl-$C_{1-6}$alkyl, halogen, cyano, hydroxyl, $C_{1-6}$alkoxy, $C_{1-6}$-haloalkoxy, amino, carboxy, aminocarbonyl, —$C_{1-6}$alkyl-aminocarbonylamino, $C_{1-6}$alkyl-aminocarbonyl, —S(O)—R$^8$, —S(O)$_2$—R$^8$, —NR$^8$—S(O)$_2$—R$^8$, —S(O)$_2$—NR$^a$R$^b$, —NR$^8$—S(O)$_2$—NR$^a$R$^b$, —$C_{1-6}$alkyl-aryl, —$C_{1-6}$alkyl-heteroaryl, —$C_{1-6}$alkyl-heterocycle, and —$C_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, $CF_3$, aminocarbonyl, —$C_{1-6}$alkyl-aminocarbonylamino, and $C_{3-6}$cycloalkyl;

$R^7$ is B-$L^2$-$R^{10}$, or $R^7$ is aryl or heteroaryl, wherein the aryl or heteroaryl is optionally substituted with one to four $R^{17}$;

each $R^8$ is independently selected from the group consisting of hydrogen, $C_{1-6}$alkyl, $C_{1-6}$haloalkyl, hydroxy, $C_{1-6}$alkoxy, and —O—$C_{1-6}$haloalkyl; $R^9$ is selected from the group consisting of hydrogen, cycloalkyl, heterocycloalkyl, aryl, and heteroaryl, wherein any non-hydrogen $R^9$ is optionally substituted with one to four $R^{17}$;

$R^{10}$ is selected from the group consisting of hydrogen, cyano, hydroxyl, $C_{1-6}$haloalkyl, $C_{1-6}$alkoxy, —O—$C_{1-6}$-haloalkyl, cycloalkyl, heterocycloalkyl, aryl, heteroaryl, —C(O)— heterocycloalkyl, and —S(O)$_2$-heterocycloalkyl, wherein any $R^{10}$ other than hydrogen, cyano, and hydroxyl is optionally substituted with one to four $R^{17}$;

$R^{11}$, $R^{12}$, $R^{13}$, $R^{14}$, $R^{15}$, and $R^{16}$ are each independently selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, halogen, cyano, hydroxyl, $C_{1-6}$alkoxy, amino, carboxy, aminocarbonyl, —$C_{1-6}$alkyl-aryl, —$C_{1-6}$alkyl-heteroaryl, —$C_{1-6}$alkyl-heterocycle, and $C_{1-6}$alkyl-cycloalkyl, wherein said alkyl is optionally substituted with one or more substituents independently selected from the group consisting of halo, hydroxyl, methoxy, alkylamino, dialkylamino, $CF_3$, and $C_{3-6}$cycloalkyl;

$R^{17}$ is, independently for each occurrence, selected from the group consisting of halogen, cyano, hydroxyl, —$NR^aR^b$, $C_{1-6}$alkyl, $C_{2-6}$alkenyl, $C_{2-6}$alkynyl, $C_{1-6}$haloalkyl, $C_{1-6}$alkoxy, $CF_3$, —SH, —S—$C_{1-6}$alkyl, —COOH, —CO$_2$—$C_{1-6}$alkyl, —$C_{1-6}$alkyl-CN, —C(O)$NR^aR^b$, —C(O)—$C_{1-6}$alkyl-$NR^aR^b$, —C(O)$NR^a$—S(O)$_2$—$C_{1-6}$alkyl, —S(O)$_2$—$C_{1-6}$alkyl, —S(O)$_2$ —$NR^aR^b$, —S(O)$_2$—$C_{1-6}$alkyl-$NR^aR^b$;

A is selected from the group consisting of —C(O)—, —S(O)—, and —S(O)$_2$—, or A is absent;

B is selected from the group consisting of —C(O)—, —S(O)$_2$—$NR^8$—, —CH$_2$—$NR^8$—, and —C(O)$NR^8$—;

$L^1$ is selected from the group consisting of a bond, $C_{1-6}$alkylene, $C_{1-6}$heteroalkylene, $C_{2-6}$alkenylene, and $C_{2-6}$alkynylene, wherein $L^1$ is optionally substituted with one to four $R^{17}$ groups;

$L^2$ is selected from the group consisting of a bond, $C_{1-6}$alkylene, $C_{2-6}$alkenylene, and $C_{2-6}$alkynylene, wherein any CH$_2$ group of $C_{1-6}$alkylene can be replaced with a moeity selected from the group consisting of —O—, —$NR^a$—, and —S(O)$_2$—, and one CH$_2$ group of $C_{1-6}$alkylene can be replaced with a moiety selected from the group consisting of cycloalkylene, heterocycloalkylene, arylene, and heteroarylene, and wherein $L^2$ is optionally substituted with one to four $R^{17}$ groups; and each of $R^a$ and $R^b$ are, independently for each occurrence, selected from the group consisting of hydrogen, $C_{1-6}$alkyl, and $C_{1-6}$haloalkyl, or $R^a$ and $R^b$ are taken together, including the nitrogen to which they are attached, to form a heterocycloalkyl ring.

In yet another aspect, provided herein is a pharmaceutical composition comprising a compound of the disclosure and a pharmaceutically acceptable carrier.

In yet another aspect, provided herein is a method of treating a disease, the method comprising administering a pharmaceutically effective amount of a compound or composition of any one of the preceding claims to a patient in need thereof, wherein the disease is selected from the group consisting of rheumatoid arthritis, myositis, vasculitis, pemphigus, bullous pemphigoid, inflammatory bowel disease including Crohn's disease and ulcerative colitis, celiac diseases, proctitis, eosinophilic gastroenteritis, or mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis *nodosa*, dry eye syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation, including Cogan's syndrome, ankylosing spondylitis, Wegener's granulomatosis, autoimmune alopecia, Type I or juvenile onset diabetes, and complications from diabetes, or thyroiditis, chronic pulmonary obstructive disorder, acute respiratory disease, cachexia, cancer, including alimentary/gastrointestinal tract cancer, colon cancer, liver cancer, skin cancer including mast cell tumor and squamous cell carcinoma, breast and mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma including oral and metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, or angiogenic-associated disorders including solid tumors, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotropic Lateral Sclerosis, Huntington's disease, cerebral ischemia, fronto-temporal lobe dementia, and with neuropsychiatric disorders including schizophrenia, bipolar disorder, treatment resistant depression, Post Traumatic Stress Disorder, anxiety, and auto-antibodies mediated encephalopathies, Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization.

DETAILED DESCRIPTION OF CERTAIN EMBODIMENTS OF THE INVENTION

As generally described herein, the present invention provides bicyclic compounds designed, for example, to act as modulators of the JAK family kinases. In certain embodiments, such compounds are envisioned to be useful as therapeutic agents for treating a neurodegenerative disorder

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Isomers, e.g., stereoisomers, can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers. Racemates and Resolutions (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-position/center/carbon compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The articles "a" and "an" may be used herein to refer to one or to more than one (i.e. at least one) of the grammatical objects of the article. By way of example "an analog" means one analog or more than one analog.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-6}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-6}$alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

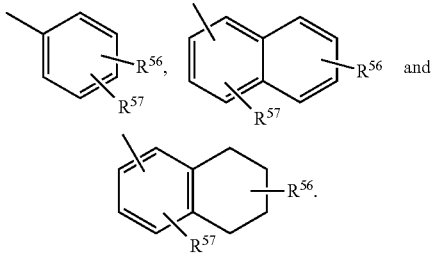

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{59}SOR^{59}$, $NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system.

"Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

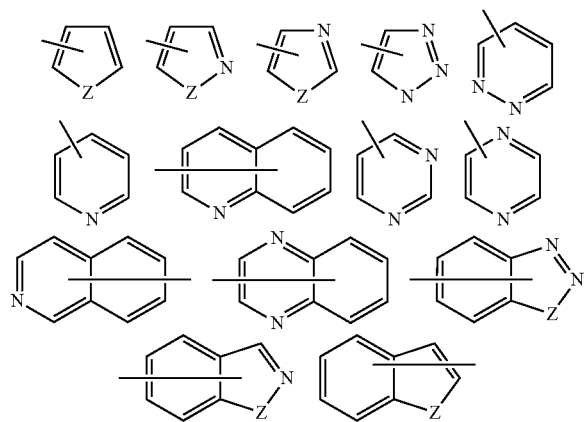

wherein each Z is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_5$), cyclooctenyl ($C_5$), bicyclo[2.2.1]heptanyl ($C_7$), bicyclo[2.2.2]octanyl ($C_5$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-4}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups herein, a heteroatom sulfur may also be an —S(O)— or —S(O)$_2$— group. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur. A "cyclooxyalkyl" group is a heterocyclic ring, for example, a 3- to 7-membered ring, that includes several carbon ring atoms and one oxygen ring atom, but no other heteroatoms.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cyclohetereoalkenyl, and the like having from 1 to 5, and particularly from 1 to 3 heteroatoms.

"Spiro" cyclic group means a 3- to 7-membered ring in which exactly one of the ring atoms is shared with a second ring. The spiro group may be spiro cycloakyl if all ring atoms are carbon. The spiro group may be spiroheterocyclyl if one or more of the ring atoms are non carbon, for example 1-3 ring atoms independently selected from N, O, and S.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^2$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$($C_6$-$C_{10}$ aryl), —O—(CH$_2$)(5-10 membered heteroaryl), —O—(CH$_2$)($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo group" refers to —C(=O)—.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —NR$^3$—C$_1$-C$_8$ alkyl, —NR$^3$—(CH$_2$)$_t$(C$_6$-C$_{10}$ aryl), —NR$^3$—(CH$_2$)(5-10 membered heteroaryl), —NR$^3$—(CH$_2$)(C$_3$-C$_{10}$ cycloalkyl), and —NR$^3$—(CH$_2$)$_t$(4-10 membered heterocyclyl), wherein t is an integer from 0 to 4, for instance 1 or 2, each R$^3$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl, difluoromethyl, fluoromethyl, chloromethyl, dichloromethyl, dibromoethyl, tribromomethyl, tetrafluoroethyl, and the like.

"Hydroxy" refers to the radical —OH.

"Nitro" refers to the radical —NO$_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction.

Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ haloalkyl, C$_{2-10}$ alkenyl, C$_{2-10}$ alkynyl, $C_{3-40}$ carbocyclyl, 3-14 membered heterocyclyl, $C_{6-14}$ aryl, and 5-14 membered heteroaryl, or two $R^a$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-40}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

These and other exemplary substituents are described in more detail in the Detailed Description, and Claims. The invention is not intended to be limited in any manner by the above exemplary listing of substituents.

Other Definitions

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammoniun cations, and the like. See, e.g., Berge, et al. *J. Pharm. Sci.* (1977) 66(1): 1-79.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the subject.

In some embodiments, the compound of Formula (I), (II), (III), or (IV) is a prodrug, wherein the prodrug includes a cleavable moiety. Exemplary hydroxyl containing prodrugs include, for example, esters.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of x electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g. infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{cc})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on a sulfur atom is a sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R$, $-C(=O)N(R^{bb})_2$, $-C(=NR^{bb})R^{aa}$, $-C(=NR)OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

In certain embodiments, the substituent present on a nitrogen atom is an amino protecting group (also referred to herein as a nitrogen protecting group). Amino protecting groups include, but are not limited to, $-OH$, $-OR^{aa}$, $-N(R^{cc})_2$, $-C(=O)R^{aa}$, $-C(=O)OR^{aa}$, $-C(=O)N(R^{cc})_2$, $-S(=O)_2R^{aa}$, $-C(=NR^{cc})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $C_{1-10}$ alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary amino protecting groups include, but are not limited to amide groups (e.g., $-C(=O)R^{aa}$), which include, but are not limited to, formamide and acetamide; carbamate groups (e.g., $-C(=O)OR^{aa}$), which include, but are not limited to, 9-fluorenylmethyl carbamate (Fmoc), t-butyl carbamate (BOC), and benzyl carbamate (Cbz); sulfonamide groups (e.g., $-S(=O)_2R^{aa}$), which include, but are not limited to, p-toluenesulfonamide (Ts), methanesulfonamide (Ms), and N-[2-(trimethylsilyl)ethoxy]methylamine (SEM).

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response, e.g., to treat an immune disorder, is sufficient to reduce progress or symptoms. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Compounds

In one aspect, provided herein is compound of formula I, formula II, formula III or formula IV:

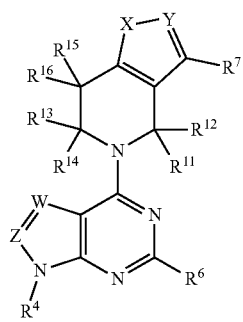

(I)

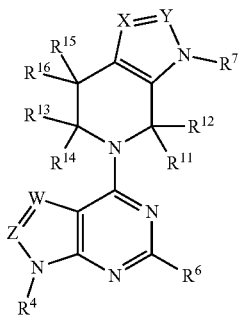

(II)

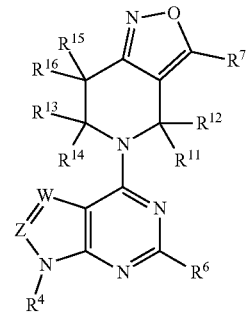

(III)

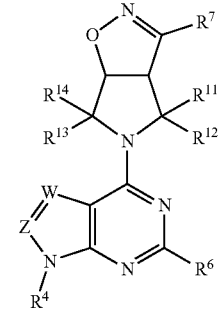

(IV)

or a pharmaceutically acceptable salt thereof, wherein

For formula I: X is $NR^1$, $C(R^8)R^1$, O, S, S(O), or $S(O)_2$;

For formula II: X is N or $CR^1$; and

For formula I, formula II, formula III, and formula IV:

W is N or $CR^5$;

Y is N or $CR^2$;

Z is N or $CR^3$;

wherein W and Z are not both N;

$R^1$ is selected from the group consisting of cyano, hydroxyl, $NR^aR^b$, $C_{1-6}$alkoxy, and -A-$L^1$-$R^9$;

$R^2$, $R^3$, $R^4$, and $R^6$ are each independently selected from the group consisting of hydrogen, deuterium, halogen, cyano, hydroxyl, —$NR^aR^b$, $C_{1-6}$alkyl, $C_{2-6}$alkenyl, $C_{2-6}$alkynyl, $C_{1-6}$haloalkyl, and $C_{1-6}$alkoxy;

$R^5$ is selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, -heterocyclyl-$C_{1-6}$alkyl, halogen, cyano, hydroxyl, $C_{1-6}$alkoxy, $C_{1-6}$-haloalkoxy, amino, carboxy, aminocarbonyl, —$C_{1-6}$alkyl-aminocarbonylamino, $C_{1-6}$alkyl-aminocarbonyl, —S(O)—$R^8$, —$S(O)_2$—$R^8$, —$NR^8$—$S(O)_2$—$R^8$, —$S(O)_2$—$NR^aR^b$, —$NR^8$—$S(O)_2$—$NR^aR^b$, —$C_{1-6}$alkyl-aryl, —$C_{1-6}$alkyl-heteroaryl, —$C_{1-6}$alkyl-heterocycle, and —$C_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, CF$_3$, aminocarbonyl, —C$_{1-6}$alkyl-aminocarbonylamino, and C$_{3-6}$cycloalkyl;

R$^7$ is B-L$^2$-R$^{10}$, or R$^7$ is aryl or heteroaryl, wherein the aryl or heteroaryl is optionally substituted with one to four R$^{17}$;

each R$^8$ is independently selected from the group consisting of hydrogen, C$_{1-6}$alkyl, C$_{1-6}$haloalkyl, hydroxy, C$_{1-6}$alkoxy, and —O—C$_{1-6}$haloalkyl;

R$^9$ is selected from the group consisting of hydrogen, cycloalkyl, heterocycloalkyl, aryl, and heteroaryl, wherein any non-hydrogen R$^9$ is optionally substituted with one to four R$^{17}$;

R$^{10}$ is selected from the group consisting of hydrogen, cyano, hydroxyl, C$_{1-6}$haloalkyl, C$_{1-6}$alkoxy, —O—C$_{1-6}$-haloalkyl, cycloalkyl, heterocycloalkyl, aryl, heteroaryl, —C(O)— heterocycloalkyl, and —S(O)$_2$-heterocycloalkyl, wherein any R$^{10}$ other than hydrogen, cyano, and hydroxyl is optionally substituted with one to four R$^{17}$;

R$^{11}$, R$^{12}$, R$^{13}$, R$^{14}$, R$^{15}$, and R$^{16}$ are each independently selected from the group consisting of hydrogen, C$_{1-6}$alkyl, C$_{2-6}$alkenyl, C$_{2-6}$alkynyl, C$_{1-6}$haloalkyl, aryl, heteroaryl, cycloalkyl, heterocycloalkyl, heterocyclyl, -aryl-C$_{1-6}$alkyl, -heteroaryl-C$_{1-6}$alkyl, halogen, cyano, hydroxyl, C$_{1-6}$alkoxy, amino, carboxy, aminocarbonyl, —C$_{1-6}$alkyl-aryl, —C$_{1-6}$alkyl-heteroaryl, —C$_{1-6}$alkyl-heterocycle, and C$_{1-6}$alkyl-cycloalkyl, wherein said alkyl is optionally substituted with one or more substituents independently selected from the group consisting of halo, hydroxyl, methoxy, alkylamino, dialkylamino, CF$_3$, and C$_{3-6}$cycloalkyl; or R$^{11}$ and R$^{12}$, R$^{13}$ and R$^{14}$, or R$^{15}$ and R$^{16}$ can be taken together including the atom to which they are attached to form a 3-6-membered spiro-fused ring optionally substituted by 1-3 substituents independently selected from the group consisting of halogen, C$_{1-6}$alkyl, and C$_{1-6}$haloalkyl;

R$^{17}$ is, independently for each occurrence, selected from the group consisting of halogen, cyano, hydroxyl, —NR$^a$R$^b$, C$_{1-6}$alkyl, C$_{2-6}$alkenyl, C$_{2-6}$alkynyl, C$_{1-6}$haloalkyl, C$_{1-6}$alkoxy, CF$_3$, —SH, —S—C$_{1-6}$alkyl, —COOH, —CO$_2$—C$_{1-6}$alkyl, —C$_{1-6}$alkyl-CN, —C(O)NR$^a$R$^b$, —C(O)—C$_{1-6}$alkyl-NR$^a$R$^b$, —C(O)—NR$^a$—S(O)$_2$—C$_{1-6}$alkyl, —S(O)$_2$—C$_{1-6}$alkyl, —S(O)$_2$—NR$^a$R$^b$, —S(O)$_2$—C$_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR$^8$—, —CH$_2$—NR$^8$—, and —C(O)NR$^8$—;

L$^1$ is selected from the group consisting of a bond, C$_{1-6}$alkylene, C$_{1-6}$heteroalkylene, C$_{2-6}$alkenylene, and C$_{2-6}$alkynylene, wherein L$^1$ is optionally substituted with one to four R$^{17}$ groups;

L$^2$ is selected from the group consisting of a bond, C$_{1-6}$alkylene, C$_{2-6}$alkenylene, and C$_{2-6}$alkynylene, wherein any CH$_2$ group of C$_{1-6}$alkylene can be replaced with a moeity selected from the group consisting of —O—, —NR$^a$—, and —S(O)$_2$—, and one CH$_2$ group of C$_{1-6}$alkylene can be replaced with a moiety selected from the group consisting of cycloalkylene, heterocycloalkylene, arylene, and heteroarylene, and wherein L$^2$ is optionally substituted with one to four R$^{17}$ groups; or when B is —S(O)$_2$—NR$^8$—, —CH$_2$—NR$^8$—, or —C(O)NR$^8$—, R$^8$ and L$^2$ can be taken together including the nitrogen atom to which they are attached to form a 3-7-membered heterocycloalkyl optionally substituted with one to four R$^{17}$ groups; and each of R$^a$ and R$^b$ are, independently for each occurrence, selected from the group consisting of hydrogen, C$_{1-6}$alkyl, and C$_{1-6}$-haloalkyl, or R$^a$ and R$^b$ are taken together, including the nitrogen to which they are attached, to form a heterocycloalkyl ring.

In another aspect, provided herein is a compound of formula I or formula II:

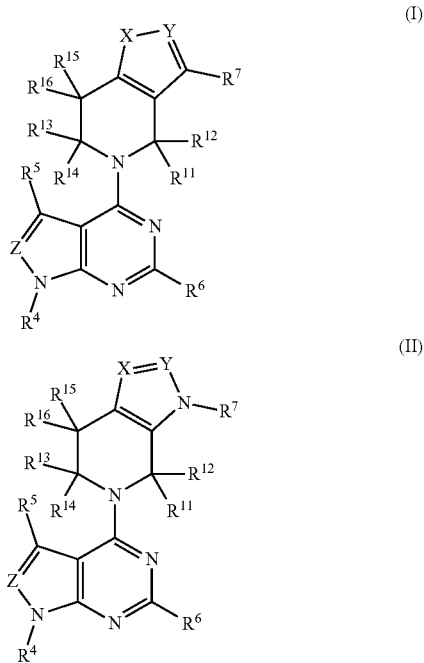

or a pharmaceutically acceptable salt thereof, wherein

For formula I: X is NR$^1$, C(R$^8$)R$^1$, O, S, S(O), or S(O)$_2$;

For formula II: X is N or CR$^1$; and

For both formula I and formula II:

Y is N or CR$^2$;

Z is N or CR$^3$;

R$^1$ is selected from the group consisting of cyano, hydroxyl, NR$^a$R$^b$, C$_{1-6}$alkoxy, and -A-L$^1$-R$^9$;

R$^2$, R$^3$, R$^4$, and R$^6$ are each independently selected from the group consisting of hydrogen, deuterium, halogen, cyano, hydroxyl, —NR$^a$R$^b$, C$_{1-4}$alkyl, C$_{2-6}$alkenyl, C$_{2-6}$alkynyl, C$_{1-6}$haloalkyl, and C$_{1-6}$alkoxy;

R$^5$ is selected from the group consisting of hydrogen, C$_{1-6}$alkyl, C$_{2-6}$alkenyl, C$_{2-6}$alkynyl, C$_{1-6}$haloalkyl, aryl, heteroaryl, cycloalkyl, heterocyclyl, -aryl-C$_{1-6}$alkyl, -heteroaryl-C$_{1-6}$alkyl, -heterocyclyl-C$_{1-6}$alkyl, halogen, cyano, hydroxyl, C$_{1-6}$alkoxy, C$_{1-6}$haloalkoxy, amino, carboxy, aminocarbonyl, —C$_{1-6}$alkyl-aminocarbonylamino, C$_{1-6}$alkyl-aminocarbonyl, —S(O)—R$^8$, —S(O)$_2$—R$^8$, —NR$^8$—S(O)$_2$—R$^8$, —S(O)$_2$—NR$^a$R$^b$, —NR$^8$—S(O)$_2$—NR$^a$R$^b$, —C$_{1-6}$alkyl-aryl, —C$_{1-6}$alkyl-heteroaryl, —C$_{1-6}$alkyl-heterocycle, and —C$_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, CF$_3$, aminocarbonyl, —C$_{1-6}$alkyl-aminocarbonylamino, and C$_{3-6}$cycloalkyl;

$R^7$ is $B$-$L^2$-$R^{10}$, or $R^7$ is aryl or heteroaryl, wherein the aryl or heteroaryl is optionally substituted with one to four $R^{17}$;

each $R^8$ is independently selected from the group consisting of hydrogen, $C_{1-6}$alkyl, $C_{1-6}$haloalkyl, hydroxy, $C_{1-6}$alkoxy, and —O—$C_{1-6}$haloalkyl;

$R^9$ is selected from the group consisting of hydrogen, cycloalkyl, heterocycloalkyl, aryl, and heteroaryl, wherein any non-hydrogen $R^9$ is optionally substituted with one to four $R^{17}$;

$R^{10}$ is selected from the group consisting of hydrogen, cyano, hydroxyl, $C_{1-6}$haloalkyl, $C_{1-6}$alkoxy, —O—$C_{1-6}$ haloalkyl, cycloalkyl, heterocycloalkyl, aryl, heteroaryl, —C(O)— heterocycloalkyl, and —S(O)$_2$-heterocycloalkyl, wherein any $R^{10}$ other than hydrogen, cyano, and hydroxyl is optionally substituted with one to four $R^{17}$;

$R^{11}$, $R^{12}$, $R^{13}$, $R^{14}$, $R^{15}$, and $R^{16}$ are each independently selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, halogen, cyano, hydroxyl, $C_{1-6}$alkoxy, amino, carboxy, aminocarbonyl, —$C_{1-6}$alkyl-aryl, —$C_{1-6}$alkyl-heteroaryl, —$C_{1-6}$alkyl-heterocycle, and $C_{1-6}$alkyl-cycloalkyl, wherein said alkyl is optionally substituted with one or more substituents independently selected from the group consisting of halo, hydroxyl, methoxy, alkylamino, dialkylamino, CF$_3$, and $C_{3-6}$cycloalkyl;

$R^{17}$ is, independently for each occurrence, selected from the group consisting of halogen, cyano, hydroxyl, —NR$^a$R$^b$, $C_{1-6}$alkyl, $C_{2-6}$alkenyl, $C_{2-6}$alkynyl, $C_{1-6}$haloalkyl, $C_{1-6}$alkoxy, CF$_3$, —SH, —S—$C_{1-6}$alkyl, —COOH, —CO$_2$—$C_{1-6}$alkyl, —$C_{1-6}$alkyl-CN, —C(O)NR$^a$R$^b$, —C(O)—$C_{1-6}$alkyl-NR$^a$R$^b$, —C(O)—NR$^a$—S(O)$_2$—$C_{1-6}$alkyl, —S(O)$_2$—$C_{1-6}$alkyl, —S(O)$_2$—NR$^a$R$^b$, —S(O)$_2$—$C_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR$^8$—, —CH$_2$—NR$^8$—, and —C(O)NR$^8$—;

$L^1$ is selected from the group consisting of a bond, $C_{1-6}$alkylene, $C_{1-6}$heteroalkylene, $C_{2-6}$alkenylene, and $C_{2-6}$alkynylene, wherein $L^1$ is optionally substituted with one to four $R^{17}$ groups;

$L^2$ is selected from the group consisting of a bond, $C_{1-6}$alkylene, $C_{2-6}$alkenylene, and $C_{2-6}$alkynylene, wherein any CH$_2$ group of $C_{1-6}$alkylene can be replaced with a moeity selected from the group consisting of —O—, —NR$^a$—, and —S(O)$_2$—, and one CH$_2$ group of $C_{1-6}$alkylene can be replaced with a moiety selected from the group consisting of cycloalkylene, heterocycloalkylene, arylene, and heteroarylene, and wherein $L^2$ is optionally substituted with one to four $R^{17}$ groups; and each of R$^a$ and R$^b$ are, independently for each occurrence, selected from the group consisting of hydrogen, $C_{1-6}$alkyl, and $C_{1-6}$haloalkyl, or R$^a$ and R$^b$ are taken together, including the nitrogen to which they are attached, to form a heterocycloalkyl ring.

In another aspect, provided herein is compound of formula I:

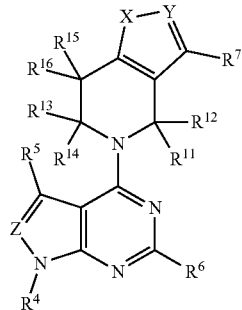

(I)

or a pharmaceutically acceptable salt thereof, wherein

X is NR$^1$, C(R$^8$)R$^1$, O, S, S(O), or S(O)$_2$;

Y is N or CR$^2$;

Z is N or CR$^3$;

$R^1$ is selected from the group consisting of cyano, hydroxyl, NR$^a$R$^b$, $C_{1-6}$alkoxy, and -A-$L^1$-R$^9$;

$R^2$, $R^3$, $R^4$, $R^5$, and $R^6$ are each independently selected from the group consisting of hydrogen, halogen, cyano, hydroxyl, —NR$^a$R$^b$, $C_{1-6}$alkyl, $C_{2-6}$alkenyl, $C_{2-6}$alkynyl, $C_{1-6}$haloalkyl, and $C_{1-6}$alkoxy;

$R^7$ is $B$-$L^2$-$R^{10}$, or $R^7$ is aryl or heteroaryl, wherein the aryl or heteroaryl is optionally substituted with one to four $R^{17}$;

each $R^8$ is independently selected from the group consisting of hydrogen, $C_{1-6}$alkyl, $C_{1-6}$haloalkyl, hydroxy, $C_{1-6}$alkoxy, and —O—$C_{1-6}$haloalkyl;

$R^9$ is selected from the group consisting of hydrogen, cycloalkyl, heterocycloalkyl, aryl, and heteroaryl, wherein any non-hydrogen $R^9$ is optionally substituted with one to four $R^{17}$;

$R^{10}$ is selected from the group consisting of hydrogen, cyano, hydroxyl, $C_{1-6}$haloalkyl, $C_{1-6}$alkoxy, —O—$C_{1-6}$ haloalkyl, cycloalkyl, heterocycloalkyl, aryl, heteroaryl, —C(O)— heterocycloalkyl, and —S(O)$_2$-heterocycloalkyl, wherein any $R^{10}$ other than hydrogen, cyano, and hydroxyl is optionally substituted with one to four $R^{17}$;

$R^{11}$, $R^{12}$, $R^{13}$, $R^{14}$, $R^{15}$, and $R^{16}$ are each independently selected from the group consisting of hydrogen, halogen, hydroxy, cyano, $C_{1-6}$alkyl, $C_{2-6}$alkenyl, $C_{2-6}$alkynyl, $C_{1-6}$haloalkyl, and $C_{1-6}$alkoxy;

$R^{17}$ is, independently for each occurrence, selected from the group consisting of halogen, cyano, hydroxyl, —NR$^a$R$^b$, $C_{1-6}$alkyl, $C_{2-6}$alkenyl, $C_{2-6}$alkynyl, $C_{1-6}$haloalkyl, $C_{1-6}$alkoxy, CF$_3$, —SH, —S—$C_{1-6}$alkyl, —COOH, —CO$_2$—$C_{1-6}$alkyl, —$C_{1-6}$alkyl-CN, —C(O)NR$^a$R$^b$, —C(O)—$C_{1-6}$alkyl-NR$^a$R$^b$, —C(O)—NR$^a$—S(O)$_2$—$C_{1-6}$alkyl, —S(O)$_2$—$C_{1-6}$alkyl, —S(O)$_2$—NR$^a$R$^b$, —S(O)$_2$—$C_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR$^8$—, —CH$_2$—NR$^8$—, and —C(O)NR$^8$—;

$L^1$ is selected from the group consisting of a bond, $C_{1-6}$alkylene, $C_{1-6}$heteroalkylene, $C_{2-6}$alkenylene, and $C_{2-6}$alkynylene, wherein $L^1$ is optionally substituted with one to four $R^{17}$ groups;

$L^2$ is selected from the group consisting of a bond, $C_{1-6}$alkylene, $C_{2-6}$alkenylene, and $C_{2-6}$alkynylene, wherein any CH$_2$ group of $C_{1-6}$alkylene can be replaced with a moeity selected from the group consisting of —O—, —NR$^a$—, and —S(O)$_2$—, and one CH$_2$ group of C$_{1-6}$alkylene can be replaced with a moiety selected from the group consisting of cycloalkylene, heterocycloalkylene, arylene, and heteroarylene, and wherein L$^2$ is optionally substituted with one to four R$^{17}$ groups; and each of R$^a$ and R$^b$ are, independently for each occurrence, selected from the group consisting of hydrogen, C$_{1-6}$alkyl, and C$_{1-6}$haloalkyl, or R$^a$ and R$^b$ are taken together, including the nitrogen to which they are attached, to form a heterocycloalkyl ring.

In some embodiments, the compound is of formula I or formula II.

In some embodiments, the compound is of formula I.
In some embodiments, the compound is of formula II.
In some embodiments, the compound is of formula III.
In some embodiments, the compound is of formula IV.
In some embodiments, W is CR$^5$.
In some embodiments, X is NR$^1$ or O. In some embodiments, X is O. In some embodiments, X is NR$^1$.
In some embodiments, Y is N.
In some embodiments, Z is CR$^3$.
In some embodiments, R$^3$ is hydrogen.
In some embodiments, R$^4$ is hydrogen.
In some embodiments, R$^5$ is hydrogen.
In some embodiments, R$^6$ is hydrogen.
In some embodiments, R$^{11}$, R$^{12}$, R$^{13}$, R$^{14}$, R$^{15}$, and R$^{16}$ are each hydrogen.
In some embodiments, R$^3$, R$^4$, R$^5$, and R$^6$ are each hydrogen.
In some embodiments, R$^1$ is -L$^1$-R$^9$.
In some embodiments, L$^1$ is C$_{1-6}$-alkylene optionally substituted with one to four substituents. In some embodiments, L$^1$ is unsubstituted C$_{1-6}$-alkylene.
In some embodiments, R$^9$ is aryl or heteroaryl.
In some embodiments, R$^1$ is C$_{1-6}$alkyl, e.g., methyl. In some embodiments, R$^1$ is hydrogen. In some embodiments, R$^1$ is C$_{1-6}$alkyl, e.g. methyl, or hydrogen.
In some embodiments, R$^1$ is selected from the group consisting of hydrogen, methyl, ethyl, propyl, isopropyl, —CH$_2$—CH=CH$_2$, —CH$_2$CH$_2$—OMe, CH$_2$CH$_2$—OH, S(O)$_2$Et, phenyl,

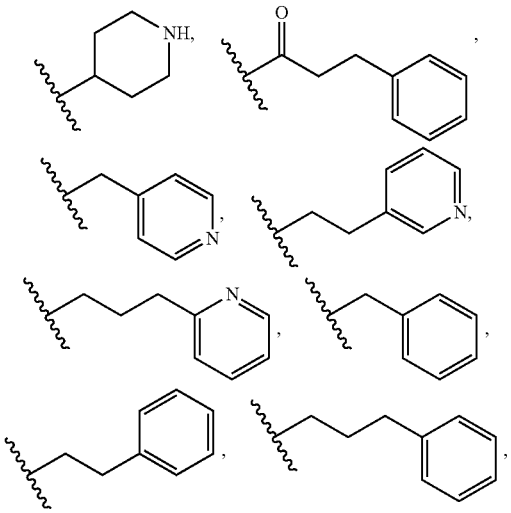

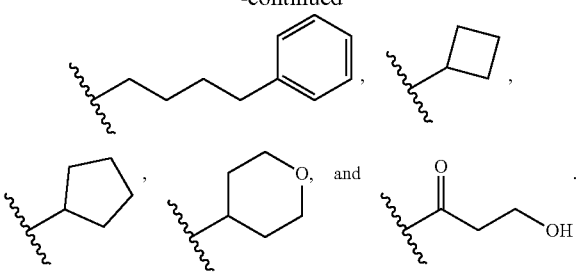

In some embodiments, R$^7$ is B-L$^2$-R$^{10}$.

In some embodiments, B is —C(O)NH—.

In some embodiments, L$^2$ is C$_{1-6}$-alkylene substituted with one R$^{17}$ at a terminal carbon position.

In some embodiments, R$^7$ is —C(O)NR$^8$—C$_{1-6}$alkyl-CF$_3$, e.g., —C(O)NH—CH$_2$CH$_2$—CF$_3$. In some embodiments, R$^7$ is —C(O)NR$^8$—C$_{3-7}$cycloalkyl-R$^{17}$. In some embodiments, R$^7$ is selected from the group consisting of —C(O)NH—CH$_2$—CF$_3$, —C(O)NH—CH$_2$CH$_2$—CF$_3$, —C(O)NH—CH$_2$CH$_2$CH$_2$—CF$_3$, —CH$_2$NH—CH$_2$CH$_2$—CF$_3$, —C(O)—CH$_2$—CN, p-cyanopenyl,

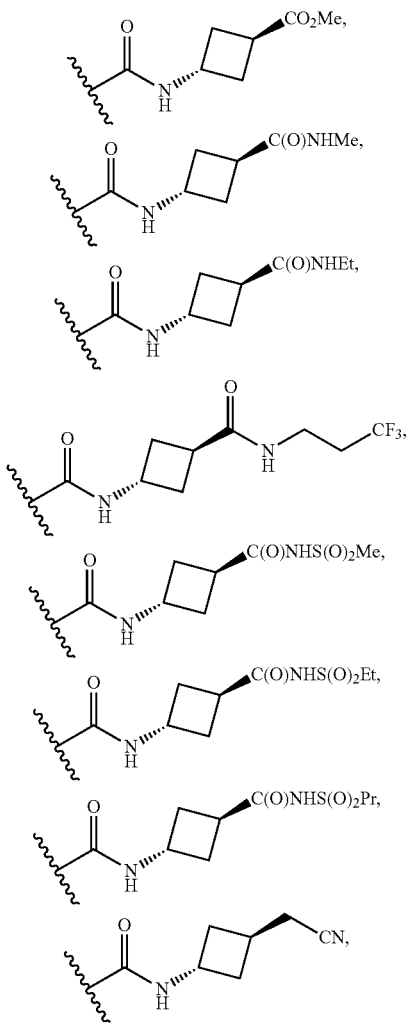

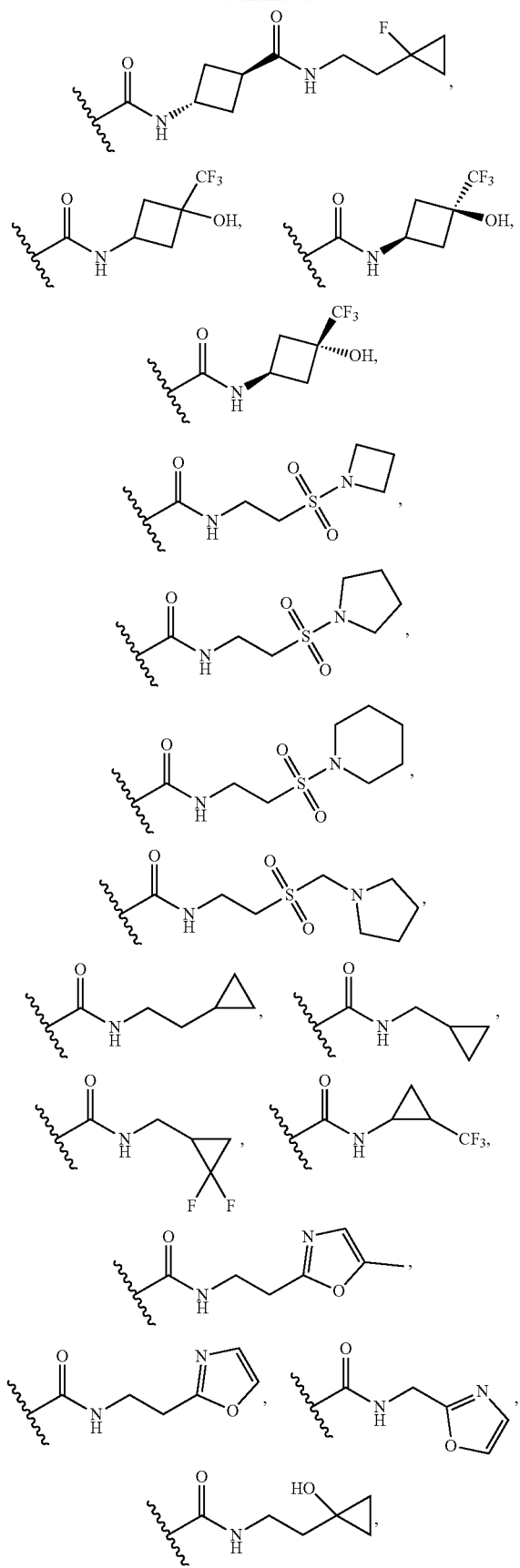
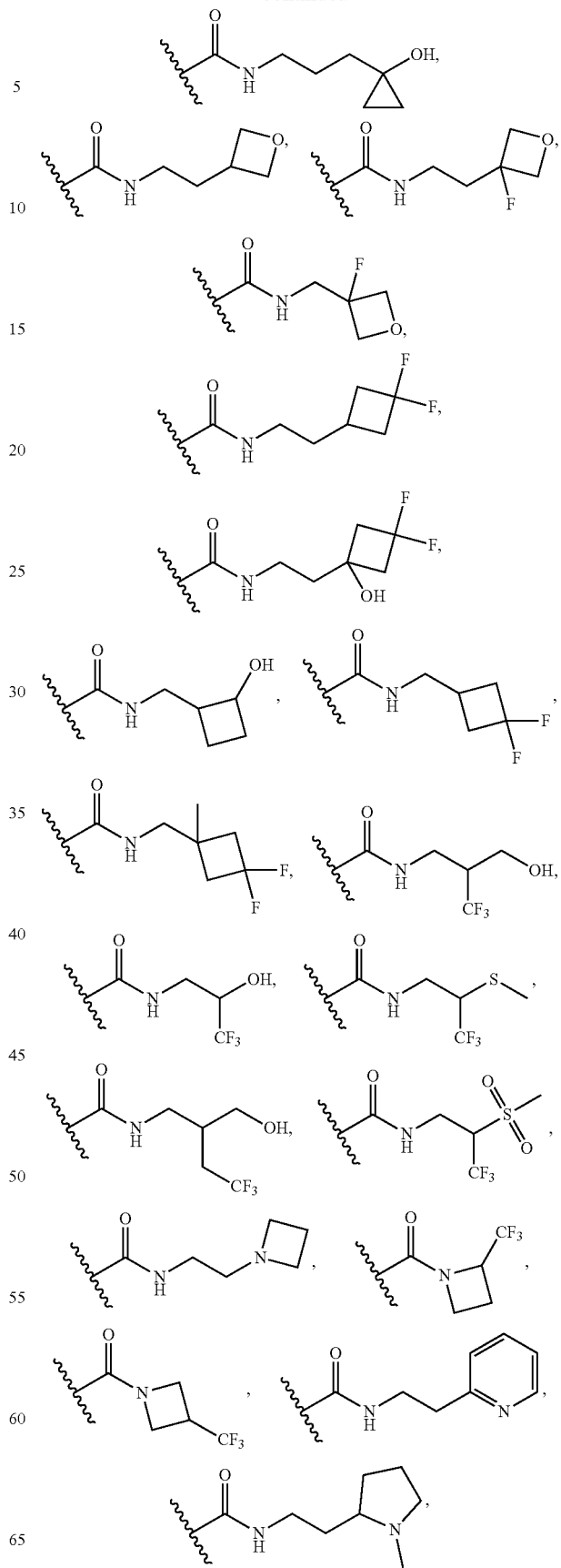

-continued

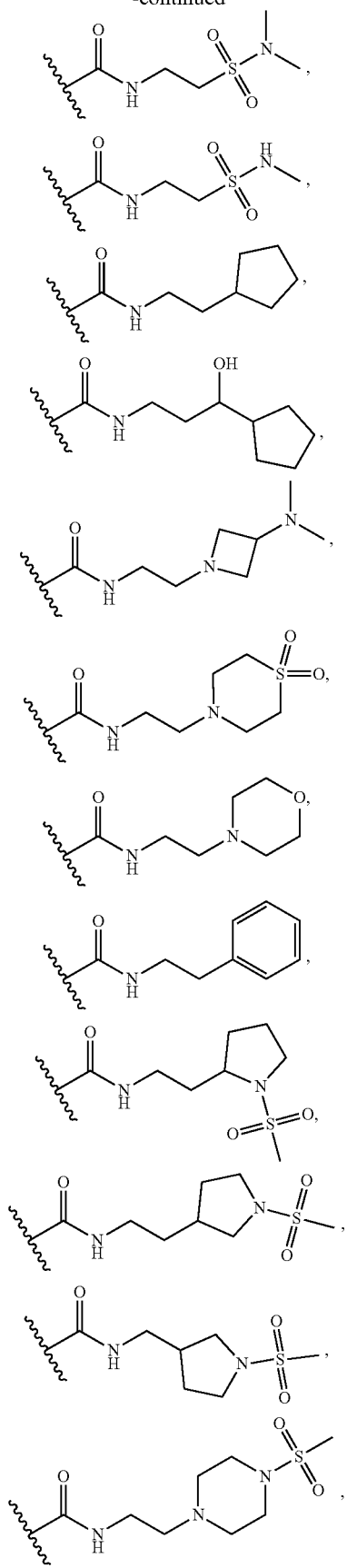

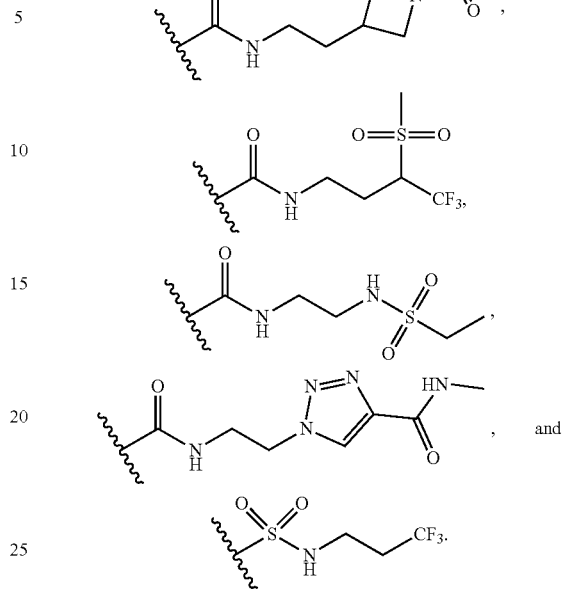

In some embodiments, R⁷ is

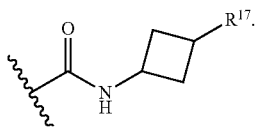

In some embodiments, R⁷ is

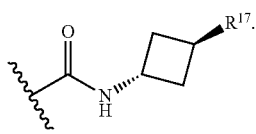

In some embodiments, R⁷ is

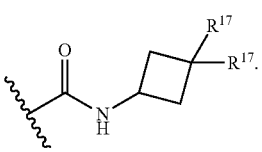

In some embodiments, $R^{17}$ is selected from the group consisting of $C_{1-6}$haloalkyl, $-CO_2-C_{1-6}$alkyl, $-C_{1-6}$alkyl-CN, $-C(O)NR^aR^b$, and $-C(O)-NR^a-S(O)_2-C_{1-6}$alkyl.

In some embodiments, $R^{17}$ is selected from the group consisting of hydroxy, CN, halogen, $C_{1-6}$alkyl, $C_{1-6}$haloalkyl, $-CO_2-C_{1-6}$alkyl, $-SO_2-C_{1-6}$alkyl, $-S(O)_2-NR^aR^b$, $-C_{1-6}$alkyl-CN, $-C(O)NR^aR^b$, and $-C(O)-NR^a-S(O)_2-C_{1-6}$alkyl.

In some embodiments, $R^{17}$ is selected from the group consisting of hydroxy, CN, F, Me, SMe, $CF_3$, —$CO_2$—$C_{1-6}$alkyl, —$SO_2$-Me, —$S(O)_2$—$NMe_2$, —$C(O)NMe_2$, and —$C(O)$—NH—$S(O)_2$-Me.

In some embodiments, the compound is a compound of formula Ia:

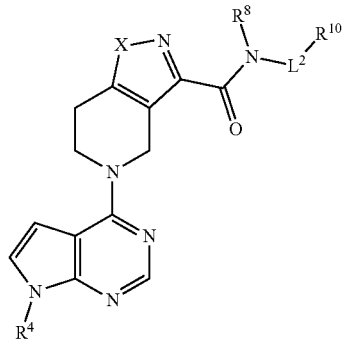

(Ia)

or a pharmaceutically acceptable salt thereof, wherein
X is $NR^1$ or O;
$R^1$ is selected from the group consisting of hydrogen, cyano, hydroxyl, $NR^aR^b$, $C_{1-6}$alkoxy, $C_{1-6}$alkyl, $C_{2-6}$alkenyl, $C_{2-6}$alkynyl, —C(O)—$C_{1-6}$alkyl-aryl, —C(O)—$C_{1-6}$alkyl-heteroaryl, —$C_{1-6}$alkyl-aryl, $C_{1-6}$alkyl-heteroaryl, aryl, heteroaryl, cycloakyl, heterocycloalkyl, and —$S(O)_2$—$C_{1-6}$alkyl, wherein any non-hydrogen $R^1$ is optionally substituted with one $R^{17}$;
$R^4$ is selected from the group consisting of hydrogen and $C_{1-6}$alkyl;
$R^8$ is selected from the group consisting of hydrogen and $C_{1-6}$alkyl;
$R^{10}$ is selected from the group consisting of hydrogen, $CF_3$, cyano, cycloalkyl, heterocycloalkyl, aryl, heteroaryl, wherein any $R^{10}$ other than hydrogen, cyano, and hydroxyl is optionally substituted with one to three $R^{17}$;
$R^{17}$ is, independently for each occurrence, selected from the group consisting of halogen, cyano, hydroxyl, —$NR^aR^b$, $C_{1-6}$alkyl, $C_{2-6}$alkenyl, $C_{2-6}$alkynyl, $C_{1-6}$haloalkyl, $C_{1-6}$alkoxy, $CF_3$, —SH, —S—$C_{1-6}$alkyl, —COOH, —$CO_2$—$C_{1-6}$alkyl, —$C_{1-6}$alkyl-CN, —$C(O)NR^aR^b$, —C(O)—$C_{1-6}$alkyl-$NR^aR^b$, —C(O)—$NR^a$—$S(O)_2$—$C_{1-6}$alkyl, —$S(O)_2$—$C_{1-6}$alkyl, —$S(O)_2$ —$NR^aR^b$, —$S(O)_2$—$C_{1-6}$alkyl-$NR^aR^b$;
$L^2$ is selected from the group consisting of a bond, $C_{1-6}$alkylene, cycloalkylene, and cycloalkylene-$C_{1-6}$alkylene; and
each of $R^a$ and $R^b$ are, independently for each occurrence, selected from the group consisting of hydrogen, $C_{1-6}$alkyl, and $C_{1-6}$haloalkyl, or $R^a$ and $R^b$ are taken together, including the nitrogen to which they are attached, to form a heterocycloalkyl ring.

In some embodiments the compound is a compound of formula Ib:

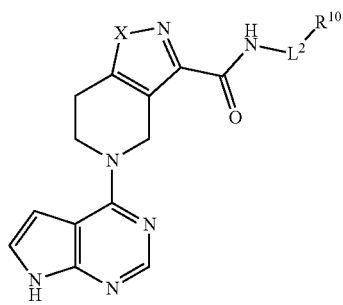

(Ib)

or a pharmaceutically acceptable salt thereof, wherein
X is $NR^1$ or O;
$R^1$ is selected from the group consisting of hydrogen and $C_{1-6}$alkyl;
$R^{10}$ is selected from the group consisting of $CF_3$, cyano, cycloalkyl, heterocycloalkyl, aryl, heteroaryl, wherein any $R^{10}$ other than hydrogen and cyano is optionally substituted with one to three $R^{17}$;
$R^{17}$ is, independently for each occurrence, selected from the group consisting of halogen, cyano, hydroxyl, —$NR^aR^b$, $C_{1-6}$alkyl, $C_{2-6}$alkenyl, $C_{2-6}$alkynyl, $C_{1-6}$haloalkyl, $C_{1-6}$alkoxy, $CF_3$, —SH, —S—$C_{1-6}$alkyl, —COOH, —$CO_2$—$C_{1-6}$alkyl, —$C_{1-6}$alkyl-CN, —$C(O)NR^aR^b$, —C(O)—$C_{1-6}$alkyl-$NR^aR^b$, —C(O)—$NR^a$—$S(O)_2$—$C_{1-6}$alkyl, —$S(O)_2$—$C_{1-6}$alkyl, —$S(O)_2$ —$NR^aR^b$, —$S(O)_2$—$C_{1-6}$alkyl-$NR^aR^b$;
$L^2$ is selected from the group consisting of a bond, $C_{1-6}$alkylene, 1,3-cyclobutylene, and 1,3-cyclobutylene-$CH_2$—; and
each of $R^a$ and $R^b$ are, independently for each occurrence, selected from the group consisting of hydrogen, $C_{1-6}$alkyl, and $C_{1-6}$haloalkyl, or $R^a$ and $R^b$ are taken together, including the nitrogen to which they are attached, to form a heterocycloalkyl ring.

In some embodiments the compound is a compound of formula Ic:

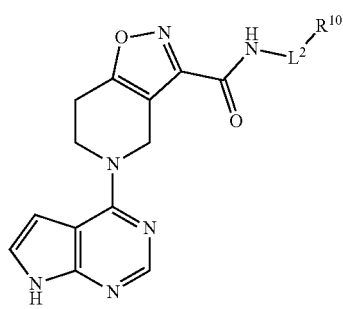

(Ic)

or a pharmaceutically acceptable salt thereof, wherein
$R^1$ is selected from the group consisting of hydrogen and $C_{1-6}$alkyl;
$R^{10}$ is selected from the group consisting of $CF_3$, cyano, cycloalkyl, heterocycloalkyl, aryl, heteroaryl, wherein any $R^{10}$ other than hydrogen and cyano is optionally substituted with one to three $R^{17}$;
$R^{17}$ is, independently for each occurrence, selected from the group consisting of halogen, cyano, hydroxyl, —$NR^aR^b$, $C_{1-6}$alkyl, $C_{2-6}$alkenyl, $C_{2-6}$alkynyl, $C_{1-6}$haloalkyl, $C_{1-6}$alkoxy, $CF_3$, —SH, —S—$C_{1-6}$alkyl, —COOH, —CO$_2$—C$_{1-6}$alkyl, —C$_{1-6}$alkyl-CN, —C(O)NR$^a$R$^b$, —C(O)—C$_{1-6}$alkyl-NR$^a$R$^b$, —C(O)—NR$^a$—S(O)$_2$—C$_{1-6}$alkyl, —S(O)$_2$—C$_{1-6}$alkyl, —S(O)$_2$—NR$^a$R$^b$, —S(O)$_2$—C$_{1-6}$alkyl-NR$^a$R$^b$;

L$^2$ is selected from the group consisting of a bond, C$_{1-6}$alkylene, 1,3-cyclobutylene, and 1,3-cyclobutylene-CH$_2$—; and each of R$^a$ and R$^b$ are, independently for each occurrence, selected from the group consisting of hydrogen, C$_{1-6}$alkyl, and C$_{1-6}$haloalkyl, or R$^a$ and R$^b$ are taken together, including the nitrogen to which they are attached, to form a heterocycloalkyl ring.

In some embodiments, the compound is a compound of formula II:

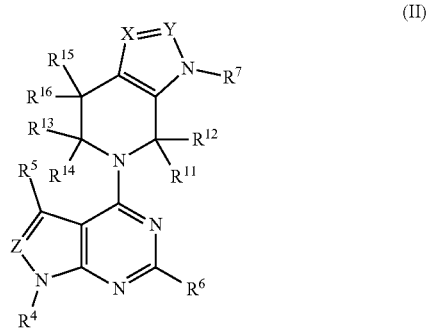

(II)

or a pharmaceutically acceptable salt thereof, wherein

X is N or CR$^1$;
Y is N or CR$^2$;
Z is N or CR$^3$;
R$^1$ is selected from the group consisting of cyano, hydroxyl, NR$^a$R$^b$, C$_{1-6}$alkoxy, and -A-L$^1$-R$^9$;
R$^2$, R$^3$, R$^4$, R$^5$, and R$^6$ are each independently selected from the group consisting of hydrogen, halogen, cyano, hydroxyl, —NR$^a$R$^b$, C$_{1-6}$alkyl, C$_{2-6}$alkenyl, C$_{2-6}$alkynyl, C$_{1-6}$haloalkyl, and C$_{1-6}$alkoxy;
R$^7$ is B-L$^2$-R$^{10}$, or R$^7$ is aryl or heteroaryl, wherein the aryl or heteroaryl is optionally substituted with one to four R$^{17}$;
R$^8$ is selected from the group consisting of hydrogen, C$_{1-6}$alkyl, C$_{1-6}$haloalkyl, hydroxy, C$_{1-6}$alkoxy, and —O—C$_{1-6}$haloalkyl;
R$^9$ is selected from the group consisting of hydrogen, cycloalkyl, heterocycloalkyl, aryl, and heteroaryl, wherein any non-hydrogen R$^9$ is optionally substituted with one to four R$^{17}$;
R$^{10}$ is selected from the group consisting of hydrogen, cyano, hydroxyl, C$_{1-6}$haloalkyl, C$_{1-6}$alkoxy, —O—C$_{1-6}$ haloalkyl, cycloalkyl, heterocycloalkyl, aryl, heteroaryl, —C(O)— heterocycloalkyl, and —S(O)$_2$-heterocycloalkyl, wherein any R$^{10}$ other than hydrogen, cyano, and hydroxyl is optionally substituted with one to four R$^{17}$;
R$^{11}$, R$^{12}$, R$^{13}$, R$^{14}$, R$^{15}$, and R$^{16}$ are each independently selected from the group consisting of hydrogen, halogen, hydroxy, cyano, C$_{1-6}$alkyl, C$_{2-6}$alkenyl, C$_{2-6}$alkynyl, C$_{1-6}$haloalkyl, and C$_{1-6}$alkoxy;
R$^{17}$ is, independently for each occurrence, selected from the group consisting of halogen, cyano, hydroxyl, —NR$^a$R$^b$, C$_{1-6}$alkyl, C$_{2-6}$alkenyl, C$_{2-6}$alkynyl, C$_{1-6}$haloalkyl, C$_{1-6}$alkoxy, CF$_3$, —SH, —S—C$_{1-6}$alkyl, —COOH, —CO$_2$—C$_{1-6}$alkyl, —C$_{1-6}$alkyl-CN, —C(O)NR$^a$R$^b$, —C(O)—C$_{1-6}$alkyl-NR$^a$R$^b$, —C(O)—NR$^a$—S(O)$_2$—C$_{1-6}$-alkyl, —S(O)$_2$—C$_{1-6}$alkyl, —S(O)$_2$—NR$^a$R$^b$, —S(O)$_2$—C$_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR$^8$—, and —C(O)NR$^8$—;

L$^1$ is selected from the group consisting of a bond, C$_{1-6}$alkylene, C$_{1-6}$heteroalkylene, C$_{2-6}$alkenylene, and C$_{2-6}$alkynylene, wherein L$^1$ is optionally substituted with one to four R$^{17}$ groups;

L$^2$ is selected from the group consisting of a bond, C$_{1-6}$alkylene, C$_{2-6}$alkenylene, and C$_{2-6}$alkynylene, wherein any CH$_2$ group of C$_{1-6}$alkylene can be replaced with a moiety selected from the group consisting of —O—, —NR$^a$—, and —S(O)$_2$—, and one CH$_2$ group of C$_{1-6}$alkylene can be replaced with a moiety selected from the group consisting of cycloalkylene, heterocycloalkylene, arylene, and heteroarylene, and wherein L$^2$ is optionally substituted with one to four R$^{17}$ groups; and each of R$^a$ and R$^b$ are, independently for each occurrence, selected from the group consisting of hydrogen, C$_{1-6}$alkyl, and C$_{1-6}$haloalkyl, or R$^a$ and R$^b$ are taken together, including the nitrogen to which they are attached, to form a heterocycloalkyl ring.

In some embodiments, the compound is a compound of formula II, wherein

X is CR$^1$;
Y is CH;
Z is CH;
R$^1$ is selected from the group consisting of hydrogen and C$_{1-6}$alkyl;
R$^4$, R$^5$, and R$^6$ are each hydrogen;
R$^7$ is B-L$^2$-R$^{10}$;
R$^8$ is hydrogen;
R$^{10}$ is selected from the group consisting of CF$_3$, cyano, cycloalkyl, heterocycloalkyl, aryl, heteroaryl, wherein any R$^{10}$ other than hydrogen and cyano is optionally substituted with one to three R$^{17}$;
R$^{11}$, R$^{12}$, R$^{13}$, R$^{14}$, R$^{15}$, and R$^{16}$ are each hydrogen;
R$^{17}$ is, independently for each occurrence, selected from the group consisting of halogen, cyano, hydroxyl, —NR$^a$R$^b$, C$_{1-6}$alkyl, C$_{2-6}$alkenyl, C$_{2-6}$alkynyl, C$_{1-6}$haloalkyl, C$_{1-6}$alkoxy, CF$_3$, —SH, —S—C$_{1-6}$alkyl, —COOH, —CO$_2$—C$_{1-6}$alkyl, —C$_{1-6}$alkyl-CN, —C(O)NR$^a$R$^b$, —C(O)—C$_{1-6}$alkyl-NR$^a$R$^b$, —C(O)—NR$^a$—S(O)$_2$—C$_{1-6}$alkyl, —S(O)$_2$—C$_{1-6}$alkyl, —S(O)$_2$—NR$^a$R$^b$, —S(O)$_2$—C$_{1-6}$alkyl-NR$^a$R$^b$;

B is —C(O)NR$^8$—;

L$^2$ is selected from the group consisting of a bond, C$_{1-6}$alkylene, 1,3-cyclobutylene, and 1,3-cyclobutylene-CH$_2$—; and each of R$^a$ and R$^b$ are, independently for each occurrence, selected from the group consisting of hydrogen, C$_{1-6}$alkyl, and C$_{1-6}$haloalkyl, or R$^a$ and R$^b$ are taken together, including the nitrogen to which they are attached, to form a heterocycloalkyl ring.

In yet another aspect, provided herein is a pharmaceutical composition comprising a pharmaceutically acceptable carrier and a compound of formula I, formula II, formula III, or formula IV:

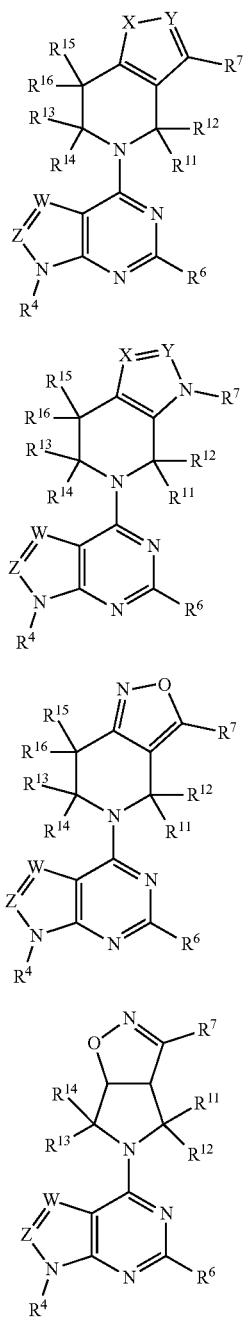

or a pharmaceutically acceptable salt thereof, wherein
For formula I: X is $NR^1$, $C(R^8)R^1$, O, S, S(O), or $S(O)_2$;
For formula II: X is N or $CR^1$; and
For formula I, formula II, formula III, and formula IV:
W is N or $CR^5$;
Y is N or $CR^2$;
Z is N or $CR^3$;
wherein W and Z are not both N;
$R^1$ is selected from the group consisting of cyano, hydroxyl, $NR^aR^b$, $C_{1-6}$alkoxy, and $-A-L^1-R^9$;
$R^2$, $R^3$, $R^4$, and $R^6$ are each independently selected from the group consisting of hydrogen, deuterium, halogen, cyano, hydroxyl, $-NR^aR^b$, $C_{1-6}$alkyl, $C_{2-6}$alkenyl, $C_{2-6}$alkynyl, $C_{1-6}$haloalkyl, and $C_{1-6}$alkoxy;

$R^5$ is selected from the group consisting of hydrogen, $C_{1-6}$alkyl, $C_{2-6}$alkenyl, $C_{2-6}$alkynyl, $C_{1-6}$-haloalkyl, aryl, heteroaryl, cycloalkyl, heterocyclyl, -aryl-$C_{1-6}$alkyl, -heteroaryl-$C_{1-6}$alkyl, -heterocyclyl-$C_{1-6}$alkyl, halogen, cyano, hydroxyl, $C_{1-6}$alkoxy, $C_{1-6}$haloalkoxy, amino, carboxy, aminocarbonyl, $-C_{1-6}$alkyl-aminocarbonylamino, $C_{1-6}$alkyl-aminocarbonyl, $-S(O)-R^8$, $-S(O)_2-R^8$, $-NR^8-S(O)_2-R^8$, $-S(O)_2-NR^aR^b$, $-NR^8-S(O)_2-NR^aR^b$, $-C_{1-6}$alkyl-aryl, $-C_{1-6}$alkyl-heteroaryl, $-C_{1-6}$alkyl-heterocycle, and $-C_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, $CF_3$, aminocarbonyl, $-C_{1-6}$alkyl-aminocarbonylamino, and $C_{3-6}$cycloalkyl;

$R^7$ is $B-L^2-R^{10}$, or $R^7$ is aryl or heteroaryl, wherein the aryl or heteroaryl is optionally substituted with one to four $R^{17}$;

each $R^8$ is independently selected from the group consisting of hydrogen, $C_{1-6}$alkyl, $C_{1-6}$haloalkyl, hydroxy, $C_{1-6}$alkoxy, and $-O-C_{1-6}$haloalkyl;

$R^9$ is selected from the group consisting of hydrogen, cycloalkyl, heterocycloalkyl, aryl, and heteroaryl, wherein any non-hydrogen $R^9$ is optionally substituted with one to four $R^{17}$;

$R^{10}$ is selected from the group consisting of hydrogen, cyano, hydroxyl, $C_{1-6}$haloalkyl, $C_{1-6}$alkoxy, $-O-C_{1-6}$ haloalkyl, cycloalkyl, heterocycloalkyl, aryl, heteroaryl, $-C(O)-$ heterocycloalkyl, and $-S(O)_2$-heterocycloalkyl, wherein any $R^{10}$ other than hydrogen, cyano, and hydroxyl is optionally substituted with one to four $R^{17}$;

$R^{11}$, $R^{12}$, $R^{13}$, $R^{14}$, $R^{15}$, and $R^{16}$ are each independently selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, halogen, cyano, hydroxyl, $C_{1-6}$alkoxy, amino, carboxy, aminocarbonyl, $-C_{1-6}$alkyl-aryl, $-C_{1-6}$alkyl-heteroaryl, $-C_{1-6}$alkyl-heterocycle, and $C_{1-6}$alkyl-cycloalkyl, wherein said alkyl is optionally substituted with one or more substituents independently selected from the group consisting of halo, hydroxyl, methoxy, alkylamino, dialkylamino, $CF_3$, and $C_{3-6}$cycloalkyl; or $R^{11}$ and $R^{12}$, $R^{13}$ and $R^{14}$, or $R^{15}$ and $R^{16}$ can betaken together including the atom to which they are attached to form a 3-6-membered spiro-fused ring optionally substituted by 1-3 substituents independently selected from the group consisting of halogen, $C_{1-6}$alkyl, and $C_{1-6}$haloalkyl;

$R^{17}$ is, independently for each occurrence, selected from the group consisting of halogen, cyano, hydroxyl, $-NR^aR^b$, $C_{1-6}$alkyl, $C_{2-6}$alkenyl, $C_{2-6}$alkynyl, $C_{1-6}$haloalkyl, $C_{1-6}$alkoxy, $CF_3$, $-SH$, $-S-C_{1-6}$alkyl, $-COOH$, $-CO_2-C_{1-6}$alkyl, $-C_{1-6}$alkyl-CN, $-C(O)NR^aR^b$, $-C(O)-C_{1-6}$alkyl-$NR^aR^b$, $-C(O)-NR^a-S(O)_2-C_{1-6}$alkyl, $-S(O)_2-C_{1-6}$alkyl, $-S(O)_2-NR^aR^b$, $-S(O)_2-C_{1-6}$alkyl-$NR^aR^b$;

A is selected from the group consisting of $-C(O)-$, $-S(O)-$, and $-S(O)_2-$, or A is absent;

B is selected from the group consisting of $-C(O)-$, $-S(O)_2-NR^8-$, $-CH_2-NR^8-$, and $-C(O)NR^8-$;

$L^1$ is selected from the group consisting of a bond, $C_{1-6}$alkylene, $C_{1-6}$heteroalkylene, $C_{2-6}$alkenylene, and $C_{2-6}$alkynylene, wherein $L^1$ is optionally substituted with one to four $R^{17}$ groups;

$L^2$ is selected from the group consisting of a bond, $C_{1-6}$alkylene, $C_{2-6}$alkenylene, and $C_{2-6}$alkynylene, wherein any CH$_2$ group of $C_{1-6}$alkylene can be replaced with a moeity selected from the group consisting of —O—, —NR$^a$—, and —S(O)$_2$—, and one CH$_2$ group of $C_{1-6}$alkylene can be replaced with a moiety selected from the group consisting of cycloalkylene, heterocycloalkylene, arylene, and heteroarylene, and wherein $L^2$ is optionally substituted with one to four $R^{17}$ groups; or when B is —S(O)$_2$—NR$^8$—, —CH$_2$—NR$^8$—, or —C(O)NR$^8$—, $R^8$ and $L^2$ can be taken together including the nitrogen atom to which they are attached to form a 3-7-membered heterocycloalkyl optionally substituted with one to four $R^{17}$ groups; and each of $R^a$ and $R^b$ are, independently for each occurrence, selected from the group consisting of hydrogen, $C_{1-6}$alkyl, and $C_{1-6}$haloalkyl, or $R^a$ and $R^b$ are taken together, including the nitrogen to which they are attached, to form a heterocycloalkyl ring.

In yet another aspect, provided herein is a pharmaceutical composition comprising a pharmaceutically acceptable carrier and a compound of formula I or formula II:

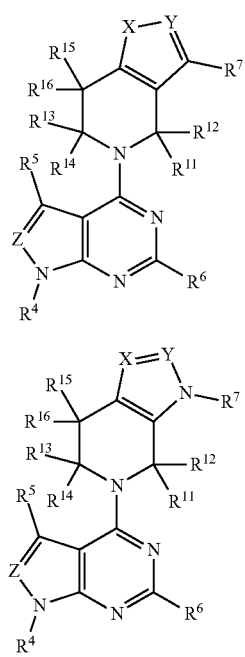

or a pharmaceutically acceptable salt thereof, wherein
For formula I: X is NR$^1$, C(R$^8$)R$^1$, O, S, S(O), or S(O)$_2$;
For formula II: X is N or CR$^1$; and
For both formula I and formula II:
Y is N or CR$^2$;
Z is N or CR$^3$;
$R^1$ is selected from the group consisting of cyano, hydroxyl, NR$^a$R$^b$, $C_{1-6}$alkoxy, and -A-L$^1$-R$^9$;
$R^2$, $R^3$, $R^4$, and $R^6$ are each independently selected from the group consisting of hydrogen, deuterium, halogen, cyano, hydroxyl, —NR$^a$R$^b$, $C_{1-6}$alkyl, $C_{2-6}$alkenyl, $C_{2-6}$alkynyl, $C_{1-6}$haloalkyl, and $C_{1-6}$alkoxy;

$R^5$ is selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, -heterocyclyl-$C_{1-6}$alkyl, halogen, cyano, hydroxyl, $C_{1-6}$alkoxy, $C_{1-6}$-haloalkoxy, amino, carboxy, aminocarbonyl, —$C_{1-6}$alkyl-aminocarbonylamino, $C_{1-6}$alkyl-aminocarbonyl, —S(O)—R$^8$, —S(O)$_2$—R$^8$, —NR$^8$—S(O)$_2$—R$^8$, —S(O)$_2$—NR$^a$R$^b$, —NR$^8$—S(O)$_2$—NR$^a$R$^b$, —$C_{1-6}$alkyl-aryl, —$C_{1-6}$alkyl-heteroaryl, —$C_{1-6}$alkyl-heterocycle, and —$C_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, CF$_3$, aminocarbonyl, —$C_{1-6}$alkyl-aminocarbonylamino, and $C_{3-6}$cycloalkyl;

$R^7$ is B-L$^2$-R$^{10}$, or $R^7$ is aryl or heteroaryl, wherein the aryl or heteroaryl is optionally substituted with one to four $R^{17}$;

each $R^8$ is independently selected from the group consisting of hydrogen, $C_{1-6}$alkyl, $C_{1-6}$haloalkyl, hydroxy, $C_{1-6}$alkoxy, and —O—$C_{1-6}$haloalkyl; $R^9$ is selected from the group consisting of hydrogen, cycloalkyl, heterocycloalkyl, aryl, and heteroaryl, wherein any non-hydrogen $R^9$ is optionally substituted with one to four $R^{17}$;

$R^{10}$ is selected from the group consisting of hydrogen, cyano, hydroxyl, $C_{1-6}$haloalkyl, $C_{1-6}$alkoxy, —O—$C_{1-6}$-haloalkyl, cycloalkyl, heterocycloalkyl, aryl, heteroaryl, —C(O)— heterocycloalkyl, and —S(O)$_2$-heterocycloalkyl, wherein any $R^{10}$ other than hydrogen, cyano, and hydroxyl is optionally substituted with one to four $R^{17}$;

$R^{11}$, $R^{12}$, $R^{13}$, $R^{14}$, $R^{15}$, and $R^{16}$ are each independently selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, halogen, cyano, hydroxyl, $C_{1-6}$alkoxy, amino, carboxy, aminocarbonyl, —$C_{1-6}$alkyl-aryl, —$C_{1-6}$alkyl-heteroaryl, —$C_{1-6}$alkyl-heterocycle, and $C_{1-6}$alkyl-cycloalkyl, wherein said alkyl is optionally substituted with one or more substituents independently selected from the group consisting of halo, hydroxyl, methoxy, alkylamino, dialkylamino, CF$_3$, and $C_{3-6}$cycloalkyl;

$R^{17}$ is, independently for each occurrence, selected from the group consisting of halogen, cyano, hydroxyl, —NR$^a$R$^b$, $C_{1-6}$alkyl, $C_{2-6}$alkenyl, $C_{2-6}$alkynyl, $C_{1-6}$haloalkyl, $C_{1-6}$alkoxy, CF$_3$, —SH, —S—$C_{1-6}$alkyl, —COOH, —CO$_2$—$C_{1-6}$alkyl, —$C_{1-6}$alkyl-CN, —C(O)NR$^a$R$^b$, —C(O)—$C_{1-6}$alkyl-NR$^a$R$^b$, —C(O)—NR$^a$—S(O)$_2$—$C_{1-6}$alkyl, —S(O)$_2$—$C_{1-6}$alkyl, —S(O)$_2$—NR$^a$R$^b$, —S(O)$_2$—$C_{1-6}$alkyl-NR$^a$R$^b$;

A is selected from the group consisting of —C(O)—, —S(O)—, and —S(O)$_2$—, or A is absent;

B is selected from the group consisting of —C(O)—, —S(O)$_2$—NR$^8$—, —CH$_2$—NR$^8$—, and —C(O)NR$^8$—;

$L^1$ is selected from the group consisting of a bond, $C_{1-6}$alkylene, $C_{1-6}$heteroalkylene, $C_{2-6}$alkenylene, and $C_{2-6}$alkynylene, wherein $L^1$ is optionally substituted with one to four $R^{17}$ groups; $L^2$ is selected from the group consisting of a bond, $C_{1-6}$alkylene, $C_{2-6}$alkenylene, and $C_{2-6}$alkynylene, wherein any CH$_2$ group of $C_{1-6}$alkylene can be replaced with a moeity selected from the group consisting of —O—, —NR$^a$—, and —S(O)$_2$—, and one CH$_2$ group of $C_{1-6}$alkylene can be replaced with a moiety selected from the group consisting of cycloalkylene, heterocycloalkylene, arylene, and heteroarylene, and wherein $L^2$ is optionally substituted with one to four $R^{17}$ groups; and each of $R^a$ and $R^b$ are, independently for each occurrence, selected from the group consisting of hydrogen, $C_{1-6}$alkyl, and $C_{1-6}$haloalkyl, or $R^a$ and $R^b$ are taken together, including the nitrogen to which they are attached, to form a heterocycloalkyl ring.

In some embodiments, the composition comprises a pharmaceutically acceptable carrier and a compound of formula I or formula II:

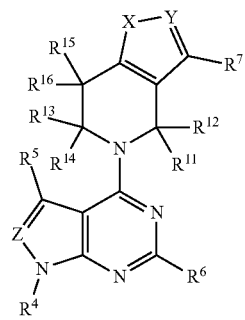

(I)

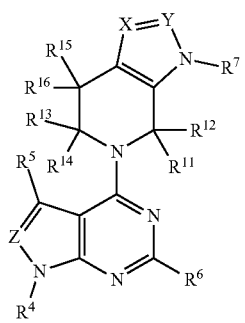

(II)

or a pharmaceutically acceptable salt thereof, wherein
for formula I: X is $NR^1$, $C(R^8)R^1$, O, S, S(O), or $S(O)_2$;
for formula II: X is N or $CR^1$;
for both formula I and formula II:
Y is N or $CR^2$;
Z is N or $CR^3$;
$R^1$ is selected from the group consisting of cyano, hydroxyl, $NR^aR^b$, $C_{1-6}$alkoxy, and $-A-L^1-R^9$;
$R^2$, $R^3$, $R^4$, $R^5$, and $R^6$ are each independently selected from the group consisting of hydrogen, halogen, cyano, hydroxyl, $-NR^aR^b$, $C_{1-6}$alkyl, $C_{2-6}$alkenyl, $C_{2-6}$alkynyl, $C_{1-6}$haloalkyl, and $C_{1-6}$alkoxy;
$R^7$ is selected from the group consisting of cyano, hydroxyl, $NR^aR^b$, $C_{1-6}$alkoxy, and $B-L^2-R^{10}$;
each $R^8$ is independently selected from the group consisting of hydrogen, $C_{1-6}$alkyl, $C_{1-6}$haloalkyl, hydroxy, $C_{1-6}$alkoxy, and $-O-C_{1-6}$haloalkyl; $R^9$ is selected from the group consisting of hydrogen, cycloalkyl, heterocycloalkyl, aryl, and heteroaryl, wherein any non-hydrogen $R^9$ is optionally substituted with one to four $R^{17}$;
$R^{10}$ is selected from the group consisting of hydrogen, cyano, hydroxyl, $C_{1-6}$haloalkyl, $C_{1-6}$alkoxy, $-O-C_{1-6}$ haloalkyl, cycloalkyl, heterocycloalkyl, aryl, heteroaryl, $-C(O)-$ heterocycloalkyl, and $-S(O)_2$-heterocycloalkyl, wherein any $R^{10}$ other than hydrogen, cyano, and hydroxyl is optionally substituted with one to four $R^{17}$;
$R^{11}$, $R^{12}$, $R^{13}$, $R^{14}$, $R_{15}$, and $R^{16}$ are each independently selected from the group consisting of hydrogen, halogen, hydroxy, cyano, $C_{1-6}$alkyl, $C_{2-6}$alkenyl, $C_{2-6}$alkynyl, $C_{1-6}$haloalkyl, and $C_{1-6}$alkoxy;
$R^{17}$ is, independently for each occurrence, selected from the group consisting of halogen, cyano, hydroxyl, $-NR^aR^b$, $C_{1-6}$alkyl, $C_{2-6}$alkenyl, $C_{2-6}$alkynyl, $C_{1-6}$haloalkyl, $C_{1-6}$alkoxy, $CF_3$, $-SH$, $-S-C_{1-6}$alkyl, $-COOH$, $-CO_2-C_{1-6}$alkyl, $-C_{1-6}$alkyl-CN, $-C(O)NR^aR^b$, $-C(O)-C_{1-6}$alkyl-$NR^aR^b$, $-C(O)-NR^a-S(O)_2-C_{1-6}$alkyl, $-S(O)_2-C_{1-6}$alkyl, $-S(O)_2-NR^aR^b$, $-S(O)_2-C_{1-6}$alkyl-$NR^aR^b$;
A is selected from the group consisting of $-C(O)-$, $-S(O)-$, and $-S(O)_2-$, or A is absent;
B is selected from the group consisting of $-C(O)-$, $-S(O)_2-NR^8-$, $-C(O)NR^8-$, and $-CH_2-NR^8-$;
$L^1$ is selected from the group consisting of a bond, $C_{1-6}$alkylene, $C_{1-6}$heteroalkylene, $C_{2-6}$alkenylene, and $C_{2-6}$alkynylene, wherein $L^1$ is optionally substituted with one to four $R^{17}$ groups;
$L^2$ is selected from the group consisting of a bond, $C_{1-6}$alkylene, $C_{2-6}$alkenylene, and $C_{2-6}$alkynylene, wherein any $CH_2$ group of $C_{1-6}$alkylene can be replaced with a moiety selected from the group consisting of $-O-$, $-NR^a-$, and $-S(O)_2-$, and one $CH_2$ group of $C_{1-6}$alkylene can be replaced with a moiety selected from the group consisting of cycloalkylene, heterocycloalkylene, arylene, and heteroarylene, and wherein $L^2$ is optionally substituted with one to four $R^{17}$ groups; and each of $R^a$ and $R^b$ are, independently for each occurrence, selected from the group consisting of hydrogen, $C_{1-6}$alkyl, and $C_{1-6}$haloalkyl, or $R^a$ and $R^b$ are taken together, including the nitrogen to which they are attached, to form a heterocycloalkyl ring.

In some embodiments, the compound is of formula I or formula II.
In some embodiments, the compound is of formula I.
In some embodiments, the compound is of formula II.
In some embodiments, the compound is of formula III.
In some embodiments, the compound is of formula IV.
In some embodiments, W is $CR^5$.

In yet another aspect, provided herein is a pharmaceutical composition comprising a compound of the disclosure and a pharmaceutically acceptable carrier. In yet another aspect, provided herein is a method of treating a disease which can be treated with a JAK3 inhibitor, the method comprising administering a pharmaceutically effective amount of a compound or composition of any one of the preceding claims to a patient in need thereof.

In yet another aspect, provided herein is a method of treating a disease, the method comprising administering a pharmaceutically effective amount of a compound or composition of any one of the preceding claims to a patient in need thereof, wherein the disease is selected from the group consisting of rheumatoid arthritis, myositis, vasculitis, pemphigus, bullous pemphigoid, inflammatory bowel disease including Crohn's disease and ulcerative colitis, celiac diseases, proctitis, eosinophilic gastroenteritis, or mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis nodosa, dry eye syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation, including Cogan's syndrome, ankylosing spondylitis, Wegener's granulomatosis, autoimmune alopecia, Type I or juvenile onset diabetes, and complications from diabetes, or thyroiditis, chronic pulmonary obstructive disorder, acute respiratory disease, cachexia, cancer, including alimentary/gastrointestinal tract cancer, colon cancer, liver cancer, skin cancer including mast cell tumor and squamous cell carcinoma, breast and mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma including oral and metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, or angiogenic-associated disorders including solid tumors, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotropic Lateral Sclerosis, Huntington's disease, cerebral ischemia, fronto-temporal lobe dementia, and with neuropsychiatric disorders including schizophrenia, bipolar disorder, treatment resistant depression, Post Traumatic Stress Disorder, anxiety, and auto-antibodies mediated encephalopathies, Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization. In some embodiments, the disease is selected from the group consisting of autoimmune disease, an inflammatory disease, or cancer.

In some embodiments, the disease is cancer. In some embodiments, the cancer is selected from the group consisting of T-ALL, CTCL, NK-T cell lymphoma, and Sezary syndrome.

In some embodiments, the disease is an autoimmune disease. In some embodiments, the autoimmune disease is selected from the group consisting of inflammatory bowel disease, lupus, psoriasis, transplantation, graft vs. host disease, arthritis, rheumatoid arthritis, juvenile rheumatoid arthritis, diabetes, myasthenia gravis, Grave's disease, multiple sclerosis, Guillain-Barre syndrome, ankylosing spondylitis, autoimmune hepatitis, celiac disease, scleroderma, psoriasis, allergy, anaphylaxis, atopic dermatitis, and chronic fatigue syndrome. In some embodiments, the autoimmune disease is inflammatory bowel disease.

In some embodiments, the disease is an inflammatory disease. In some embodiments, the inflammatory disease is selected from the group consisting of asthma, blepharitis, bronchiolitis, bronchitis, bursitis, cholecystitis, colitis, conjunctivitis, dermatitis, eczema, endocarditis, enteritis, gastritis, hepatitis, meningitis, nephritis, pancreatitis, peritonitis, pleuritis, pneumonia, prostatitis, rhinitis, sinusitis, and tendonitis.

In some embodiments, the compound is a compound from Table 1.

TABLE 1

Selected Compounds of Formulas I and II

| Compound No. | structure |
|---|---|
| 101 | 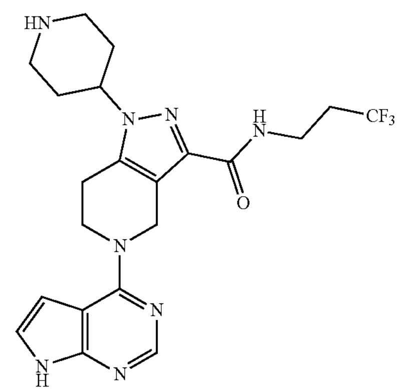 [SMILES: O=C(NCCC(F)(F)F)c1nn(C2CCNCC2)c2c1CN(c1ncnc3[nH]ccc13)CC2] |
| 102 | 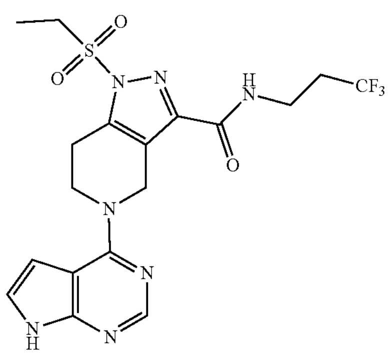 [SMILES: CCS(=O)(=O)n1nc(C(=O)NCCC(F)(F)F)c2c1CCN(c1ncnc3[nH]ccc13)C2] |
| 103 | 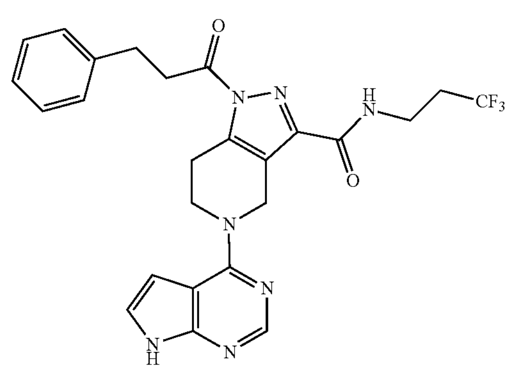 [SMILES: O=C(NCCC(F)(F)F)c1nn(C(=O)CCc2ccccc2)c2c1CN(c1ncnc3[nH]ccc13)CC2] |

TABLE 1-continued

Selected Compounds of Formulas I and II

| Compound No. | structure |
|---|---|
| 104 | 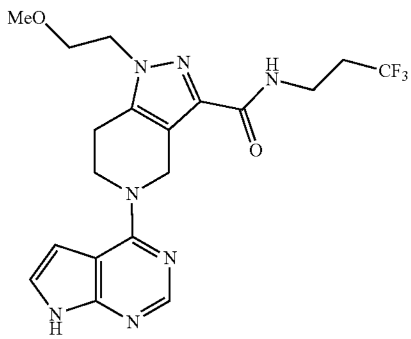 [SMILES: COCCn1nc(C(=O)NCCC(F)(F)F)c2c1CCN(c1ncnc3[nH]ccc13)C2] |
| 105 | 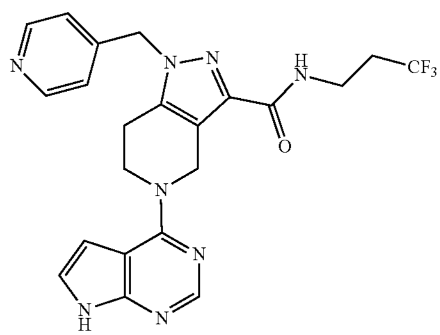 [SMILES: O=C(NCCC(F)(F)F)c1nn(Cc2ccncc2)c2c1CN(c1ncnc3[nH]ccc13)CC2] |
| 106 | 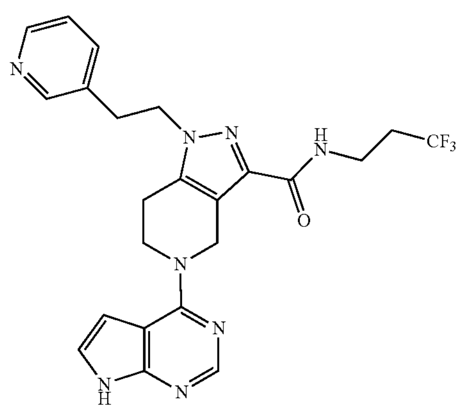 [SMILES: O=C(NCCC(F)(F)F)c1nn(CCc2cccnc2)c2c1CN(c1ncnc3[nH]ccc13)CC2] |
| 107 | 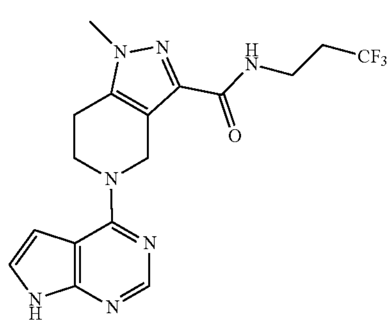 [SMILES: Cn1nc(C(=O)NCCC(F)(F)F)c2c1CCN(c1ncnc3[nH]ccc13)C2] |
| 108 | |
| 109 | |
| 110 | |
| 111 | |

TABLE 1-continued

Selected Compounds of Formulas I and II

| Compound No. | structure |
|---|---|
| 112 | 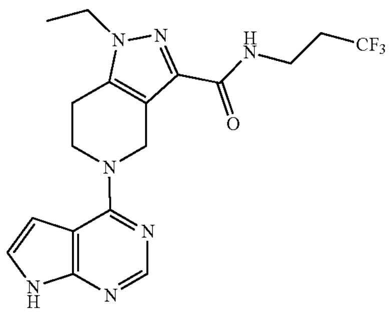 [SMILES: CCn1nc(C(=O)NCCC(F)(F)F)c2c1CCN(c1ncnc3[nH]ccc13)C2] |
| 113 | 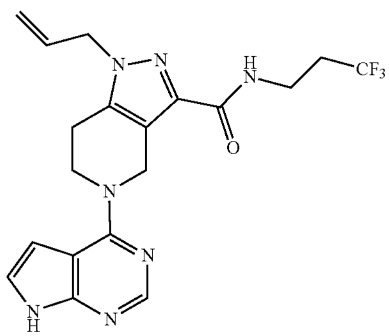 [SMILES: C=CCn1nc(C(=O)NCCC(F)(F)F)c2c1CCN(c1ncnc3[nH]ccc13)C2] |
| 114 | 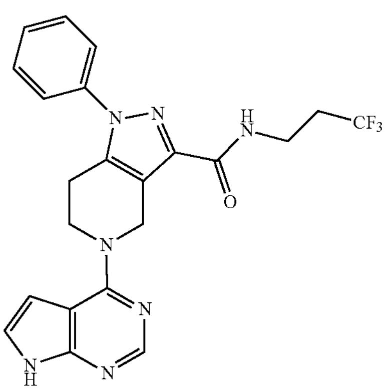 [SMILES: O=C(NCCC(F)(F)F)c1nn(-c2ccccc2)c2c1CN(c1ncnc3[nH]ccc13)CC2] |
| 115 | 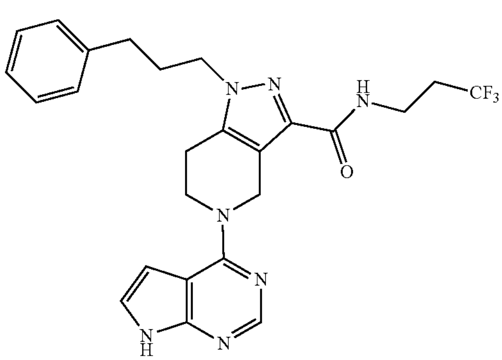 [SMILES: O=C(NCCC(F)(F)F)c1nn(CCCc2ccccc2)c2c1CN(c1ncnc3[nH]ccc13)CC2] |
| 116 | 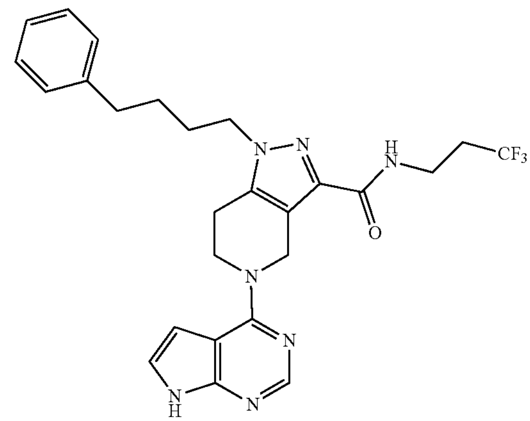 [SMILES: O=C(NCCC(F)(F)F)c1nn(CCCCc2ccccc2)c2c1CN(c1ncnc3[nH]ccc13)CC2] |
| 117 | 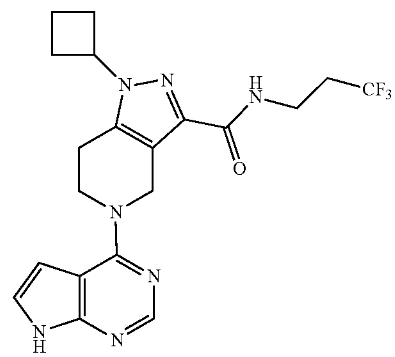 [SMILES: O=C(NCCC(F)(F)F)c1nn(C2CCC2)c2c1CN(c1ncnc3[nH]ccc13)CC2] |
| 118 | 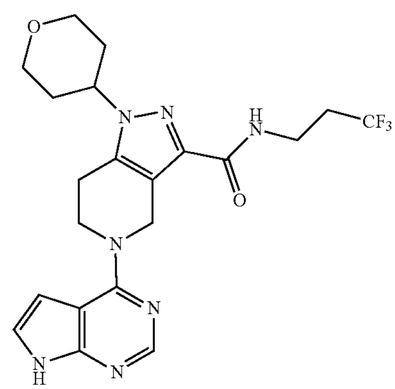 [SMILES: O=C(NCCC(F)(F)F)c1nn(C2CCOCC2)c2c1CN(c1ncnc3[nH]ccc13)CC2] |
| 119 | 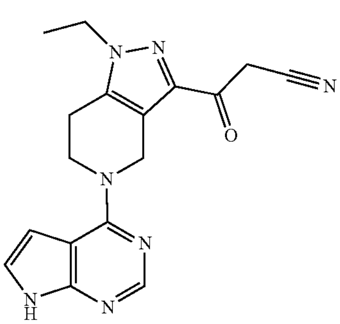 [SMILES: CCn1nc(C(=O)CC#N)c2c1CCN(c1ncnc3[nH]ccc13)C2] |

TABLE 1-continued

Selected Compounds of Formulas I and II

| Compound No. | structure |
|---|---|
| 120 | |
| 121 | |
| 122 | |
| 123 | |
| 124 | 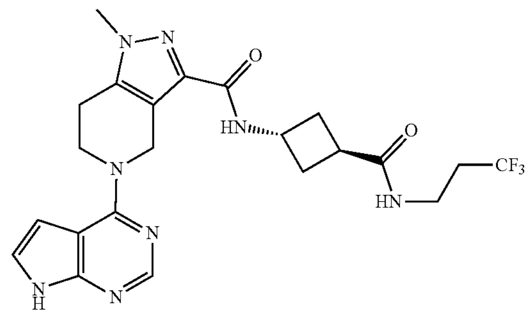 [SMILES: Cn1nc(C(=O)N[C@H]2C[C@H](C(=O)NCCC(F)(F)F)C2)c2c1CCN(c1ncnc3[nH]ccc13)C2] |
| 125 | 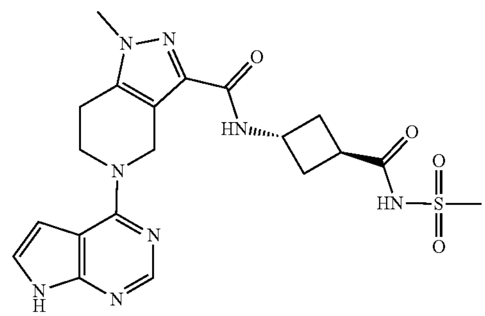 [SMILES: Cn1nc(C(=O)N[C@H]2C[C@H](C(=O)NS(C)(=O)=O)C2)c2c1CCN(c1ncnc3[nH]ccc13)C2] |
| 126 | 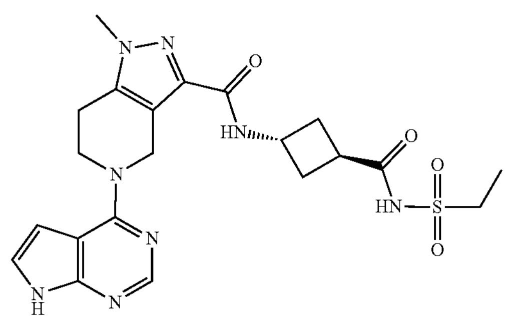 [SMILES: CCS(=O)(=O)NC(=O)[C@H]1C[C@H](NC(=O)c2nn(C)c3c2CN(c2ncnc4[nH]ccc24)CC3)C1] |
| 127 | 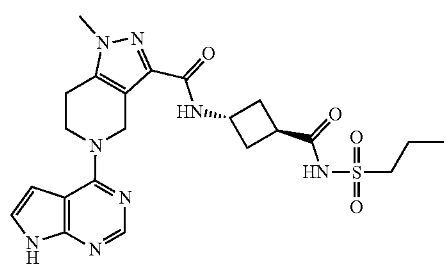 [SMILES: CCCS(=O)(=O)NC(=O)[C@H]1C[C@H](NC(=O)c2nn(C)c3c2CN(c2ncnc4[nH]ccc24)CC3)C1] |
| 128 | 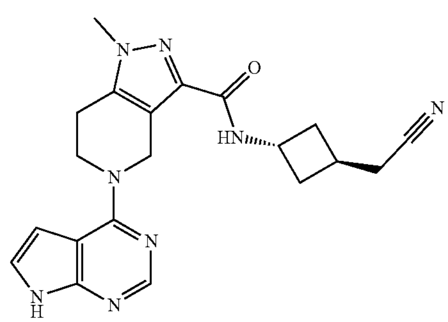 [SMILES: Cn1nc(C(=O)N[C@H]2C[C@H](CC#N)C2)c2c1CCN(c1ncnc3[nH]ccc13)C2] |

TABLE 1-continued
Selected Compounds of Formulas I and II
| Compound No. | structure |
|---|---|
| 129 | 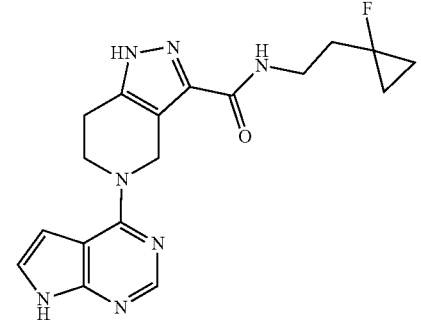 [SMILES: O=C(NCCC1(F)CC1)c1n[nH]c2c1CN(c1ncnc3[nH]ccc13)CC2] |
| 130 | 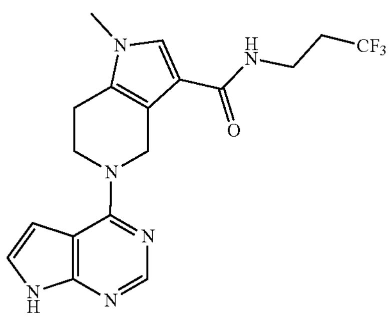 [SMILES: Cn1cc(C(=O)NCCC(F)(F)F)c2c1CCN(c1ncnc3[nH]ccc13)C2] |
| 131 | 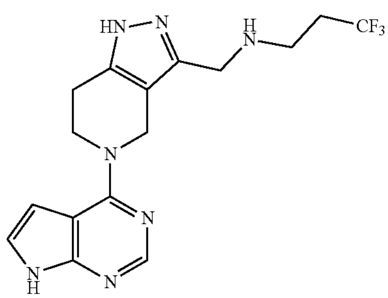 [SMILES: FC(F)(F)CCNCc1n[nH]c2c1CN(c1ncnc3[nH]ccc13)CC2] |
| 132 | 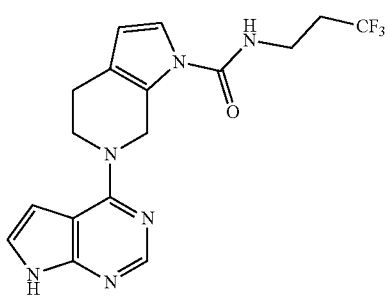 [SMILES: O=C(NCCC(F)(F)F)n1ccc2c1CN(c1ncnc3[nH]ccc13)CC2] |
| 133 | 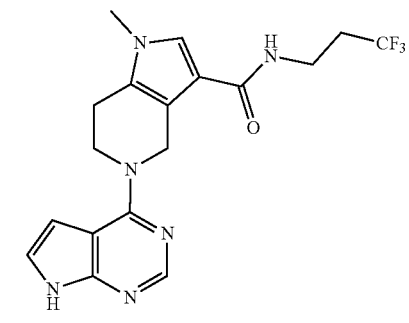 |
| 134 | |
| 135 | |
| 136 | |

TABLE 1-continued
Selected Compounds of Formulas I and II
| Compound No. | structure |
|---|---|
| 137 | 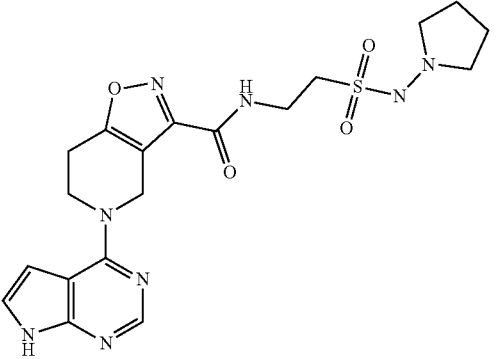 [SMILES: O=C(NCCS(=O)(=O)NN1CCCC1)c1noc2c1CN(c1ncnc3[nH]ccc13)CC2] |
| 138 | 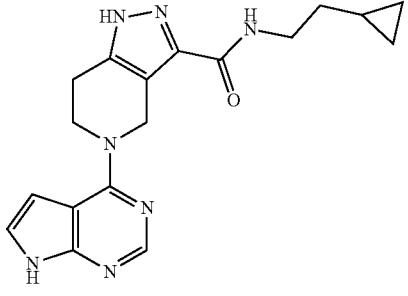 [SMILES: O=C(NCCC1CC1)c1n[nH]c2c1CN(c1ncnc3[nH]ccc13)CC2] |
| 139 | 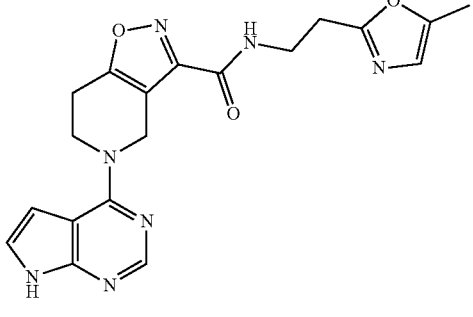 |
| 140 | 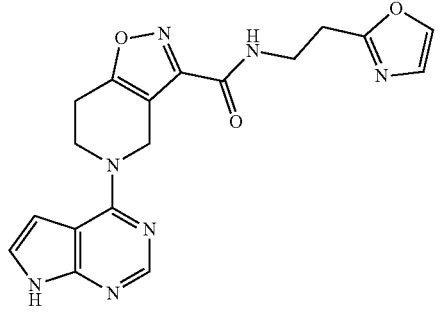 [SMILES: O=C(NCCc1ncco1)c1noc2c1CN(c1ncnc3[nH]ccc13)CC2] |
| 141 | 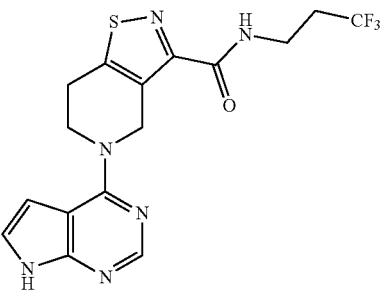 [SMILES: O=C(NCCC(F)(F)F)c1nsc2c1CN(c1ncnc3[nH]ccc13)CC2] |
| 142 | 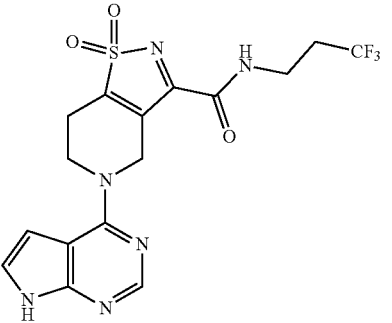 [SMILES: O=C(NCCC(F)(F)F)C1=NS(=O)(=O)C2=C1CN(c1ncnc3[nH]ccc13)CC2] |
| 143 | 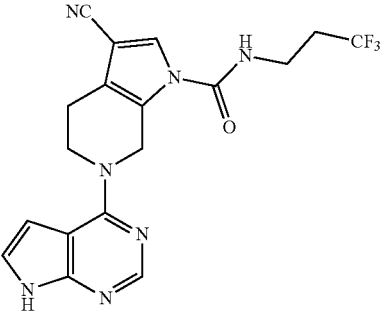 [SMILES: N#Cc1cn(C(=O)NCCC(F)(F)F)c2c1CCN(c1ncnc3[nH]ccc13)C2] |
| 144 | 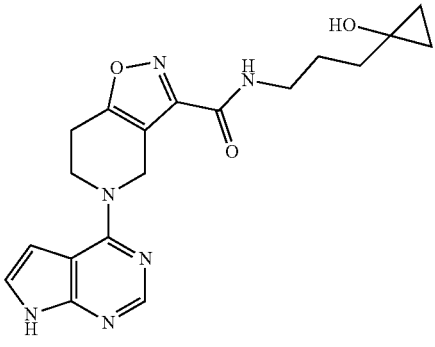 [SMILES: O=C(NCCCC1(O)CC1)c1noc2c1CN(c1ncnc3[nH]ccc13)CC2] |

TABLE 1-continued

Selected Compounds of Formulas I and II

| Compound No. | structure |
|---|---|
| 145 | 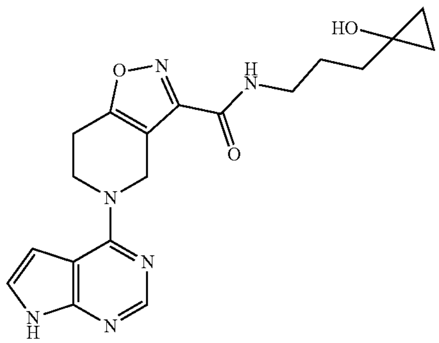 [SMILES: O=C(NCCCC1(O)CC1)c1noc2c1CN(c1ncnc3[nH]ccc13)CC2] |
| 146 | 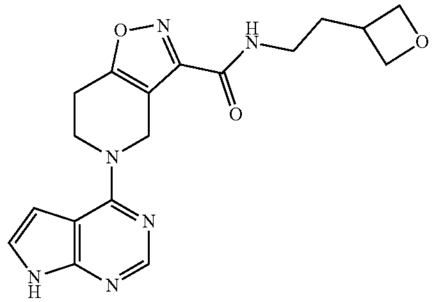 [SMILES: O=C(NCCC1COC1)c1noc2c1CN(c1ncnc3[nH]ccc13)CC2] |
| 147 | 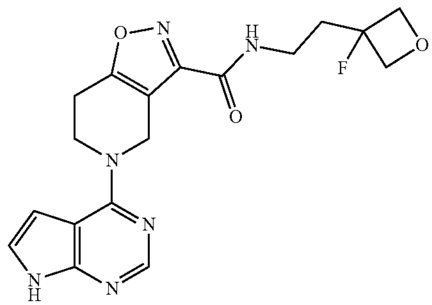 [SMILES: O=C(NCCC1(F)COC1)c1noc2c1CN(c1ncnc3[nH]ccc13)CC2] |
| 148 | 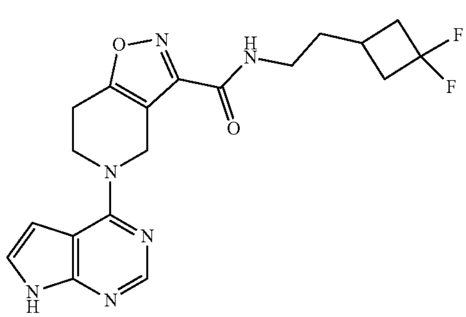 [SMILES: O=C(NCCC1CC(F)(F)C1)c1noc2c1CN(c1ncnc3[nH]ccc13)CC2] |
| 149 | |
| 150 | |
| 151 | |
| 152 | |

TABLE 1-continued

Selected Compounds of Formulas I and II

| Compound No. | structure |
|---|---|
| 153 | 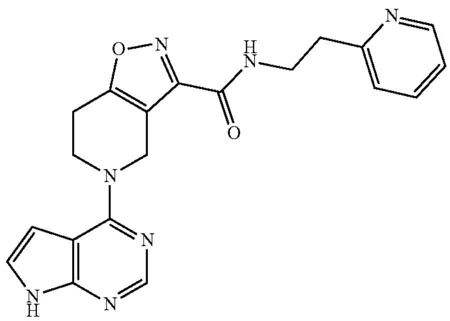 [SMILES: O=C(NCCc1ccccn1)c1noc2c1CN(c1ncnc3[nH]ccc13)CC2] |
| 154 | 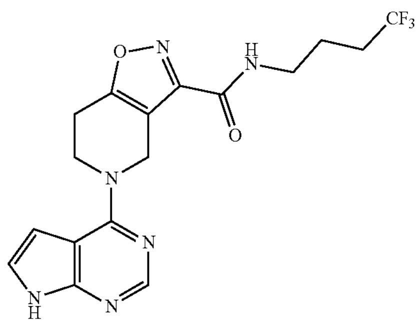 [SMILES: O=C(NCCCC(F)(F)F)c1noc2c1CN(c1ncnc3[nH]ccc13)CC2] |
| 155 | 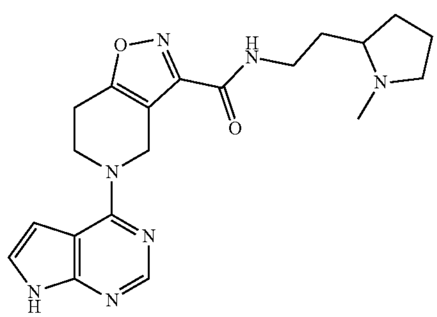 [SMILES: CN1CCCC1CCNC(=O)c1noc2c1CN(c1ncnc3[nH]ccc13)CC2] |
| 156 | 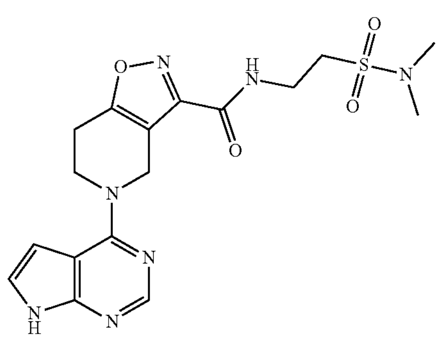 [SMILES: CN(C)S(=O)(=O)CCNC(=O)c1noc2c1CN(c1ncnc3[nH]ccc13)CC2] |
| 157 | |
| 158 | |
| 159 | |
| 160 | |

TABLE 1-continued

Selected Compounds of Formulas I and II

| Compound No. | structure |
|---|---|
| 161 | 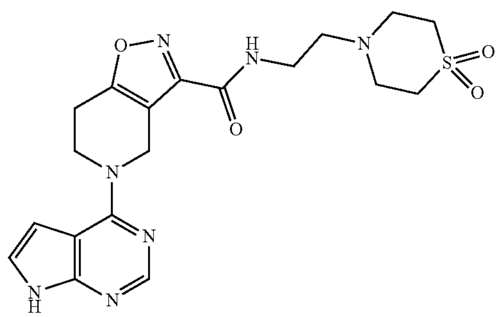 [SMILES: O=C(NCCN1CCS(=O)(=O)CC1)c1noc2c1CN(c1ncnc3[nH]ccc13)CC2] |
| 162 | 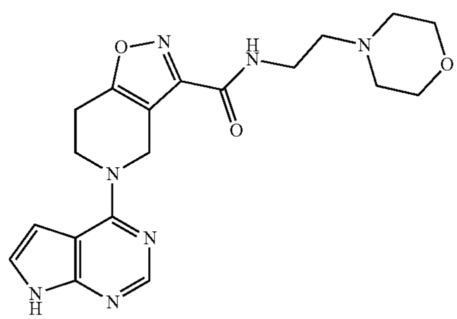 [SMILES: O=C(NCCN1CCOCC1)c1noc2c1CN(c1ncnc3[nH]ccc13)CC2] |
| 163 | 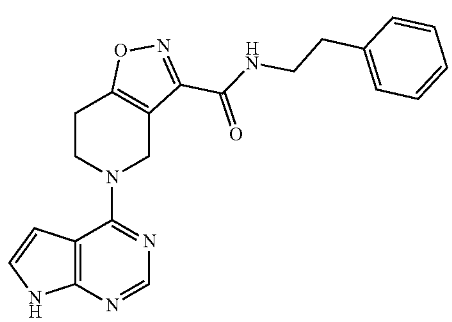 [SMILES: O=C(NCCc1ccccc1)c1noc2c1CN(c1ncnc3[nH]ccc13)CC2] |
| 164 | |ـ

TABLE 1-continued

Selected Compounds of Formulas I and II

| Compound No. | structure |
|---|---|
| 165 | 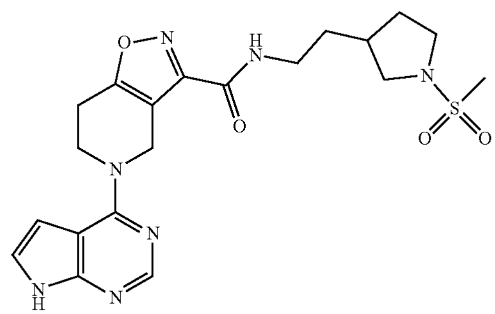 [SMILES: CS(=O)(=O)N1CCC(CCNC(=O)c2noc3c2CN(c2ncnc4[nH]ccc24)CC3)C1] |
| 166 | 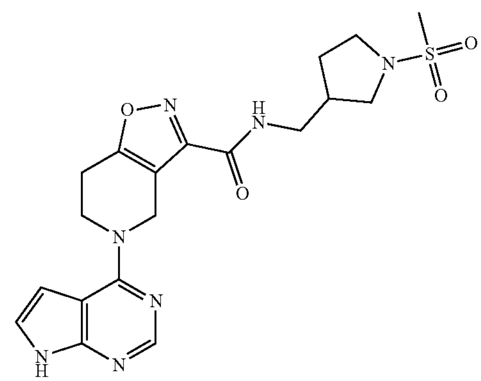 [SMILES: CS(=O)(=O)N1CCC(CNC(=O)c2noc3c2CN(c2ncnc4[nH]ccc24)CC3)C1] |
| 167 | 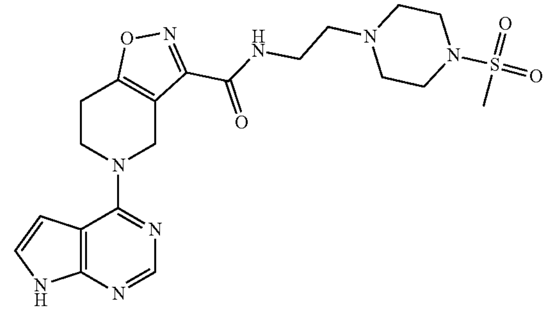 [SMILES: CS(=O)(=O)N1CCN(CCNC(=O)c2noc3c2CN(c2ncnc4[nH]ccc24)CC3)CC1] |
| 168 | 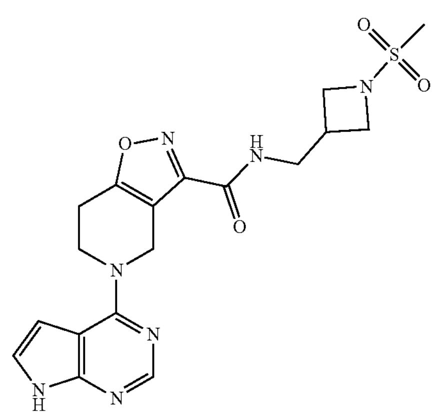 [SMILES: CS(=O)(=O)N1CC(CNC(=O)c2noc3c2CN(c2ncnc4[nH]ccc24)CC3)C1] |

TABLE 1-continued

Selected Compounds of Formulas I and II

| Compound No. | structure |
|---|---|
| 169 | |
| 170 | |
| 171 | |
| 172 | |
| 173 | |
| 174 | 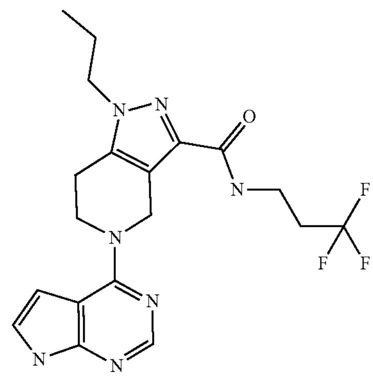 |
| 175 | 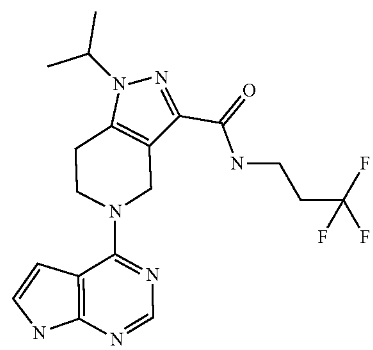 |
| 176 | 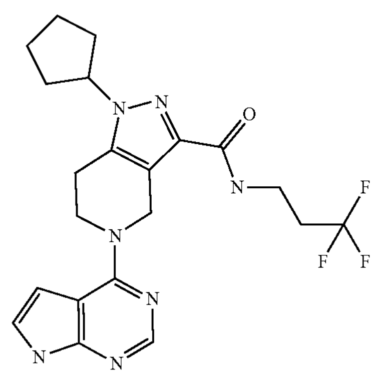 |
| 177 | 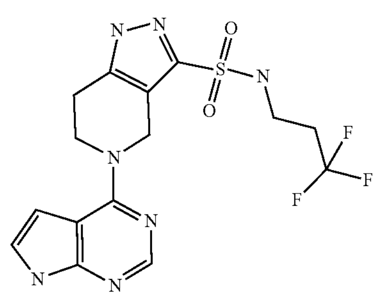 |
| 178 | |
| 179 | |

TABLE 1-continued
Selected Compounds of Formulas I and II
| Compound No. | structure |
|---|---|
| 180 | 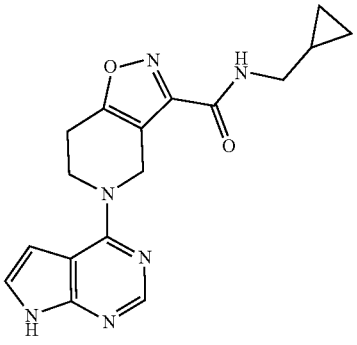 [SMILES: O=C(NCC1CC1)c1noc2c1CN(c1ncnc3[nH]ccc13)CC2] |
| 181 | 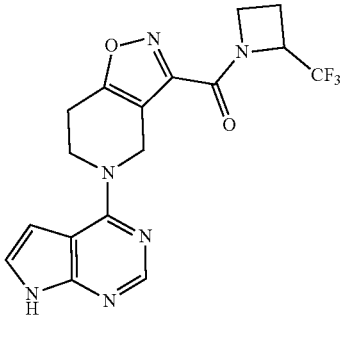 [SMILES: O=C(c1noc2c1CN(c1ncnc3[nH]ccc13)CC2)N1CCC1C(F)(F)F] |
| 182 | 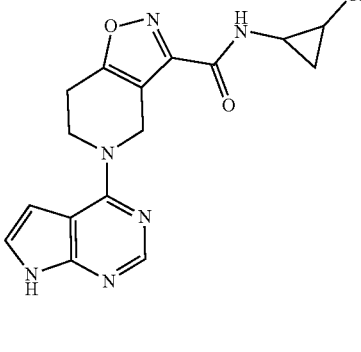 |
| 183 | 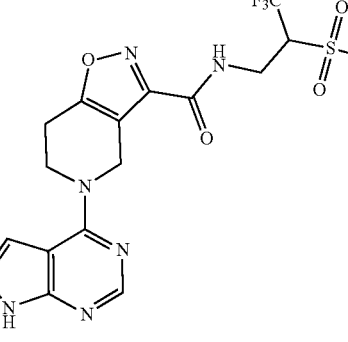 |
| 185 | 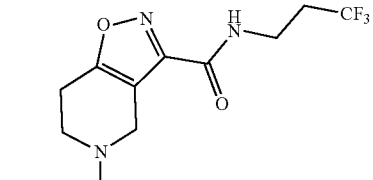 |
| 186 | 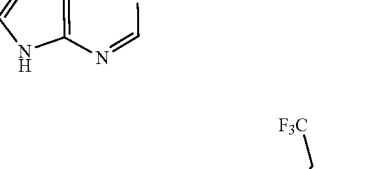 |
| 187 | 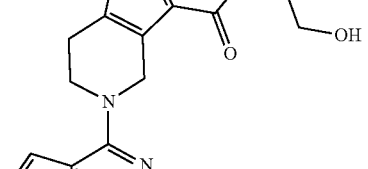 |
| 188 | 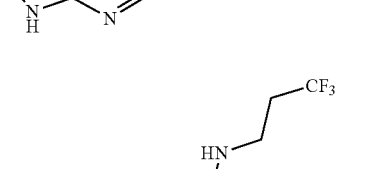 |

TABLE 1-continued

Selected Compounds of Formulas I and II

| Compound No. | structure |
| --- | --- |
| 189 | 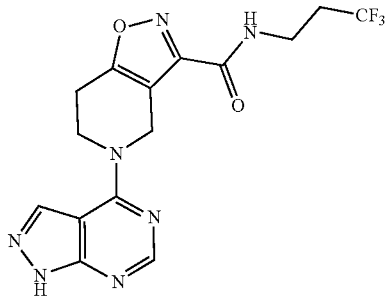 [SMILES: O=C(NCCC(F)(F)F)c1noc2c1CN(c1ncnc3[nH]ncc13)CC2] |
| 190 | 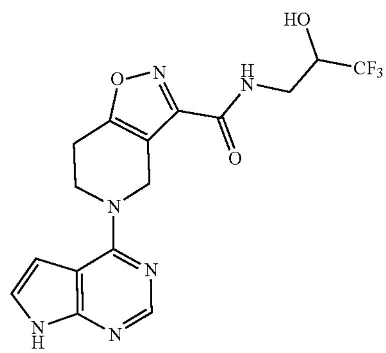 [SMILES: O=C(NCC(O)C(F)(F)F)c1noc2c1CN(c1ncnc3[nH]ccc13)CC2] |
| 191 | 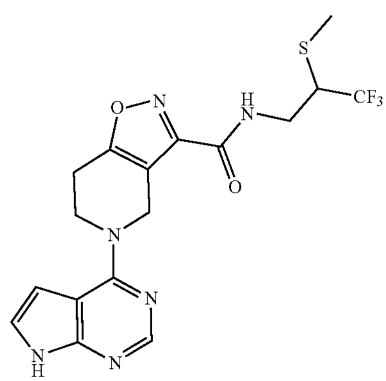 [SMILES: CSC(CNC(=O)c1noc2c1CN(c1ncnc3[nH]ccc13)CC2)C(F)(F)F] |
| 192 | 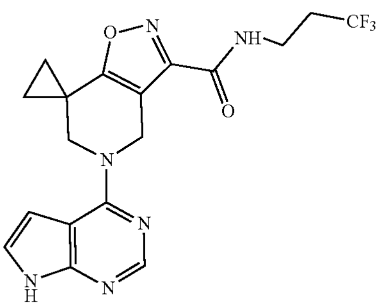 [SMILES: O=C(NCCC(F)(F)F)c1noc2c1CN(c1ncnc3[nH]ccc13)CC21CC1] |
| 193 | |
| 194 | |
| 196 | |
| 197 | |

TABLE 1-continued

Selected Compounds of Formulas I and II

| Compound No. | structure |
|---|---|
| 198 | (structure) |
| 199 | (structure) |
| 200 | (structure) |
| 201 | (structure) |
| 202 | (structure) |

In certain embodiments, the compound is administered orally, subcutaneously, intravenously, or intramuscularly. In certain embodiments, the compound is administered orally. In certain embodiments, the compound is administered chronically. In certain embodiments, the compound is administered continuously, e.g., by continuous intravenous infusion.

Exemplary compounds of the invention may be synthesized from the following known starting materials using methods known to one skilled in the art or certain references. In one aspect, provided herein is a pharmaceutically acceptable salt of a compound described herein (e.g., a compound of Formula (I), (II), (III), or (IV)).

Alternative Embodiments

In an alternative embodiment, compounds described herein may also comprise one or more isotopic substitutions. For example, hydrogen may be $^2$H (D or deuterium) or 3H (T or tritium); carbon may be, for example, $^{13}$C or $^{14}$C; oxygen may be, for example, $^{18}$O; nitrogen may be, for example, $^{13}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

In another alternative embodiment, compounds of the disclosure may include pharmaceutically acceptable salts, solvates, enantiomers, or stereoisomers of the compound.

Pharmaceutical Compositions

In one aspect, provided herein is a pharmaceutical composition comprising a compound described herein (e.g., a compound of Formula (I), (II), (III), or (IV)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether O-cyclodextrin, e.g., for example, sulfobutyl ether β-cyclodextrin, also known as CAPTISOL®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

In one aspect, provided is a kit comprising a composition (e.g., a solid composition) comprising a compound of Formula (I), (II), (III), or (IV)

Methods of Use and Treatment

The compounds described herein can be used to treat or prevent a disorder described herein. For example, compounds which modulate JAK family kinases are provided herein for the prevention, treatment, or alleviating symptoms of a disease or condition associated with JAK family kinases. A compound of formula (I), (II), (III), or (IV), or pharmaceutical compositions containing a compound of formula (I), (II), (III), or (IV), can be administered to treat disorders, conditions, or diseases described herein such as those treatable by the modulation of JAK family kinases. For example, a pharmaceutical composition comprising a therapeutically effective dose of a compound of formula (I), (II), (III), or (IV) or pharmaceutically acceptable salts thereof can be administered (e.g., intravenously) to a subject in need thereof multiple times per day (e.g., BID) over a course of treatment of one or more days to treat a disease in the subject.

Those of skill in the treatment of diseases linked to the mediation of the JAK family kinases will be able to determine the therapeutically effective amount of a compound of formula (I), (II), (III), or (IV) from the test results presented hereinafter. In general, a suitable daily dose of a compound of the invention will be that amount of the compound that is the lowest dose able to produce a therapeutic effect. Such an effective dose will generally depend upon various factors. Generally, oral, sublingual, rectal, intravenous, topical, transdermal, inhaled and intracerebroventricular doses of the compounds of this invention for a patient will range from about 0.0001 to about 100 mg per kilogram of body weight per day. For example, the dose can be 1-50, 1-25, or 5-10 mg/kg. It is contemplated, for instance, that a therapeutically effective dose will be from about 0.001 mg/kg to about 50 mg/kg per kg of body weight, more preferably from about 0.01 mg/kg to about 10 mg/kg per kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

The exact dosage and frequency of administration depends on the particular form of a compound of formula (I), (II), (III), or (IV) used, the particular condition being treated, the severity of the condition being treated, the age, weight and general physical condition of the particular patient as well as the other medication the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines. A physician or veterinarian having ordinary skill in the art can readily determine and prescribe the effective amount of the pharmaceutical composition required.

Exemplary disorders suitable for treatment with a compound or composition described herein are provided herein.

There are substantial needs for safe and efficacious agents to control disorders related to JAK family kinases, such as atopic dermatitis, both in human and animals. The market for treating atopic dermatitis in animals is currently dominated by corticosteroids, which cause distressing and undesirable side effects in animals, specifically in companion animals such as dogs APOQUEL™ is a pan-JAK inhibitor recently approved for atopic dermatitis in canines. Antihistamines are also used, but are poorly effective. A canine formulation of cyclosporine (ATOPICA™) is currently being marketed for atopic dermatitis, but is expensive and has a slow onset of efficacy. In addition, there are G1 toleration issues with ATOPICA™. Compounds of the present invention are JAK inhibitors, in some cases with selective efficacy against JAK3. These compounds are expected to provide an alternative to steroid usage and provide resolution of chronic pruritus and inflammation that would either persist in atopic dermatitis or slowly regress following removal of allergen or causative agent, such as fleas in flea-allergic dermatitis.

Compounds of the present invention may be administered in a pharmaceutically acceptable form either alone or in combination with one or more additional agents which modulate a mammalian immune system or with anti-inflammatory agents. These agents may include but are not limited to cyclosporin A (e.g., Sandimmune™ or Neoral™, rapamycin. FK-506 (tacrolimus), leflunomide, deoxyspergualin, mycophenolate (e.g., Cellcept™, azathioprine (e.g., Imuran™), daclizumab (e.g., Zenapax™), OKT3 (e.g., Orthocolone™), AtGam™, aspirin, acetaminophen, ibuprofen, naproxen, piroxicam, and anti-inflammatory steroids (e.g., prednisolone or dexamethasone), IFN-beta, teriflunomide. Laquinimod, glatiramer acetate, dimethyl fumerate, rituximab, fingolimod, natalizumab, alemtuzumab, mitoxantrone. Sulfasalazine (Azulfidine), Mesalamine (Apriso, Asacol, Lialda, others), balsalazide (Colazal) and olsalazine (Dipentum), and mercaptopurine (Purinethol), antibiotics (antimycobacterial drugs, e.g., Metronidazole, ciprofloxacin), Ustekinumab and vedolizumab These agents may be administered as part of the same or separate dosage forms, via the same or different routes of administration, and on the same or different administration schedules according to standard pharmaceutical practice known to one skilled in the art.

Accordingly, the invention provides methods of treating or preventing a disease, condition or disorder associated with JAK family kinases in a subject, such as a human or non-human mammal, comprising administering an effective amount of one or more compounds described herein to the subject. Suitable subjects that can be treated include domestic or wild animals, companion animals, such as dogs, cats, horses and the like: livestock including, cows and other ruminants, pigs, poultry, rabbits and the like: primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier.

Another embodiment provides a method of selectively inhibiting a JAK3 enzyme, which includes contacting the JAK3 enzyme with either a non-therapeutic amount or a therapeutically effective amount of one or more of the presently taught compounds. Such methods can occur in vivo or in vitro. In vitro contact can involve a screening assay to determine the efficacy of the one or more compounds against a selected enzyme at various amounts or concentrations. In vivo contact with a therapeutically effective amount of the one or more compounds can involve treatment of a described disease, disorder or condition or prophylaxis of organ transplant rejection in the animal in which the contact occurs. The effect of the one or more compounds on the JAK enzyme and/or host animal can also be determined or measured. Methods for determining JAK activity include those described in the Examples as well as those disclosed in WO99/65908, WO 99/65909, WO01/42246, WO02/00661, WO02/096909, WO2004/046112 and WO2007/012953.

Examples

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Reagents were purchased from available commercial sources. The structures of all the desired products were in full accordance with the spectral data provided.

$^1$H NMR spectra (supporting information) were recorded using a 400-Bruker spectrometer (400 MHz, in listed solvent.) $^1$H-NMR data reported herein (e.g., for the region between δ (ppm) of about 0.5 to about 4 ppm) will be understood to be an exemplary interpretation of the NMR spectrum (e.g., exemplary peak integrations) of a compound.

LC/MS spectra were obtained using Agilent 1200\G1956A or SHIMADZU LCMS-2020. Standard LC/MS conditions were as follows (running time 1.55 minutes): Acidic condition: Mobile Phase A: 0.0375% TFA in water (v/v). Mobile Phase B: 0.01875% TFA in acetonitrile (v/v); Column: Kinetex EVO C18 30*2.1 mm, 5 μm. Basic condition: Mobile Phase A: 0.025% NH$_3$·H$_2$O in water (v/v). Mobile Phase B: Acetonitrile; Column: Kinetex EVO C18 2.1×30 mm, 5 μm. The gradient ran from 5% to 95% mobile phase B or 0 to 60% mobile phase B.

Abbreviations: PE: petroleum ether; EtOAc: ethyl acetate; THF: tetrahydrofuran; TLC: thin layer chromatography; Me: methyl; i-Pr: iso-propyl; t-Bu: tert-butyl; Ph: phenyl; Et: ethyl; DCM: dichloromethane; DMAP: 4-dimethylaminopyridine; EtOAc: ethyl acetate; Boc: t-butoxycarbonyl. THF: tetrahydrofuran; LAH: Lithium Aluminium Hydride; MeCN: acetonitrile; ACN: acetonitrile; Tos: 4-toluenesulfonyl; Ms: methanesulfonyl; FA: formic acid; DMF: dimethylformamide; TFA: trifluoroacetic acid; EDCI: 1-ethyl-3-(3-dimethylaminopropyl)carbodiimide; LDA: lithium diisopropylamide; HATU: 1-[bis(dimethylamino)methylene]-1H-1,2,3-triazolo[4,5-b]pyridinium 3-oxid hexafluorophosphate; SEM: 2-(trimethylsilyl)ethoxymethyl; TEA: triethylamine; DIEA: N. N-diisopropylethylamine; MTBE: methyl tert-butyl ether; T3P: propylphosphonic anhydride; hr: hour; Rr retention factor, TLC: thin layer chromatography; LCMS: liquid chromatography mass spectroscopy; HPLC: high-performance liquid chromatography.

Example 1: Synthesis of Compound 105

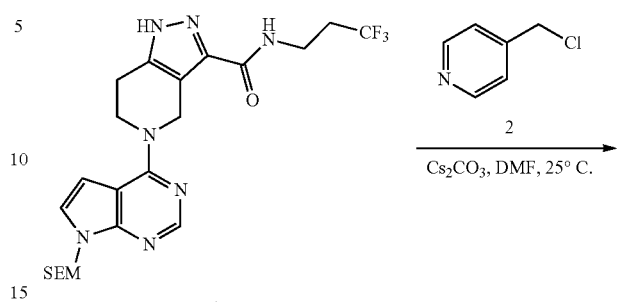

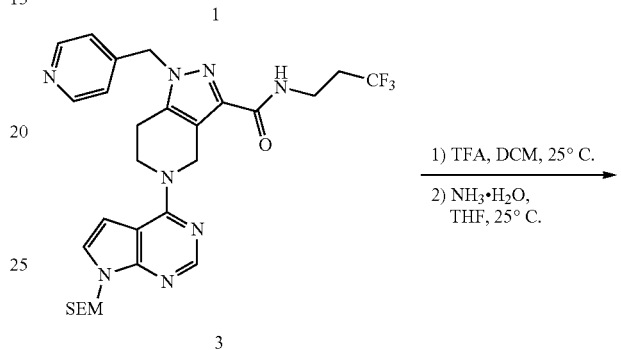

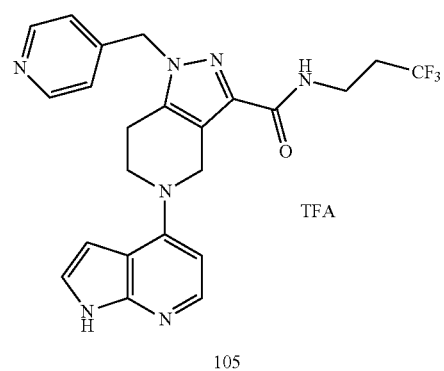

Preparation of Compound 3

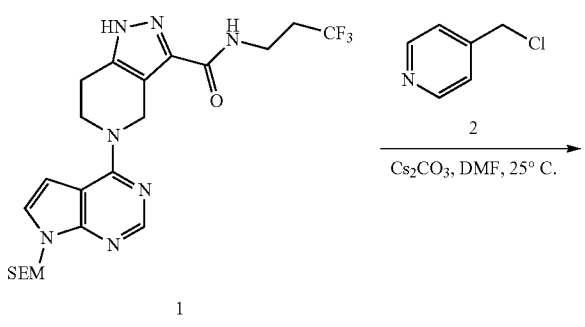

-continued

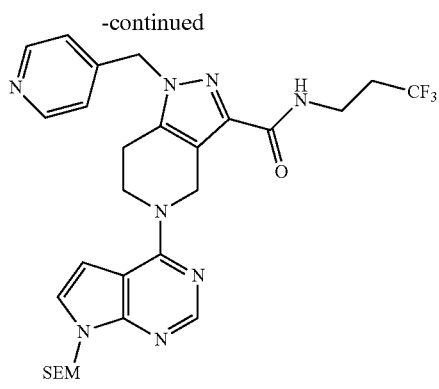

3

A mixture of Compound 1 (150 mg, 294.35 umol, 1 eq), Compound 2 (53.11 mg, 323.78 umol, 1.1 eq, HCl) and Cs$_2$CO$_3$ (383.62 mg, 1.18 mmol, 4 eq) in DMF (3 mL) was stirred at 50° C. for 1 hr. LCMS showed Compound 1 was consumed, and a major peak with desired MS was detected. The mixture was diluted with water (20 mL), extracted with EtOAc (20 mL*2), washed with brine (50 mL), dried with Na$_2$SO$_4$, filtered and concentrated to give Compound 3 (180 mg, crude) as yellow oil.

$^1$H NMR (400 MHz, CDCl$_3$)

δ=8.59 (d, J=6.0 Hz, 2H), 8.35 (s, 1H), 7.13 (d, J=2.6 Hz, 1H), 7.05 (t, J=6.2 Hz, 1H), 6.99 (d, J=5.9 Hz, 2H), 6.82 (d, J=2.3 Hz, 1H), 5.58 (s, 2H), 5.26 (s, 4H), 4.28 (br. s, 2H), 3.71 (q, J=6.6 Hz, 2H), 3.59-3.47 (m, 2H), 2.77 (br. s, 2H), 2.48 (td, J=6.7, 10.8 Hz, 2H), 0.95-0.88 (m, 2H), −0.05 (s, 9H) LCMS: Rt=0.863 min, [M+H]$^+$=601.3

Preparation of Compound 105

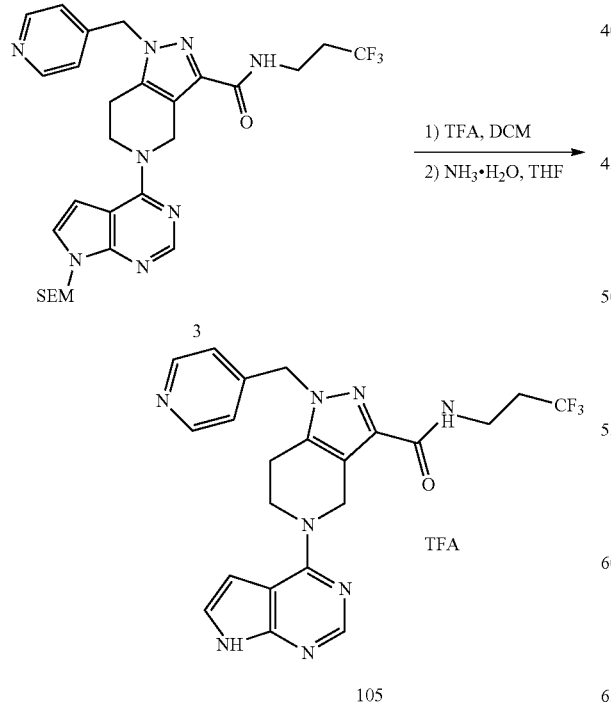

A solution of Compound 3 (170 mg, 283.00 umol, 1 eq) in TFA (1 mL) and DCM (1 mL) was stirred at 25° C. for 1 hr. The mixture was concentrated. Then dissolve the mixture in THF (1.5 mL), NH$_3$·H$_2$O (1.5 mL) was added, the mixture was stirred at 25° C. for 13 hr. LCMS showed Compound 3 was consumed and desired MS was detected. The mixture was diluted with water (40 mL), extracted with EtOAc (25 mL*3), washed with brine (40 mL*2), dried over Na$_2$SO$_4$, filtered and concentrated. The residue was purified by prep-HPLC (column: Phenomenex Synergi C18 150*25*10 um; mobile phase: [water(0.1% TFA)-ACN]; B %: 8%-38%, 10 min) to give Compound 105 (147 mg, 248.24 umol, 87.72% yield, 98.7% purity, TFA) as yellow solid.

$^1$H NMR (400 MHz, MeOD)

δ=8.74 (d, J=6.6 Hz, 2H), 8.38 (s, 1H), 7.71-7.70 (m, 1H), 7.67 (s, 1H), 7.71-7.63 (m, 1H), 7.42 (d, J=3.7 Hz, 1H), 7.05 (d, J=3.8 Hz, 1H), 5.71 (s, 2H), 5.33 (s, 2H), 4.39 (t, J=5.7 Hz, 2H), 3.62 (t, J=7.1 Hz, 2H), 3.02 (br t, J=5.6 Hz, 2H), 2.51 (tq, J=7.1, 11.0 Hz, 2H)

$^{13}$C NMR (101 MHz, MeOD)

δ=162.86, 161.25, 160.89, 154.43, 154.21, 144.13, 142.80, 141.42, 139.57, 130.61, 127.87, 125.13, 124.30, 123.74, 122.65, 114.86, 103.61, 102.57, 51.36, 44.92, 43.73, 33.34, 33.06, 32.78, 32.50, 32.50, 32.18, 32.11, 32.07, 21.27.

LCMS: Rt=0.693 min, [M+H]$^+$=471.0

Example 2: Synthesis of Compound 101

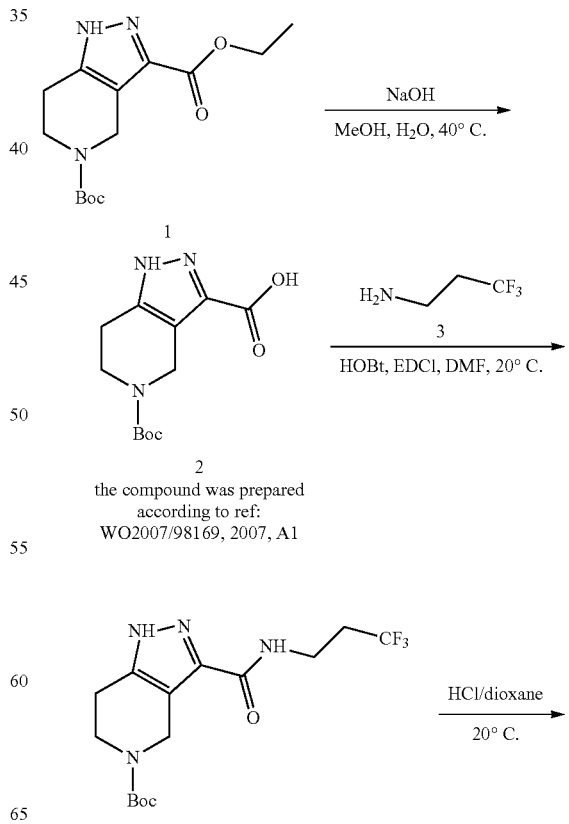

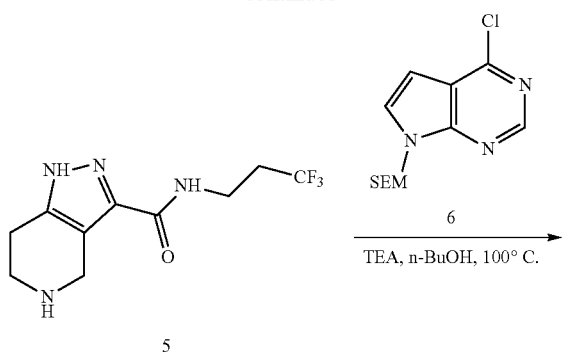
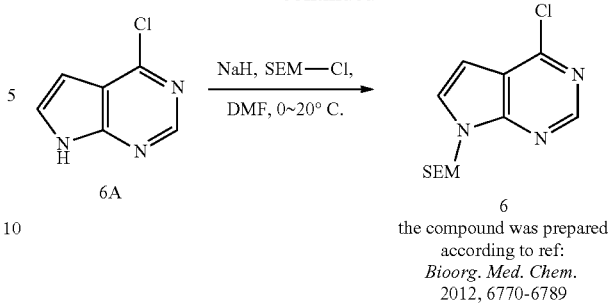
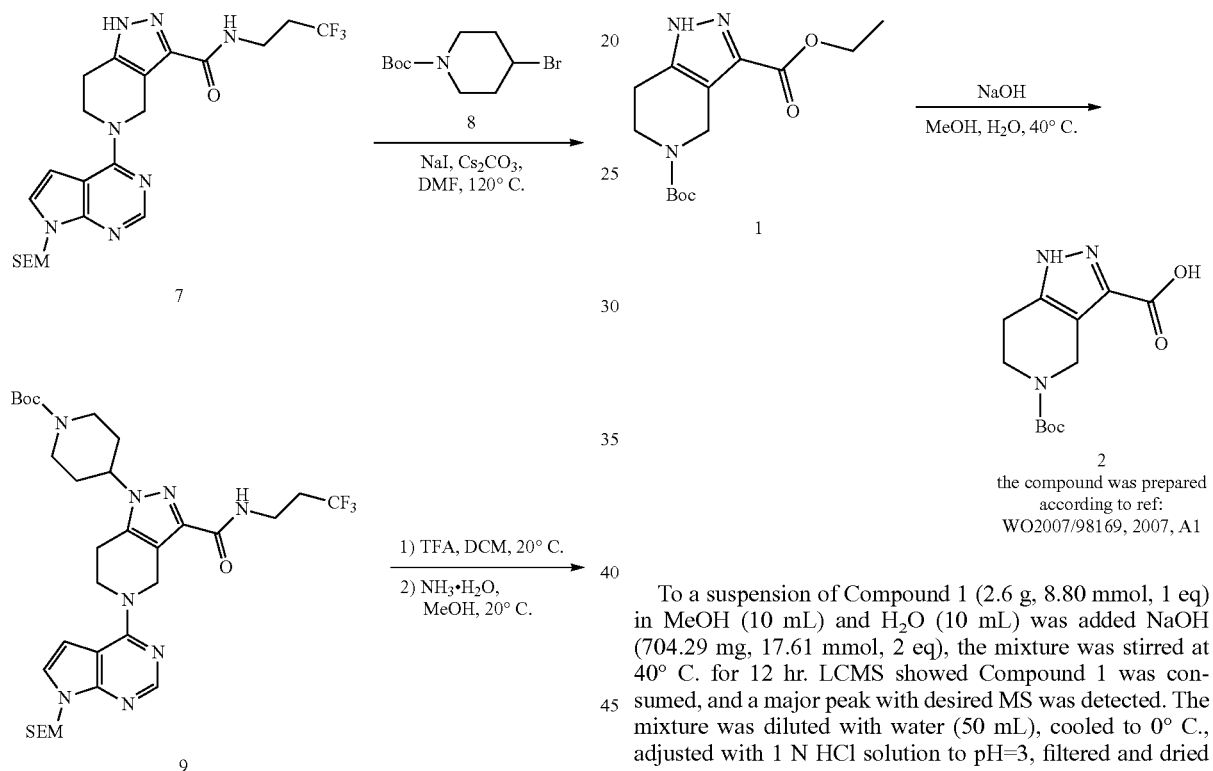

Preparation of Compound 2

To a suspension of Compound 1 (2.6 g, 8.80 mmol, 1 eq) in MeOH (10 mL) and H$_2$O (10 mL) was added NaOH (704.29 mg, 17.61 mmol, 2 eq), the mixture was stirred at 40° C. for 12 hr. LCMS showed Compound 1 was consumed, and a major peak with desired MS was detected. The mixture was diluted with water (50 mL), cooled to 0° C., adjusted with 1 N HCl solution to pH=3, filtered and dried under vacuum to give Compound 2 (2.34 g, 8.75 mmol, 99.45% yield) as off-white solid.

$^1$H NMR (400 MHz, DMSO-d$_6$)

δ=4.49 (s, 2H), 3.59 (t, J=5.8 Hz, 2H), 2.73-2.59 (m, 3H), 1.42 (s, 9H)

LCMS: Rt=0.615 min, [M+H]$^+$=268.1

Preparation of Compound 4

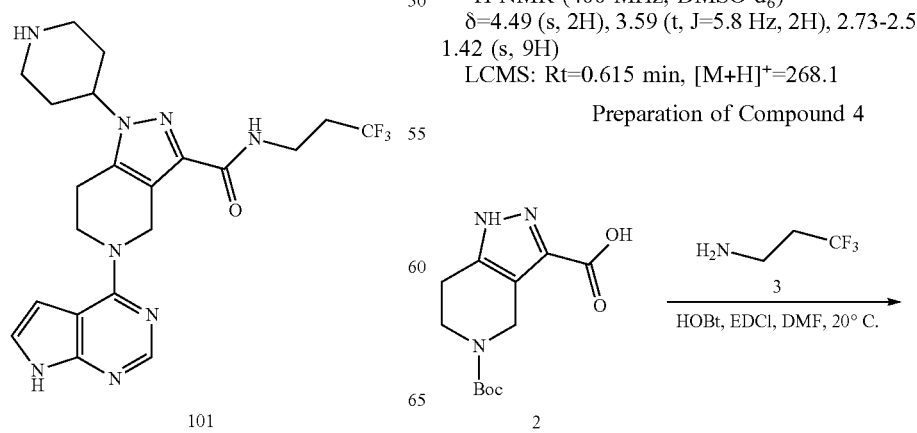

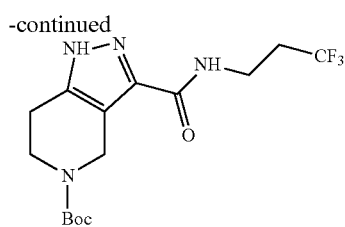

4

To a mixture of Compound 2 (2.34 g, 8.75 mmol, 1 eq) and Compound 3 (1.57 g, 10.51 mmol, 1.2 eq, HCl) in DMF (15 mL) was added HOBt (1.42 g, 10.51 mmol, 1.2 eq), EDCI (2.52 g, 13.13 mmol, 1.5 eq) and DIEA (4.53 g, 35.02 mmol, 6.10 mL, 4 eq), the mixture was stirred at 20° C. for 12 hr. LCMS showed Compound 2 was consumed, and a major peak with desired MS was detected. The mixture was diluted with water (100 mL), extracted with EtOAc (50 mL*2), washed with brine (100 mL), dried with $Na_2SO_4$, filtered and concentrated. The residue was purified by silica gel chromatography (Petroleum ether/Ethyl acetate=1/1) to give Compound 4 (3.1 g, 8.56 mmol, 97.72% yield) as white solid.

$^1$H NMR (400 MHz, $CDCl_3$)

δ=10.07-9.73 (m, 1H), 7.18-6.95 (m, 1H), 4.69 (s, 2H), 3.76-3.72 (m, 2H), 3.69 (q, J=6.6 Hz, 2H), 2.76 (br. t, J=5.6 Hz, 2H), 2.52-2.38 (m, 2H), 1.49 (s, 9H)

LCMS: Rt=0.801 min, [M+Na]$^+$=385.1

Preparation of Compound 5

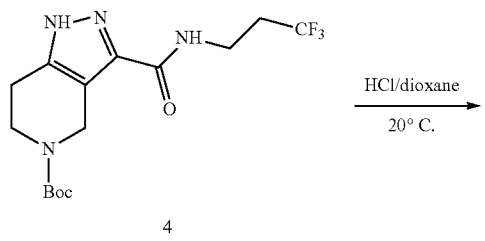

A mixture of Compound 4 (1 g, 2.76 mmol, 1 eq) in 4 N HCl/dioxane (10 mL) was stirred at 20° C. for 1 hr. TLC showed Compound 4 was consumed. The mixture was concentrated to give Compound 5 (824 mg, crude, HCl) as white solid.

Preparation of Compound 6

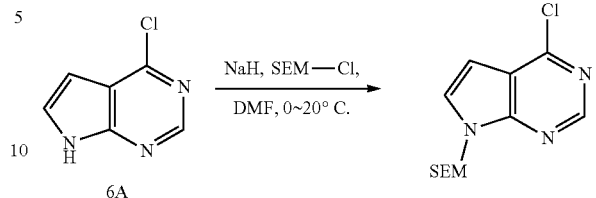

the compound was prepared according to ref:
*Bioorg. Med. Chem.*
2012, 6770-6789

To a solution of Compound 6A (1 g, 6.51 mmol, 1 eq) in DMF (10 mL) was added NaH (312.53 mg, 7.81 mmol, 60% purity, 1.2 eq), after addition, the mixture was stirred at 20° C. for 1 hr. The mixture was cooled to 0° C., SEM-Cl (1.30 g, 7.81 mmol, 1.38 mL, 1.2 eq) was added, the mixture was stirred at 20° C. for 12 hr. LCMS showed Compound 6A was consumed, and a major peak with desired MS was detected. The mixture was diluted with water (50 mL), extracted with EtOAc (20 mL*2), washed with brine (50 mL), dried with $Na_2SO_4$, filtered and concentrated. The residue was purified by flash silica gel chromatography (Petroleum ether/Ethyl acetate=5/1) to give Compound 6 (1.73 g, 6.10 mmol, 93.60% yield) as yellow oil.

$^1$H NMR (400 MHz, $CDCl_3$)

δ=8.67 (s, 1H), 7.40 (d, J=3.5 Hz, 1H), 6.68 (d, J=3.7 Hz, 1H), 5.66 (s, 2H), 3.59-3.48 (m, 2H), 0.96-0.87 (m, 2H), −0.05 (s, 9H)

LCMS: Rt=1.039 min, [M+H]$^+$=284.0

Preparation of Compound 7

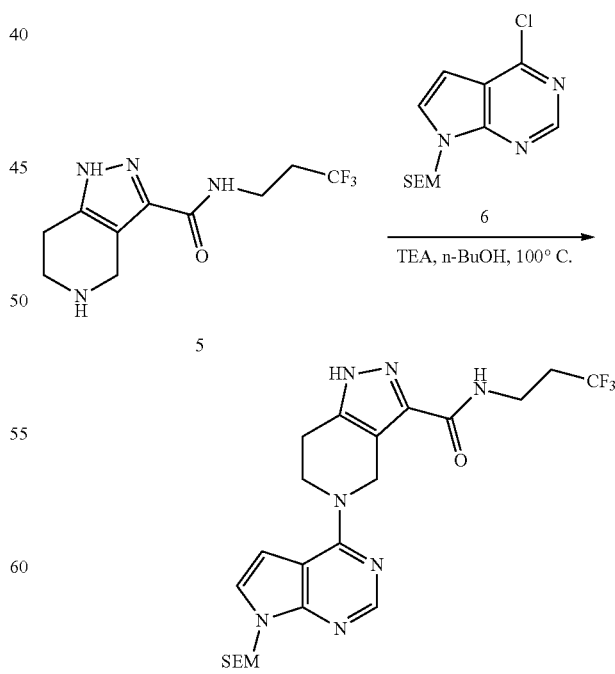

To a mixture of Compound 5 (155 mg, 518.93 umol, 1 eq, HCl) and Compound 6 (147.29 mg, 518.93 umol, 1 eq) in n-BuOH (5 mL) was added TEA (210.04 mg, 2.08 mmol, 288.92 uL, 4 eq), the mixture was stirred at 100° C. for 12 hr. LCMS showed a major peak with desired MS was detected. The mixture was concentrated. The residue was purified by flash silica gel chromatography (Petroleum ether/Ethyl acetate=1/1) to give Compound 7 (210 mg, 412.09 umol, 79.41% yield) as white solid.

$^1$H NMR (400 MHz, CDCl$_3$)

δ=10.20-9.79 (m, 1H), 8.37 (s, 1H), 7.13 (d, J=3.6 Hz, 1H), 7.11-7.05 (m, 1H), 6.83 (d, J=3.8 Hz, 1H), 5.59 (s, 2H), 5.26 (s, 2H), 4.30 (t, J=5.6 Hz, 2H), 3.72 (q, J=6.6 Hz, 2H), 3.58-3.46 (m, 2H), 2.97 (br. t, J=5.4 Hz, 2H), 2.48 (tq, J=6.6, 10.7 Hz, 2H), 0.97-0.80 (m, 2H), −0.05 (s, 9H)

LCMS: Rt=0.898 min, [M+H]$^+$=510.2

Preparation of Compound 9

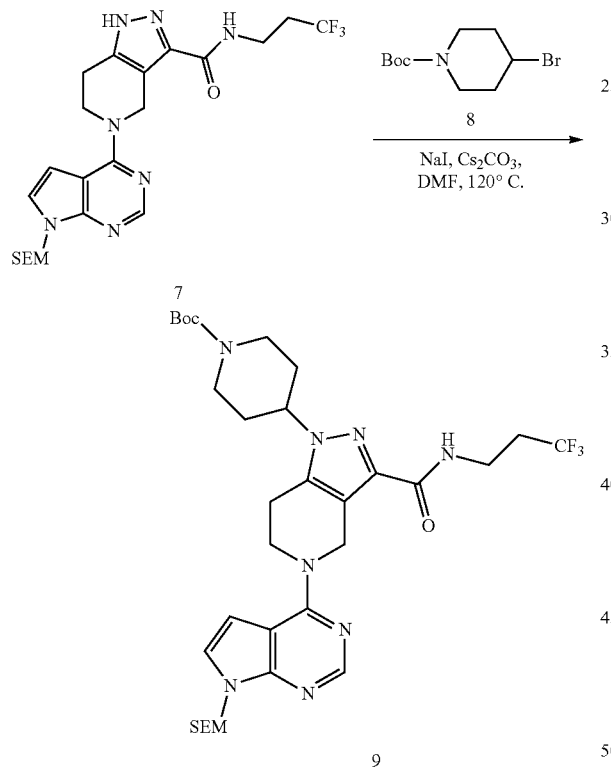

A mixture of Compound 7 (200 mg, 392.47 umol, 1 eq), Compound 8 (311.02 mg, 1.18 mmol, 3 eq), Cs$_2$CO$_3$ (639.36 mg, 1.96 mmol, 5 eq) and NaI (58.83 mg, 392.47 umol, 1 eq) in DMF (4 mL) was stirred at 120° C. for 48 hr. LCMS showed most of Compound 7 was consumed, and desired MS was detected. The mixture was diluted with water (30 mL), extracted with EtOAc (20 mL*2), washed with brine (50 mL), dried with Na$_2$SO$_4$, filtered and concentrated. The residue was purified by silica gel chromatography (Petroleum ether/Ethyl acetate=1/1~0/1) to give Compound 9 (110 mg, 158.77 umol, 40.45% yield) as colorless gum.

$^1$H NMR (400 MHz, CDCl$_3$)

δ=8.36 (s, 1H), 7.11 (d, J=3.7 Hz, 1H), 7.05 (t, J=6.4 Hz, 1H), 6.82 (d, J=3.8 Hz, 1H), 5.58 (s, 2H), 5.23 (s, 2H), 4.30 (br. t, J=5.4 Hz, 4H), 4.17-4.08 (m, 1H), 3.70 (q, J=6.7 Hz, 2H), 3.55-3.49 (m, 2H), 2.94-2.86 (m, 3H), 2.53-2.41 (m, 2H), 2.13-2.03 (m, 2H), 1.95-1.84 (m, 2H), 1.50 (s, 9H), 0.94-0.88 (m, 2H), −0.05 (s, 9H)

LCMS: Rt=1.103 min, [M+H]$^+$=693.3

Preparation of Compound 101

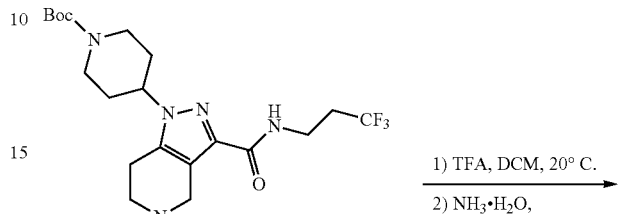

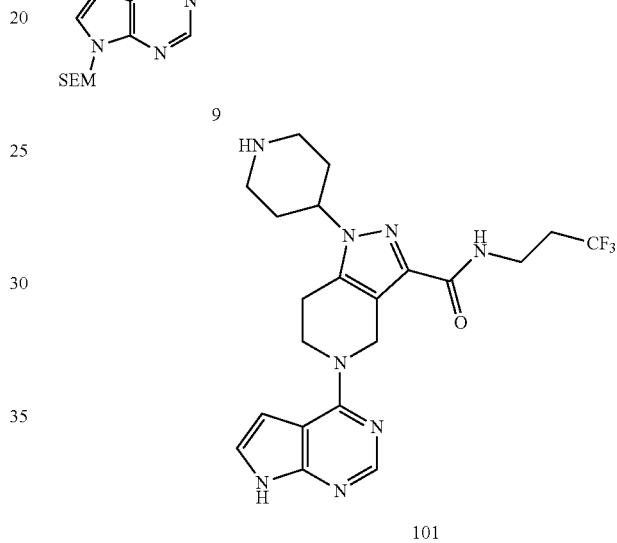

A mixture of Compound 9 (100 mg, 144.33 umol, 1 eq) in TFA (3 mL) and DCM (3 mL) was stirred at 20° C. for 3 hr. The mixture was concentrated, dissolved in MeOH (3 mL), NH$_3$·H$_2$O (3 mL) was added, stirred at 20° C. for 1 hr. LCMS showed Compound 9 was consumed, and a major peak with desired MS was detected. The mixture was concentrated, diluted with water (20 mL), extracted with EtOAc (20 mL*2), dried with Na$_2$SO$_4$, filtered and concentrated. The residue was purified by prep-HPLC (column: Phenomenex Synergi C18 150*25*10 um; mobile phase: [water(0.225% FA)-ACN]; B %: 10%-40%, 9 min) to give Compound 101 (49 mg, 103.67 umol, 71.83% yield, 97.845% purity) as off-white solid.

$^1$H NMR (400 MHz, MeOD)

δ=8.49 (br. s, 1H), 8.18 (s, 1H), 7.18 (d, J=3.7 Hz, 1H), 6.78 (d, J=3.7 Hz, 1H), 5.17 (s, 2H), 4.64-4.48 (m, 1H), 4.28 (t, J=5.6 Hz, 2H), 3.65 (t, J=7.1 Hz, 2H), 3.64-3.56 (m, 2H), 3.23 (dt, J=2.8, 12.4 Hz, 2H), 2.99 (t, J=5.5 Hz, 2H), 2.54 (ddt, J=4.0, 7.1, 11.0 Hz, 2H), 2.43-2.30 (m, 2H), 2.26-2.17 (m, 2H)

$^{13}$C NMR (101 MHz, MeOD)

δ=163.43, 157.16, 151.00, 150.20, 140.22, 138.87, 130.69, 127.95, 125.20, 122.46, 121.29, 115.72, 103.04, 101.06, 52.29, 43.62, 42.50, 42.09, 33.43, 33.16, 32.88, 32.61, 32.17, 32.13, 32.08, 32.05, 25.31, 21.29 LCMS: Rt=0.534 min, [M+H]$^+$=463.1

Example 3: Synthesis of Compound 102

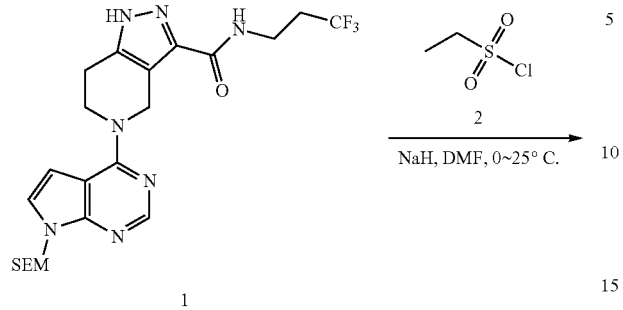

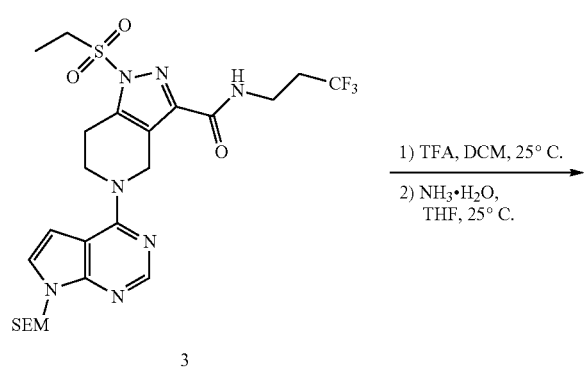

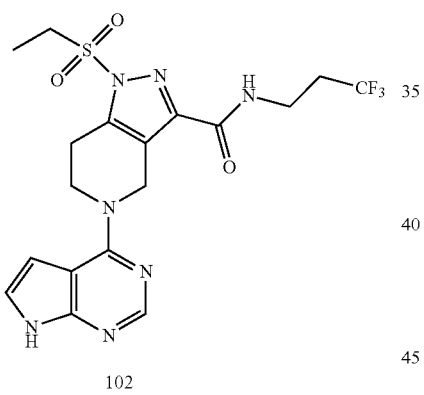

Preparation of Compound 3

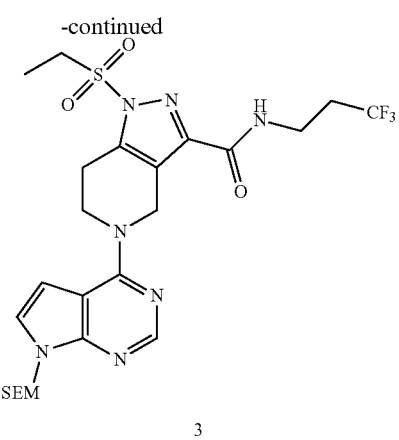

To a solution of Compound 1 (300 mg, 588.70 umol, 1 eq) in DMF (10 mL) was added NaH (35.32 mg, 883.05 umol, 60% purity, 1.5 eq) at 0° C., the mixture was stirred 0.5 hr. Then Compound 2 (83.26 mg, 647.57 umol, 61.22 uL, 1.1 eq) was added, the mixture was stirred at 25° C. for 2 hr under $N_2$ atmosphere. LCMS showed most of Compound 1 was consumed, and desired MS was detected. The residue was diluted with water (50 mL), extracted with EtOAc (100 mL*3). The combined organic layers were washed with brine (100 mL*2), dried over $Na_2SO_4$, filtered and concentrated under reduced pressure to give a residue. The residue was purified by flash silica gel chromatography (Eluent of 0-50% Ethyl acetate/Petroleum ether) to give Compound 3 (100 mg, 166.19 umol, 28.23% yield) as a white solid.

$^1$H NMR (400 MHz, $CDCl_3$)

δ=8.42 (s, 1H), 7.29 (br. t, J=6.1 Hz, 1H), 7.20 (d, J=3.7 Hz, 1H), 6.82 (d, J=3.8 Hz, 1H), 5.64 (s, 2H), 5.28 (s, 2H), 4.32 (t, J=5.7 Hz, 2H), 3.76 (q, J=6.6 Hz, 2H), 3.61-3.52 (m, 4H), 3.28 (br. t, J=5.5 Hz, 2H), 2.54 (tq, J=6.8, 10.6 Hz, 2H), 1.36 (t, J=7.4 Hz, 3H), 1.00-0.93 (m, 2H), 0.02-0.02 (m, 9H)

LCMS: Rt=0.970 min, $[M+H]^+$=602.6

Preparation of Compound 102

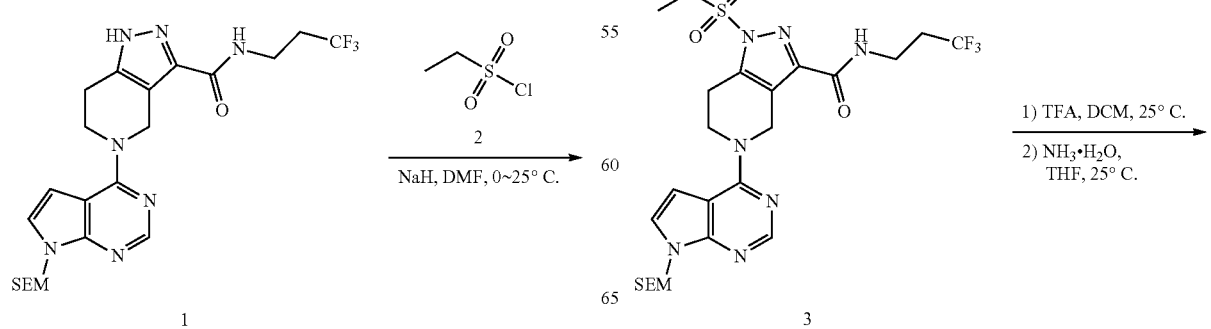

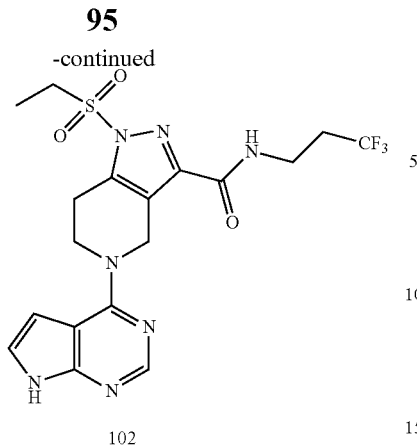

102

A solution of Compound 3 (100 mg, 166.19 umol, 1 eq) in TFA (1 mL) and DCM (1 mL) was stirred at 25° C. for 1 hr. The mixture was concentrated. Then dissolve the mixture in THF (1.5 mL), NH$_3$·H$_2$O (1.5 mL) was added, the mixture was stirred at 25° C. for 1.5 hr. LCMS showed Compound 3 was consumed, and desired MS was detected. The mixture was diluted with water (30 mL), extracted with EtOAc (30 m*2), washed with brine (50 mL*2), dried over Na$_2$SO$_4$, filtered and concentrated under reduced pressure to give a residue. The residue was purified by prep-HPLC. (column: Phenomenex Synergi C18 150*30 mm*4 um; mobile phase: [water(0.225% FA)-ACN]; B %: 20%-50%, 10 min) to give Compound 102 (55.5 mg, 117.13 umol, 70.48% yield, 99.5% purity) as off-white solid.

$^1$H NMR (400 MHz, CDCl$_3$)

δ=10.82 (br. s, 1H), 8.38 (br. s, 1H), 7.21 (br. t, J=6.2 Hz, 1H), 7.14 (d, J=3.7 Hz, 1H), 6.76 (d, J=3.4 Hz, 1H), 5.27 (s, 2H), 4.30 (t, J=5.6 Hz, 2H), 3.71 (q, J=6.6 Hz, 2H), 3.50 (q, J=7.3 Hz, 2H), 3.24 (br t, J=5.6 Hz, 2H), 2.49 (tq, J=6.8, 10.6 Hz, 2H), 1.31 (t, J=7.4 Hz, 3H)

$^{13}$C NMR (101 MHz, CDCl$_3$)

δ=161.161, 157.139, 151.443, 150.314, 145.080, 144.025, 130.327, 127.574, 124.821, 122.101, 121.285, 118.532, 103.275, 101.652, 49.420, 43.543, 41.483, 34.205, 33.925, 33.644, 33.364, 32.754, 32.721, 23.951, 7.648 LCMS: Rt=0.787 min, [M+H]$^+$=472.0

Example 4: Synthesis of Compound 106

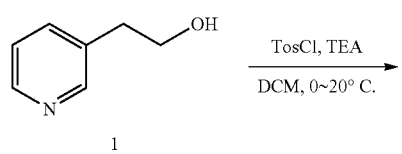

1

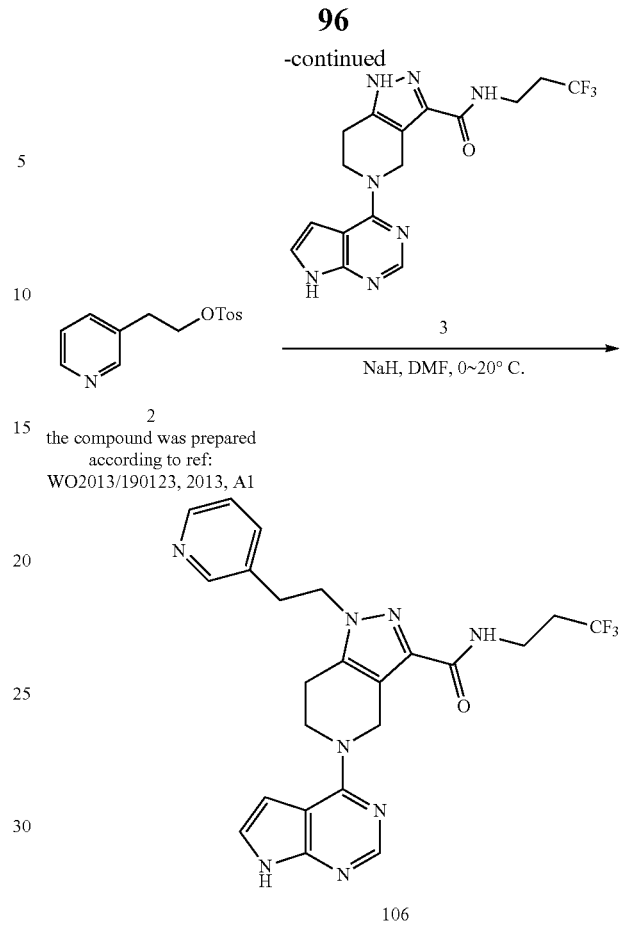

2
the compound was prepared according to ref: WO2013/190123, 2013, A1

106

Preparation of Compound 2

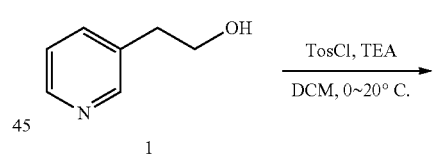

2
the compound was prepared according to ref: WO2013/190123, 2013, A1

To a solution of Compound 1 (100 mg, 812.00 umol, 1 eq) in DCM (5 mL) was added TEA (98.60 mg, 974.41 umol, 135.63 uL, 1.2 eq) and TosCl (170.29 mg, 893.21 umol, 1.1 eq) at 0° C., the mixture was stirred at 20° C. for 3 hr. TLC showed most of Compound 1 was consumed, and a new major spot was observed. The mixture was diluted with EtOAc (30 mL), washed with water (30 mL), dried with Na$_2$SO$_4$, filtered and concentrated. The residue was purified by prep-TLC (EA) to give Compound 2 (120 mg, 432.68 umol, 53.29% yield) as colorless oil.

$^1$H NMR (400 MHz, CDCl$_3$)

δ=8.41 (dd, J=1.5, 4.8 Hz, 1H), 7.73-7.57 (m, 4H), 7.22 (d, J=7.9 Hz, 1H), 7.09 (d, J=8.1 Hz, 2H), 4.32-4.24 (m, 1H), 4.16 (t, J=6.6 Hz, 1H), 3.37-3.19 (m, 1H), 2.90 (t, J=6.6 Hz, 1H), 2.27 (s, 3H)

Preparation of Compound 106

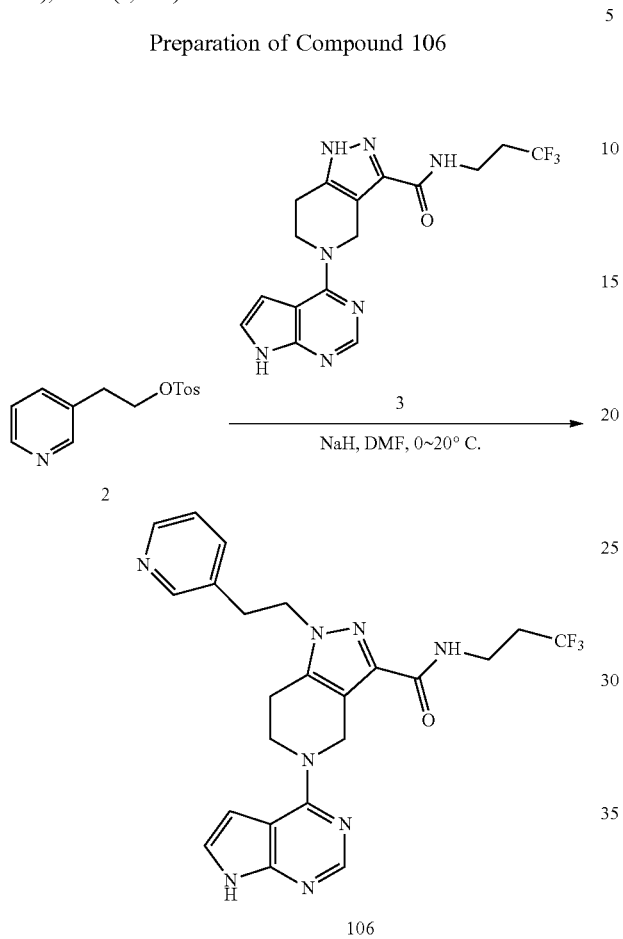

To a solution of Compound 3 (100 mg, 263.62 umol, 1 eq) in DMF (3 mL) was added NaH (12.65 mg, 316.34 umol, 60% purity, 1.2 eq) at 0° C., the mixture was stirred at 0° C. for 0.5 hr, then Compound 2 (87.73 mg, 316.34 umol, 1.2 eq) was added. The mixture was stirred at 20° C. for 2 hr. LCMS showed desired MS was detected. The mixture was quenched with saturated NH₄Cl solution (20 mL), extracted with EtOAc (20 mL*2), washed with brine (50 mL), dried with Na₂SO₄, filtered and concentrated. The residue was purified by prep-HPLC (column: Phenomenex Synergi C18 150*25*10 um; mobile phase: [water(0.225% FA)-ACN]; B %: 1%-30%, 10 min) to give Compound 106 (30 mg, 61.92 umol, 23.49% yield, 100% purity) as yellow solid.

$^1$H NMR (400 MHz, MeOD)

δ=8.19 (dd, J=1.4, 4.8 Hz, 1H), 8.16 (s, 2H), 7.33 (td, J=1.8, 7.9 Hz, 1H), 7.17 (d, J=3.7 Hz, 1H), 7.06 (dd, J=4.9, 7.6 Hz, 1H), 6.71 (d, J=3.7 Hz, 1H), 5.11 (s, 2H), 4.35 (t, J=6.4 Hz, 2H), 4.04 (t, J=5.7 Hz, 2H), 3.65 (t, J=7.1 Hz, 2H), 3.20 (t, J=6.4 Hz, 2H), 2.62-2.49 (m, 2H), 2.38 (t, J=5.6 Hz, 2H)

$^{13}$C NMR (101 MHz, MeOD)

δ=163.46, 157.14, 151.04, 150.20, 149.00, 146.90, 140.32, 139.78, 137.39, 134.58, 130.00, 129.93, 125.18, 123.55, 122.77, 121.24, 115.47, 103.09, 101.05, 49.72, 43.59, 42.12, 33.16, 32.98, 32.89, 32.14, 32.11, 32.07, 32.03, 21.08 LCMS: Rt=0.702 min, [M+H]$^+$=485.1

Example 5: Synthesis of Compound 108

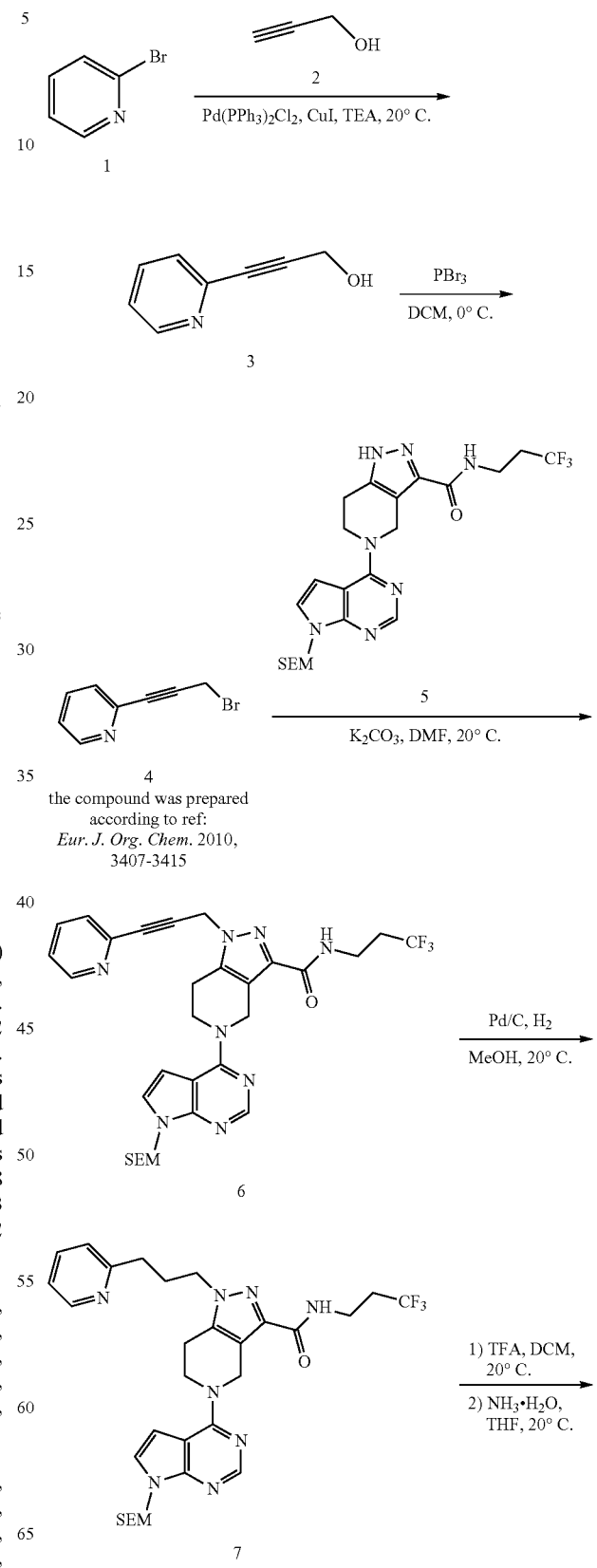

the compound was prepared according to ref: *Eur. J. Org. Chem.* 2010, 3407-3415

-continued

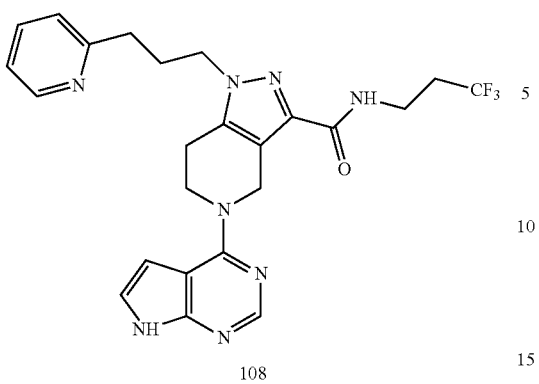

108

Preparation of Compound 3

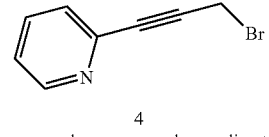

4 the compound was prepared according to ref:
Eur. J. Org. Chem. 2010, 3407-3415

To a solution of Compound 3 (330 mg, 2.48 mmol, 1 eq) in DCM (5 mL) was added a solution of PBr₃ (737.97 mg, 2.73 mmol, 1.1 eq) in DCM (3 mL) at 0° C. The mixture was stirred at 0° C. for 2 hr. TLC showed Compound 3 was consumed, and a new major spot was observed. The mixture was quenched with water (10 mL), washed with water (10 mL*3), dried with Na₂SO₄, filtered to give Compound 4 (480 mg, crude), which was stored in DCM and used in next step directly as colorless oil liquid.

Preparation of Compound 6

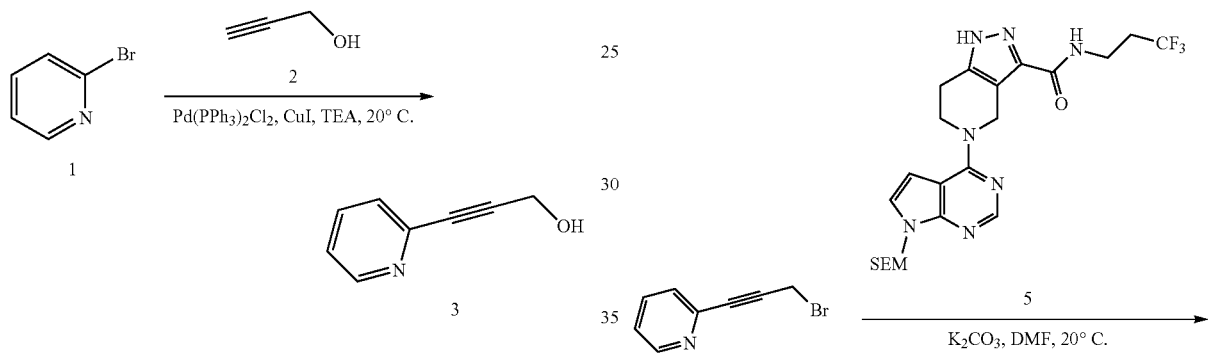

To a mixture of Pd(PPh₃)₂Cl₂ (44.42 mg, 63.29 umol, 0.01 eq), CuI (24.11 mg, 126.59 umol, 0.02 eq) in TEA (10 mL) was added Compound 1 (1 g, 6.33 mmol, 602.41 uL, 1 eq) and Compound 2 (425.81 mg, 7.60 mmol, 448.69 uL, 1.2 eq). The mixture was stirred at 20° C. for 12 hr. LCMS showed Compound 1 was consumed, and desired MS was detected. The mixture was diluted with saturated NH₄Cl solution (50 mL), extracted with EtOAc (30 mL*2), dried with Na₂SO₄, filtered and concentrated. The residue was purified by flash silica gel chromatography (Petroleum ether/Ethyl acetate=1/1) to give Compound 3 (480 mg, 3.61 mmol, 56.96% yield) as yellow solid.

¹H NMR (400 MHz, CDCl₃)

δ=8.62-8.55 (m, 1H), 7.67 (dt, J=1.8, 7.7 Hz, 1H), 7.48-7.42 (m, 1H), 7.27-7.19 (m, 1H), 4.54 (d, J=5.6 Hz, 2H), 2.00 (br. t, J=6.0 Hz, 1H)

LCMS: Rt=0.350 min, [M+H]⁺=134.2

Preparation of Compound 4

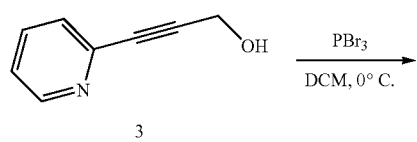

A mixture of Compound 5 (100 mg, 196.23 umol, 1 eq), Compound 4 (307.76 mg, 1.57 mmol, 8 eq) and K₂CO₃ (271.21 mg, 1.96 mmol, 10 eq) in DMF (5 mL) was stirred at 20° C. for 12 hr. LCMS showed Compound 5 was remained, and desired MS was detected. The mixture was diluted with water (20 mL), extracted with EtOAc (20 mL*2), washed with brine (50 mL), dried with Na₂SO₄, filtered and concentrated. The residue was purified by prep-TLC (Petroleum ether/Ethyl acetate=1/3) to give Compound 6 (30 mg, 48.02 umol, 24.47% yield) as yellow oil.

¹H NMR (400 MHz, CDCl₃)

δ=8.59 (br. d, J=4.6 Hz, 1H), 8.36 (s, 1H), 7.71-7.62 (m, 1H), 7.47-7.39 (m, 1H), 7.15-7.06 (m, 2H), 6.85-6.79 (m, 1H), 5.58 (s, 2H), 5.25 (s, 2H), 5.12 (s, 2H), 4.33 (br. d,

J=5.1 Hz, 2H), 3.77-3.66 (m, 2H), 3.58-3.48 (m, 2H), 3.11-2.99 (m, 2H), 2.48 (br. d, J=10.5 Hz, 2H), 0.93-0.88 (m, 2H), 0.08 (s, 9H)

LCMS: Rt=0.922 min, [M+H]⁺=625.2

Preparation of Compound 7

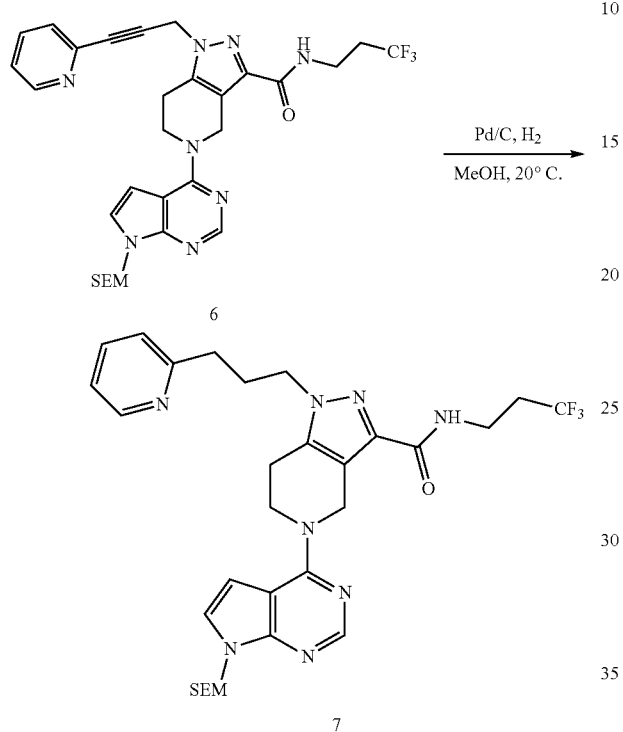

To a solution of Compound 6 (20 mg, 32.01 umol, 1 eq) in MeOH (5 mL) was added Pd/C (5 mg, 10% purity). The mixture was stirred at 20° C. under H₂ balloon for 1.5 hr at 15 psi. LCMS showed Compound 6 was consumed, and a major peak with desired MS was detected. The mixture was filtered and concentrated to give Compound 7 (20 mg, crude) as colorless oil.

LCMS: Rt=0.851 min, [M+H]⁺=629.3

Preparation of Compound 108

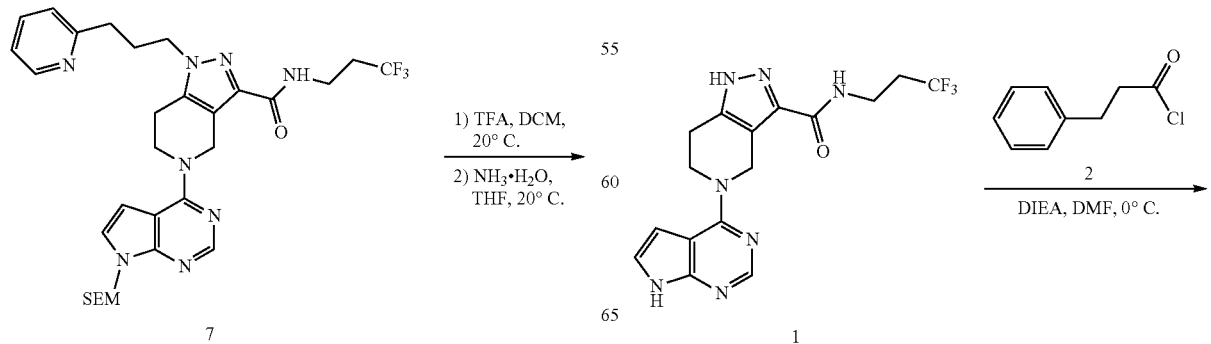

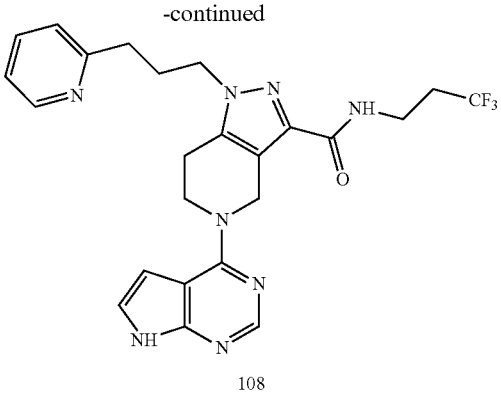

A solution of Compound 7 (20 mg, 31.81 umol, 1 eq) in TFA (1 mL) and DCM (1 mL) was stirred at 20° C. for 12 hr. The mixture was concentrated, dissolved in THF (1 mL), NH₃H₂O (1 mL) was added. The mixture was stirred at 20° C. for 1 hr. LCMS showed Compound 7 was consumed, and a major peak with desired MS was detected. The mixture was diluted with water (20 mL), extracted with EtOAc (15 mL*2), dried with Na₂SO₄, filtered and concentrated to give crude Compound 108 (15 mg, crude) as yellow oil. 21 mg crude Compound 108 was purified by prep-HPLC (column: Phenomenex Synergi C18 150*30 mm*4 um; mobile phase: [water(0.225% FA)-ACN]; B %: 5%-35%, 10 min) to give Compound 108 (13 mg, 26.08 umol, 61.90% yield, 100% purity) as white solid.

¹H NMR (400 MHz, MeOD)

δ=8.36-8.27 (m, 2H), 8.19 (s, 1H), 7.62 (dt, J=1.7, 7.7 Hz, 1H), 7.24-7.18 (m, 2H), 7.10 (dd, J=5.5, 7.0 Hz, 1H), 6.79 (d, J=3.7 Hz, 1H), 5.12 (s, 2H), 4.23 (t, J=5.6 Hz, 2H), 4.18 (t, J=6.8 Hz, 2H), 3.64 (t, J=7.2 Hz, 2H), 2.87 (br. t, J=5.5 Hz, 2H), 2.82 (t, J=7.4 Hz, 2H), 2.54 (tq, J=7.2, 11.0 Hz, 2H), 2.32 (quin, J=7.1 Hz, 2H)

¹³C NMR (101 MHz, MeOD)

δ=183.58, 160.25, 157.16, 150.95, 150.20, 148.06, 139.69, 138.98, 137.18, 130.23, 129.16, 127.92, 126.75, 123.25, 121.42, 121.24, 115.59, 103.05, 101.14, 48.40, 43.67, 42.11, 34.20, 33.17, 32.89, 32.10, 32.07, 32.03, 32.00, 29.00, 21.39 LCMS: Rt=0.706 min, [M+H]⁺=499.1

Example 6: Synthesis of Compound 103

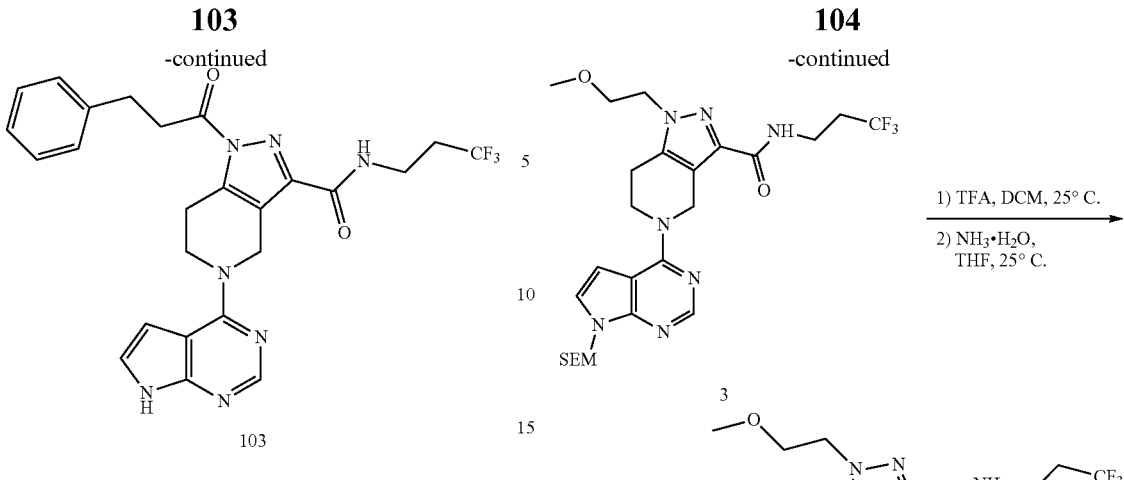

To a solution of Compound 1 (50 mg, 131.81 umol, 1 eq) and DIEA (51.10 mg, 395.43 umol, 68.87 uL, 3 eq) in DMF (3 mL) was added Compound 2 (33.34 mg, 197.72 umol, 29.24 uL, 1.5 eq) at 0° C., the mixture was stirred at 0° C. for 1 hr. LCMS showed Compound 1 was consumed, and a major peak with desired MS was detected. The mixture was adjusted with AcOH (several drops) to pH=7, filtered. The residue was purified by prep-HPLC (column: Luna C18 150*25 5 u; mobile phase: [water(0.075% TFA)-ACN]; B %: 30%-60%, 9 min) and prep-TLC (EA) to give Compound 103 (15 mg, 26.60 umol, 20.18% yield, 90.713% purity) as yellow solid.

$^1$H NMR (400 MHz, CDCl$_3$)

δ=10.89 (br. s, 1H), 8.24 (s, 1H), 7.27-7.19 (m, 3H), 7.17-7.12 (m, 2H), 7.03 (d, J=3.7 Hz, 1H), 7.02-6.96 (m, 1H), 6.65 (d, J=3.7 Hz, 1H), 5.15 (s, 2H), 4.18 (t, J=5.7 Hz, 2H), 3.64 (q, J=6.5 Hz, 2H), 3.40-3.33 (m, 2H), 3.24 (br. t, J=5.6 Hz, 2H), 3.01 (t, J=7.7 Hz, 2H), 2.41 (ddt, J=4.0, 6.6, 10.7 Hz, 2H)

$^{13}$C NMR (101 MHz, CDCl$_3$)

δ=172.56, 161.62, 157.25, 151.62, 150.39, 143.82, 142.68, 140.11, 130.45, 128.65, 128.44, 127.70, 126.53, 126.18, 124.95, 121.10, 119.52, 103.22, 101.65, 43.52, 41.66, 36.46, 34.25, 33.98, 33.70, 33.42, 32.71, 32.67, 32.64, 32.61, 30.06, 25.24 LCMS: Rt=0.806 min, [M+H]$^+$= 512.2

Example 7: Synthesis of Compound 104

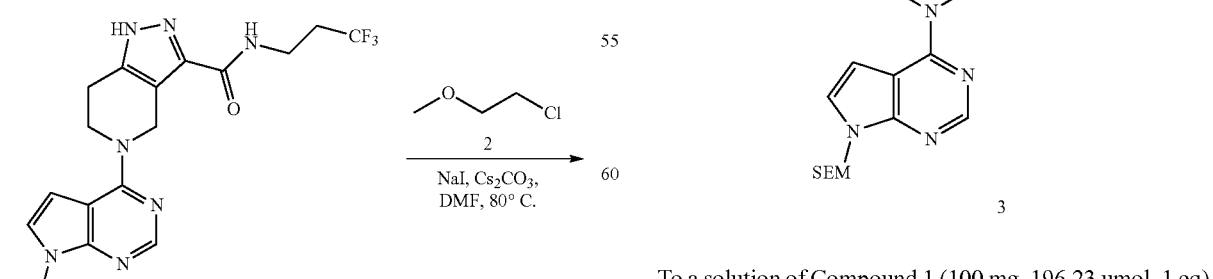

Preparation of Compound 3

To a solution of Compound 1 (100 mg, 196.23 umol, 1 eq) in DMF (2 mL) was added NaI (29.41 mg, 196.23 umol, 1 eq), Cs$_2$CO$_3$ (191.81 mg, 588.70 umol, 3 eq) and Compound 2 (37.10 mg, 392.47 umol, 35.68 uL, 2 eq). The mixture was stirred at 80° C. for 3 hr under N₂ atmosphere. LCMS showed Compound 1 was consumed, and a major peak with desired MS was detected. The mixture was diluted with water (30 mL), extracted with EtOAc (30 mL*3), washed with brine (35 mL*2), dried over Na₂SO₄, filtered and concentrated under reduced pressure to give Compound 3 (115 mg, crude) as yellow oil.

LCMS: Rt=0.916 min, [M+H]⁺=568.2

Preparation of Compound 104

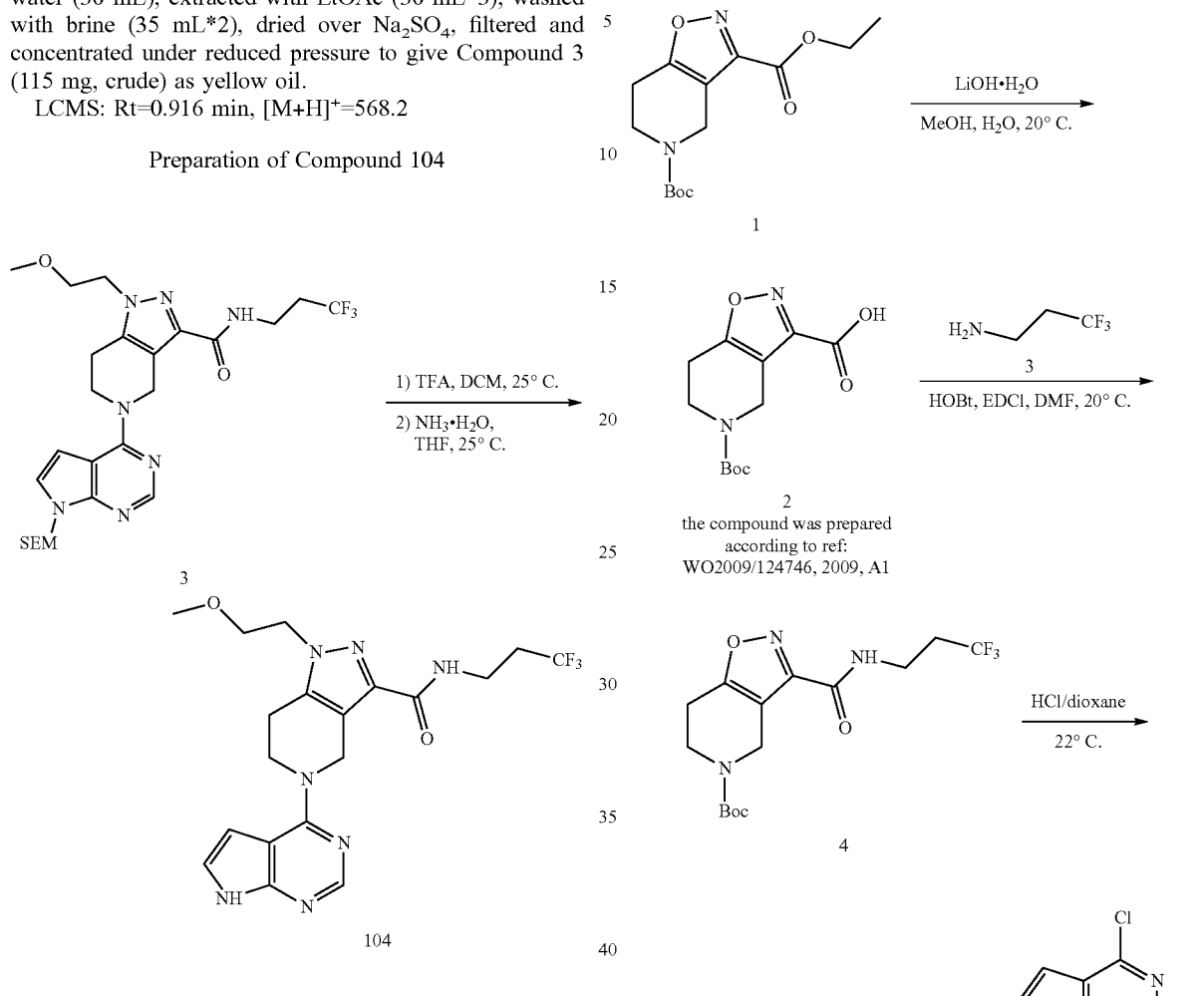

A solution of Compound 3 (70 mg, 123.31 umol, 1 eq) in TFA (1 mL) and DCM (1 mL) was stirred at 25° C. for 1 hr. The mixture was concentrated. Then dissolve the mixture in THF (1.5 mL), NH₃·H₂O (1.5 mL) was added, the mixture was stirred at 25° C. for 1.5 hr. LCMS showed Compound 3 was consumed, and a major peak with desired MS was detected. The mixture was diluted with water (35 mL), extracted with EtOAc (30 mL*3), washed with brine (30 mL*2), dried over Na₂SO₄, filtered and concentrated. The residue was purified by prep-HPLC (column: Phenomenex Gemini 150*25 mm*10 um; mobile phase: [water(10 mM NH₄HCO₃)-ACN]; B %: 24%-54%, 10 min) to give Compound 104 (26.5 mg, 59.73 umol, 48.44% yield, 98.6% purity) as white solid.

¹H NMR (400 MHz, CDCl₃)
δ=10.82 (br s, 1H), 8.40-8.21 (m, 1H), 7.17-6.97 (m, 2H), 6.80 (d, J=3.4 Hz, 1H), 5.25 (s, 2H), 4.30 (t, J=5.7 Hz, 2H), 4.18 (t, J=5.3 Hz, 2H), 3.76-3.64 (m, 4H), 3.30 (s, 3H), 2.91 (t, J=5.6 Hz, 2H), 2.47 (tq, J=6.7, 10.8 Hz, 2H)

¹³C NMR (101 MHz, CDCl₃)
δ=162.74, 157.41, 152.16, 150.95, 140.36, 140.09, 130.54, 127.80, 125.05, 122.13, 120.70, 115.93, 103.31, 102.08, 71.17, 59.10, 49.56, 44.14, 41.59, 34.49, 34.21, 33.94, 33.67, 32.45, 32.41, 21.98

LCMS: Rt=0.770 min, [M+H]⁺=438.0

Example 8: Synthesis of Compound 110

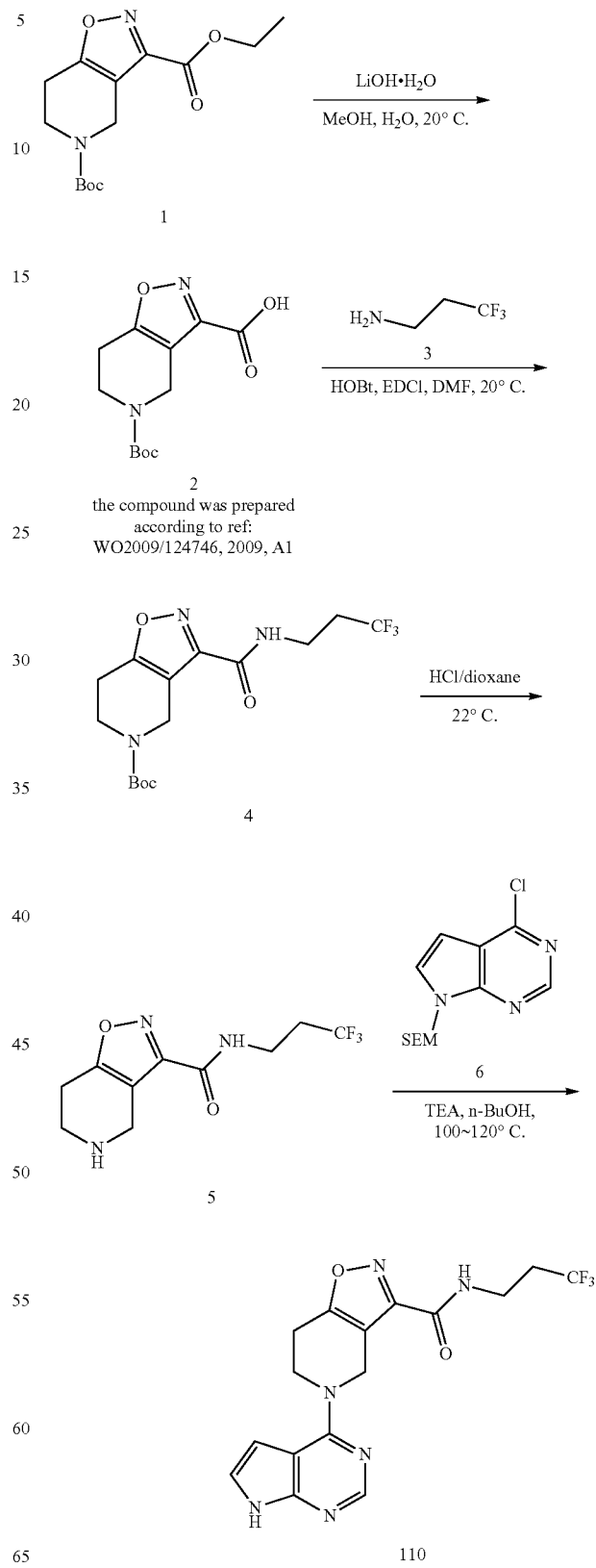

Preparation of Compound 2

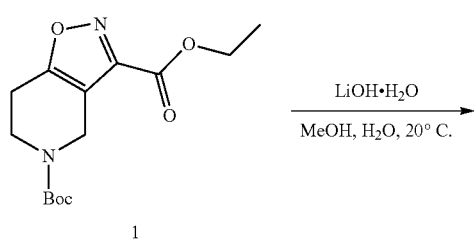

To a solution of Compound 1 (360 mg, 1.21 mmol, 1 eq) in EtOH (4 mL) and H₂O (4 mL) was added LiOH·H₂O (76.47 mg, 1.82 mmol, 1.5 eq), the mixture was stirred at 20° C. for 14 hr. TLC showed Compound 1 was consumed, and one major new spot with larger polarity was detected. The mixture was diluted with water (25 mL), adjusted with 1 N HCl solution to pH=3, extracted with EtOAc (30 mL*3), washed with brine (30 mL*2), dried over Na₂SO₄, filtered and concentrated under reduced pressure to give Compound 2 (346 mg, crude) as off-white solid.

Preparation of Compound 4

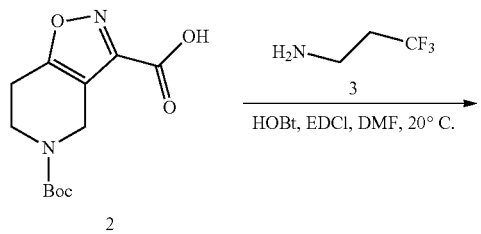

To a mixture of Compound 2 (346 mg, 1.29 mmol, 1 eq) and Compound 3 (231.45 mg, 1.55 mmol, 1.2 eq, HCl) in DMF (10 mL) was added HOBt (209.13 mg, 1.55 mmol, 1.2 eq), EDCI (370.87 mg, 1.93 mmol, 1.5 eq) and DIEA (666.76 mg, 5.16 mmol, 898.60 uL, 4 eq), the mixture was stirred at 20° C. for 16 hr. LCMS showed Compound 2 was consumed, and a major peak with desired MS was detected. The mixture was diluted with water (45 mL), extracted with EtOAc (40 mL*2), washed with brine (40 mL), dried with Na₂SO₄, filtered and concentrated. The residue was purified by column chromatography (SiO₂, Petroleum ether/Ethyl acetate=10/1 to 5:1) to give Compound 4 (286 mg, 787.16 umol, 61.03% yield) as a colorless oil.

¹H NMR (400 MHz, CDCl₃)

δ=7.09-6.96 (m, 1H), 4.59 (br. s, 2H), 3.76 (br. t, J=5.1 Hz, 2H), 3.70 (q, J=6.6 Hz, 2H), 2.85 (br. t, J=5.1 Hz, 2H), 2.53-2.38 (m, 2H), 1.49 (s, 9H).

LCMS: Rt=0.944 min, [M+H]⁺=308.0

Preparation of Compound 5

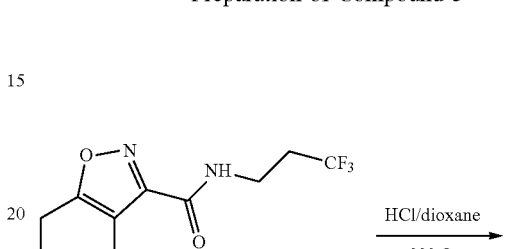

A mixture of Compound 4 (150 mg, 412.85 umol, 1 eq) in 4 N HCl/dioxane (3 mL) was stirred at 22° C. for 1 hr. TLC showed Compound 4 was consumed, and one major new spot with larger polarity was detected. The mixture was concentrated to give Compound 5 (140 mg, crude, HCl) as white solid.

Preparation of Compound 110

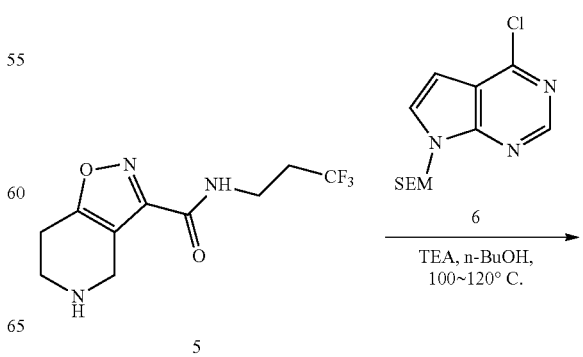

109
-continued

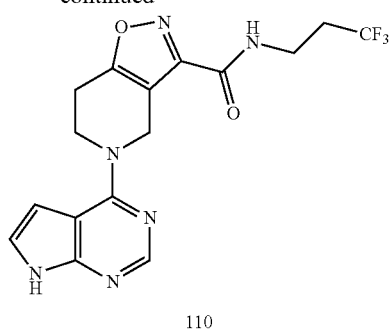

110

110
-continued

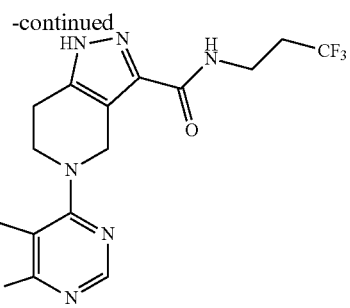

109

To a mixture of Compound 5 (140 mg, 467.17 umol, 1 eq, HCl) in n-BuOH (5 mL) was added TEA (189.09 mg, 1.87 mmol, 260.10 uL, 4 eq) and Compound 6 (71.74 mg, 467.17 umol, 1 eq), the mixture was stirred at 100° C. for 14 hr. Additional TEA (72.70 mg, 718.45 umol, 0.1 mL, 1.54 eq) was added, the mixture was stirred at 120° C. for 4 hr. LCMS showed most of Compound 5 was consumed, and desired MS was detected. The mixture was concentrated. The residue was purified by prep-HPLC (column: Waters Xbridge 150*25 5 u; mobile phase: [water(10 mM $NH_4HCO_3$)-ACN]; B %: 20%-50%, 10 min) to give Compound 110 (29.5 mg, 77.57 umol, 16.60% yield, 100% purity) as white solid.

$^1$H NMR (400 MHz, DMSO)

δ=11.80 (br. s, 1H), 8.98 (t, J=5.7 Hz, 1H), 8.21 (s, 1H), 7.34-7.24 (m, 1H), 6.65 (dd, J=1.7, 3.4 Hz, 1H), 4.99 (s, 2H), 4.22 (t, J=5.6 Hz, 2H), 3.52 (q, J=6.8 Hz, 2H), 3.04 (br. t, J=5.1 Hz, 2H), 2.60 (br. s, 2H).

$^{13}$C NMR (101 MHz, DMSO)

δ=169.38, 159.49, 156.97, 154.56, 152.50, 151.01, 131.32, 128.56, 125.81, 122.58, 112.09, 102.96, 100.86, 42.18, 41.84, 33.10, 32.83, 32.76, 32.71, 32.57, 32.30, 23.63.

LCMS: Rt=0.757 min, [M+H]$^+$=381.0

Example 9: Synthesis of Compound 109

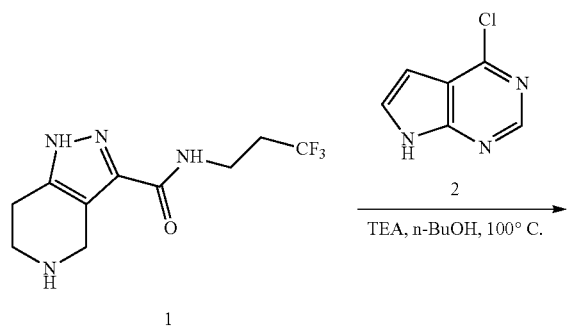

To a mixture of Compound 1 (824 mg, 2.76 mmol, 1 eq, HCl) and Compound 2 (423.65 mg, 2.76 mmol, 1 eq) in n-BuOH (10 mL) was added TEA (1.12 g, 11.03 mmol, 1.54 mL, 4 eq), the mixture was stirred at 100° C. for 12 hr. LCMS showed Compound 1 was consumed, and a major peak with desired MS was detected. The mixture was concentrated. The residue was triturated with water (20 mL) and MeOH (4 mL) to give Compound 109 (800 mg, 2.11 mmol, 76.45% yield) as yellow solid.

$^1$H NMR (400 MHz, DMSO-d)

δ=13.08 (s, 1H), 11.74 (br. s, 1H), 8.32 (t, J=5.9 Hz, 1H), 8.17 (s, 1H), 7.26-7.21 (m, 1H), 6.64 (dd, J=1.6, 3.4 Hz, 1H), 5.06 (s, 2H), 4.15 (t, J=5.6 Hz, 2H), 3.49 (q, J=6.8 Hz, 2H), 2.87 (br. t, J=5.3 Hz, 2H), 2.61-2.52 (m, 2H)

$^{13}$C NMR (101 MHz, DMSO-d4)

δ=162.98, 157.14, 152.40, 151.12, 141.45, 131.42, 128.67, 152.91, 123.16, 122.10, 114.76, 102.81, 101.12, 43.62, 42.52, 33.54, 33.27, 33.01, 32.75, 32.26, 32.23

LCMS: Rt=0.713 min, [M+H]$^+$=380.0

Example 10: Synthesis of Compound 132

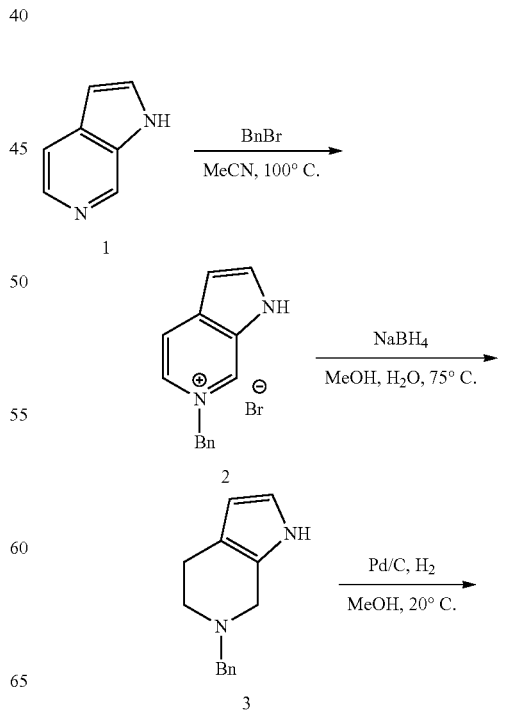

-continued

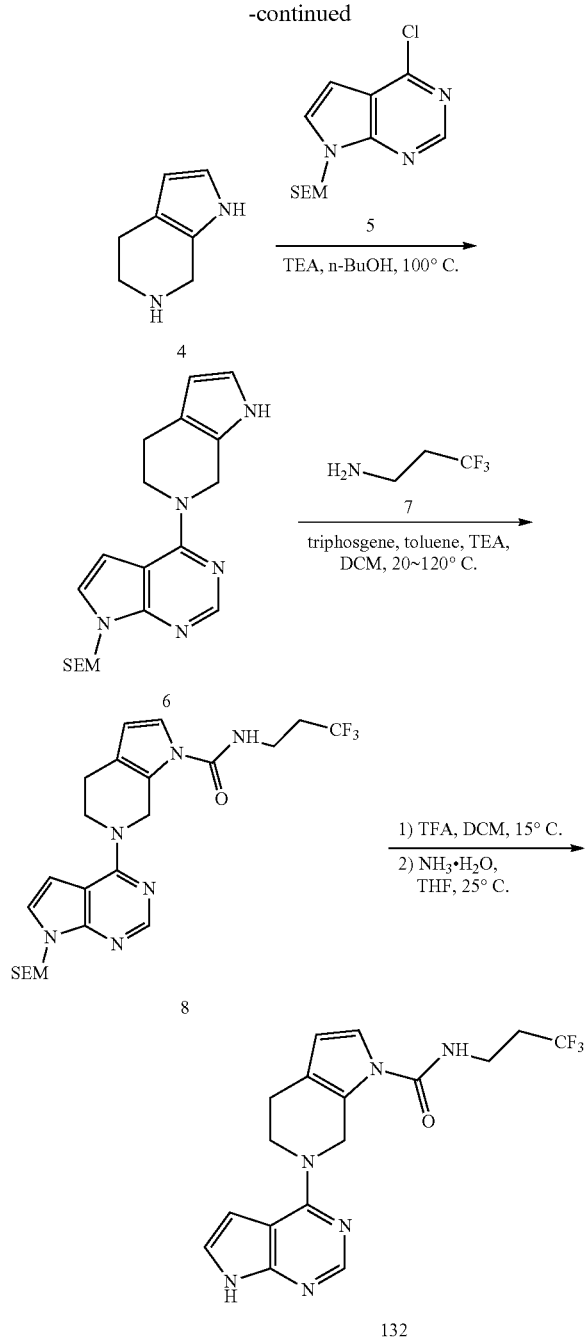

Preparation of Compound 2

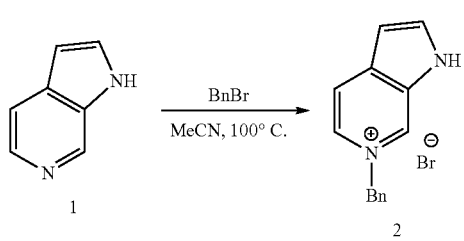

To a solution of Compound 1 (1.5 g, 12.70 mmol, 1 eq) in MeCN (15 mL) was added BnBr (2.61 g, 15.24 mmol, 1.81 mL, 1.2 eq). Then the mixture was warmed to 100° C., stirred for 14 hr under $N_2$ atmosphere. TLC showed most of Compound 1 was consumed, and obvious larger polar spot was observed. The mixture was concentrated under reduced pressure to give Compound 2 (3.63 g, 12.55 mmol, 98.87% yield) as pink solid.

$^1$H NMR (400 MHz, MeOD)

δ=9.31-9.21 (m, 1H), 8.34 (br. d, J=6.7 Hz, 1H), 8.20 (d, J=2.8 Hz, 1H), 8.11 (d, J=6.6 Hz, 1H), 7.51-7.39 (m, 5H), 6.98 (d, J=2.3 Hz, 1H), 5.89-5.77 (m, 2H)

Preparation of Compound 3

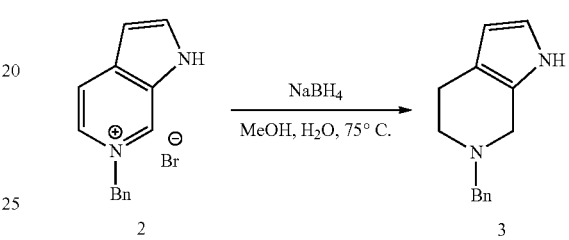

To a solution of Compound 2 (2.63 g, 9.09 mmol, 1 eq) in $H_2O$ (20 mL) and MeOH (20 mL) was added slowly $NaBH_4$ (1.72 g, 45.47 mmol, 5 eq). Then the mixture was warmed to 75° C., stirred for 14 hr. LCMS showed Compound 2 was consumed, and 95% of desired MS was detected. The mixture was diluted with water (60 mL), extracted with EtOAc (60 mL*2), washed with brine (60 mL*2), dried with $Na_2SO_4$, filtered and concentrated. The residue was purified by silica gel column chromatography (Petroleum ether/Ethyl acetate=5/1~2/1) to give Compound 3 (1.4 g, 6.59 mmol, 72.51% yield) as yellow oil.

LCMS: Rt=0.262 min, [M+H]$^+$=213.1

Preparation of Compound 4

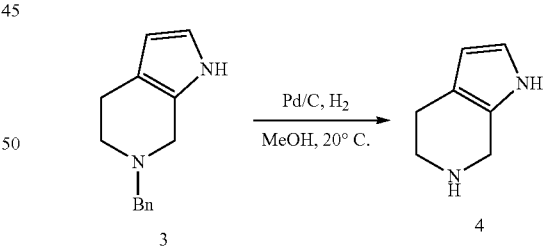

To a solution of Compound 3 (900 mg, 4.24 mmol, 1 eq) in MeOH (15 mL) was added Pd/C (200 mg, 10% purity). The mixture was stirred at 20° C. for 14 hr under $H_2$ balloon at 15 psi. LCMS showed most of Compound 3 was consumed, and desired MS was detected. The mixture was filtered and concentrated under reduced pressure to give Compound 4 (400 mg, crude) as orange solid.

$^1$H NMR (400 MHz, MeOD)

δ=5.00 (d, J=2.8 Hz, 1H), 4.30 (d, J=2.7 Hz, 1H), 2.26 (s, 2H), 1.44 (t, J=5.8 Hz, 2H), 1.01 (t, J=5.8 Hz, 2H).

LCMS: Rt=0.110 min, [M+H]$^+$=123.1

Preparation of Compound 6

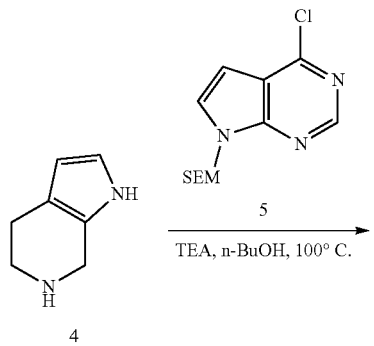

To a mixture of Compound 4 (350 mg, 2.86 mmol, 1 eq) and Compound 5 (813.15 mg, 2.86 mmol, 1 eq) in n-BuOH (5 mL) was added TEA (869.70 mg, 8.59 mmol, 1.20 mL, 3 eq), the mixture was stirred at 100° C. for 12 hr. LCMS showed 11% of Compound 5 was remained, and 70% of desired MS was detected. The mixture was concentrated. The mixture was diluted with water (45 mL), extracted with EtOAc (40 mL*3), washed with brine (40 mL*2), dried over Na₂SO₄, filtered and concentrated. The residue was purified by silica gel column chromatography (Petroleum ether/Ethyl acetate=10/1~2/1) to give Compound 6 (750 mg, 2.03 mmol, 70.84% yield) as yellow oil.

¹H NMR (400 MHz, CDCl₃)

δ=8.38 (s, 1H), 8.10-7.83 (m, 1H), 7.12 (d, J=3.6 Hz, 1H), 6.72 (t, J=2.6 Hz, 1H), 6.63 (d, J=3.6 Hz, 1H), 6.08 (t, J=2.5 Hz, 1H), 5.60 (s, 2H), 5.01 (s, 2H), 4.19 (t, J=5.6 Hz, 2H), 3.64-3.47 (m, 2H), 2.84 (br t, J=5.6 Hz, 2H), 0.97-0.87 (m, 2H), 0.02-0.09 (m, 9H).

LCMS: Rt=1.076 min, [M+H]⁺=370.1

Preparation of Compound 8

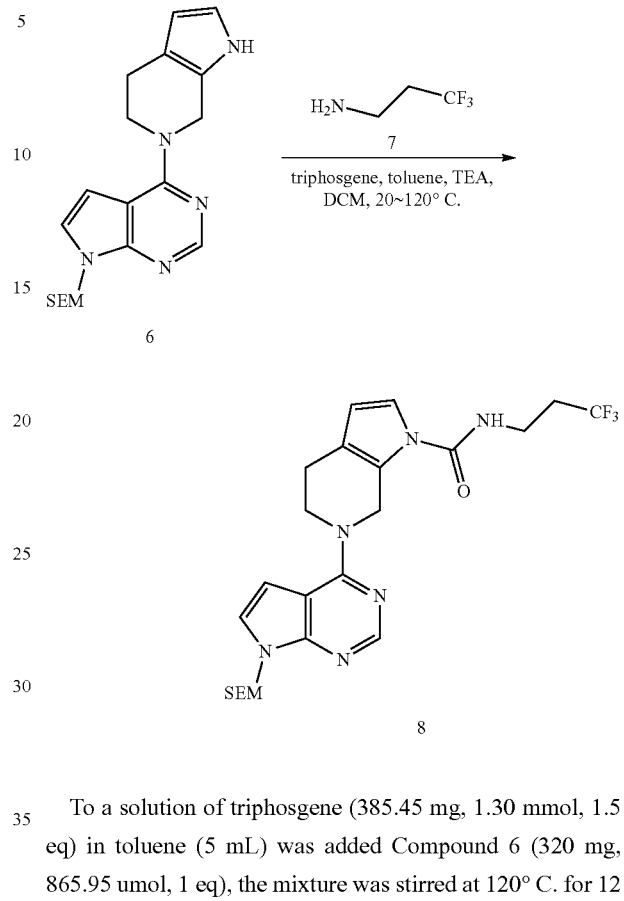

To a solution of triphosgene (385.45 mg, 1.30 mmol, 1.5 eq) in toluene (5 mL) was added Compound 6 (320 mg, 865.95 umol, 1 eq), the mixture was stirred at 120° C. for 12 hr under N₂ atmosphere. The mixture was concentrated, dissolved in DCM (5 mL), Compound 7 (194.25 mg, 1.30 mmol, 1.5 eq, HCl) and TEA (350.50 mg, 3.46 mmol, 482.12 uL, 4 eq) was added, the mixture was stirred at 20° C. for 2 hr under N₂ atmosphere. LCMS showed Compound 6 was consumed, and desired MS was detected. The mixture was filtered, diluted with water (60 mL), extracted with EtOAc (60 mL*3), dried over Na₂SO₄, filtered and concentrated. The residue was purified by silica gel column chromatography (Petroleum ether/Ethyl acetate=10/1~1/2) to give Compound 8 (240 mg, 471.87 umol, 27.25% yield) as orange oil.

¹H NMR (400 MHz, CDCl₃)

δ=9.35-9.09 (m, 1H), 8.38 (s, 1H), 7.14 (d, J=3.8 Hz, 1H), 6.61 (d, J=3.8 Hz, 1H), 6.38 (d, J=2.1 Hz, 1H), 5.98 (s, 1H), 5.60 (s, 2H), 5.03 (s, 2H), 4.23-4.15 (m, 2H), 3.70 (q, J=6.4 Hz, 2H), 3.59-3.46 (m, 2H), 2.81 (br. t, J=5.5 Hz, 2H), 2.45 (td, J=6.3, 10.8 Hz, 2H), 0.98-0.85 (m, 2H), −0.02-0.08 (m, 9H).

LCMS: Rt=1.070 min, [M+H]⁺=509.4

115
Preparation of Compound 132

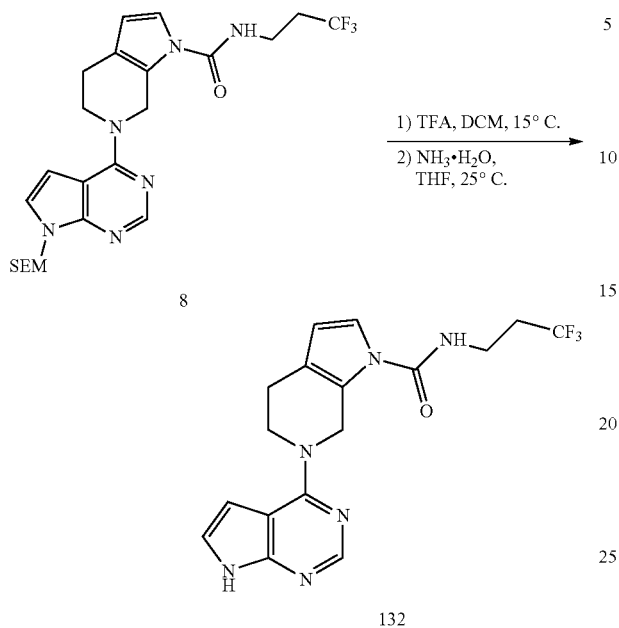

A solution of Compound 8 (100 mg, 196.61 umol, 1 eq) in TFA (1 mL) and DCM (1 mL) was stirred at 15° C. for 1 hr. The mixture was concentrated, dissolved in THF (1 mL), concentrated NH$_3$·H$_2$O (1 mL) was added, the mixture was stirred at 25° C. for 1 hr. LCMS showed Compound 8 was consumed, and a major peak with desired MS was detected. The mixture diluted with water (30 mL), extracted with EtOAc (30 mL*2), washed with brine (30 mL*2), dried with Na$_2$SO$_4$, filtered and concentrated. The residue was purified by prep-HPLC (column: Xtimate C18 150*25 mm*5 um; mobile phase: [water(0.05% ammonia hydroxide v/v)-ACN]; B %: 18%-48%, 10 min) to give Compound 132 (40 mg, 101.49 umol, 51.62% yield, 96% purity) as white solid.

$^1$H NMR (400 MHz, DMSO-d6)
δ=11.94-11.54 (m, 1H), 11.46-11.16 (m, 1H), 8.16 (s, 1H), 8.10 (t, J=5.7 Hz, 1H), 7.23 (d, J=3.5 Hz, 1H), 6.63 (d, J=3.7 Hz, 1H), 6.56 (s, 1H), 4.91 (s, 2H), 4.10 (br t, J=5.5 Hz, 2H), 3.44 (br d, J=6.0 Hz, 2H), 2.66 (br t, J=5.2 Hz, 2H), 2.50-2.40 (m, 2H). $^{13}$C NMR (101 MHz, DMSO-d6)
δ=161.34, 157.07, 152.34, 151.10, 131.44, 128.77, 125.93, 125.20, 123.17, 121.97, 116.16, 108.83, 102.69, 101.15, 44.48, 44.07, 40.65, 40.34, 33.69, 33.16, 32.90, 32.58, 32.55, 23.06.
LCMS: Rt=0.852 min, [M+H]$^+$=379.3

Example 11: Synthesis of Compound 130

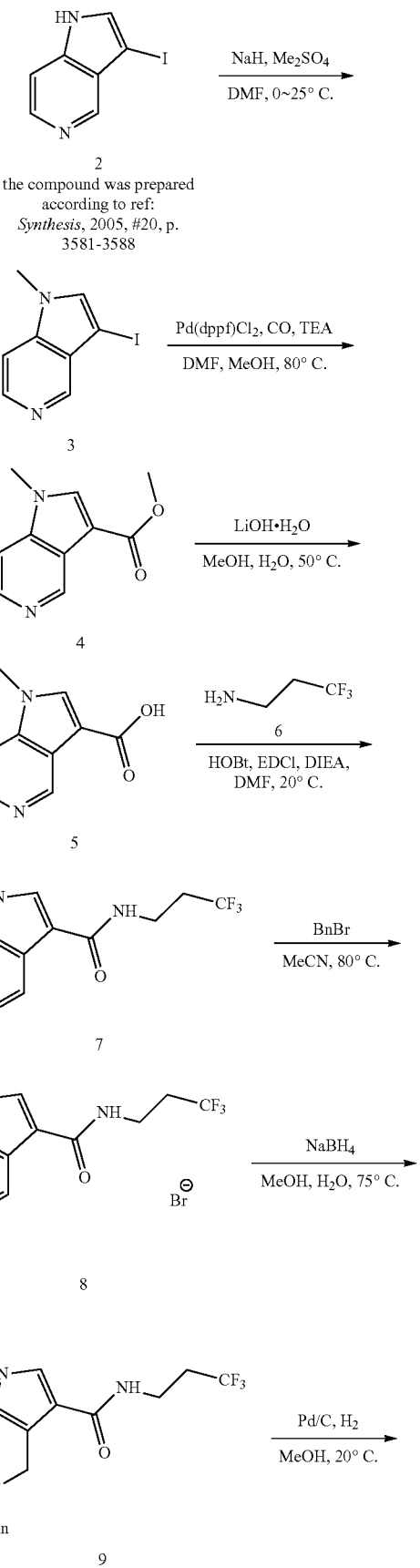

Preparation of Compound 3

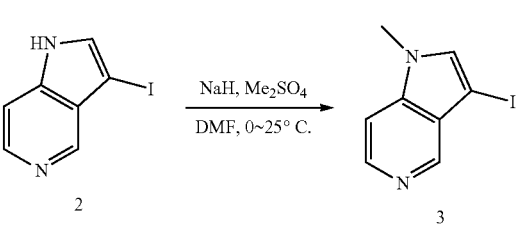

To a solution of Compound 2 (3 g, 12.29 mmol, 1 eq) in DMF (40 mL) was added NaH (737.54 mg, 18.44 mmol, 60% purity, 1.5 eq), the reaction was stirred at 0° C. for 15 min. Then Me$_2$SO$_4$ (1.55 g, 12.29 mmol, 1.17 mL, 1 eq) was added at 0° C. The reaction mixture was stirred at 25° C. for 16 hr. TLC indicated one new major spot with lower polarity was detected, and LCMS showed desired MS was detected. The reaction mixture was quenched by EtOH (8 mL), diluted with water (80 mL), extracted with EtOAc (240 mL*3). The combined organic layers were washed with brine (120 mL*3), dried over anhydrous Na$_2$SO$_4$, filtered and concentrated to give Compound 3 (3.66 g, crude) as a yellow solid.

$^1$H NMR (400 MHz, DMSO-d)

δ=8.59-8.50 (m, 1H), 8.34-8.20 (m, 1H), 7.69-7.60 (m, 1H), 7.54-7.41 (m, 1H), 3.95-3.73 (m, 3H).

LCMS: Rt=0.668 min, [M+H]$^+$=259.0

Preparation of Compound 4

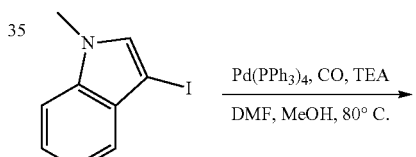

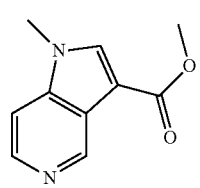

CO was bubbled into a solution of Compound 3 (3.56 g, 13.80 mmol, 1 eq), TEA (4.19 g, 41.39 mmol, 5.76 mL, 3 eq) and Pd(PPh$_3$)$_4$ (1.59 g, 1.38 mmol, 0.1 eq) in DMF (20 mL) and MeOH (20 mL), the reaction mixture was stirred at 80° C. under CO (50 psi) for 16 hr. LCMS showed desired mass was detected. The reaction mixture was diluted with H$_2$O (80 mL), extracted with EtOAc (100 mL*3), washed with brine (200 mL*3), dried over anhydrous Na$_2$SO$_4$, filtered and concentrated. The residue was purified by silica gel column chromatography (Petroleum ether/Ethyl acetate=5/ 1~0/1) to give Compound 4 (1.31 g, 6.20 mmol, 44.93% yield, 90% purity) as a yellow solid.

$^1$H NMR (400 MHz, CDCl$_3$)

δ=9.41 (s, 1H), 8.46 (d, J=5.9 Hz, 1H), 7.80 (s, 1H), 7.30-7.28 (m, 1H), 3.95 (s, 3H), 3.86 (s, 3H)

LCMS: Rt=0.929 min, [M+H]$^+$=191.2

-continued

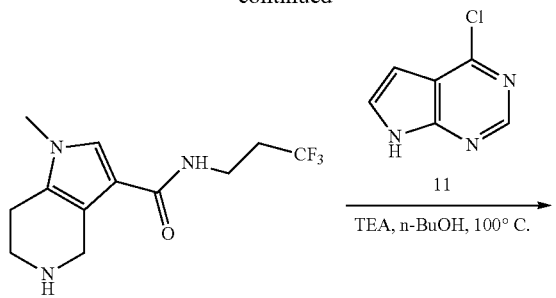

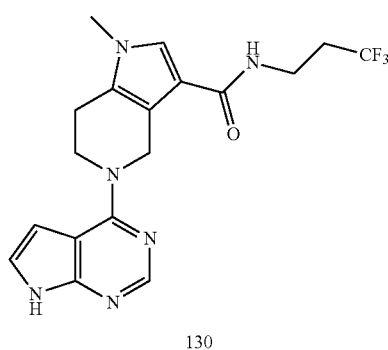

130

Preparation of Compound 2

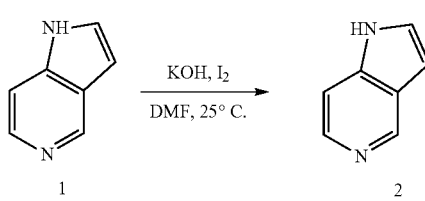

the compound was prepared according to ref: *Synthesis*, 2005, #20, p. 3581-3588

To a solution of Compound 1 (4 g, 33.86 mmol, 1 eq) in DMF (16 mL) was added KOH (7.18 g, 128.00 mmol, 3.78 eq), the mixture was stirred at 25° C. for 0.25 hr, and then a solution of 12 (8.59 g, 33.86 mmol, 6.82 mL, 1 eq) in DMF (16 mL) was added. The mixture was stirred at 25° C. for 0.25 hr. TLC indicated Compound 1 was consumed, and one major new spot with lower polarity was detected. The reaction mixture was quenched by saturated Na$_2$S$_2$O$_3$ solution (50 mL), diluted with H$_2$O (50 mL), extracted with EtOAc (100 mL*3). The combined organic layers were dried over Na$_2$SO$_4$, filtered and concentrated to give Compound 2 (7 g, crude) as a yellow solid.

$^1$H NMR (400 MHz, MeOD)

δ=8.54 (s, 1H), 8.28-8.13 (m, 1H), 7.55-7.46 (m, 1H), 7.43-7.37 (m, 1H)

Preparation of Compound 5

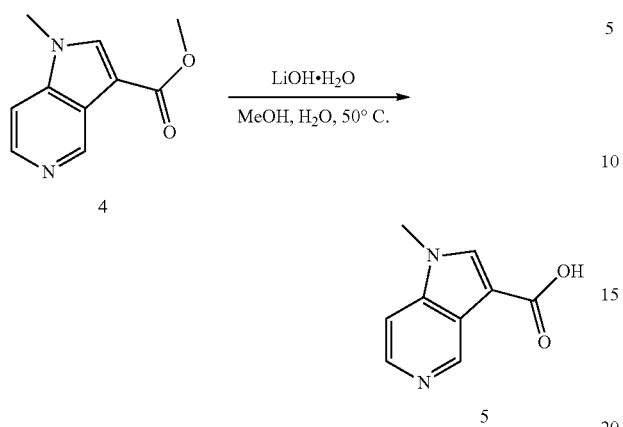

To a solution of Compound 4 (1.31 g, 6.89 mmol, 1 eq) in MeOH (9 mL) and H₂O (3 mL) was added LiOH·H₂O (867.01 mg, 20.66 mmol, 3 eq), the reaction mixture was stirred at 50° C. for 2 hr. LCMS showed the desired mass was detected. The reaction mixture was concentrated, the residue was purified by prep-HPLC (TFA condition, column: Waters Xbridge 150*50 10 u; mobile phase: [water (0.05% ammonia hydroxide v/v)-ACN]; B %: 1%-8%, 11.5 min) to give Compound 5 (1.21 g, crude) as a white solid.

LCMS: Rt=0.149 min, [M+H]$^+$=177.2

Preparation of Compound 7

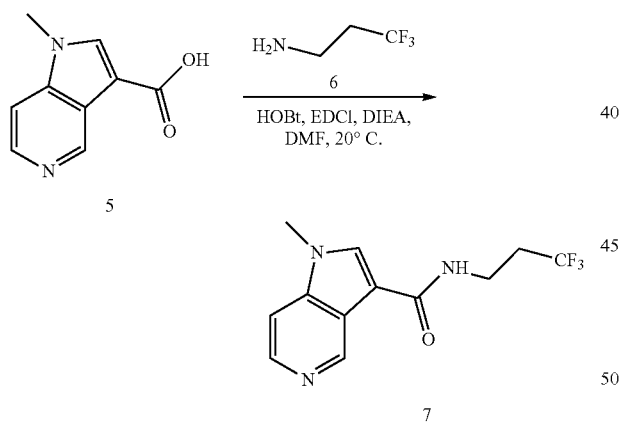

To a solution of Compound 5 (900 mg, 5.11 mmol, 1 eq), Compound 6 (916.75 mg, 6.13 mmol, 1.2 eq, HCl) and DIEA (3.30 g, 25.54 mmol, 4.45 mL, 5 eq) in DMF (10 mL) and was added HOBt (690.28 mg, 5.11 mmol, 1 eq) and EDCI (1.47 g, 7.66 mmol, 1.5 eq), then the reaction mixture was stirred at 20° C. for 12 hr. LCMS showed desired mass was detected. The reaction mixture was diluted with H₂O (20 mL), extracted with EtOAc (15 mL*3), washed with brine (20 mL*3), dried over anhydrous Na₂SO₄, filtered and concentrated. The residue was purified by silica gel column chromatography (DCM/MeOH=1/0~10/1) to give Compound 7 (680 mg, 2.51 mmol, 49.07% yield) as a light yellow solid.

LCMS: Rt=0.953 min, [M+H]$^+$=272.2

Preparation of Compound 8

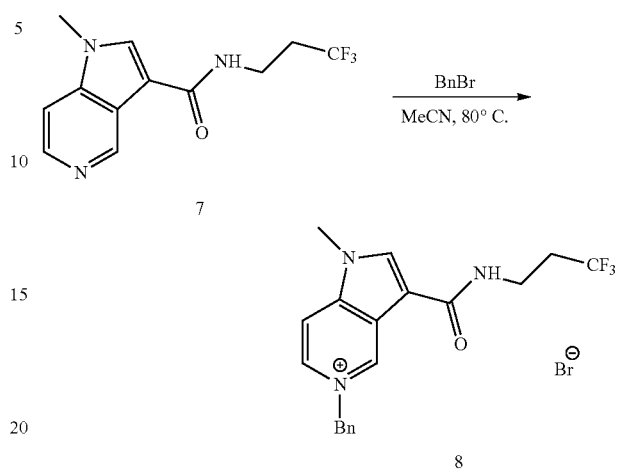

To a solution of Compound 7 (370 mg, 1.36 mmol, 1 eq) in MeCN (4 mL) was added BnBr (349.97 mg, 2.05 mmol, 243.03 uL, 1.5 eq), the reaction was stirred at 80° C. for 8 hr. LCMS showed desired mass was detected. The reaction mixture was concentrated, triturated with PE (20 mL*3) at 20° C. for 15 min to give Compound 8 (603.31 mg, crude) as white solid.

LCMS: Rt=0.770 min, [M+H]$^+$=362.2

Preparation of Compound 9

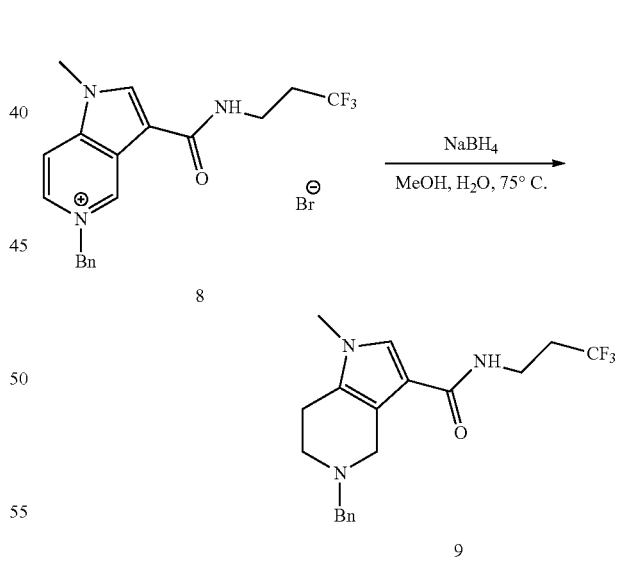

To a solution of Compound 8 (603.31 mg, 1.36 mmol, 1 eq) in MeOH (4 mL) and H₂O (4 mL) was added NaBH₄ (258.02 mg, 6.82 mmol, 5 eq), then the reaction mixture was stirred at 75° C. for 12 hr.

TLC showed most of Compound 8 was consumed, and one obvious new spot was observed. LCMS showed 99% of desired MS was detected. The mixture was diluted with water (60 mL), extracted with EtOAc (60 mL*3), washed with brine (60 mL*2), dried over Na₂SO₄, filtered and concentrated. The residue was purified by prep-TLC (DCM:MeOH=10:1) to give Compound 9 (204 mg, 541.56 umol, 39.70% yield, 97% purity) as a light yellow oil.

LCMS: Rt=1.193 min, [M+H]⁺=366.4

Preparation of Compound 10

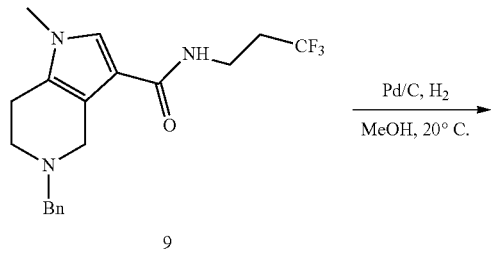

9

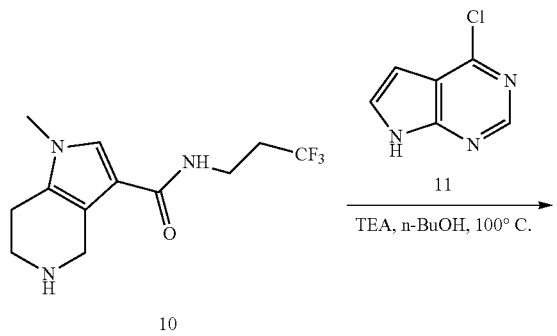

10

To a solution of Compound 9 (200 mg, 547.36 umol, 1 eq in MeOH (2 mL) was added Pd/C (4 mg, 10% purity), the mixture was stirred at 20° C. for 12 hr under H₂ balloon at 15 psi. TLC showed one major new spot with larger polarity was detected. The mixture was filtered and concentrated under reduced pressure to give Compound 10 (150.67 mg, crude) as a light yellow solid.

LCMS: Rt=1.026 min, [M+H]⁺=276.3

Preparation of Compound 130

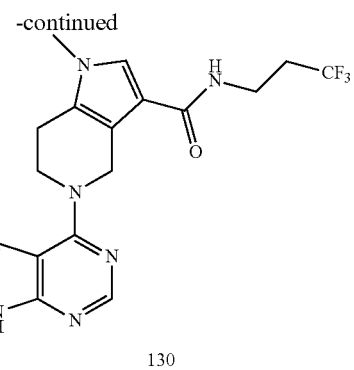

130

To a solution of Compound 10 (150 mg, 544.92 umol, 1 eq) in n-BuOH (3 mL) was added Compound 11 (100.42 mg, 653.90 umol, 1.2 eq) and TEA (165.42 mg, 1.63 mmol, 227.54 uL, 3 eq), the reaction mixture was stirred at 100° C. for 12 hr. LCMS showed desired mass was detected. The reaction mixture was concentrated, diluted with H₂O (20 mL), extracted with EtOAc (15 mL*3), washed with brine (20 mL*3), dried over anhydrous Na₂SO₄, filtered and concentrated. The residue was purified by prep-HPLC (column: Waters Xbridge 150*25 5 u; mobile phase: [water(10 mM NH₄HCO₃)-ACN]; B %: 20%-50%, 10 min) to give Compound 130 (20 mg, 48.93 umol, 67.35% yield, 96% purity) as a white solid.

¹H NMR (400 MHz, DMSO-d)

δ=11.69 (br s, 1H), 8.15 (s, 1H), 7.90 (t, J=5.6 Hz, 1H), 7.23 (s, 1H), 7.21-7.18 (m, 1H), 6.64 (dd, J=1.7, 3.4 Hz, 1H), 5.03 (s, 2H), 4.15 (br t, J=5.6 Hz, 2H), 3.50 (s, 3H), 3.45-3.39 (m, 2H), 2.72 (br t, J=5.2 Hz, 2H), 2.49-2.43 (m, 2H)

¹³C NMR (101 MHz, DMSO-d)

δ=169.95, 157.05, 152.18, 150.93, 131.50, 128.74, 127.79, 125.99, 122.52, 121.84, 116.46, 114.56, 102.76, 101.43, 45.27, 42.84, 33.77, 33.50, 33.24, 32.97, 32.44, 32.40, 21.70

LCMS: Rt=0.945 min, [M+H]⁺=393.2

Example 12: Synthesis of Compound 131

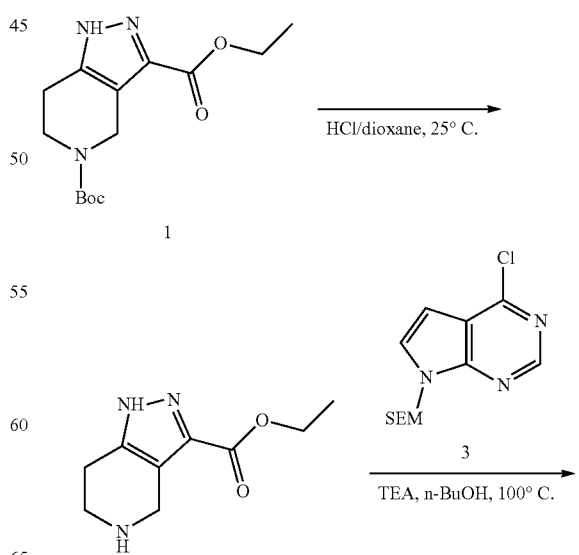

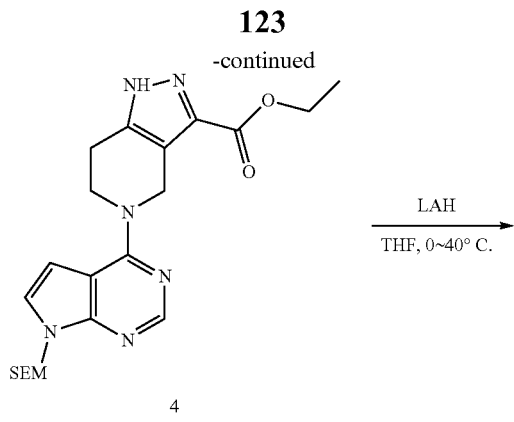
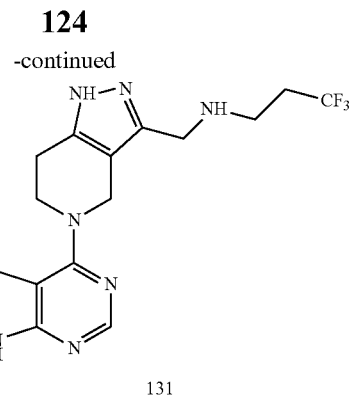
Preparation of Compound 2
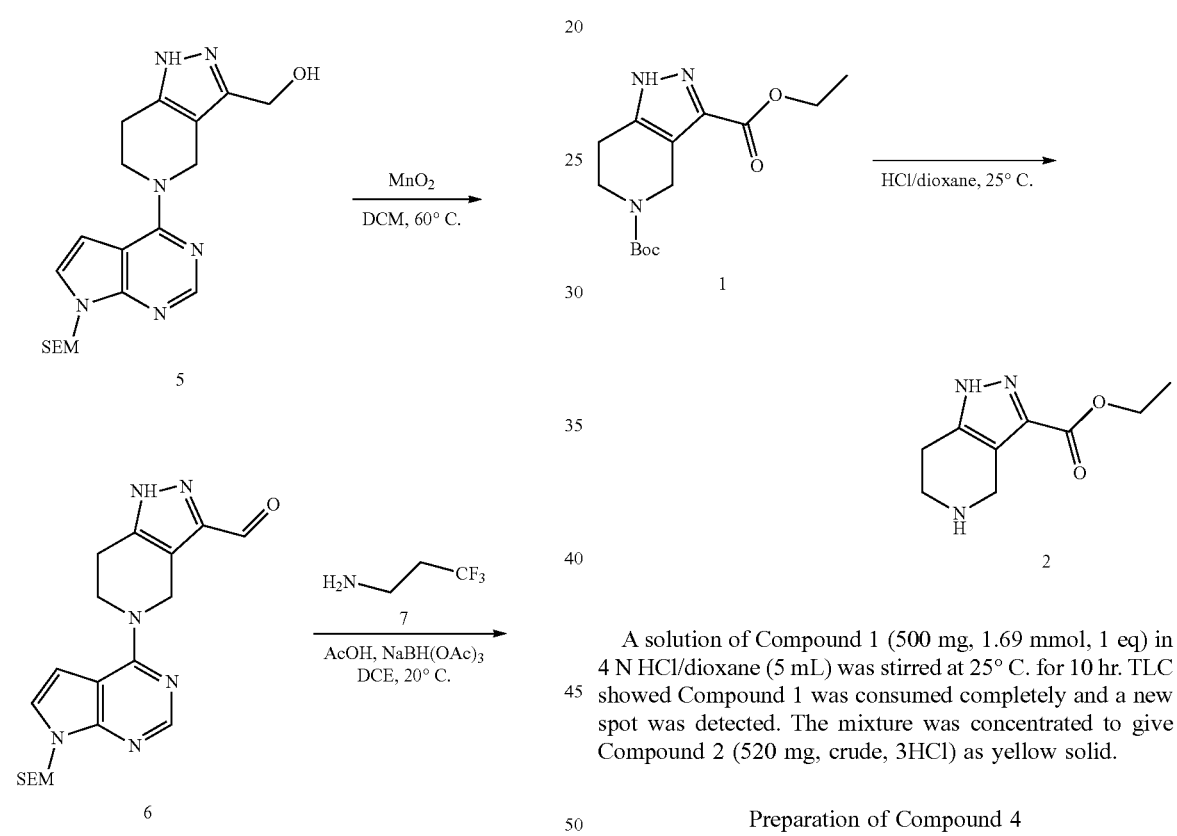
A solution of Compound 1 (500 mg, 1.69 mmol, 1 eq) in 4 N HCl/dioxane (5 mL) was stirred at 25° C. for 10 hr. TLC showed Compound 1 was consumed completely and a new spot was detected. The mixture was concentrated to give Compound 2 (520 mg, crude, 3HCl) as yellow solid.
Preparation of Compound 4
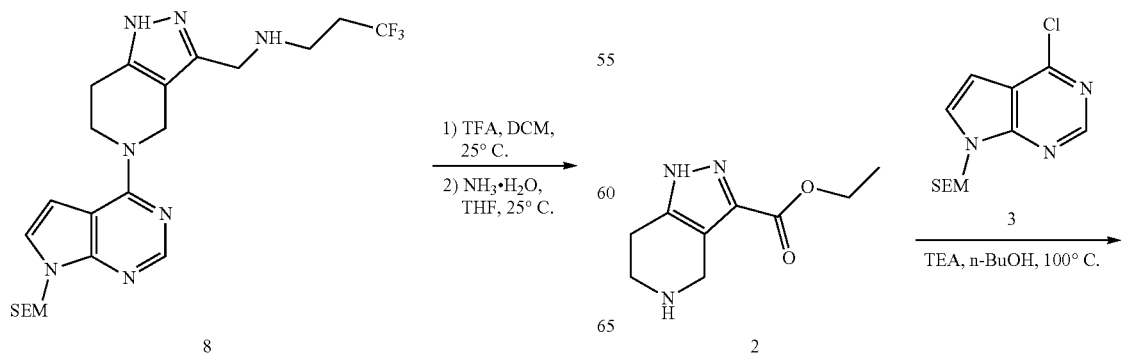

-continued

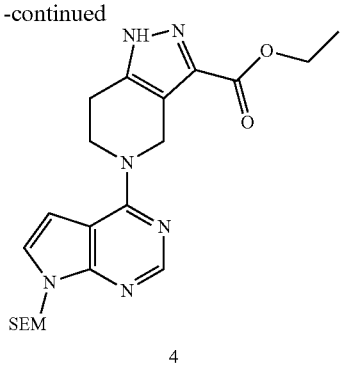

4

To a solution of Compound 2 (330 mg, 1.08 mmol, 1 eq) and Compound 3 (307.50 mg, 1.08 mmol, 1 eq) in n-BuOH (5 mL) was added TEA (877.02 mg, 8.67 mmol, 1.21 mL, 8 eq), the mixture was stirred at 100° C. for 12 hr. LCMS showed Compound 2 was consumed completely and desired MS was detected. The reaction mixture was diluted with water (50 mL), extracted with EtOAc (50 mL*3), washed with brine (30 mL), dried over anhydrous sodium sulfate, filtered and concentrated. The residue was purified by column chromatography (Petroleum ether/Ethyl acetate=10/1~1:1) to give Compound 4 (220 mg, 497.08 umol, 45.88% yield) as yellow solid.

LCMS: Rt=1.105 min, [M+H]⁺=443.3

Preparation of Compound 5

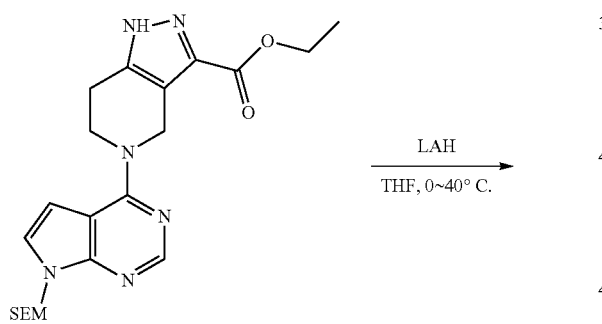

To a solution of Compound 4 (200 mg, 451.89 umol, 1 eq) in THF (4 mL) was added LAH (34.30 mg, 903.78 umol, 2 eq) at 0° C., then the mixture was stirred at 40° C. for 5 hr. LCMS showed Compound 4 was consumed completely and desired MS was detected. The mixture was quenched with water (0.4 mL), follow by 15% NaOH solution (0.4 mL) and water (1.2 mL). The mixture was filtered and concentrated, purified by prep-TLC (EA) to give Compound 5 (170 mg, 424.42 umol, 93.92% yield) as a yellow solid.

LCMS: Rt=0.426 min, [M+H]⁺=401.1

Preparation of Compound 6

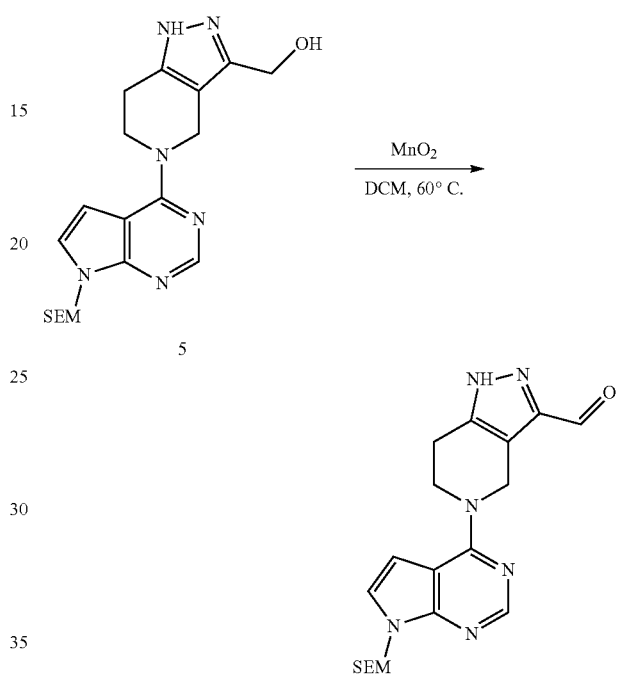

To a solution of Compound 5 in DCM (3 mL) was added MnO₂ (368.97 mg, 4.24 mmol, 10 eq), the mixture was stirred at 60° C. for 72 hr. LCMS showed that 60% of Compound 5 was consumed and desired MS was detected. The mixture was filtered and concentrated, purified by prep-TLC (EA) to give Compound 6 (60 mg, 150.55 umol, 35.47% yield) as a white oil.

LCMS: Rt=0.835 min, [M+H]⁺=399.1

Preparation of Compound 8

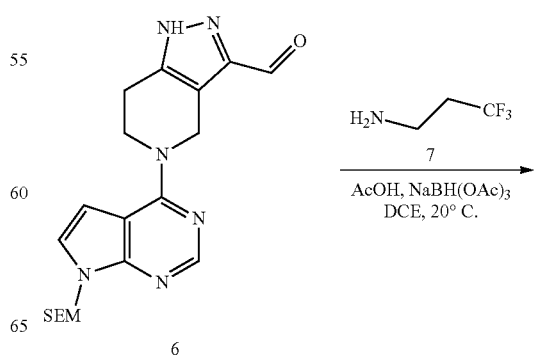

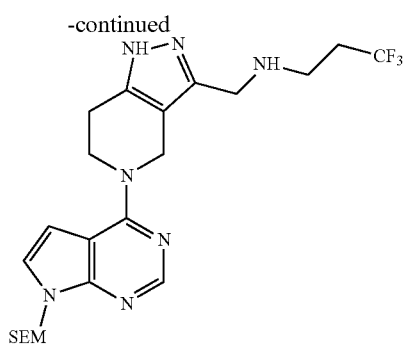

8

To a solution of Compound 6 (56 mg, 140.52 umol, 1 eq) and Compound 7 (39.72 mg, 351.29 umol, 2.5 eq) in DCE (5 mL) was added AcOH (25.31 mg, 421.55 umol, 24.11 uL, 3 eq), which was stirred at 20° C. for 1 hr, then NaBH(OAc)$_3$ (59.56 mg, 281.03 umol, 2 eq) was added, the mixture was stirred at 20° C. for 12 hr. LCMS showed Compound 7 was consumed and desired MS was detected. The reaction mixture was added 50 mL water, extracted with EtOAc (20 mL), washed with brine (20 mL), dried over anhydrous sodium sulfate, filtered and concentrated. The residue was purified by prep-HPLC (column: Phenomenex Synergi C18 150*25*10 um; mobile phase: [water(0.225% FA)-ACN]; B %: 17%-41%, 8 min) to give Compound 8 (25 mg, 50.44 umol, 35.90% yield) as a brown oil.

LCMS: Rt=0.810 min, [M+H]$^+$=496.2

Preparation of Compound 131

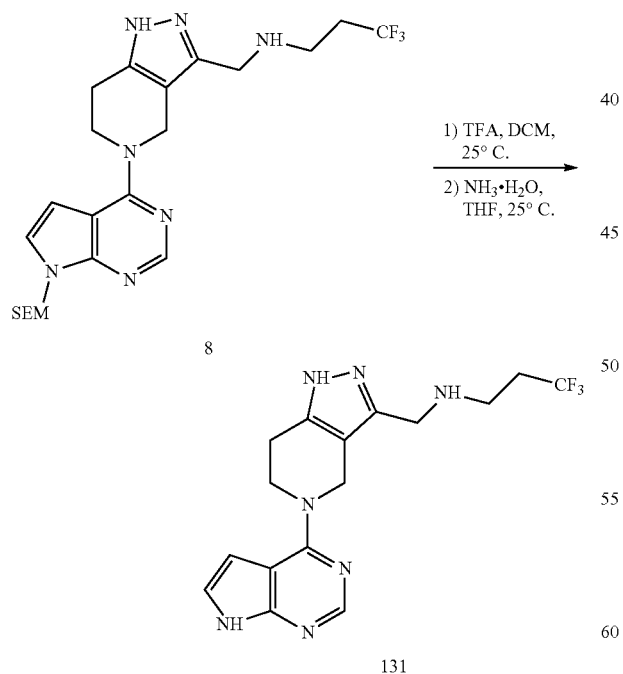

To a solution of Compound 8 (25 mg, 50.44 umol, 1 eq) in DCM (0.5 mL) was added TFA (11.50 mg, 100.88 umol, 7.47 uL, 2 eq), the mixture was stirred at 25° C. for 0.5 h, The mixture was concentrated, dissolved in DCM (0.5 mL), NH$_3$·H$_2$O (14.14 mg, 100.88 umol, 15.54 uL, 25% purity, 2 eq) was added, the mixture was stirred at 25° C. for 9.5 hr. LCMS showed Compound 8 was consumed completely and desired MS was detected. The mixture was diluted with water (10 mL), extracted with EtOAc (20 mL), washed with brine (20 mL), dried with Na$_2$SO$_4$, filtered and concentrated. The residue was purified by prep-HPLC (column: Waters Xbridge 150*25 5 u; mobile phase: [water(10 mM NH$_4$HCO$_3$)-ACN]; B %: 15%-39%, 10 min) to give Compound 131 (2 mg, 5.09 umol, 10.09% yield, 93% purity) as colorless oil.

$^1$H NMR (400 MHz, MeOD)

δ=8.18 (s, 1H), 7.18 (d, J=3.7 Hz, 1H), 6.77 (d, J=3.5 Hz, 1H), 5.00 (s, 2H), 4.25 (t, J=5.7 Hz, 2H), 3.86 (s, 2H), 2.94 (t, J=5.7 Hz, 2H), 2.90-2.82 (m, 2H), 2.42 (tq, J=7.6, 11.2 Hz, 2H)

$^{13}$C NMR (101 MHz, MeOD) 157.28, 150.97, 150.23, 121.17, 111.07, 103.00, 101.04, 42.33, 41.42, 33.69, 33.41, 33.14, 33.86

LCMS: Rt=0.823 min, [M+H]$^+$=366.4

Example 13: Synthesis of Compound 135

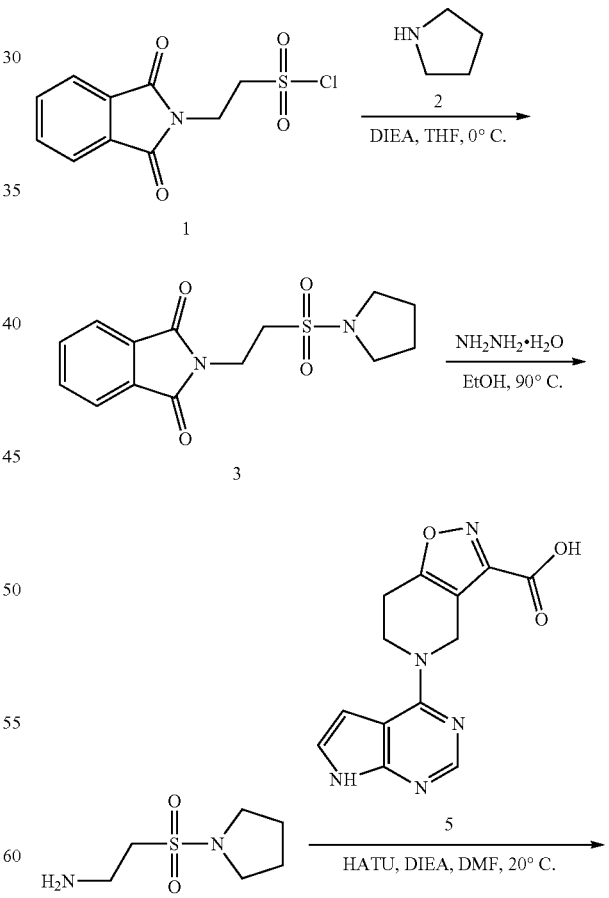

the compound was prepared according to ref:
Bioorg. Med. Chem. Lett., 1998, 1607-1612

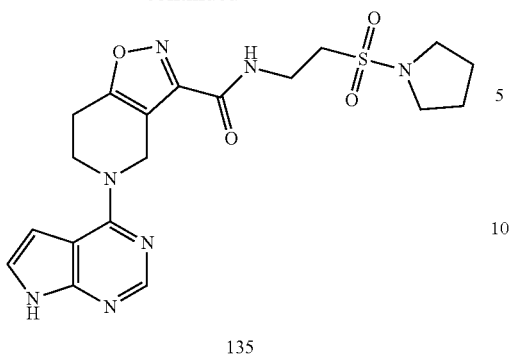

135

Preparation of Compound 3

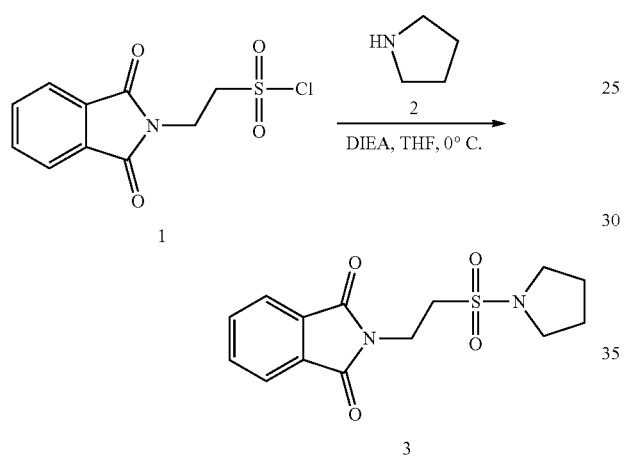

To a solution of Compound 1 (400 mg, 1.46 mmol, 1 eq) in THF (5 mL) was added DIEA (566.65 mg, 4.38 mmol, 763.68 uL, 3 eq) and Compound 2 (155.91 mg, 2.19 mmol, 183.00 uL, 1.5 eq) at 0° C., the mixture was stirred at 0° C. for 1 hr. LCMS showed Compound 1 was consumed, and desired MS was detected. The mixture was diluted with water (30 mL), extracted with EtOAc (30 mL*3), washed with brine (35 mL*2), dried over Na$_2$SO$_4$, filtered and concentrated to give Compound 3 (500 mg, crude) as a yellow solid.

LCMS: Rt=0.824 min, [M+H]$^+$=309.2

Preparation of Compound 4

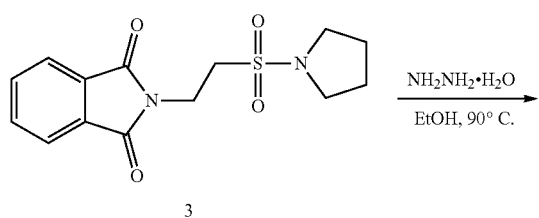

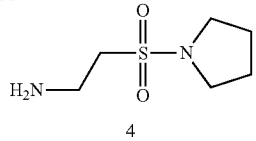

the compound was prepared according to ref:
*Bioorg. Med. Chem. Lett.*,
1998, 1607-1612

To a solution of Compound 3 (500 mg, 1.62 mmol, 1 eq) in EtOH (8 mL) was added NH$_2$NH$_2$·H$_2$O (114.60 mg, 1.95 mmol, 111.26 uL, 85% purity, 1.2 eq), the mixture was stirred at 90° C. for 12 hr. LCMS showed Compound 3 was consumed, and white precipitate was formed. The reaction mixture was filtered and concentrated, water (20 mL) was added, adjusted with 1 N HCl solution to pH=3. Residual insoluble material was filtered off. The clear filtrate was lyophilized to give Compound 4 (250 mg, crude, HCl) as a white solid.

$^1$H NMR (400 MHz, D$_2$O)
δ=3.60-3.44 (m, 4H), 3.42-3.25 (m, 4H), 2.01-1.90 (m, 4H).

Preparation of Compound 135

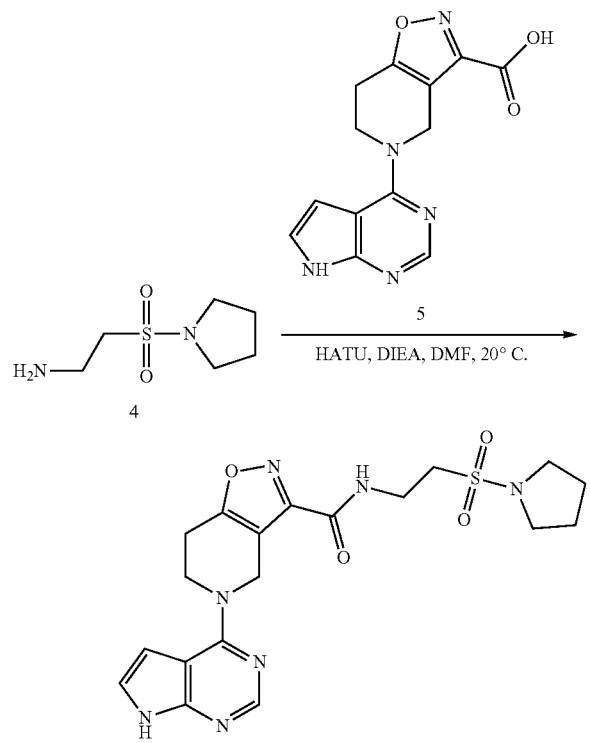

135

To a mixture of Compound 5 (133.36 mg, 467.50 umol, 1 eq) and Compound 4 (100 mg, 561.00 umol, 1.2 eq, HCl) in DMF (2.5 mL) was added HATU (266.64 mg, 701.25 umol, 1.5 eq) and DIEA (241.68 mg, 1.87 mmol, 325.71 uL, 4 eq), the mixture was stirred at 20° C. for 14 hr. LCMS showed Compound 5 was consumed, and desired MS was detected. The mixture was diluted with water (40 mL), filtered. The filter cake was purified by prep-HPLC (column: Phenomenex Synergi C18 150*25*10 um; mobile phase: [water(0.225% FA)-ACN]; B %: 8%-38%, 10 min) to give Compound 135 (32 mg, 69.32 umol, 14.83% yield, 96.5% purity) as yellow solid.

$^1$H NMR (400 MHz, DMSO-d6)

δ=11.82 (br s, 1H), 8.88 (t, J=5.6 Hz, 1H), 8.21 (s, 1H), 7.27 (br d, J=2.4 Hz, 1H), 6.65 (d, J=2.1 Hz, 1H), 4.99 (s, 2H), 4.22 (br t, J=5.5 Hz, 2H), 3.75-3.60 (m, 2H), 3.37-3.33 (m, 2H), 3.26 (br t, J=6.7 Hz, 4H), 3.04 (br t, J=5.0 Hz, 2H), 1.89-1.79 (m, 4H)

$^{13}$C NMR (101 MHz, DMSO-d6)

δ=169.41, 159.45, 156.97, 154.54, 152.50, 151.00, 122.59, 112.09, 102.98, 100.86, 47.80, 46.71, 42.22, 41.84, 34.03, 25.75, 23.65

LCMS: Rt=0.742 min, [M+H]$^+$=446.0

Example 14: Synthesis of Compound 136

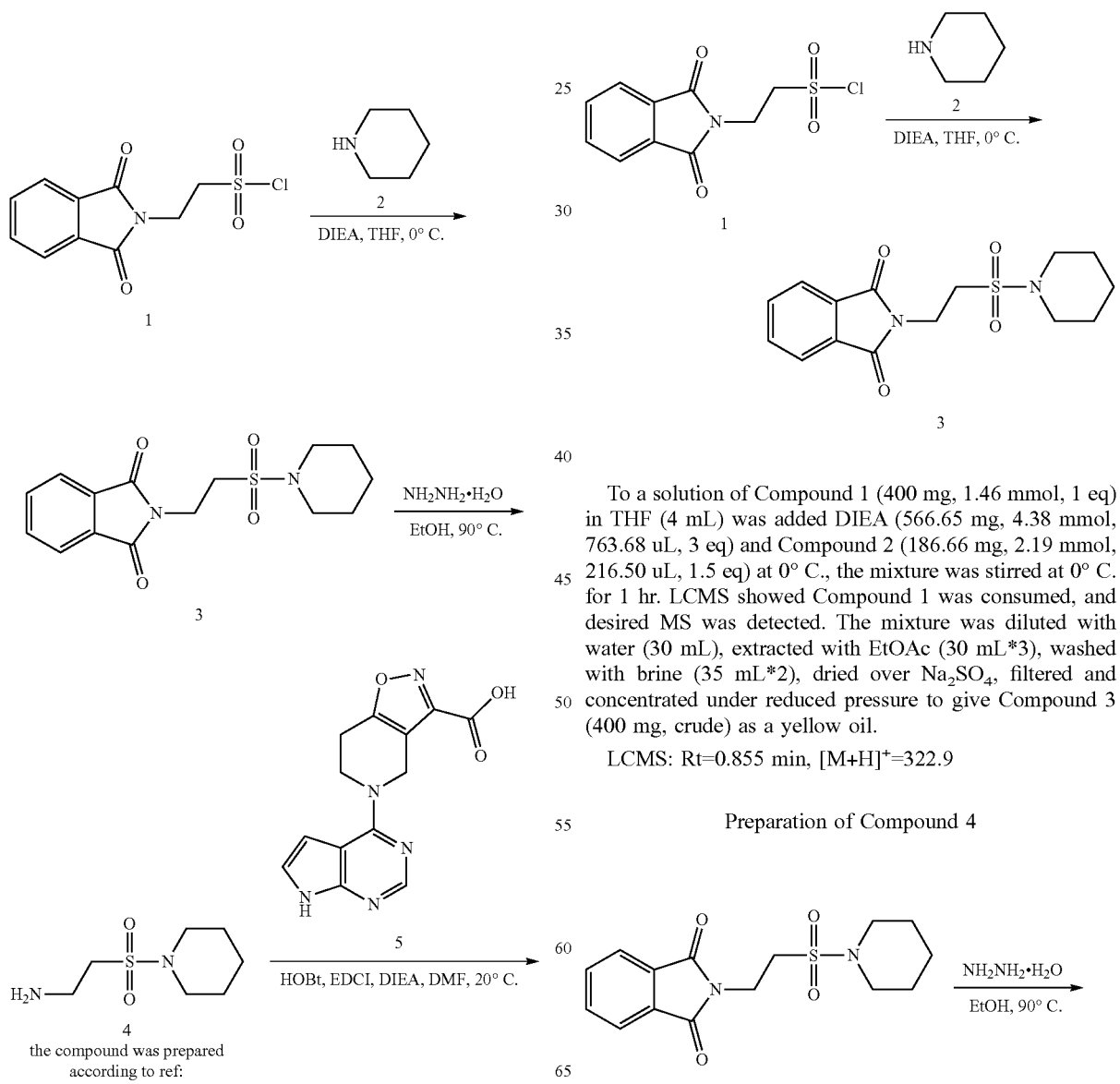

Preparation of Compound 3

To a solution of Compound 1 (400 mg, 1.46 mmol, 1 eq) in THF (4 mL) was added DIEA (566.65 mg, 4.38 mmol, 763.68 uL, 3 eq) and Compound 2 (186.66 mg, 2.19 mmol, 216.50 uL, 1.5 eq) at 0° C., the mixture was stirred at 0° C. for 1 hr. LCMS showed Compound 1 was consumed, and desired MS was detected. The mixture was diluted with water (30 mL), extracted with EtOAc (30 mL*3), washed with brine (35 mL*2), dried over Na$_2$SO$_4$, filtered and concentrated under reduced pressure to give Compound 3 (400 mg, crude) as a yellow oil.

LCMS: Rt=0.855 min, [M+H]$^+$=322.9

Preparation of Compound 4

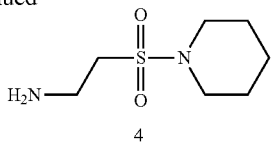

the compound was prepared according to ref:
Chem. Abstr., 1973, 79, 31884

To a solution of Compound 3 (400 mg, 1.24 mmol, 1 eq) in EtOH (5 mL) was added NH$_2$NH$_2$·H$_2$O (87.69 mg, 1.49 mmol, 85.14 uL, 85% purity, 1.2 eq), the mixture was stirred at 90° C. for 12 hr. LCMS showed Compound 3 was consumed. The mixture was filtered and concentrated, diluted with water (10 mL), adjusted with 1 N HCl solution to pH=3. Residual insoluble material was filtered off. The clear filtrate was lyophilized to give Compound 4 (200 mg, crude, HCl) as brown solid.

$^1$H NMR (400 MHz, D$_2$O)

δ=3.60-3.40 (m, 4H), 3.32-3.16 (m, 4H), 1.69-1.49 (m, 6H).

Preparation of Compound 136

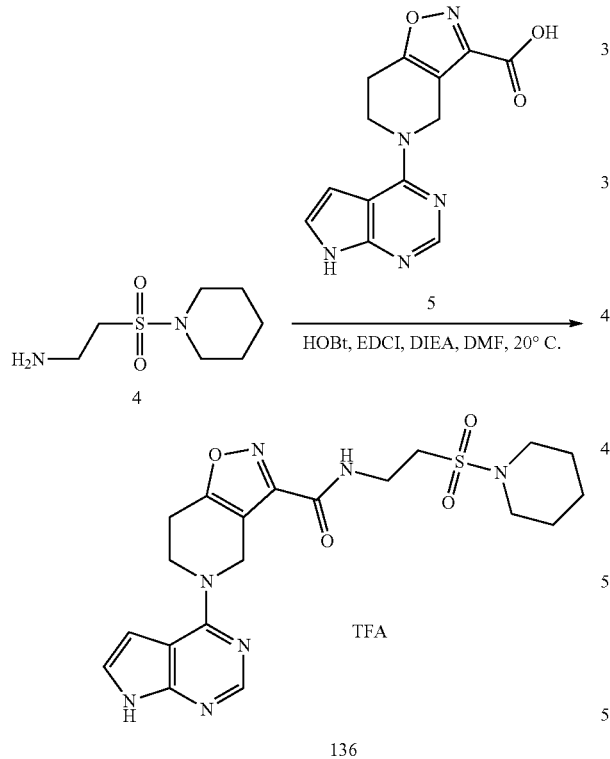

To a mixture of Compound 5 (103.92 mg, 364.32 umol, 1 eq) and Compound 4 (100 mg, 437.18 umol, 1.2 eq, HCl) in DMF (3 mL) was added HOBt (59.07 mg, 437.18 umol, 1.2 eq), EDCI (104.76 mg, 546.47 umol, 1.5 eq) and DIEA (188.34 mg, 1.46 mmol, 253.82 uL, 4 eq), the mixture was stirred at 20° C. for 15 hr. LCMS showed Compound 5 was consumed, and desired MS was detected. The mixture was diluted with water (30 mL), extracted with DCM/IPA (3:1, 40 mL*3), washed with brine (40 mL), dried with Na$_2$SO$_4$, filtered and concentrated. The residue was purified by prep-HPLC (column: Phenomenex Synergi C18 150*25*10 um; mobile phase: [water(0.1% TFA)-ACN]; B %: 18%-38%, 10 min) to give Compound 136 (50.9 mg, 88.48 umol, 24.29% yield, 99.7% purity, TFA) as yellow oil.

$^1$H NMR (400 MHz, DMSO-d6)

δ=12.38 (br. s, 1H), 8.93 (t, J=5.6 Hz, 1H), 8.37 (s, 1H), 7.42 (br. s, 1H), 6.81 (br. d, J=2.5 Hz, 1H), 5.05 (s, 2H), 4.27 (br. t, J=5.5 Hz, 2H), 3.73-3.57 (m, 2H), 3.29 (t, J=7.2 Hz, 2H), 3.17 (br. t, J=4.8 Hz, 4H), 3.12-3.04 (m, 2H), 1.60-1.49 (m, 6H)

$^{13}$C NMR (101 MHz, DMSO-d6)

δ=169.06, 159.34, 158.97, 158.62, 158.27, 155.62, 154.50, 148.80, 147.54, 123.85, 120.71, 117.96, 115.04, 112.13, 111.49, 102.81, 102.36, 47.28, 46.32, 43.15, 42.71, 40.65, 40.44, 33.92, 25.63, 23.63

LCMS: Rt=0.521 min, [M+H]$^+$=460.0

Example 15: Synthesis of Compound 138

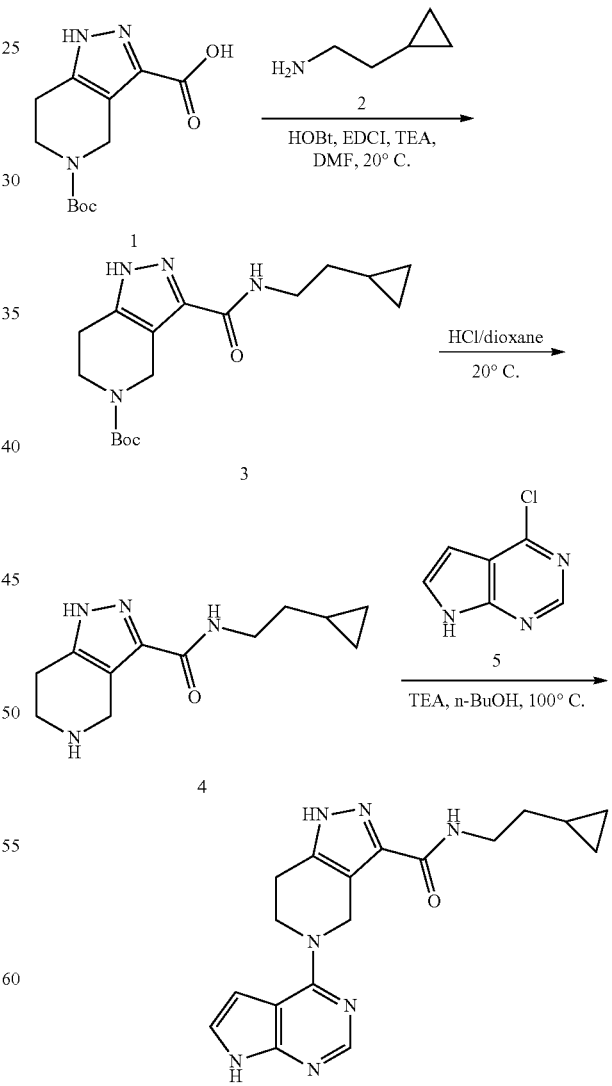

Preparation of Compound 3

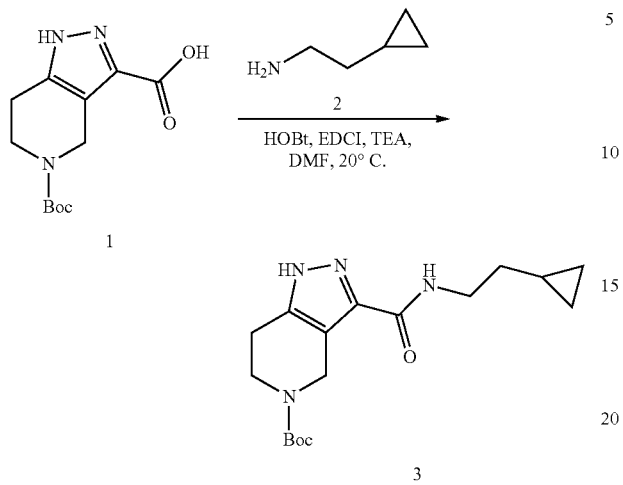

To a solution of Compound 1 (200 mg, 748.28 umol, 1 eq) and Compound 2 (109.20 mg, 897.93 umol, 1.2 eq) in DMF (3 mL) was added HOBt (121.33 mg, 897.93 umol, 1.2 eq), EDCI (172.14 mg, 897.93 umol, 1.2 eq) and TEA (302.87 mg, 2.99 mmol, 416.61 uL, 4 eq), then the reaction mixture was stirred at 20° C. for 12 hr. LCMS showed desired mass was detected. The reaction mixture was diluted with H₂O (20 mL), extracted with EtOAc (15 mL*3), washed with brine (20 mL*3), dried over anhydrous Na₂SO₄, filtered and concentrated The residue was purified by silica gel column chromatography (Petroleum ether/ethyl acetate=10/1~5/1) to give Compound 3 (100 mg, 299.03 umol, 39.96% yield) as a white solid.

¹H NMR (400 MHz, CDCl₃)

δ=10.14-9.50 (m, 1H), 7.25-6.53 (m, 1H), 4.71 (s, 2H), 3.73 (br. t, J=5.5 Hz, 2H), 3.51 (q, J=6.8 Hz, 2H), 2.76 (br. t, J=5.6 Hz, 2H), 1.54-1.50 (m, 2H), 1.49 (s, 9H), 0.83-0.65 (m, 1H), 0.57-0.42 (m, 2H), 0.20-0.01 (m, 2H)

LCMS: Rt=0.890 min, [M+H]⁺=279.2

Preparation of Compound 4

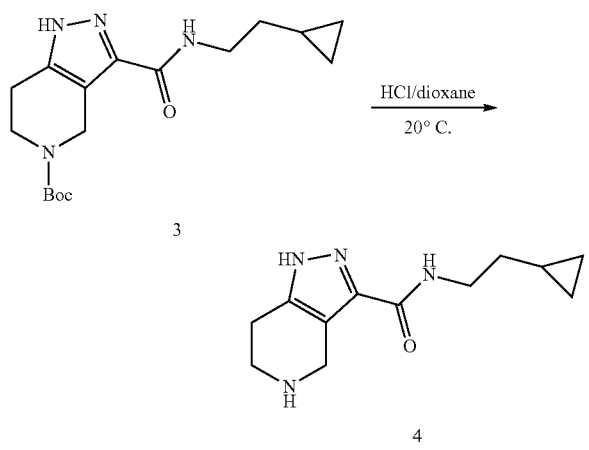

A solution of Compound 3 (96 mg, 287.07 umol, 1 eq) in 4N HCl/dioxane (2 mL) was stirred at 20° C. for 1 hr. TLC indicated Compound 3 was consumed and one new major spot with larger polarity was detected. The reaction mixture was concentrated under reduced pressure to give Compound 4 (77.73 mg, crude, HCl) as a white solid.

Preparation of Compound 138

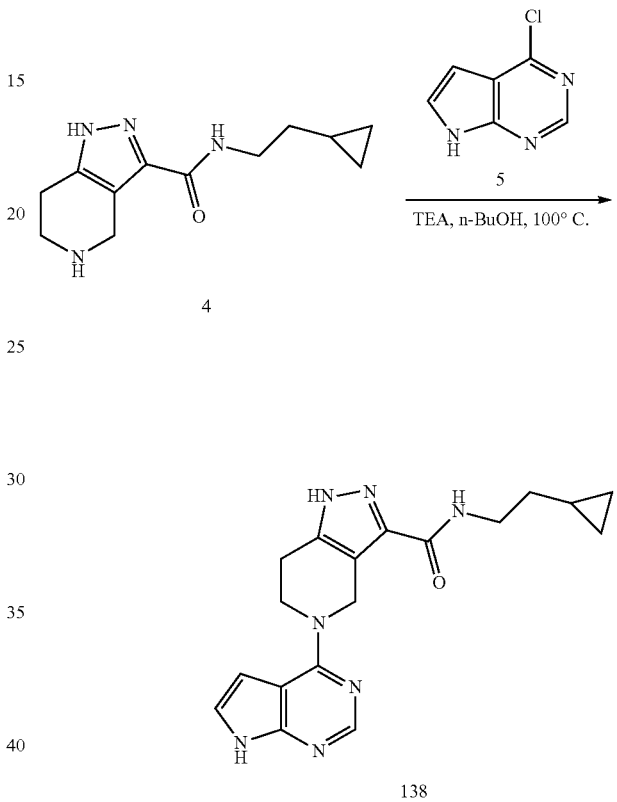

To a solution of Compound 4 (60 mg, 221.60 umol, 1 eq, HCl) and Compound 5 (34.03 mg, 221.60 umol, 1 eq) in n-BuOH (2 mL) was added TEA (89.69 mg, 886.40 umol, 123.38 uL, 4 eq), then the reaction mixture was stirred at 100° C. for 12 hr. LCMS showed desired mass was detected. The reaction mixture was concentrated, purified by prep-HPLC (column: Waters Xbridge 150*25 5 u; mobile phase: [water(10 mM NH₄HCO₃)-ACN]; B %: 15%-45%, 10 min) to give Compound 138 (17.05 mg, 47.06 umol, 21.24% yield, 97% purity) as a white solid.

¹H NMR (400 MHz, DMSO-d)

δ=12.53-11.28 (m, 1H), 8.16 (s, 1H), 8.01 (br. t, J=5.6 Hz, 1H), 7.22 (d, J=3.3 Hz, 1H), 6.63 (br d, J=3.4 Hz, 1H), 5.05 (s, 2H), 4.14 (br. t, J=4.9 Hz, 2H), 3.35-3.25 (m, 2H), 2.85 (br. s, 2H), 1.41 (q, J=7.0 Hz, 2H), 0.82-0.58 (m, 1H), 0.39 (br. d, J=7.0 Hz, 2H), 0.05 (br. d, J=4.3 Hz, 2H)

¹³C NMR (101 MHz, DMSO-d)

δ=162.52, 157.17, 152.42, 151.12, 141.31, 139.52, 122.04, 114.63, 102.83, 101.15, 43.72, 42.61, 38.97, 34.69, 21.83, 9.06, 4.56

LCMS: Rt=0.751 min, [M+H]⁺=352.3

Example 16: Synthesis of Compound 139

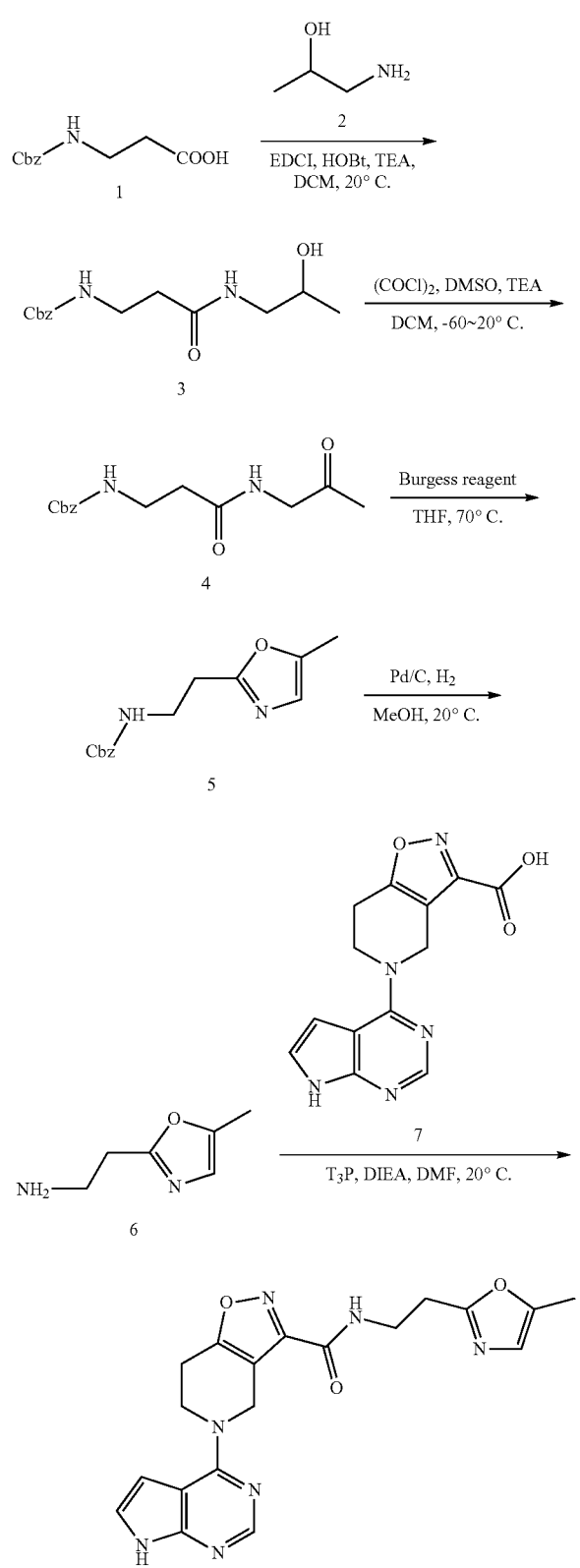

Preparation of Compound 3

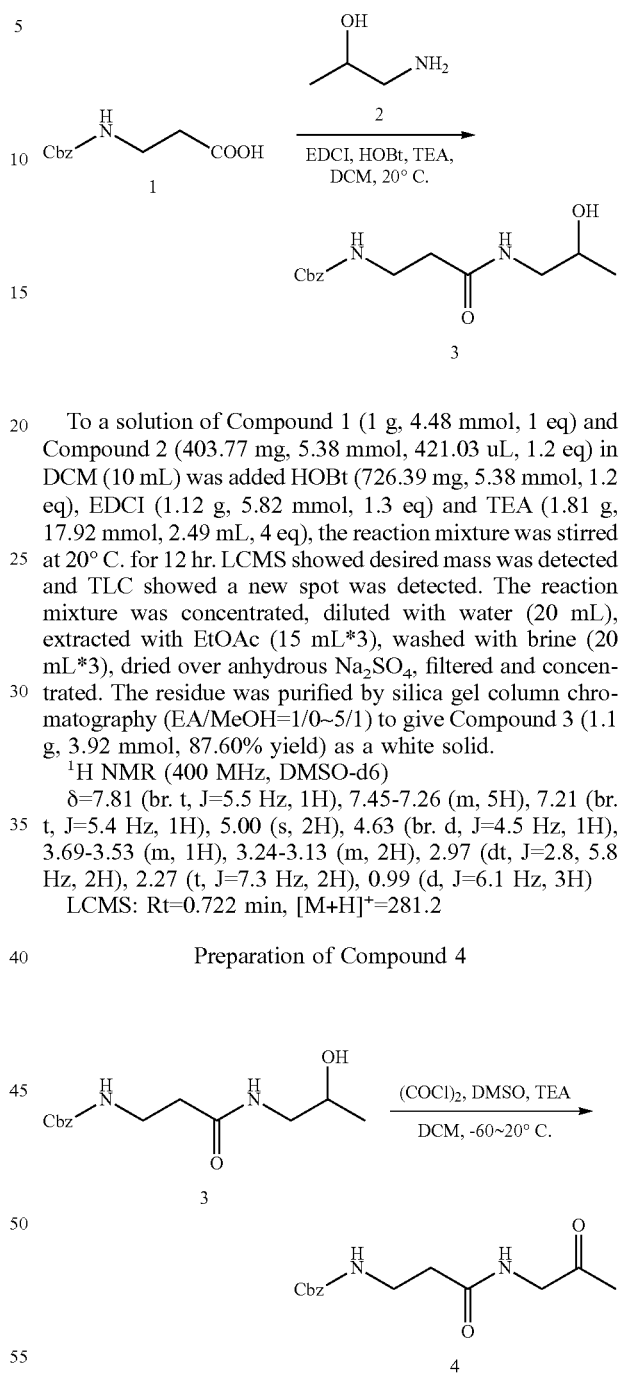

To a solution of Compound 1 (1 g, 4.48 mmol, 1 eq) and Compound 2 (403.77 mg, 5.38 mmol, 421.03 uL, 1.2 eq) in DCM (10 mL) was added HOBt (726.39 mg, 5.38 mmol, 1.2 eq), EDCI (1.12 g, 5.82 mmol, 1.3 eq) and TEA (1.81 g, 17.92 mmol, 2.49 mL, 4 eq), the reaction mixture was stirred at 20° C. for 12 hr. LCMS showed desired mass was detected and TLC showed a new spot was detected. The reaction mixture was concentrated, diluted with water (20 mL), extracted with EtOAc (15 mL*3), washed with brine (20 mL*3), dried over anhydrous $Na_2SO_4$, filtered and concentrated. The residue was purified by silica gel column chromatography (EA/MeOH=1/0~5/1) to give Compound 3 (1.1 g, 3.92 mmol, 87.60% yield) as a white solid.

$^1$H NMR (400 MHz, DMSO-d6)

δ=7.81 (br. t, J=5.5 Hz, 1H), 7.45-7.26 (m, 5H), 7.21 (br. t, J=5.4 Hz, 1H), 5.00 (s, 2H), 4.63 (br. d, J=4.5 Hz, 1H), 3.69-3.53 (m, 1H), 3.24-3.13 (m, 2H), 2.97 (dt, J=2.8, 5.8 Hz, 2H), 2.27 (t, J=7.3 Hz, 2H), 0.99 (d, J=6.1 Hz, 3H)

LCMS: Rt=0.722 min, [M+H]$^+$=281.2

Preparation of Compound 4

To a solution of (COCl)$_2$ (869.39 mg, 6.85 mmol, 599.58 uL, 1.2 eq) in DCM (15 mL) was added a solution of DMSO (713.52 mg, 9.13 mmol, 713.52 uL, 1.6 eq) in DCM (10 mL) at −53° C., the mixture was stirred at −53° C. for 15 min. Then a solution of Compound 3 (1.6 g, 5.71 mmol, 1 eq) in DCM (15 mL) was added, the mixture was stirred at −60° C. for 1.5 hr. TEA (2.44 g, 24.14 mmol, 3.36 mL, 4.23 eq) was added dropwise and the suspension was stirred for 1 hr at −50° C., then warmed to 20° C., stirred for 16 hr. LCMS showed desired mass was detected and TLC showed new spots was detected. The reaction mixture was concentrated, diluted with H₂O (20 mL), extracted with DCM (15 mL*3), washed with brine (20 mL*3), dried over anhydrous Na₂SO₄, filtered and concentrated. The residue was purified by prep-TLC (DCM/MeOH=10/1) to give Compound 4 (107 mg, 384.47 umol, 35.93% yield) as a white solid.

¹H NMR (400 MHz, CDCl₃)

δ=7.40-7.31 (m, 5H), 6.22 (br. d, J=0.9 Hz, 1H), 5.42 (br. d, J=1.8 Hz, 1H), 5.10 (s, 2H), 4.15 (d, J=4.6 Hz, 2H), 3.51 (q, J=6.1 Hz, 2H), 2.49 (br. t, J=5.7 Hz, 2H), 2.21 (s, 3H)

LCMS: Rt=0.762 min, [M+H]⁺=279.2

Preparation of Compound 5

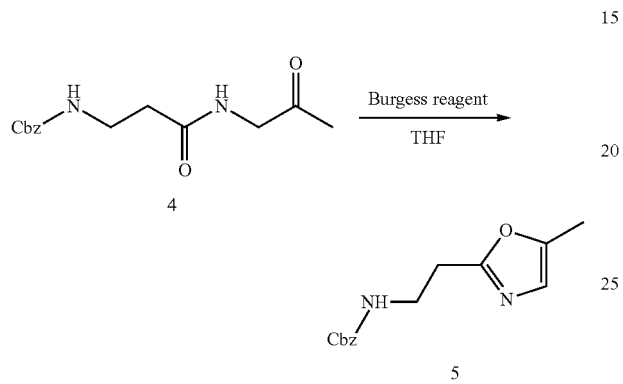

To a mixture of Compound 4 (0.35 g, 1.26 mmol, 1 eq) in THF (10 mL) was added Burgess reagent (599.40 mg, 2.52 mmol, 2 eq), the mixture was stirred at 70° C. for 10 hr. TLC showed the desired product. The mixture was concentrated to dry. The residue was purified by silica gel column chromatography (Petroleum ether/Ethyl acetate=5/1) to give Compound 5 (252 mg, 968.16 umol, 76.98% yield) as a colorless oil.

¹H NMR (400 MHz, CDCl₃)

δ=7.39-7.31 (m, 5H), 6.60 (d, J=1.1 Hz, 1H), 5.46 (br. s, 1H), 5.10 (s, 2H), 3.63 (q, J=6.1 Hz, 2H), 2.92 (t, J=6.1 Hz, 2H), 2.27 (d, J=0.9 Hz, 3H)

Preparation of Compound 6

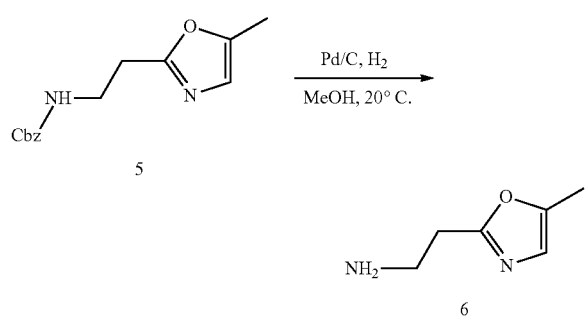

A mixture of Compound 5 (220 mg, 845.22 umol, 1 eq) and Pd/C (30 mg, 10% purity) in MeOH (5 mL) was stirred at 20° C. under H₂ balloon for 12 hr at 15 psi. TLC showed Compound 5 was consumed, and a new major spot was observed. The mixture was filtered and concentrated to give Compound 6 (85 mg, crude) as colorless oil.

¹H NMR (400 MHz, CDCl₃)

δ=6.62 (d, J=1.1 Hz, 1H), 3.17-3.07 (m, 2H), 2.86 (t, J=6.4 Hz, 2H), 2.29 (d, J=1.0 Hz, 3H)

Preparation of Compound 139

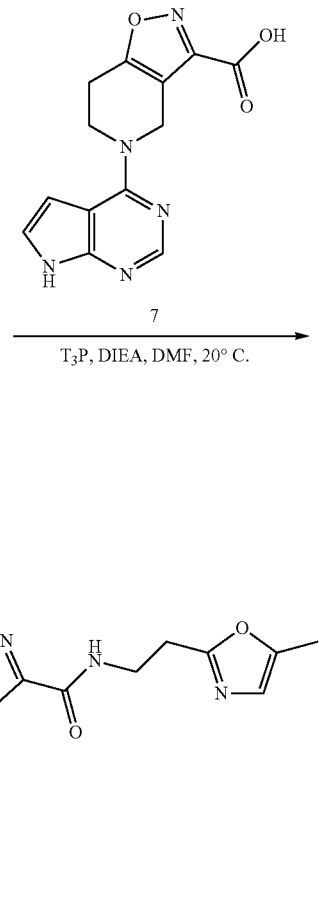

A mixture of Compound 7 (130 mg, 455.73 umol, 1 eq), Compound 6 (68.99 mg, 546.87 umol, 7.62 uL, 1.2 eq), T3P (435.01 mg, 683.59 umol, 406.55 uL, 50% purity, 1.5 eq) and DIEA (176.70 mg, 1.37 mmol, 238.14 uL, 3 eq) in DMF (2 mL) was stirred at 20° C. for 12 hr. LCMS showed a major peak with desired MS was detected. The mixture was filtered. The residue was purified by prep-HPLC (column: Phenomenex Luna C18 150*25 mm*10 um; mobile phase: [water(0.1% TFA)-ACN]; B %: 10%-40%, 10 min) to give Compound 139 (65 mg, 125.54 umol, 27.55% yield, 98% purity, TFA) as yellow solid.

¹H NMR (400 MHz, MeOD)

δ=8.42 (s, 1H), 7.46 (d, J=3.6 Hz, 1H), 7.06 (d, J=3.6 Hz, 1H), 6.70 (d, J=1.1 Hz, 1H), 5.21 (s, 2H), 4.44 (t, J=5.7 Hz, 2H), 3.77 (t, J=6.9 Hz, 2H), 3.20 (br. t, J=5.6 Hz, 2H), 3.07 (t, J=6.8 Hz, 2H) ¹³C NMR (101 MHz, MeOD)

δ=168.08, 161.55, 159.87, 159.84, 154.01, 149.68, 142.71, 124.00, 121.50, 114.54, 110.28, 103.52, 102.70, 43.51, 36.50, 27.46, 22.89, 9.21

LCMS: Rt=0.742 min, [M+H]⁺=394.1

Example 17: Synthesis of Compound 141

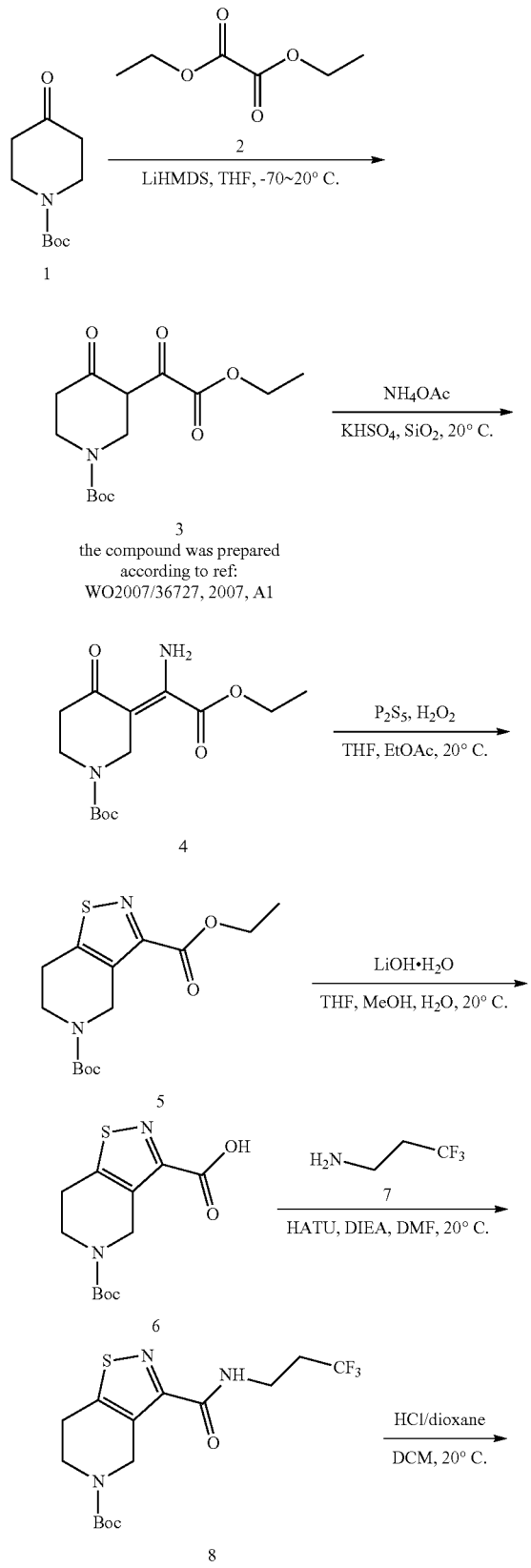

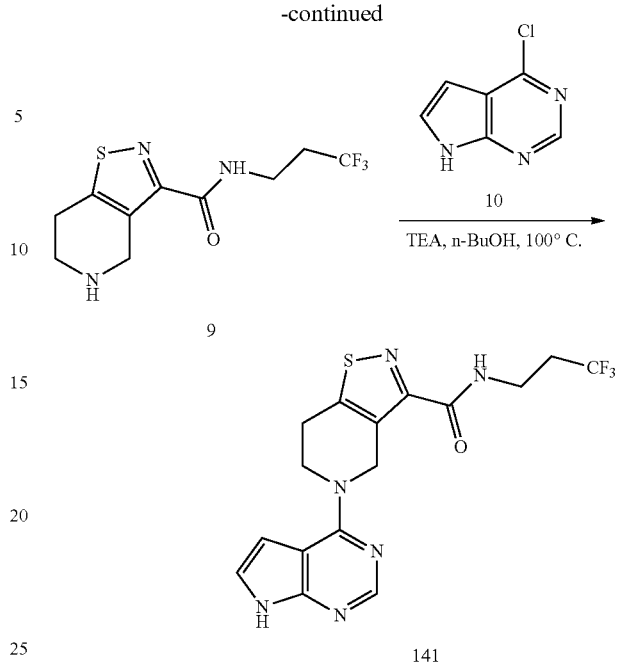

Preparation of Compound 3

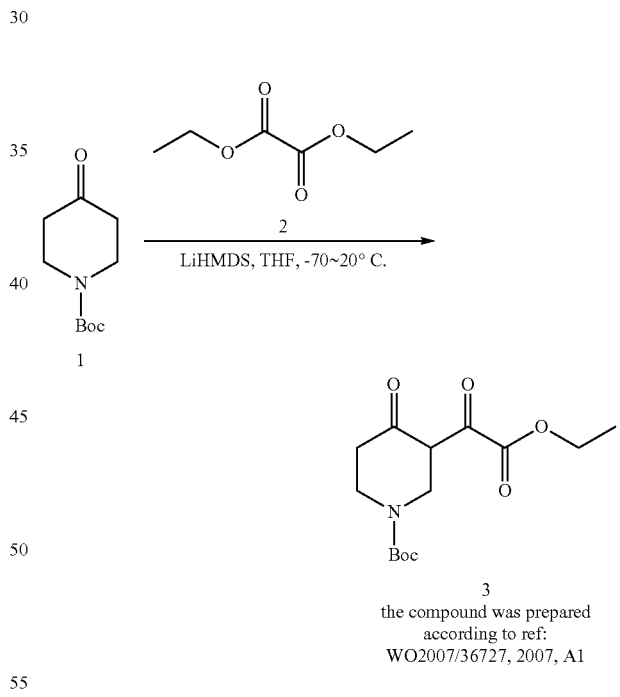

To a solution of Compound 1 (200 g, 1.00 mol, 1 eq) in THF (2000 mL) was added LiHMDS (1 M, 1.20 L, 1.2 eq) dropwise at −70° C. The mixture was stirred at −70° C. for 0.5 hr. Then Compound 2 (190.70 g, 1.30 mol, 178.23 mL, 1.3 eq) was added dropwise at −70° C. The mixture was stirred for at −70° C. 1 hr, then at 20° C. for 2 hr. TLC (PE/EA=1/1, Rf=0.6) indicated one major new spot was detected. The mixture was quenched by 1N HCl (2 L), extracted with EtOAc (1 L*3), dried with Na$_2$SO$_4$, filtered and concentrated. The residue was purified by silica gel column chromatography (Petroleum ether/Ethyl acetate=1:

0~1:1) to afford Compound 3 (180 g, 312.71 mmol, 31.15% yield, 52% purity) as yellow oil.

LCMS: Rt=0.797 min, [M+H]⁺=300.1

Preparation of Compound 4

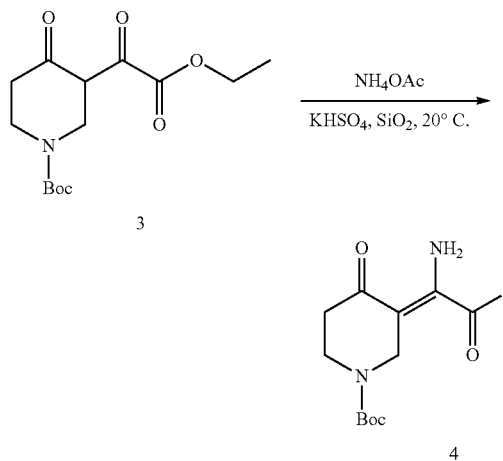

To a mixture of KHSO₄ (1 g, 7.34 mmol, 431.03 uL, 0.11 eq) and SiO₂ (1 g, 16.64 mmol, 2.49e−1 eq) was added Compound 3 (20 g, 66.82 mmol, 1 eq) and NH₄OAc (5.15 g, 66.82 mmol, 1 eq) at 20° C. The mixture was reacted at 20° C. for 12 hr. LCMS showed desired mass was detected. The reaction mixture was diluted with EtOAc (100 mL), filtered and concentrated. The residue was purified by silica gel column chromatography (Petroleum ether/Ethyl acetate=1/0~1/3) to afford Compound 4 (3.3 g, 8.96 mmol, 13.41% yield, 81% purity) as yellow oil.

LCMS: Rt=0.761 min, [M+H]⁺=299.1

Preparation of Compound 5

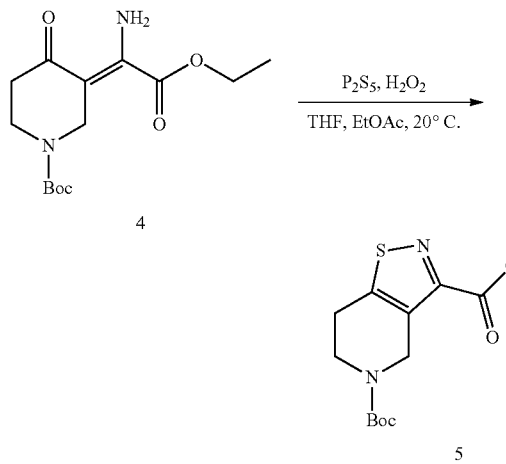

A mixture of Compound 4 (3.3 g, 11.06 mmol, 1 eq) and P₂S₅ (1.23 g, 5.53 mmol, 588.20 uL, 0.5 eq) in THF (33 mL) was reacted at 20° C. for 12 hr. The reaction mixture was concentrated under vacuum. The residue was diluted with EtOAc (33 mL), H₂O₂ (5.64 g, 49.78 mmol, 4.78 mL, 30% purity, 4.5 eq) was added dropwise at 0° C. Then the reaction mixture was stirred at 20° C. for 10 min. LCMS showed desired mass was detected. The reaction mixture was quenched by saturated Na₂SO₃ aqueous solution (40 mL), extracted with EtOAc (40 mL*3), dried over Na₂SO₄, filtered and concentrated. The residue was purified by silica gel column chromatography (Petroleum ether/Ethyl acetate=1/3) to afford Compound 5 (1.5 g, 34.73% yield, 80% purity) as yellow solid.

LCMS: Rt=0.871 min, [M+H]⁺=313.1

Preparation of Compound 6

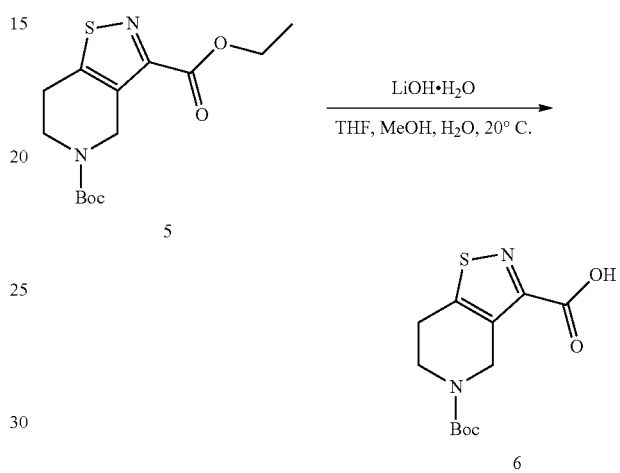

To a solution of Compound 5 (500 mg, 1.60 mmol, 1 eq) in THF (2 mL) and MeOH (2 mL) was added a solution of LiOH·H₂O (201.50 mg, 4.80 mmol, 3 eq) in H₂O (2 mL) at 20° C. The reaction mixture was stirred at 20° C. for 0.5 hr. LCMS showed desired mass was detected. The reaction mixture was adjusted to pH=5 with citric acid aqueous solution, extracted with EtOAc (15 mL*3), washed with brine (30 mL), dried over Na₂SO₄, filtered and concentrated to afford Compound 6 (631 mg, crude) as yellow solid.

LCMS: Rt=0.697 min, [M+H]⁺=285.1

Preparation of Compound 8

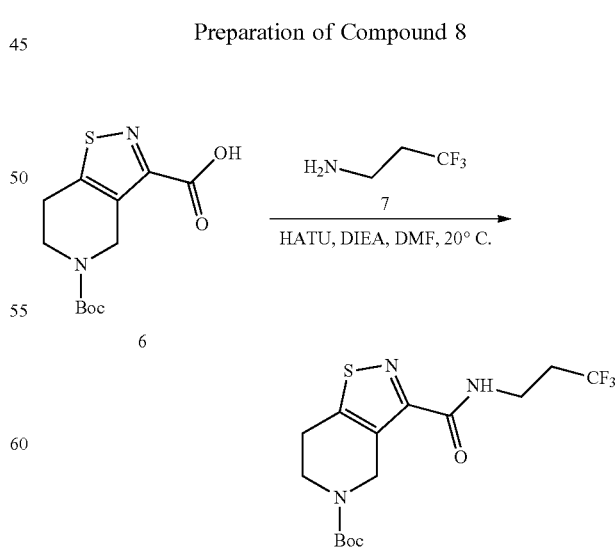

145

To a solution of Compound 6 (600 mg, 2.11 mmol, 1 eq) and HATU (2.41 g, 6.33 mmol, 3 eq) in DMF (5 mL) was added Compound 7 (631.13 mg, 4.22 mmol, 2 eq, HCl) and DIEA (1.77 g, 13.72 mmol, 2.39 mL, 6.5 eq). The mixture was stirred at 20° C. for 1 hr. LCMS showed desired mass was detected. The reaction mixture was diluted with H$_2$O (8 mL), extracted with EtOAc (10 mL*3), dried over Na$_2$SO$_4$, filtered and concentrated. The residue was purified by silica gel column chromatography (Petroleum ether/Ethyl acetate=3/1) to afford Compound 8 (600 mg, purity: 97.95%, yield: 74.9%) as yellow oil.

$^1$H NMR (400 MHz, CDCl$_3$)

δ=7.48 (s, 1H), 4.88 (s, 2H), 3.78-3.63 (m, 4H), 3.03-2.93 (t, J=5.4 Hz, 2H), 2.53-2.38 (m, 2H), 1.50 (s, 9H)

LCMS: Rt=0.948 min, [M+H]$^+$=380.0

Preparation of Compound 9

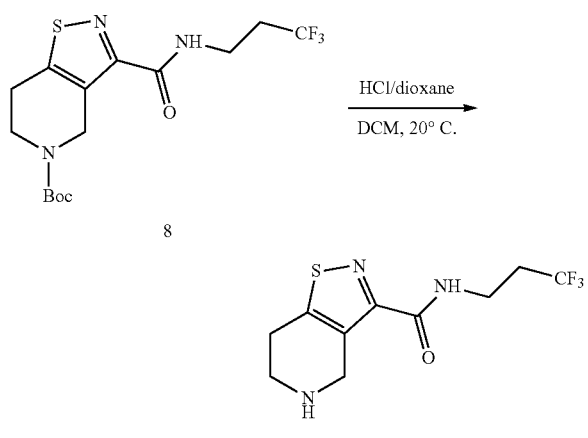

A mixture of Compound 8 (180 mg, 474.44 umol, 1 eq), HCl/dioxane (4 M, 0.6 mL) in DCM (1.2 mL) was stirred at 20° C. for 0.5 hr. LCMS showed desired mass was detected. The reaction mixture was concentrated to afford Compound 9 (180 mg, crude, HCl) as a yellow solid.

LCMS: Rt=0 min, [M+H]$^+$=280.1

Preparation of Compound 141

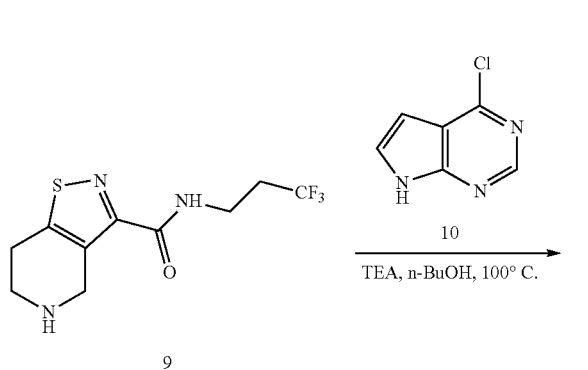

146

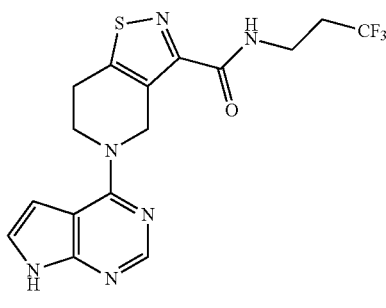

141

A mixture of Compound 9 (180 mg, 644.51 umol, 1 eq), Compound 10 (98.98 mg, 644.51 umol, 1 eq) and TEA (260.87 mg, 2.58 mmol, 358.83 uL, 4 eq) in n-BuOH (1.8 mL) was stirred at 100° C. for 12 hr. LCMS showed desired mass was detected. The reaction mixture was concentrated, the residue was purified by prep-HPLC (Column: Waters Xbridge BEH C18 250*50 mm*10 um; Condition: water (10 mM NH$_4$HCO$_3$)-ACN; FlowRate (ml/min): 60 mL) to afford Compound 141 (65.55 mg, 25.40% yield, 99% purity) as white solid.

$^1$H NMR (400 MHz, DMSO-d6)

δ=8.97-8.69 (t, J=6.2 Hz, 1H), 8.19 (s, 1H), 7.35-7.13 (d, J=3.6 Hz, 1H), 6.88-6.53 (d, J=3.6 Hz, 1H), 5.30 (s, 2H), 4.29-4.01 (t, J=5.6 Hz, 2H), 3.60-3.48 (m, 2H), 3.19-3.10 (t, J=5.4 Hz, 2H), 2.64-2.54 (m, 2H)

$^{13}$C NMR (101 MHz, DMSO-d6)

δ=161.46, 161.44, 157.93, 156.88, 152.44, 151.08, 132.83, 128.63, 125.87, 122.34, 102.90, 101.08, 46.17, 41.88, 40.58, 40.37, 40.15, 39.95, 39.74, 39.53, 39.32, 33.01, 32.75, 24.41

Example 18: Synthesis of Compound 146

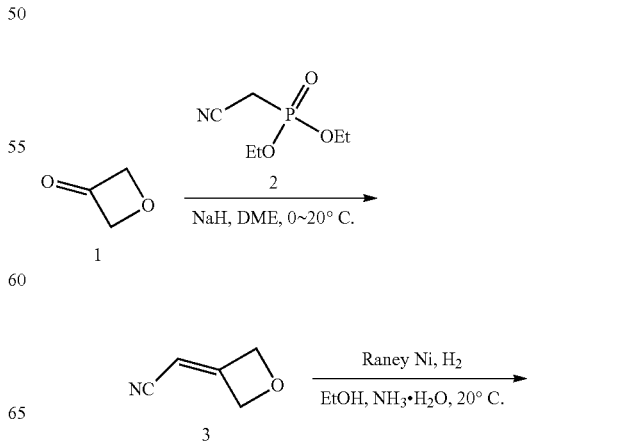

147

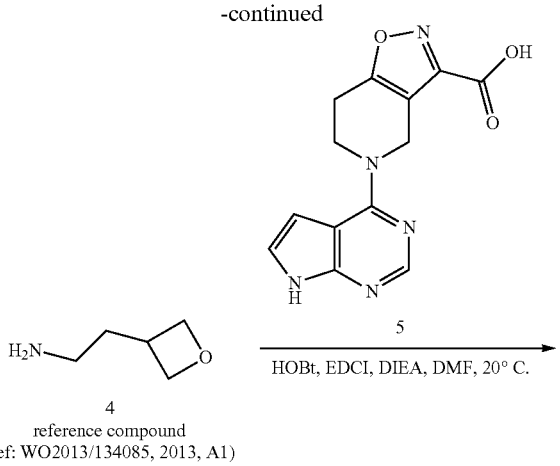

4
reference compound
(ref: WO2013/134085, 2013, A1)
used different strategy

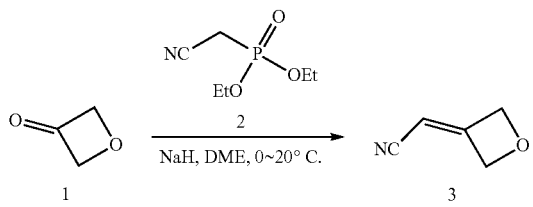

146

Preparation of Compound 3

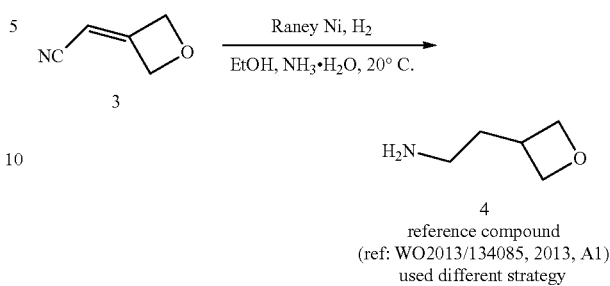

To a mixture of NaH (555.02 mg, 13.88 mmol, 60% purity, 1 eq) in THF (10 mL) was added a solution of Compound 2 (2.46 g, 13.88 mmol, 2.23 mL, 1 eq) in THF (5 mL) at 0° C. The mixture was stirred at 0° C. for 1 hr, then a solution of Compound 1 (1 g, 13.88 mmol, 1 eq) in THF (5 mL) was added at 0° C. After addition, the mixture was warmed to 20° C. smoothly, stirred for 12 hr. TLC showed a new major spot was observed. The mixture was concentrated, diluted with water (20 mL), extracted with EtOAc (20 mL*2), dried with $Na_2SO_4$, filtered and concentrated. The residue was triturated with PE/EA (3:1, 30 mL) to give Compound 3 (860 mg, 9.04 mmol, 65.17% yield) as white solid.

$^1$H NMR (400 MHz, DMSO-d)

δ=5.74 (quin, J=2.5 Hz, 1H), 5.36-5.30 (m, 2H), 5.28-5.22 (m, 2H).

148

Preparation of Compound 4

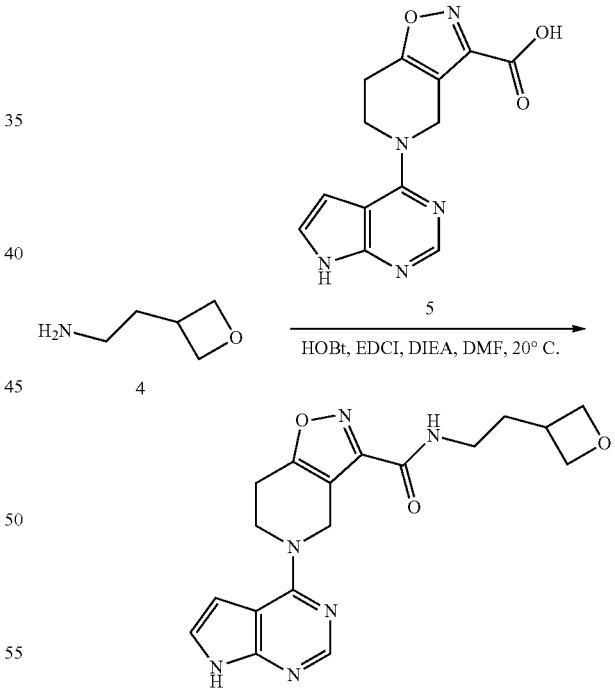

A mixture of Compound 3 (500 mg, 5.26 mmol, 1 eq) and Raney Nickel (1 g) in EtOH (16 mL) and concentrated $NH_3 \cdot H_2O$ (4 mL) was stirred at 20° C. under $H_2$ balloon at 15 psi for 12 hr. TLC showed Compound 3 was consumed. The mixture was filtered and concentrated to give Compound 4 (300 mg, crude) as yellow solid.

$^1$H NMR (400 MHz, $CDCl_3$)

δ=4.88 (br. d, J=7.2 Hz, 1H), 4.84-4.77 (m, 4H), 4.48-4.38 (m, 6H)

Preparation of Compound 146

A mixture of Compound 5 (150 mg, 525.84 umol, 1 eq), Compound 4 (106.37 mg, 1.05 mmol, 2 eq), HOBt (85.26 mg, 631.01 umol, 1.2 eq), EDCI (151.21 mg, 788.76 umol, 1.5 eq) and DIEA (203.88 mg, 1.58 mmol, 274.78 uL, 3 eq) in DMF (2 mL) was stirred at 20° C. for 12 hr. LCMS showed desired MS was detected. The mixture was filtered. The residue was purified by prep-HPLC (column: Xtimate C18 10 u 250 mm*80 mm; mobile phase: [water(0.05% ammonia hydroxide v/v)-ACN]; B %: 10%-40%, 10 min) and (column: Shim-pack C18 150*25*10 um; mobile phase: [water(0.225% FA)-ACN]; B %: 8%-38%, 10 min) to give Compound 146 (7.39 mg, 19.28 umol, 3.67% yield, 96.086% purity) as off-white solid.

¹H NMR (400 MHz, MeOD)

δ=8.13 (d, J=3.1 Hz, 1H), 7.13 (t, J=3.9 Hz, 1H), 6.69 (d, J=3.7 Hz, 1H), 5.00 (br. d, J=7.8 Hz, 2H), 4.76 (dd, J=6.1, 7.8 Hz, 1H), 4.39 (t, J=6.2 Hz, 1H), 4.24 (t, J=5.6 Hz, 2H), 4.08-3.35 (m, 3H), 3.29 (t, J=6.9 Hz, 1H), 3.10-3.03 (m, 0.5H), 2.99 (br. t, J=5.4 Hz, 2H), 2.43 (s, 0.5H), 2.04 (br. dd, J=6.9, 11.7 Hz, 0.5H), 1.95 (q, J=7.3 Hz, 1H), 1.81-1.68 (m, 0.5H)

LCMS: Rt=0.690 min, [M+H]⁺=369.1

Example 19: Synthesis of Compound 148

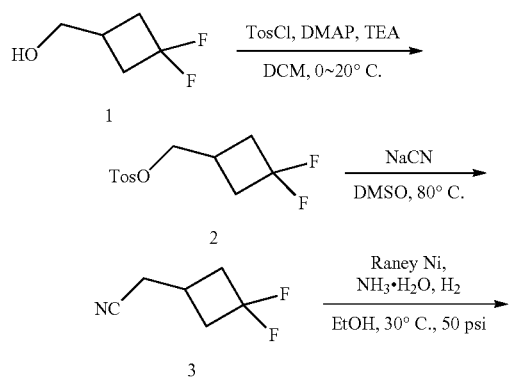

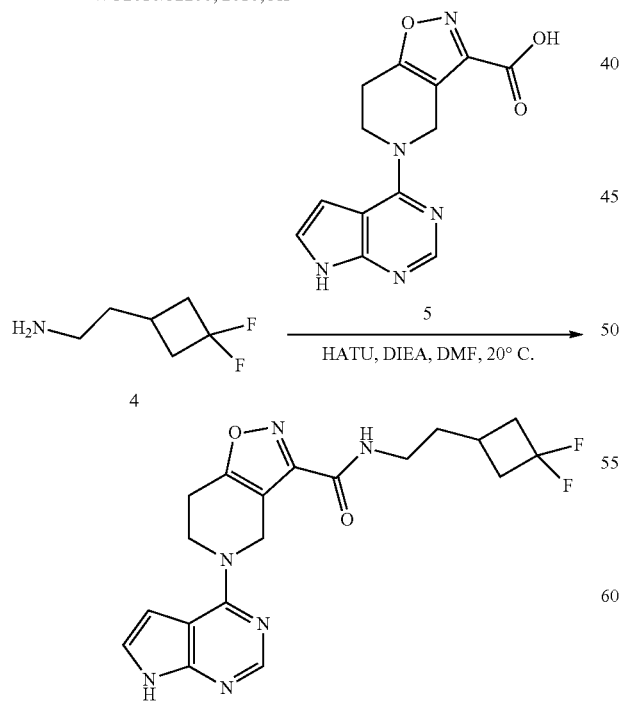

148

Preparation of Compound 2

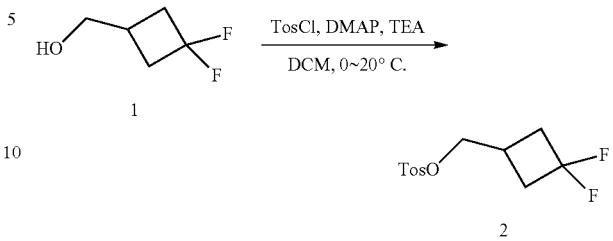

To a solution of Compound 1 (200 mg, 1.64 mmol, 1 eq), DMAP (320.14 mg, 2.62 mmol, 1.6 eq) and TEA (265.17 mg, 2.62 mmol, 364.75 uL, 1.6 eq) in DCM (1 mL) was added a solution of TosCl (405.92 mg, 2.13 mmol, 1.3 eq) in DCM (1 mL) at 0° C. The mixture was stirred at 20° C. for 2 hr. TLC (PE:EA=3:1) showed Compound 1 was consumed and a new spot was observed. The mixture was poured into water (20 mL), extracted with EtOAc (20 mL*2), washed with brine (10 mL*2), dried over Na₂SO₄, filtered and concentrated. The residue was purified by silica gel chromatography (Petroleum ether/ethyl acetate=100/1~5/1) to give Compound 2 (370 mg, 1.34 mmol, 81.76% yield) as colorless oil.

¹H NMR (400 MHz, CDCl₃)

δ=7.86-7.76 (m, 2H), 7.37 (d, J=8.0 Hz, 2H), 4.07 (d, J=6.8 Hz, 2H), 2.72-2.56 (m, 2H), 2.54-2.42 (m, 4H), 2.38-2.21 (m, 2H)

Preparation of Compound 3

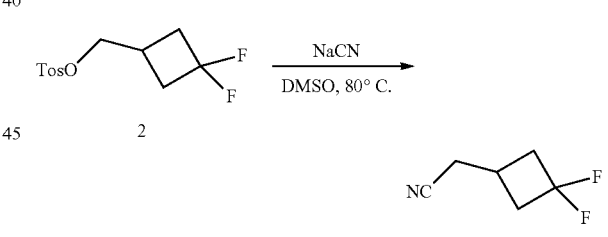

To a solution of Compound 2 (370 mg, 1.34 mmol, 1 eq) in DMSO (2 mL) was added NaCN (164.07 mg, 3.35 mmol, 2.5 eq). The mixture was stirred at 80° C. for 3 hr. TLC (PE:EA=3:1) showed Compound 2 was consumed but no new spot was observed. The mixture was poured into brine (20 mL), extracted with EtOAc (20 mL*3), dried over Na₂SO₄, filtered and concentrated to give Compound 3 (200 mg, crude) as yellow oil.

¹H NMR (400 MHz, CDCl₃)

δ=2.83-2.68 (m, 2H), 2.53-2.49 (m, 2H), 2.49-2.41 (m, 1H), 2.40-2.24 (m, 2H)

Preparation of Compound 4

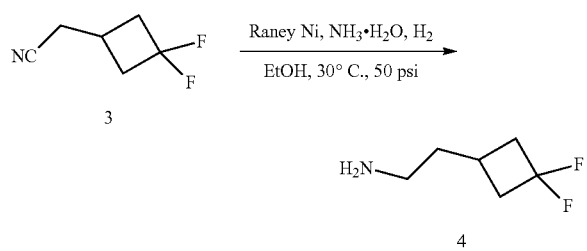

To a solution of Compound 3 (200 mg, 1.53 mmol, 1 eq) in EtOH (6 mL) and NH$_3$·H$_2$O (2.73 g, 19.47 mmol, 3 mL, 25% purity, 12.77 eq) was added Raney-Ni (200 mg, 2.33 mmol, 1.53 eq). The mixture was stirred at 30° C. for 16 h under H$_2$ atmosphere at 50 psi. TLC (MeOH:DCM=10:1) showed a new spot was observed. The mixture was filtered, the filter cake was washed with EtOH (20 mL*3), the combined filtrate was acidized by 1 N HCl solution to pH=5, concentrated to move EtOH. The resulting mixture was lyophilized to give Compound 4 (260 mg, crude, HCl) as white solid.

$^1$H NMR (400 MHz, DMSO-d$_6$)

δ=8.08 (br. s, 3H), 2.80-2.60 (m, 4H), 2.20 (br. d, J=2.2 Hz, 3H), 1.76 (br. d, J=7.3 Hz, 2H)

Preparation of Compound 148

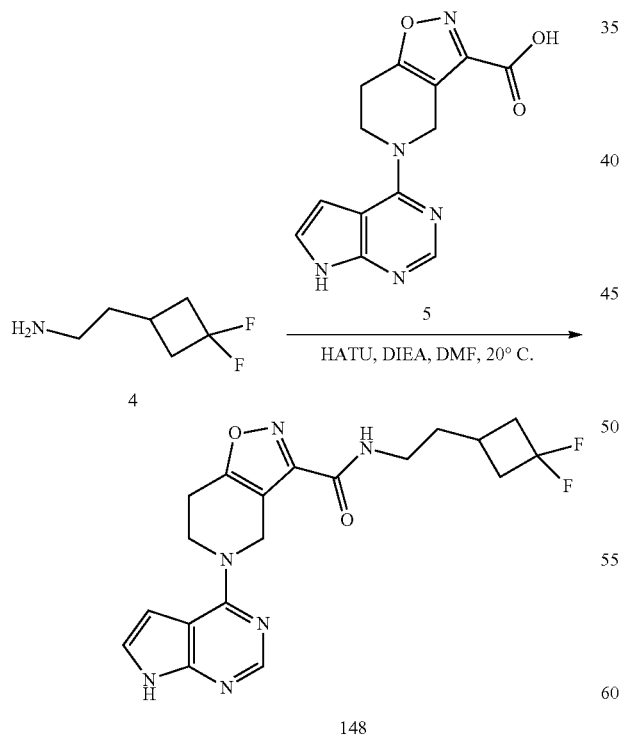

To a solution of Compound 5 (100 mg, 350.56 umol, 1 eq) and HATU (159.95 mg, 420.67 umol, 1.2 eq) in DMF (2 mL) was added DIEA (135.92 mg, 1.05 mmol, 183.18 uL, 3 eq). The mixture was stirred at 20° C. for 1 hr. Compound 4 (56.86 mg, 420.67 umol, 1.2 eq, HCl) was added, the mixture was stirred at 20° C. for 20 hr. LCMS showed Compound 5 was consumed and desired mass was detected. The mixture was poured into water (20 mL), extracted with EtOAc (20 mL*3), washed with brine (10 mL*2), dried over Na$_2$SO$_4$, filtered and concentrated. The residue was purified by prep-HPLC (column: Shim-pack C18 150*25*10 um; mobile phase: [water(0.225% FA)-ACN]; 10%: 21%-41%, 10 min) to give Compound 148 (12.34 mg, 30.67 umol, 8.75% yield, 100% purity) as white solid.

$^1$H NMR (400 MHz, CDCl$_3$)

δ=9.85-9.56 (m, 1H), 8.33 (s, 1H), 7.12 (d, J=3.7 Hz, 1H), 6.89-6.77 (m, 1H), 6.74 (d, J=3.8 Hz, 1H), 5.22-5.11 (m, 2H), 4.35 (t, J=5.6 Hz, 2H), 3.45 (q, J=6.5 Hz, 2H), 3.07 (t, J=5.6 Hz, 2H), 2.81-2.63 (m, 2H), 2.35-2.16 (m, 4H), 1.91-1.75 (m, 2H)

LCMS: Rt=0.792 min, [M+H]$^+$=403.2

Example 20: Synthesis of Compounds 150, 150-1, 150-2

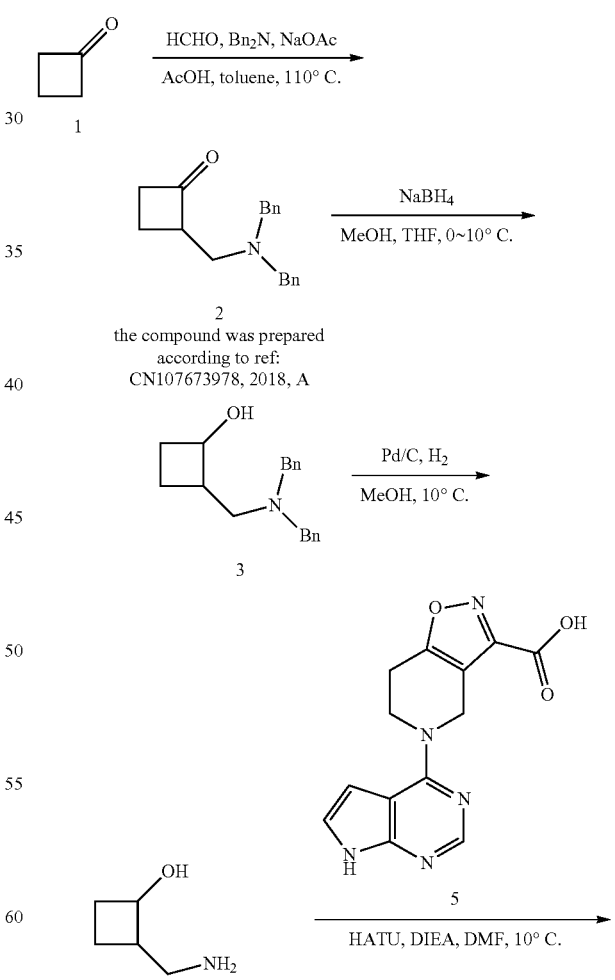

-continued

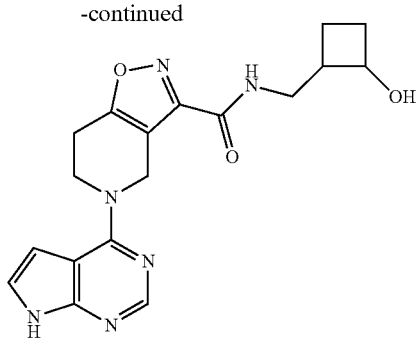

150

Preparation of Compound 2

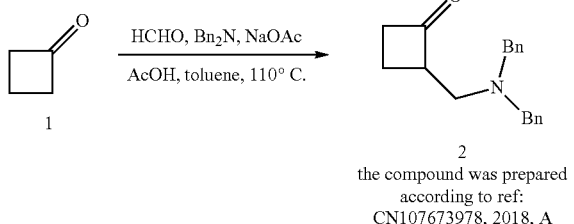

2
the compound was prepared
according to ref:
CN107673978, 2018, A

To a mixture of Compound 1 (1 g, 14.27 mmol, 1.07 mL, 1 eq) and Bn₂N (2.81 g, 14.27 mmol, 2.73 mL, 1 eq) in toluene (10 mL) was added HCHO (1.16 g, 14.27 mmol, 37% purity, 1 eq), NaOAc (234.08 mg, 2.85 mmol, 0.2 eg) and AcOH (171.36 mg, 2.85 mmol, 163.20 uL, 0.2 eq). The mixture was stirred at 110° C. for 16 hr. TLC (PE/EA=20/1, Rf=0.4) indicated a new spot was observed. The residue was purified by flash silica gel chromatography (ISCO®; 40 g SepaFlash® Silica Flash Column, Eluent of 0-20% Ethyl acetate/Petroleum ether gradient @ 80 mL/min) to give Compound 2 (1.3 g, crude) as a yellow oil.

Preparation of Compound 3

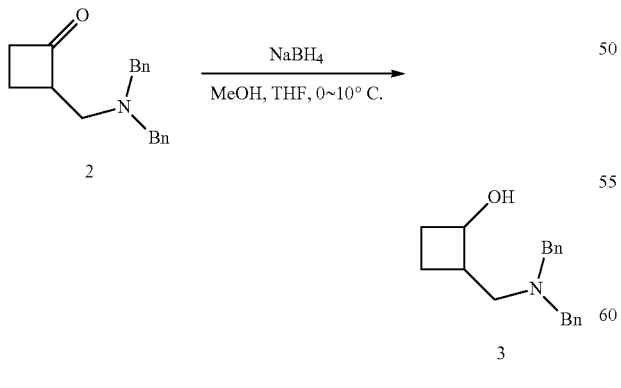

To a solution of Compound 2 (1 g, 3.58 mmol, 1 eq) in THF (5 mL) and MeOH (5 mL) was added NaBH₄ (135.42 mg, 3.58 mmol, 1 eq) at 0° C. The mixture was stirred at 10° C. for 0.5 hr. LCMS showed most of Compound 2 was consumed and 50% of desired Compound was detected. The reaction mixture was quenched by addition NH₄Cl (100 mL) at 10° C., extracted with EtOAc (10 mL*3), dried over Na₂SO₄, filtered and concentrated. The residue was purified by flash silica gel chromatography (ISCO®; 80 g SepaFlash® Silica Flash Column, Eluent of 0-30% Ethyl acetate/ Petroleum ether gradient @ 80 mL/min) to give Compound 3 (0.8 g, crude) as yellow oil.

LCMS: Rt=1.116 min, [M+H]⁺=282.2

Preparation of Compound 4

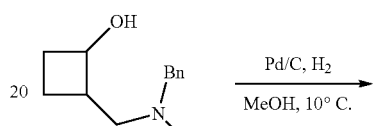

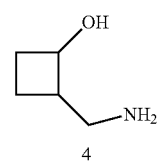

4
reference compound
(ref: WO2006/100208, 2006, A1)
used different strategy

To a solution of Compound 3 in MeOH (10 mL) was added Pd/C (100 mg, 10% purity). The mixture was stirred at 10° C. for 16 hr under H₂ balloon at 15 psi. TLC (PE/EA=1/1, Rf=0.01) indicated most of Compound 3 was consumed, and one major new spot with larger polarity was detected. The reaction mixture was filtered and concentrated to give Compound 4 (128 mg, crude) was obtained as yellow oil.

Preparation of Compound 150

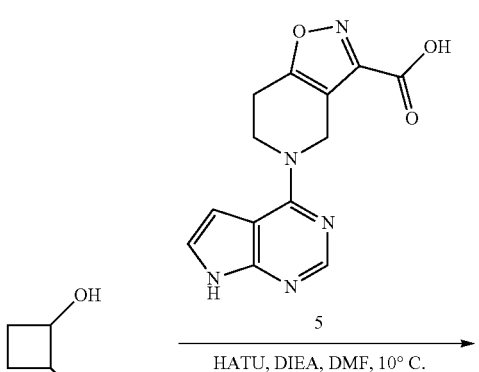

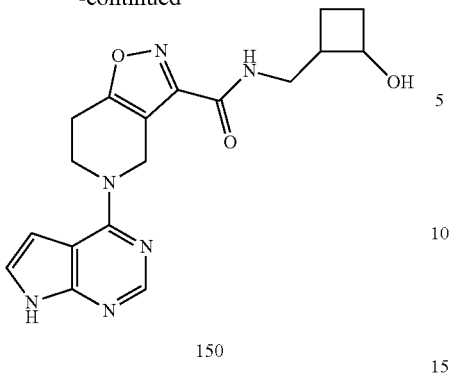

150

To a solution of Compound 4 (100 mg, 988.66 umol, 1 eq) and Compound 5 (282.02 mg, 988.66 umol, 1 eq) in DMF (2 mL) was added HATU (1.13 g, 2.97 mmol, 3 eq) and DIEA (511.11 mg, 3.95 mmol, 688.83 uL, 4 eq). The mixture was stirred at 10° C. for 0.5 hour. LCMS showed 45% of desired Compound was detected. The mixture was diluted with H$_2$O (100 mL), extracted with EtOAc (10 mL*3), dried over Na$_2$SO$_4$, filtered and concentrated. The residue combined with the batch (EW16218-28) was purified by prep-HPLC (column: Welch Xtimate C18 150*25 mm*5 um; mobile phase: [water(0.05% ammonia hydroxide v/v)-ACN]; B %: 37%-67%, 10 min) to give Compound 150-isomer 2 (compound 150-2) (5.24 mg, 13.94 umol, 1.41% yield, 98% purity) as yellow solid. The crude Compound 150-isomer 1 (30 mg, crude) further purified by prep-TLC (DCM/MeOH=5/1, Rf=0.7) to Compound 150-isomer 1 (compound 150-1)(1.52 mg, 4.13 umol, 30.40% yield) as yellow solid.

Compound 150-isomer 2 was confirmed as cis-isomer based on 2D NMR, which means Compound 150-isomer 1 was trans-isomer.

Compound 150 Isomer 1 (Compound 150-1)

$^1$H NMR (400 MHz, DMSO-d6)

δ=11.80 (br. s, 1H), 8.71 (t, J=5.6 Hz, 1H), 8.21 (s, 1H), 7.27 (s, 1H), 6.65 (s, 1H), 5.04-4.93 (m, 3H), 4.22 (t, J=5.6 Hz, 2H), 3.77-3.71 (m, 1H), 3.39-3.35 (m, 1H), 3.29-3.21 (m, 1H), 3.06-3.00 (m, 2H), 2.32-2.23 (m, 1H), 2.09-1.98 (m, 1H), 1.74-1.54 (m, 2H), 1.19-1.10 (m, 1H).

LCMS: Rt=0.806 min, [M+H]$^+$=369.3

Compound 150 Isomer 2 (Compound 150-2)

$^1$H NMR (400 MHz, DMSO-d6)

δ=11.81 (br. s, 1H), 8.58-8.46 (m, 1H), 8.20 (s, 1H), 7.27 (d, J=3.6 Hz, 1H), 6.64 (d, J=3.6 Hz, 1H), 5.10 (d, J=4.4 Hz, 1H), 4.97 (s, 2H), 4.20 (t, J=5.6 Hz, 3H), 3.56-3.52 (m, 1H), 3.47-3.39 (m, 1H), 3.02 (t, J=5.4 Hz, 2H), 2.15-2.12 (m, 1H), 2.00-1.87 (m, 1H), 1.64-1.46 (m, 2H)

LCMS: Rt=0.863 min, [M+H]$^+$=369.3

Example 21: Synthesis of Compound 151

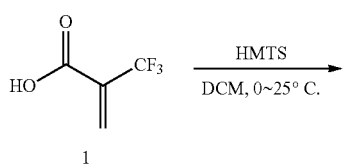

1

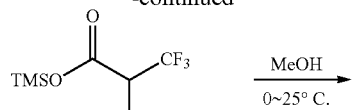

2

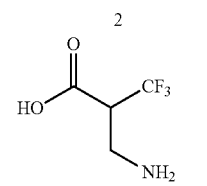

3
the compound was prepared according to ref:
J. Org. Chem., 1989, 54, 4511-4522

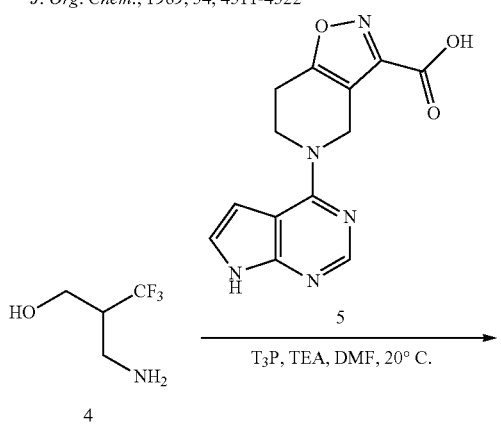

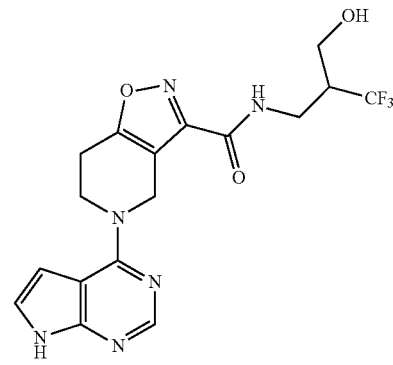

151

Preparation of Compound 2

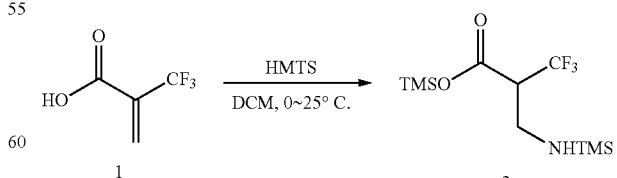

To a solution of Compound 1 (1.0 g, 7.14 mmol, 1 eq) in DCM (10 mL) was added HMTS (2.30 g, 14.28 mmol, 2.99 mL, 2 eq) dropwise at 0-5° C. After addition, the reaction mixture was stirred at 25° C. for 14 hr. TLC (PE/EA=2/1, Rf=0.05) showed Compound 1 was consumed completely and a main spot was formed. The reaction mixture was concentrated give Compound 2 (3.2 g, crude) as yellow oil.

$^{1}$H NMR (400 MHz, CDCl$_{3}$)

δ=3.30-3.23 (m, 1H), 3.22-3.12 (m, 1H), 3.03 (d, J=11.6 Hz, 1H), 0.33 (s, 9H), 0.08-0.07 (m, 6H).

Preparation of Compound 3

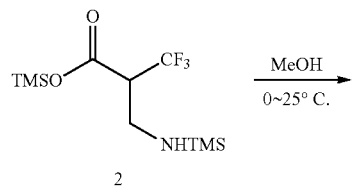

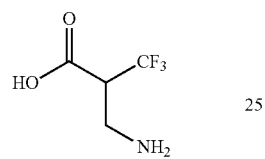

3
the compound was prepared according to ref:
J. Org. Chem., 1989, 54, 4511-4522

MeOH (15 mL) was added to Compound 2 (3.2 g, 10.62 mmol, 1 eq) dropwise at 0° C. After addition, the reaction mixture was stirred at 25° C. for 14 hr. The reaction mixture was concentrated to give Compound 3 (1.02 g, crude) as white solid.

$^{1}$H NMR (400 MHz, MeOD)

δ=3.53-3.45 (m, 1H), 3.45-3.37 (m, 1H), 3.30-3.25 (m, 1H).

LCMS: Rt=0.075 min, [M+H]$^{+}$=158.0

Preparation of Compound 4

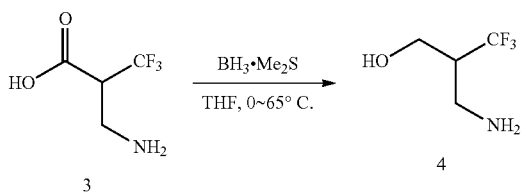 [SMILES: NCC(C(=O)O)C(F)(F)F ; "BH3·Me2S" ; NCC(CO)C(F)(F)F]

To a mixture of Compound 3 (500 mg, 3.18 mmol, 1 eq) in THF (5.0 mL) was added BH$_{3}$·Me$_{2}$S (10 M, 636.57 uL, 2 eq) dropwise at 0° C. After addition, the reaction mixture was stirred at 65° C. for 2 hr. LCMS showed a main peak which contain the starting material and the desired mass. The reaction mixture was quenched with MeOH (10 mL). The mixture was concentrated to give Compound 4 (520 mg, crude) as white solid.

LCMS: Rt=0.306 min, [M+H]$^{+}$=144.3

Preparation of Compound 151

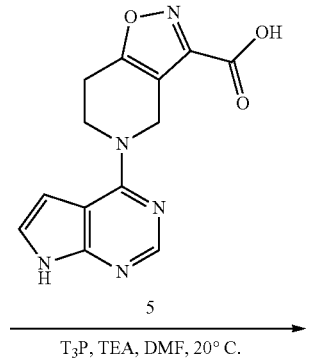

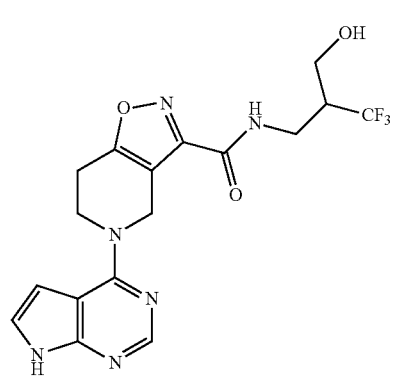

To a mixture of Compound 4 (100.34 mg, 701.12 umol, 4 eq), Compound 5 (50 mg, 175.28 umol, 1 eq) and T3P (278.85 mg, 438.20 umol, 260.61 uL, 50% purity, 2.5 eq) in DMF (0.7 mL) was added TEA (70.95 mg, 701.12 umol, 97.59 uL, 4 eq). The mixture was stirred at 20° C. for 16 hr. LCMS showed Compound 5 was consumed completely and desired mass was detected. The reaction mixture was diluted with H$_{2}$O (20 mL), extracted with EtOAc (30 mL), washed with brine (30 mL*3), dried over Na$_{2}$SO$_{4}$, filtered and concentrated. The residue was purified by prep-HPLC (column: Boston Green ODS 150*30 mm*5 um; mobile phase: [water(0.225% FA)-ACN]; B %: 8%-38%, 10 min) to give Compound 151 (6.78 mg, 14.64 umol, 8.35% yield, 98.56% purity, FA) as white solid.

$^{1}$H NMR (400 MHz, DMSO-d$_{6}$)

δ=11.80 (s, 1H), 8.92 (t, J=6.0 Hz, 1H), 8.37 (s, 1H), 8.20 (s, 1H), 7.30-7.24 (m, 1H), 6.68-6.60 (m, 1H), 4.98 (s, 2H), 4.21 (t, J=5.6 Hz, 2H), 3.68-3.63 (m, 2H), 3.62-3.56 (m, 1H), 3.53-3.48 (m, 1H), 3.03 (t, J=5.2 Hz, 2H), 2.78-2.69 (m, 1H).

$^{19}$F NMR (400 MHz, DMSO-d$_{6}$)

δ=66.76.

LCMS: Rt=0.574 min, [M+H]$^{+}$=411.1.

Example 22: Synthesis of Compound 152

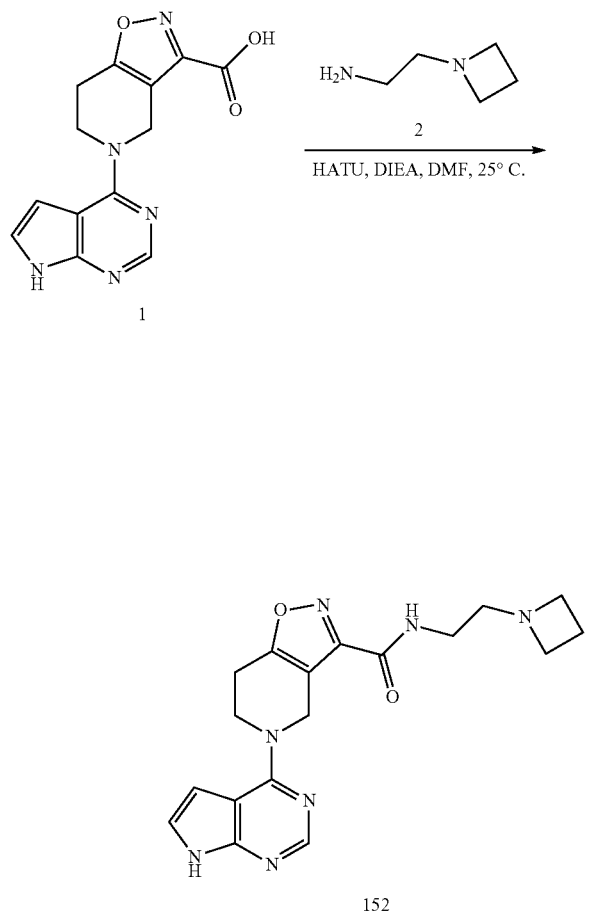

To a solution of Compound 1 (30 mg, 105.17 umol, 1 eq) and Compound 2 (21.07 mg, 210.34 umol, 2 eq) in DMF (1 mL) was added HATU (59.98 mg, 157.75 umol, 1.5 eq) and DIEA (40.78 mg, 315.50 umol, 54.96 uL, 3 eq). The mixture was stirred at 25° C. for 1 hr. LCMS showed Compound 1 was consumed and a major peak with desired mass was detected. The reaction mixture was diluted with water (10 mL), extracted with EtOAc (10 mL*2), washed with H$_2$O (10 mL) and brine (10 mL), dried over Na$_2$SO$_4$, filtered and concentrated. The residue was purified by prep-HPLC (column: Waters Xbridge 150*50 10 u; mobile phase: [water (0.05% ammonia hydroxide v/v)-ACN]; B %: 15%-35%, 10 min) to give Compound 152 (11.91 mg, 31.91 umol, 30.34% yield, 98.442% purity) as yellow solid.

$^1$H NMR (400 MHz, DMSO-d6)

δ=11.80 (br. s, 1H), 8.59 (t, J=5.7 Hz, 1H), 8.20 (s, 1H), 7.27 (d, J=3.5 Hz, 1H), 6.64 (d, J=3.7 Hz, 1H), 4.97 (s, 2H), 4.21 (t, J=5.6 Hz, 2H), 3.26-2.63 (m, 10H), 1.94 (t, J=6.9 Hz, 2H)

$^{13}$C NMR (101 MHz, DMSO-d6)

δ=169.17, 159.27, 156.97, 154.83, 152.50, 151.01, 122.56, 112.02, 102.96, 100.86, 58.30, 55.12, 42.18, 41.88, 40.77, 40.67, 40.45, 37.44, 23.62, 17.82

LCMS: Rt=0.849 min, [M+H]$^+$=368.3

Example 23: Synthesis of Compound 153

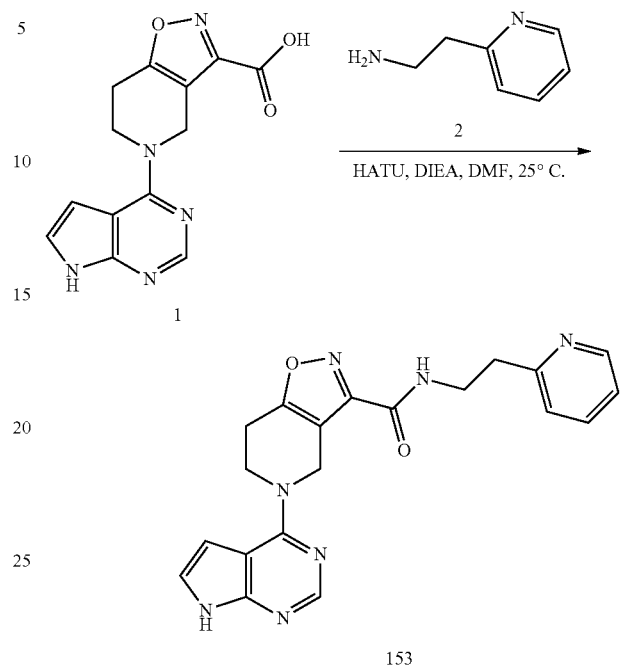

To a solution of Compound 1 (100 mg, 350.56 umol, 1 eq) in DMF (3 mL) was added HATU (266.59 mg, 701.12 u mol, 2 eq), DIEA (135.92 mg, 1.05 mmol, 183.18 uL, 3 eq) and Compound 2 (128.48 mg, 1.05 mmol, 125.96 uL, 3 eq). The mixture was stirred at 25° C. for 1 hr. LCMS showed Compound 1 was consumed and a major peak with desired mass was detected. The reaction mixture was diluted with H$_2$O (20 mL), filtered. The filter cake was purified by prep-HPLC (column: Welch Xtimate C18 150*25 mm*5 um; mobile phase: [water(0.05% ammonia hydroxide v/v)-ACN]; B %: 17%-47%, 10 min) to give Compound 153 (29.49 mg, 72.37 umol, 20.64% yield, 95.560% purity) as yellow solid.

$^1$H NMR (400 MHz, DMSO-d6)

δ=11.81 (br. s, 1H), 8.89 (br. t, J=5.7 Hz, 1H), 8.50 (br. d, J=4.3 Hz, 1H), 8.21 (s, 1H), 7.70 (dt, J=1.7, 7.6 Hz, 1H), 7.35-7.11 (m, 3H), 6.63 (d, J=3.4 Hz, 1H), 4.96 (s, 2H), 4.20 (br. t, J=5.5 Hz, 2H), 3.63 (q, J=6.9 Hz, 2H), 3.09-2.94 (m, 4H)

$^{13}$C NMR (101 MHz, DMSO-d6)

δ=169.16, 159.35, 159.31, 156.96, 154.82, 152.48, 151.01, 149.55, 136.98, 123.63, 122.57, 122.05, 112.03, 102.95, 100.88, 42.17, 41.86, 40.62, 40.41, 39.09, 37.38, 23.62

LCMS: Rt=0.843 min, [M+H]$^+$=390.3

Example 24: Synthesis of Compound 154

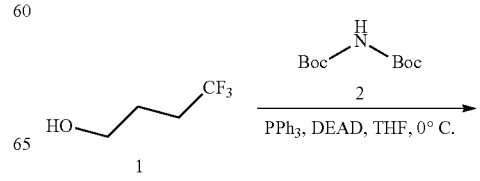

Ethylacetate/Petroleum ether gradient @ 50 mL/min) to afford Compound 3 (1.2 g, 3.67 mmol, 46.96% yield, 100% purity) as yellow oil.

$^1$H NMR (400 MHz, CDCl$_3$)

δ=3.65 (t, J=7.2 Hz, 2H), 2.18-2.02 (m, 2H), 1.85 (quin, J=7.6 Hz, 2H), 1.52 (s, 18H)

Preparation of Compound 4

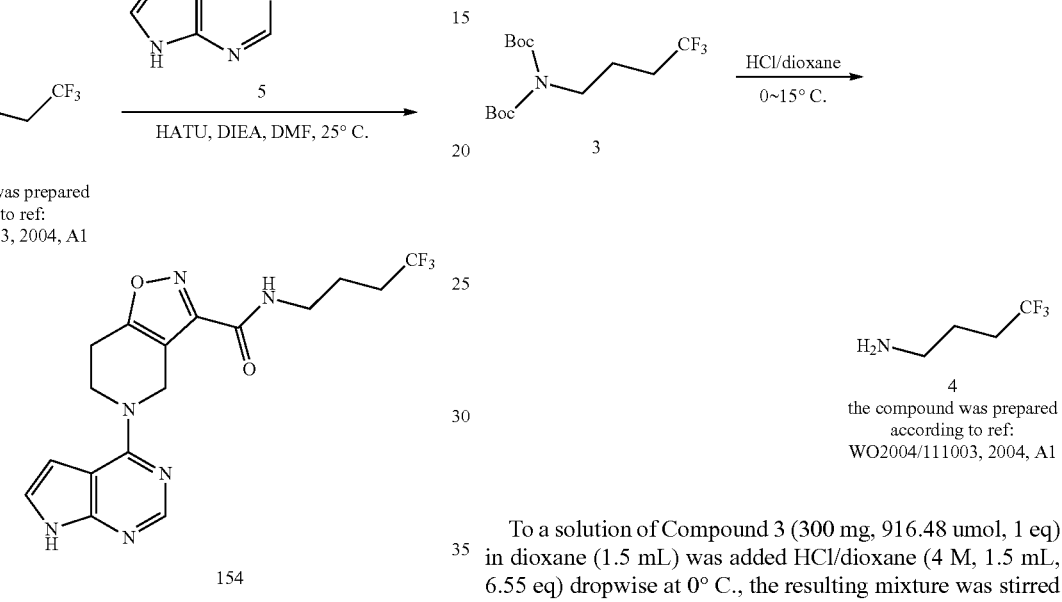

To a solution of Compound 3 (300 mg, 916.48 umol, 1 eq) in dioxane (1.5 mL) was added HCl/dioxane (4 M, 1.5 mL, 6.55 eq) dropwise at 0° C., the resulting mixture was stirred at 15° C. for 12 hr. TLC (PE:EA=10:1) showed Compound 3 was consumed, and one new spot was observed. The mixture was concentrated, re-evaporated with MTBE (5 mL*2) to give Compound 4 (150 mg, crude, HCl) as white solid.

$^1$H NMR (400 MHz, DMSO-d)

δ=8.28-7.97 (m, 3H), 2.92-2.79 (m, 2H), 2.46-2.31 (m, 2H), 1.85-1.77 (m, 2H)

Preparation of Compound 154

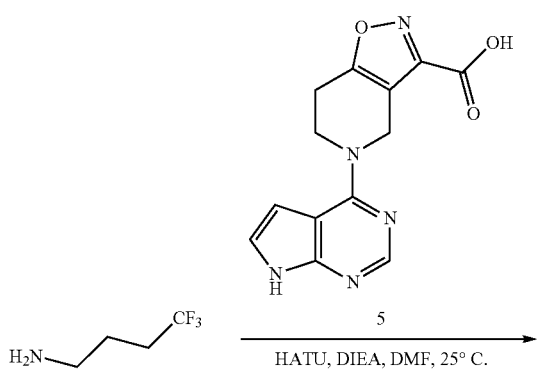

Preparation of Compound 3

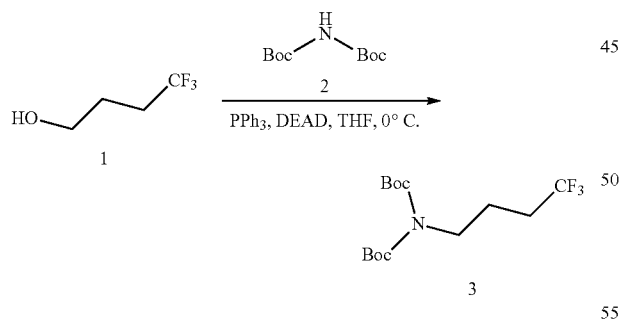

To a solution of Compound 1 (1.0 g, 7.81 mmol, 1 eq), PPh$_3$ (2.46 g, 9.37 mmol, 1.2 eq) and Compound 2 (1.70 g, 7.81 mmol, 1 eq) in THF (20 mL) was added DEAD (1.63 g, 9.37 mmol, 1.70 mL, 1.2 eq) dropwise at 0° C. under N$_2$. The reaction mixture was stirred at 0° C. for 5 hr. TLC (PE:EA=5:1) showed Compound 1 was still remained, and two new spots were formed. The mixture was quenched with H$_2$O (20 mL), extracted with EtOAc (30 mL*2), dried with anhydrous Na$_2$SO$_4$, filtered and concentrate. The residue was purified by flash silica gel chromatography (Biotage®; 40.0 g SepaFlash® Silica Flash Column, Eluent of 0-20%

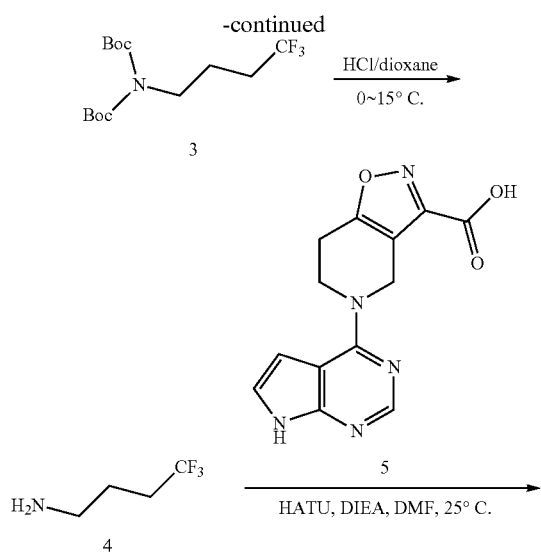

163

-continued

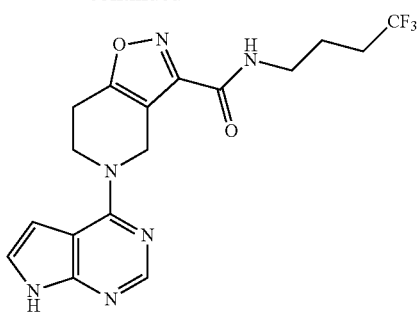

154

To a mixture of Compound 5 (100 mg, 350.56 umol, 1 eq) and DIEA (181.23 mg, 1.40 mmol, 244.25 uL, 4 eq) in DMF (5 mL) was added HATU (199.94 mg, 525.84 umol, 1.5 eq), the mixture was stirred at 25° C. for 1 hr. Then Compound 4 (86.01 mg, 525.84 umol, 1.5 eq, HCl) was added, the mixture was stirred at 25° C. for 12 hr. LCMS showed Compound 5 was consumed. The mixture was diluted with water (5 mL), extracted with EtOAc (10 mL*2), washed with brine (5 mL), dried with anhydrous $Na_2SO_4$, filtered and concentrated. The residue was purified by prep-HPLC (column: Phenomenex Synergi C18 150*25*10 um; mobile phase: [water(0.225% FA)-ACN]; B %: 14%-47%, 10 min) to give Compound 154 (34.67 mg, 86.26 umol, 24.60% yield, 98.11% purity) as light yellow solid.

$^1$H NMR (400 MHz, DMSO-d6)

δ=11.80 (br. s, 1H), 8.92 (t, J=5.6 Hz, 1H), 8.22-8.15 (m, 1H), 7.27 (dd, J=2.4, 3.2 Hz, 1H), 6.64 (dd, J=1.6, 3.6 Hz, 1H), 4.98 (s, 2H), 4.22 (t, J=5.6 Hz, 2H), 3.38-3.32 (m, 2H), 3.03 (br. t, J=5.6 Hz, 2H), 2.37-2.22 (m, 2H), 1.76 (quin, J=7.6 Hz, 2H)

$^{13}$C NMR (101 MHz, DMSO-d6)

δ=168.74, 159.13, 156.54, 154.35, 152.04, 150.58, 122.13, 111.66, 102.52, 100.43, 41.74, 41.44, 37.59, 23.18, 21.65, 21.62

LCMS: Rt=0.821 min, [M+H]$^+$=395.0

Example 25: Synthesis of Compound 155

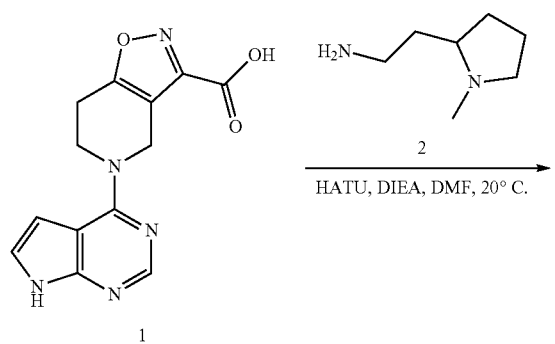

164

-continued

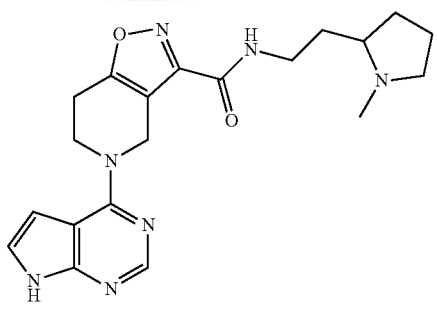

155

A mixture of Compound 1 (100 mg, 350.56 umol, 1 eq), Compound 2 (67.42 mg, 525.84 umol, 76.18 uL, 1.5 eq), HATU (159.95 mg, 420.67 umol, 1.2 eq) and DIEA (135.92 mg, 1.05 mmol, 183.18 uL, 3 eq) in DMF (2 mL) was stirred at 20° C. for 12 hr. LCMS showed a major peak with desired MS was detected. The mixture was filtered. The residue was purified by prep-HPLC (column: Welch Xtimate C18 150*25 mm*5 um; mobile phase: [water(0.05% ammonia hydroxide v/v)-ACN]; B %: 25%-55%, 10 min) to give Compound 155 (40 mg, 100.14 umol, 28.56% yield, 99% purity) as off-white solid.

$^1$H NMR (400 MHz, MeOD)

δ=8.21 (s, 1H), 7.20 (d, J=3.7 Hz, 1H), 6.76 (d, J=3.7 Hz, 1H), 5.09 (s, 2H), 4.31 (t, J=5.7 Hz, 2H), 3.49-3.40 (m, 2H), 3.11-3.03 (m, 3H), 2.35 (s, 3H), 2.27-2.18 (m, 2H), 2.16-2.01 (m, 2H), 1.87-1.72 (m, 2H), 1.64-1.50 (m, 2H)

$^{13}$C NMR (101 MHz, MeOD)

δ=168.94, 160.08, 157.17, 154.24, 151.17, 150.21, 121.60, 111.43, 103.17, 100.74, 64.26, 56.48, 42.16, 41.85, 39.17, 36.67, 32.44, 30.06, 23.04, 21.23

LCMS: Rt=0.931 min, [M+H]$^+$=396.3

Example 26: Synthesis of Compound 156

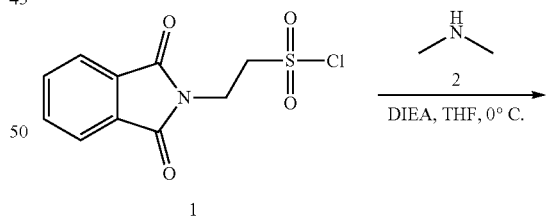

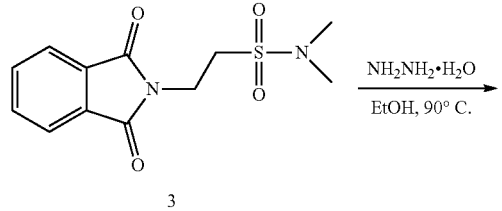

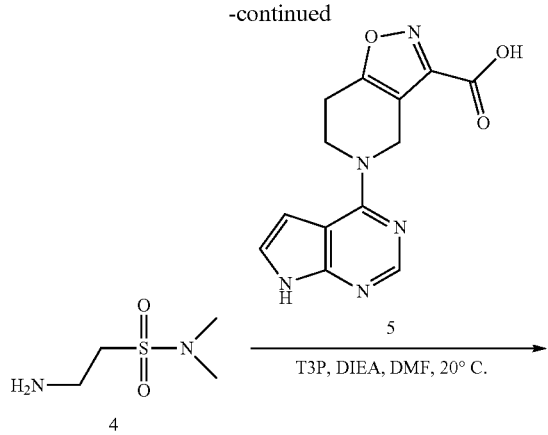

Preparation of Compound 3

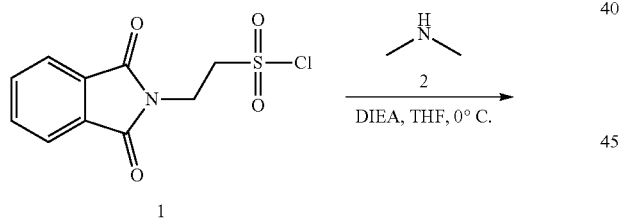

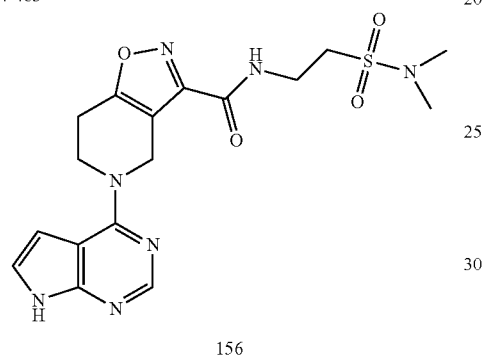

156

To a solution of Compound 1 (500 mg, 1.83 mmol, 1 eq) in THF (10 mL) was added DIEA (708.31 mg, 5.48 mmol, 954.60 uL, 3 eq) and Compound 2 (178.77 mg, 2.19 mmol, 91.35 uL, 1.2 eq, HCl) at 0° C., the mixture was stirred at 0° C. for 1 hr. LCMS showed Compound 1 was consumed, and desired MS was detected. The mixture was diluted with water (45 mL), extracted with EtOAc (40 mL*3), washed with brine (40 mL*2), dried over $Na_2SO_4$, filtered and concentrated to give Compound 3 (300 mg, crude) as a yellow solid.

$^1$H NMR (400 MHz, $CDCl_3$)

δ=7.80 (dd, J=3.0, 5.4 Hz, 2H), 7.67 (dd, J=3.1, 5.4 Hz, 2H), 4.11-4.05 (m, 2H), 3.27 (dd, J=6.6, 7.7 Hz, 2H), 2.84 (s, 6H)

Preparation of Compound 4

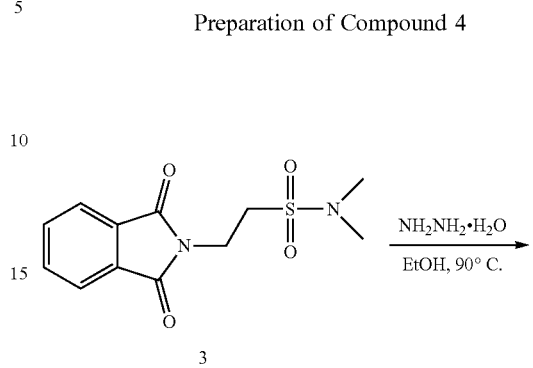

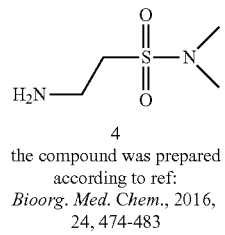

4
the compound was prepared according to ref:
Bioorg. Med. Chem., 2016, 24, 474-483

To a solution of Compound 3 (300 mg, 1.06 mmol, 1 eq) in EtOH (10 mL) was added $NH_2NH_2 \cdot H_2O$ (75.10 mg, 1.28 mmol, 72.91 uL, 85% purity, 1.2 eq), the mixture was stirred at 90° C. for 12 hr. TLC showed Compound 3 was consumed, and one major new spot with larger polarity was detected. The mixture was filtered and concentrated, diluted with water (10 mL), adjusted with 1 N HCl solution to pH=3. Residual insoluble material was filtered off. The clear filtrate was lyophilized to give Compound 4 (232 mg, crude, HCl) as brown solid.

$^1$H NMR (400 MHz, MeOD)

δ=3.43-3.37 (m, 4H), 2.93 (s, 6H)

Preparation of Compound 156

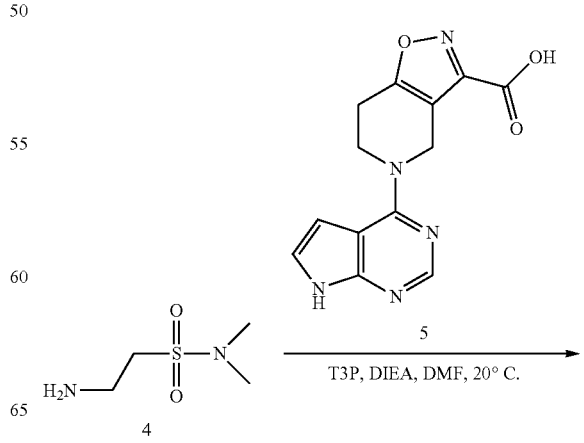

-continued

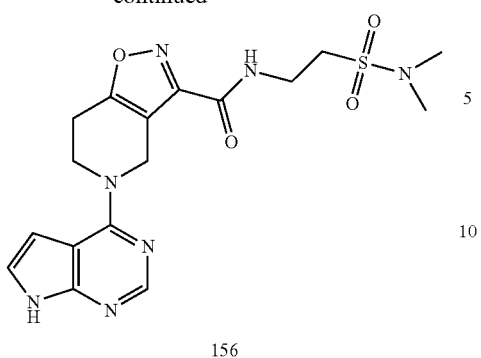

156

To a mixture of Compound 5 (151.19 mg, 530.01 umol, 1 eq) and Compound 4 (100 mg, 530.01 umol, 1 eq, HCl) in DMF (1.5 mL) was added DIEA (205.50 mg, 1.59 mmol, 276.95 uL, 3 eq) and T3P (252.96 mg, 795.01 umol, 236.41 uL, 50% purity, 0.75 eq), the mixture was stirred at 20° C. for 15 hr. LCMS showed Compound 5 was consumed, and desired MS was detected. The mixture was filtered, the residue was purified by prep-HPLC (column: Phenomenex luna C18 250*50 mm*10 um; mobile phase: [water(0.075% TFA)-ACN]; B %: 8%-38%, 9 min) to give Compound 156 (20 mg, 36.85 umol, 6.95% yield, 98.3% purity, TFA) as yellow solid.

¹H NMR (400 MHz, MeOD)

δ=8.39 (s, 1H), 7.42 (d, J=3.7 Hz, 1H), 7.02 (d, J=3.7 Hz, 1H), 5.19 (s, 2H), 4.41 (t, J=5.7 Hz, 2H), 3.82 (t, J=6.9 Hz, 2H), 3.37-3.32 (m, 2H), 3.17 (br. t, J=5.6 Hz, 2H), 2.89 (s, 6H)

¹³C NMR (101 MHz, MeOD)

δ=168.18, 153.92, 142.54, 124.06, 117.12, 114.26, 110.28, 103.59, 102.71, 45.73, 43.52, 36.21, 33.52, 22.90

LCMS: Rt=0.713 min, [M+H]⁺=420.0

Example 27: Synthesis of Compound 157

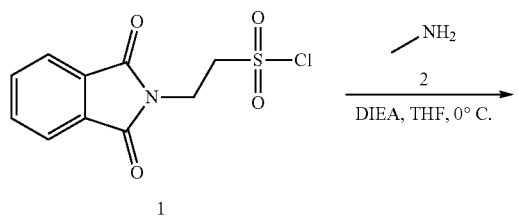

1

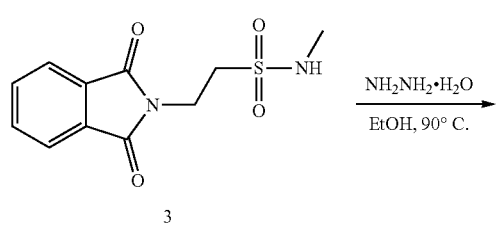

3

-continued

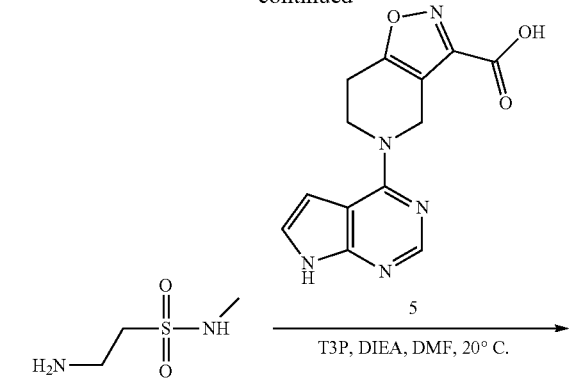

the compound was prepared according to ref:
*Bioorg. Med. Chem.*, 1998, 8, 1607-1612

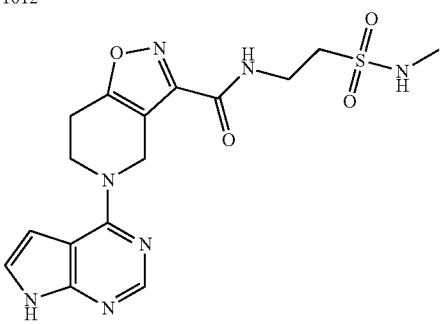

157

Preparation of Compound 3

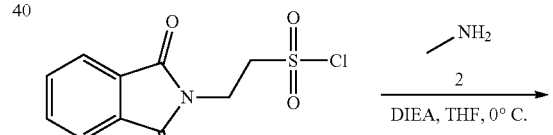

1

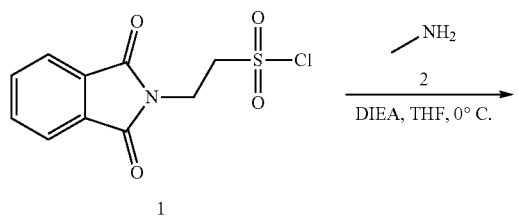

3

To a solution of Compound 1 (1 g, 3.65 mmol, 1 eq) in THF (10 mL) was added DIEA (944.42 mg, 7.31 mmol, 1.27 mL, 2 eq) and Compound 2 (2 M, 2.19 mL, 1.2 eq) at 0° C., the mixture was stirred at 0° C. for 1 hr. LCMS showed Compound 1 was consumed, and desired MS was detected. The mixture was diluted with water (45 mL), extracted with EtOAc (40 mL*3), washed with brine (40 mL*2), dried over Na₂SO₄, filtered and concentrated to give Compound 3 (770 mg, crude) as white solid.

¹H NMR (400 MHz, CDCl₃)

δ=3.54 (br. d, J=5.6 Hz, 2H), 3.44 (br. d, J=6.1 Hz, 2H), 2.72 (s, 3H)

Preparation of Compound 4

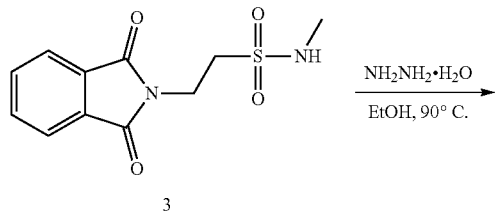

3

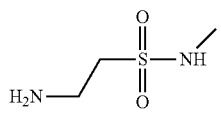

4
the compound was prepared according to ref:
*Bioorg. Med. Chem.*, 1998, 8, 1607-1612

To a solution of Compound 3 (770 mg, 2.87 mmol, 1 eq) in EtOH (15 mL) was added NH$_2$NH$_2$·H$_2$O (175.93 mg, 3.44 mmol, 170.80 uL, 98% purity, 1.2 eq), the mixture was stirred at 90° C. for 12 hr. TLC showed Compound 3 was consumed, and one major new spot with larger polarity was detected. The mixture was filtered and concentrated, diluted with water (10 mL), adjusted with 1 N HCl solution to pH=3. Residual insoluble material was filtered off. The clear filtrate was lyophilized to give Compound 4 (400 mg, crude, HCl) as a yellow solid.

$^1$H NMR (400 MHz, MeOD)

δ=3.46-3.36 (m, 4H), 2.77 (s, 3H)

Preparation of Compound 157

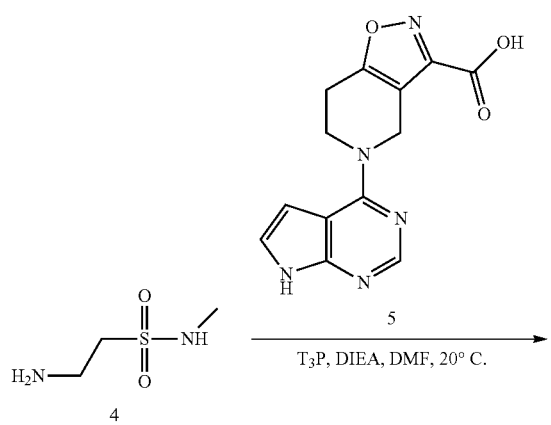

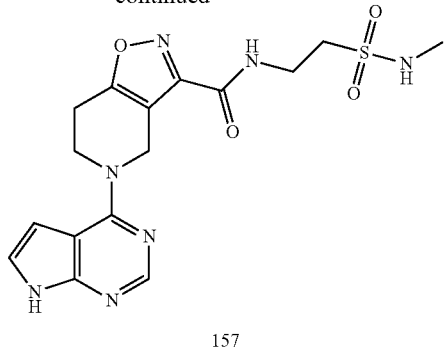

157

To a mixture of Compound 5 (163.33 mg, 572.58 umol, 1 eq) and Compound 4 (100 mg, 572.58 umol, 1 eq, HCl) in DMF (1.5 mL) was added DIEA (222.00 mg, 1.72 mmol, 299.19 uL, 3 eq) and T3P (182.18 mg, 572.58 umol, 170.26 uL, 50% purity, 0.5 eq), the mixture was stirred at 20° C. for 15 hr. LCMS showed Compound 5 was consumed, and desired MS was detected. The mixture was filtered, the residue was purified by prep-HPLC (column: Phenomenex luna C18 250*50 mm*10 um; mobile phase: [water(0.075% TFA)-ACN]; B %: 2%-32%, 9 min) to give Compound 157 (41 mg, 76.17 umol, 13.30% yield, 96.5% purity, TFA) as yellow solid.

$^1$H NMR (400 MHz, MeOD)

δ=8.40 (br. s, 1H), 7.41 (br. d, J=3.4 Hz, 1H), 7.00 (d, J=3.5 Hz, 1H), 5.17 (s, 2H), 4.41 (br. t, J=5.6 Hz, 2H), 3.79 (t, J=6.8 Hz, 2H), 3.35 (t, J=6.8 Hz, 2H), 3.16 (br. t, J=5.3 Hz, 2H), 2.74 (s, 3H)

$^{13}$C NMR (101 MHz, MeOD)

δ=168.28, 161.67, 161.32, 160.97, 160.61, 159.89, 155.02, 153.90, 144.02, 143.20, 123.81, 120.85, 117.96, 115.05, 112.05, 110.39, 103.30, 102.75, 48.41, 43.34, 33.88, 27.74, 22.91

LCMS: Rt=0.783 min, [M+H]$^+$=406.2

Example 28: Synthesis of Compound 158

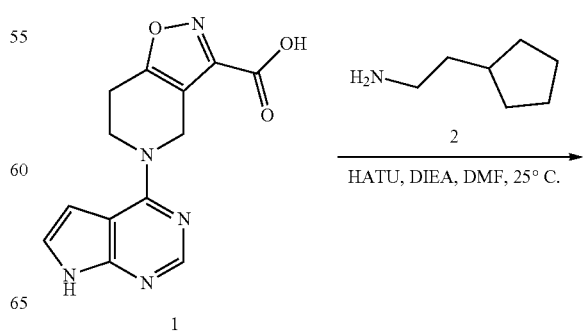

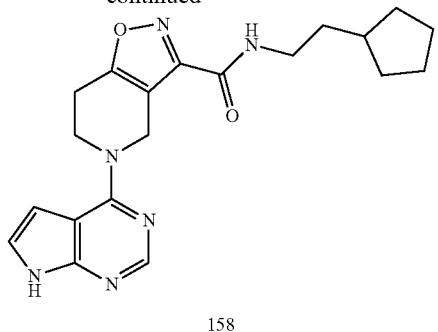

158

To a solution of Compound 1 (100 mg, 350.56 umol, 1 eq) in DMF (3 mL) was added HATU (266.59 mg, 701.12 umol, 2 eq), DIEA (135.92 mg, 1.05 mmol, 183.18 uL, 3 eq) and Compound 2 (157.40 mg, 1.05 mmol, 3 eq, HCl). The mixture was stirred at 25° C. for 1 hr. LCMS showed Compound 1 was consumed and a major peak with desired mass was detected. The reaction mixture was diluted with H$_2$O (20 mL), filtered. The filter cake was purified by prep-HPLC (column: Welch Xtimate C18 150*25 mm*5 um; mobile phase: [water(0.05% ammonia hydroxide v/v)-ACN]; B %: 37%-67%, 10 min) to give Compound 158 (27.79 mg, 72.81 umol, 20.77% yield, 99.681% purity) as off-white solid.

$^1$H NMR (400 MHz, DMSO-d6)

δ=11.81 (br. s, 1H), 8.79 (br. t, J=5.7 Hz, 1H), 8.20 (s, 1H), 7.26 (d, J=3.5 Hz, 1H), 6.63 (d, J=3.5 Hz, 1H), 4.97 (s, 2H), 4.20 (br. t, J=5.6 Hz, 2H), 3.29-3.22 (m, 2H), 3.01 (br. t, J=5.2 Hz, 2H), 1.81-1.69 (m, 3H), 1.61-1.51 (m, 4H), 1.50-1.41 (m, 2H), 1.14-1.04 (m, 2H)

$^{13}$C NMR (101 MHz, DMSO-d6)

δ=169.08, 159.21, 156.96, 154.94, 152.47, 151.01, 122.55, 112.01, 102.95, 100.87, 42.17, 41.89, 40.62, 40.41, 38.62, 37.72, 35.64, 32.59, 25.16, 23.61

LCMS: Rt=1.008 min, [M+H]$^+$=381.3

Example 29: Synthesis of Compound 159

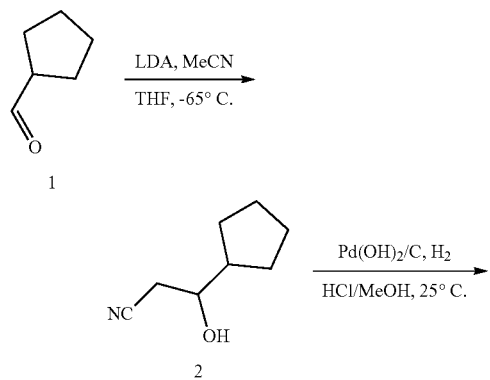

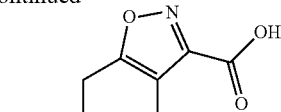

3
the compound was prepared according to ref:
ChemCatChem, 2018, 10, 2868-2872

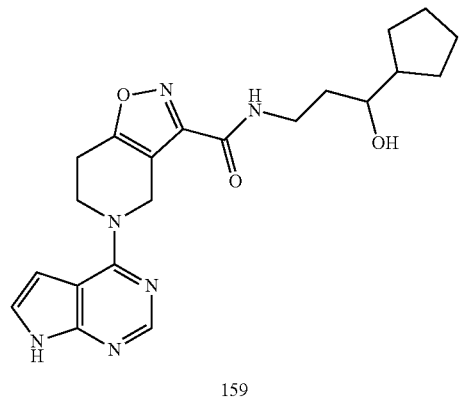

159

Preparation of Compound 2

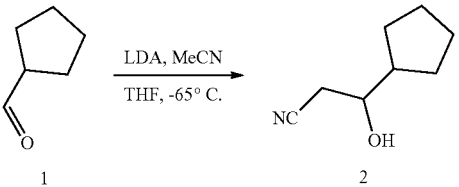 [SMILES: O=CC1CCCC1 ; "LDA, MeCN" ; N#CCC(O)C1CCCC1]

MeCN (627.43 mg, 15.28 mmol, 804.40 uL, 1.5 eq) was added to LDA (2.0 M, 7.64 mL, 1.5 eq) at −65° C. under N$_2$ atmosphere. The solution was stirred at −65° C. for 0.5 hr under N$_2$ atmosphere. Then a solution of Compound 1 (1.0 g, 10.19 mmol, 1 eq) in THF (10 mL) was added, the solution was stirred at −65° C. for 2 hr under N$_2$ atmosphere. TLC (PE/EA=3/1, Rf=0.35) indicated one new main spot was formed. The mixture was quenched with 1 N HCl solution (30 mL), extracted with EtOAc (30 ml*3), dried over Na$_2$SO$_4$, filtered and concentrated. The residue was purified by flash silica gel chromatography (80 g SepaFlash® Silica Flash Column, Eluent of 0-100% Ethylacetate/Petroleum ether gradient) to give Compound 2 (1.1 g, 6.88 mmol, 67.48% yield, 87% purity) as yellow gum.

$^1$H NMR (400 MHz, DMSO-d$_6$)

δ=5.22 (d, J=5.6 Hz, 1H), 3.59-3.45 (m, 1H), 2.65-2.58 (m, 1H), 2.49-2.45 (m, 1H), 1.93-1.79 (m, 1H), 1.74-1.64 (m, 1H), 1.63-1.41 (m, 5H), 1.40-1.29 (m, 1H), 1.20-1.14 (m, 1H).

Preparation of Compound 3

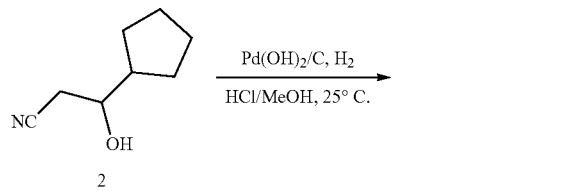

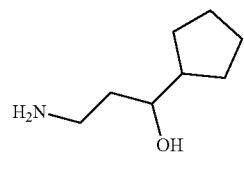

3
the compound was prepared according to ref: *ChemCatChem*, 2018, 10, 2868-2872

A mixture of Compound 2 (200 mg, 1.44 mmol, 1 eq) and Pd(OH)$_2$/C (20 mg, 28.48 umol, 20% purity) in 4 N HCl/MeOH (4 mL) was stirred at 25° C. for 18 hrs under H$_2$ atmosphere at 50 psi. TLC (PE/EA=2/1, Rf=0.01) showed Compound 2 was consumed completely and a new spot was formed. The reaction mixture was filtered and concentrated to give Compound 3 (152 mg, HCl salt) as yellow solid.

$^1$H NMR (400 MHz, DMSO-d$_6$)

δ=8.00-7.72 (m, 3H), 3.89 (s, 4H), 3.32-3.26 (m, 1H), 2.95-2.77 (m, 2H), 1.83-1.41 (m, 9H), 1.39-1.26 (m, 1H), 1.25-1.11 (m, 1H).

Preparation of Compound 159

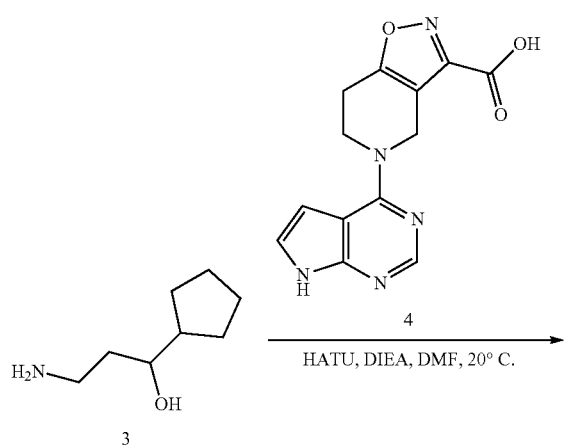

-continued

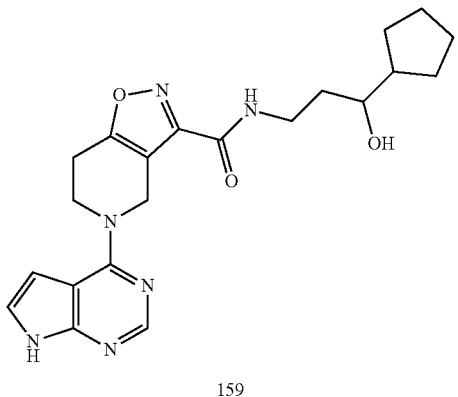

159

To a mixture of Compound 4 (60 mg, 210.34 umol, 1 eq), Compound 3 (75.59 mg, 420.67 umol, 2 eq, HCl) and HATU (319.90 mg, 841.34 umol, 4 eq) in DMF (0.5 mL) was added DIEA (163.11 mg, 1.26 mmol, 219.82 uL, 6 eq). The mixture was stirred at 20° C. for 1 hr. LCMS showed Compound 4 was consumed completely and a main peak which contain the desired MS was detected. The reaction mixture was diluted with H$_2$O (10 mL), extracted with EtOAc (20 mL), washed with brine (10 mL), dried over Na$_2$SO$_4$, filtered and concentrated. The residue was purified by prep-HPLC (column: Waters Xbridge 150*25 5um; mobile phase: [water(10 mM NH$_4$HCO$_3$)-ACN]; B %: 32%-48%, 10 min) to give Compound 159 (31.53 mg, yield 35.54%, purity 97.31%) as off-white solid.

$^1$H NMR (400 MHz, DMSO-d$_6$)

δ=11.80 (s, 1H), 8.71 (s, 1H), 8.25-8.14 (m, 1H), 7.27 (d, J=3.6 Hz, 1H), 6.64 (d, J=3.6 Hz, 1H), 4.98 (s, 2H), 4.51 (s, 1H), 4.21 (t, J=5.6 Hz, 2H), 3.46-3.35 (m, 3H), 3.02 (t, J=5.6 Hz, 2H), 1.85-1.77 (m, 1H), 1.75-1.41 (m, 8H), 1.40-1.30 (m, 1H), 1.25-1.14 (in, 1H).

$^{13}$C NMR (101 MHz, DMSO-d$_6$)

δ=168.67, 158.78, 156.51, 154.46, 152.03, 150.56, 122.11, 111.55, 102.49, 100.42, 71.69, 45.93, 41.85, 41.73, 36.54, 35.28, 28.73, 28.16, 25.43, 25.21, 23.17.

LCMS: Rt=0.792 min, [M+H]$^+$=411.2.

Example 30: Synthesis of Compound 160

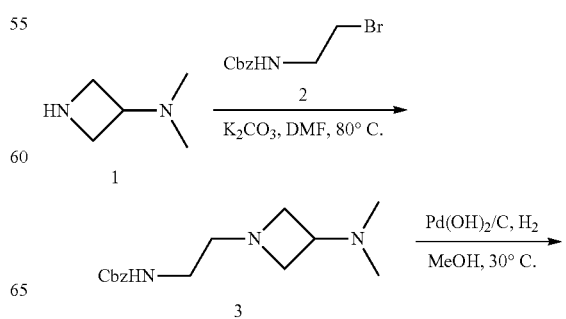

-continued

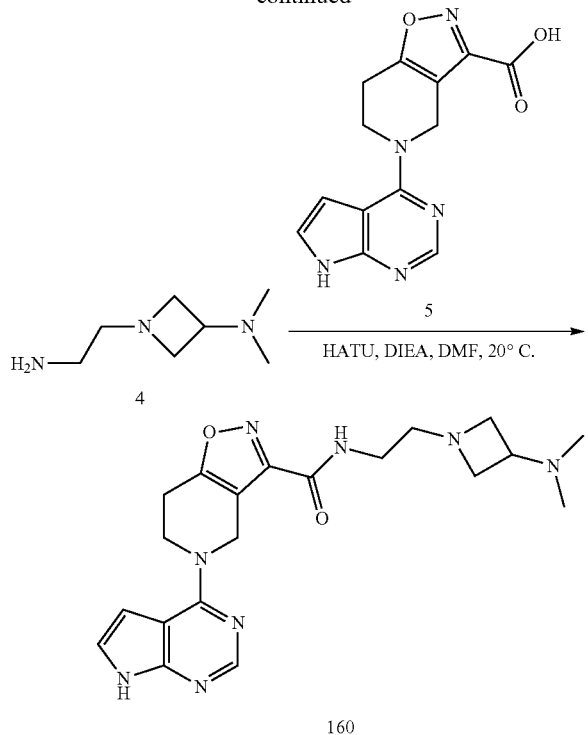

Preparation of Compound 3

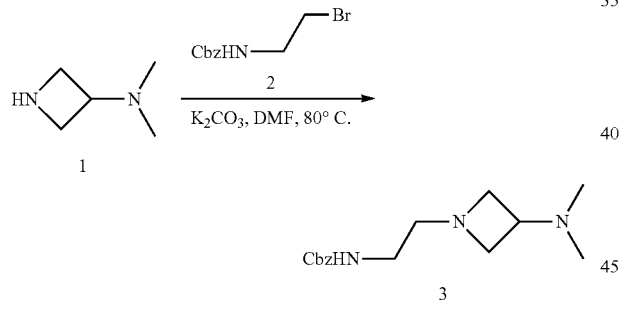

To a solution of Compound 1 (500 mg, 2.89 mmol, 1 eq, 2HCl) and Compound 2 (894.75 mg, 3.47 mmol, 1.2 eq) in MeCN (5 mL) was added $K_2CO_3$ (2.00 g, 14.44 mmol, 5 eq). The mixture was stirred at 80° C. for 3 hr. LCMS showed desired mass was detected. The reaction mixture was cooled to 0° C. and filtered. The filtrate was concentrated, purified by reversed-phase (0.1% $NH_3H_2O$) to afford Compound 3 (500 mg, 52.42% yield, 84% purity) as a yellow oil.
LCMS: Rt=0.834 min, $[M+H]^+$=278.3

Preparation of Compound 4

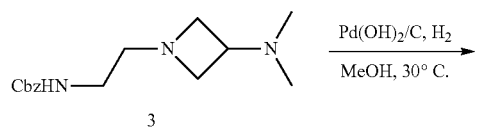

-continued

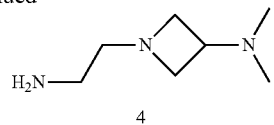

To a solution of Compound 3 (270 mg, 973.46 umol, 1 eq) in MeOH (4 mL) was added $Pd(OH)_2/C$ (54 mg, 194.69 umol, 20% purity, 0.2 eq) under $N_2$. The suspension was degassed under vacuum and purged with $H_2$ several times. The mixture was stirred at 30° C. under $H_2$ balloon for 12 hr. LCMS showed desired mass was detected. The reaction mixture was filtered and concentrated to afford Compound 4 (100 mg, 71.72% yield) as yellow solid.
LCMS: Rt=0 min, $[M+H]^+$=144.2

Preparation of Compound 160

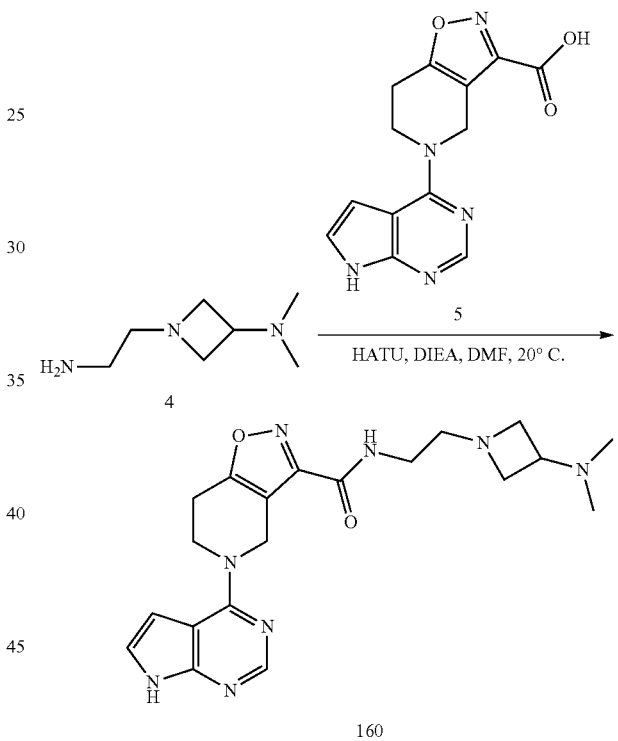

To a solution of Compound 5 (120 mg, 420.67 umol, 1 eq) and HATU (399.88 mg, 1.05 mmol, 2.5 eq) in DMF (1.2 mL) was added Compound 4 (72.30 mg, 504.81 umol, 1.2 eq) and DIEA (217.48 mg, 1.68 mmol, 293.09 uL, 4 eq). The mixture was stirred at 20° C. for 1 hr. LCMS showed desired mass was detected. The reaction mixture was filtered, purified by prep-HPLC (column: Xtimate C18 10 u 250 mm*80 mm; mobile phase: [water(0.05% ammonia hydroxide v/v)-ACN]; B %: 20%-40%, 10 min) to afford Compound 160 (18.51 mg, 42.90 umol, 10.20% yield, 95.125% purity) as yellow solid.
$^1$H NMR (400 MHz, DMSO-d6)
δ=11.82 (s, 1H), 8.85-8.52 (t, J=5.8 Hz, 1H), 8.20 (s, 1H), 7.33-7.17 (m, 1H), 6.73-6.50 (m, 1H), 4.97 (s, 2H), 4.39-4.02 (t, J=5.4 Hz, 2H), 3.45-3.41 (m, 3H), 3.25-3.16 (m, 2H), 3.07-2.96 (t, J=5.2 Hz, 2H), 2.77-2.70 (m, 2H), 2.55-2.53 (m, 2H), 2.08-1.89 (s, 6H)
$^{13}$C NMR (400 MHz, DMSO-d6)

δ=169.17, 159.30, 156.97, 154.83, 152.49, 151.01, 122.58, 112.03, 102.96, 100.86, 59.42, 58.40, 56.94, 42.16, 40.61, 40.44, 40.40, 40.19, 39.98, 39.78, 39.36, 23.62

LCMS: Rt=0.805 min, [M+H]⁺=411.3

Example 31: Synthesis of Compound 161

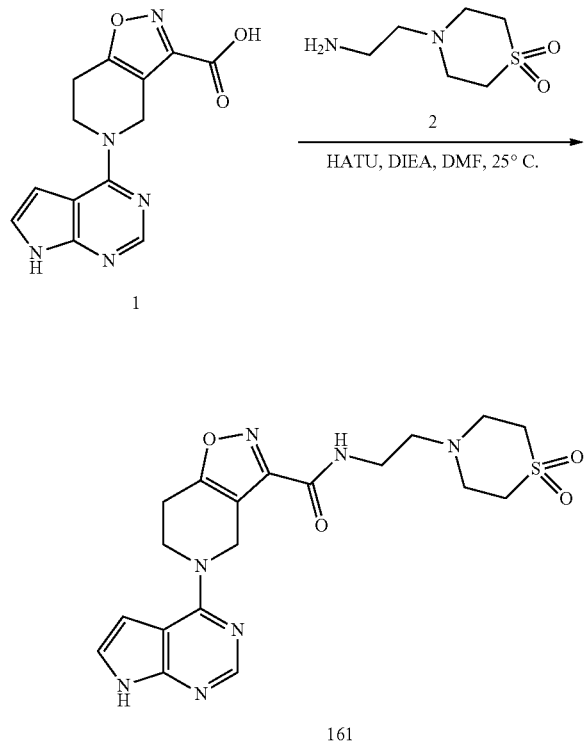

To a solution of Compound 1 (100 mg, 350.56 umol, 1 eq) in DMF (3 mL) was added HATU (266.59 mg, 701.12 umol, 2 eq), DIEA (135.92 mg, 1.05 mmol, 183.18 uL, 3 eq) and Compound 2 (93.73 mg, 525.84 umol, 1.5 eq). The mixture was stirred at 25° C. for 1 hr. LCMS showed Compound 1 was consumed and desired mass was detected. The reaction mixture was diluted with H₂O (10 mL), filtered. The filter cake was purified by prep-HPLC (column: Xtimate C18 10 u 250 mm*80 mm; mobile phase: [water(0.05% ammonia hydroxide v/v)-ACN]; B %: 18%-38%, 10 min) to give Compound 161 (6.24 mg, 13.93 u mol, 3.97% yield, 99.436% purity) as off-white solid.

¹H NMR (400 MHz, DMSO-d6)

δ=12.10-11.52 (m, 1H), 8.71 (br. t, J=5.7 Hz, 1H), 8.20 (s, 1H), 7.26 (d, J=3.4 Hz, 1H), 6.63 (d, J=3.5 Hz, 1H), 4.97 (s, 2H), 4.21 (br. t, J=5.4 Hz, 2H), 3.14-2.81 (m, 12H), 2.67 (br. t, J=6.4 Hz, 2H)

¹³C NMR (101 MHz, DMSO-d6)

δ=169.22, 159.44, 156.96, 154.85, 152.47, 151.02, 122.60, 112.04, 102.95, 100.86, 54.75, 50.84, 50.71, 42.22, 41.83, 40.61, 40.40, 36.90, 23.62

LCMS: Rt=0.808 min, [M+H]⁺=446.2

Example 32: Synthesis of Compound 162

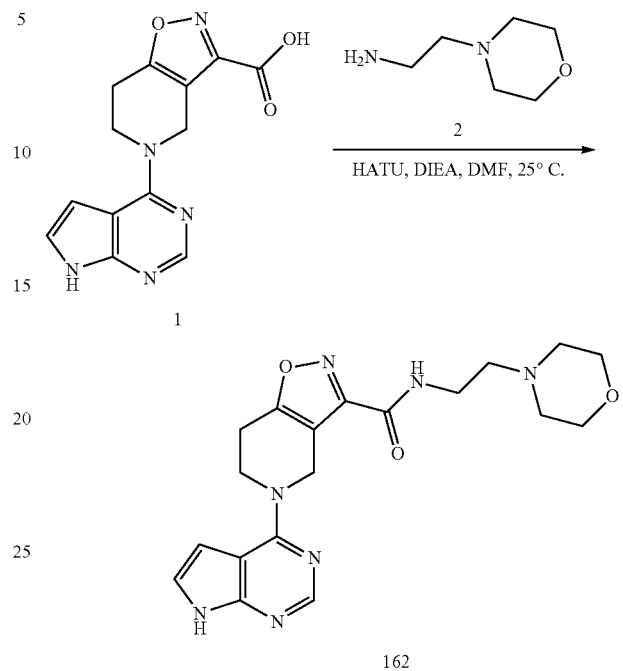

To a solution of Compound 1 (150 mg, 525.84 umol, 1 eq) in DMF (3 mL) was added HATU (399.88 mg, 1.05 mmol, 2 eq), DIEA (203.88 mg, 1.58 mmol, 274.78 uL, 3 eq) and Compound 2 (136.92 mg, 1.05 mmol, 138.02 uL, 2 eq). The mixture was stirred at 25° C. for 1 hr. LCMS showed Compound 1 was consumed and a major peak with desired mass was detected. The reaction mixture was diluted with H₂O (20 mL), filtered. The filter cake was purified by prep-HPLC (column: Xtimate C18 10 u 250 mm*80 mm; mobile phase: [water(0.05% ammonia hydroxide v/v)-ACN]; B %: 10%-40%, 10 min) to give Compound 162 (55.36 mg, 138.85 u mol, 26.40% yield, 99.677% purity) as yellow solid.

¹H NMR (400 MHz, DMSO-d6)

δ=12.29-11.08 (m, 1H), 8.67 (br. t, J=5.6 Hz, 1H), 8.20 (s, 1H), 7.27 (d, J=3.6 Hz, 1H), 6.63 (d, J=3.5 Hz, 1H), 4.97 (s, 2H), 4.20 (t, J=5.6 Hz, 2H), 3.56 (t, J=4.6 Hz, 4H), 3.47-3.40 (m, 2H), 3.02 (br. t, J=5.4 Hz, 2H), 2.46 (t, J=6.8 Hz, 2H), 2.44-2.33 (m, 4H)

¹³C NMR (101 MHz, DMSO-d6)

δ=169.21, 159.33, 156.96, 154.82, 152.46, 151.00, 122.58, 112.04, 102.95, 100.86, 66.66, 57.39, 53.65, 42.19, 41.86, 40.60, 40.39, 36.35, 23.62

LCMS: Rt=0.817 min, [M+H]⁺=398.3

Example 33: Synthesis of Compound 163

Example 34: Synthesis of Compound 164

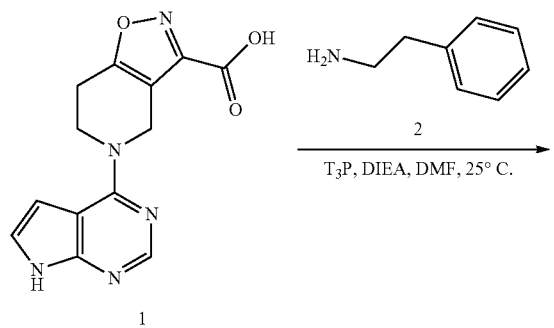

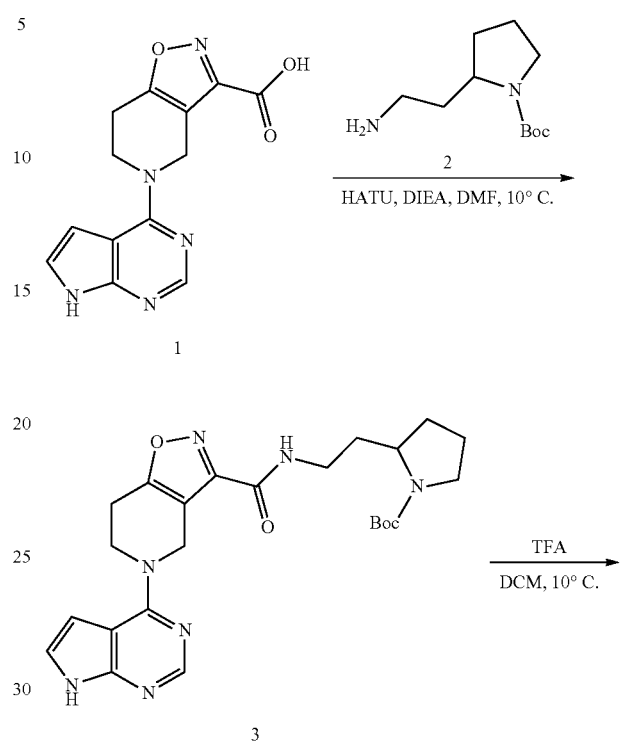

To a solution of Compound 1 (100 mg, 350.56 umol, 1 eq) and Compound 2 (127.44 mg, 1.05 m mol, 132.06 uL, 3 eq) in DMF (3 m L) was added T3P (557.71 mg, 876.40 umol, 521.22 uL, 50% purity, 2.5 eq) and DIEA (181.23 mg, 1.40 mmol, 244.25 uL, 4 eq). The mixture was stirred at 25° C. for 1 hr. LCMS showed Compound 2 was consumed and a major peak with desired mass was detected. The reaction mixture was diluted with $H_2O$ (20 mL), filtered. The filter cake was purified by prep-HPLC (column: Xtimate C18 10 u 250 mm*80 mm; mobile phase: [water(0.05% ammonia hydroxide v/v)-ACN]; B %: 32%-52%, 10 min) to give Compound 163 (35.09 mg, 89.38 u mol, 25.50% yield, 98.933% purity) as off-white solid.

$^1$H NMR (400 MHz, DMSO-d6)

δ=11.81 (br. s, 1H), 8.87 (t, J=5.7 Hz, 1H), 8.20 (s, 1H), 7.39-7.11 (m, 6H), 6.63 (d, J=3.3 Hz, 1H), 4.96 (s, 2H), 4.20 (t, J=5.6 Hz, 2H), 3.56-3.42 (m, 2H), 3.01 (br. t, J=5.4 Hz, 2H), 2.85 (t, J=7.5 Hz, 2H)

$^{13}$C NMR (101 MHz, DMSO-d6)

δ=169.16, 159.31, 156.96, 154.83, 152.47, 151.01, 139.63, 129.12, 128.83, 126.63, 122.57, 112.02, 102.95, 100.88, 42.16, 41.87, 40.74, 40.60, 40.39, 35.26, 23.61

LCMS: Rt=0.937 min, [M+H]$^+$=389.3

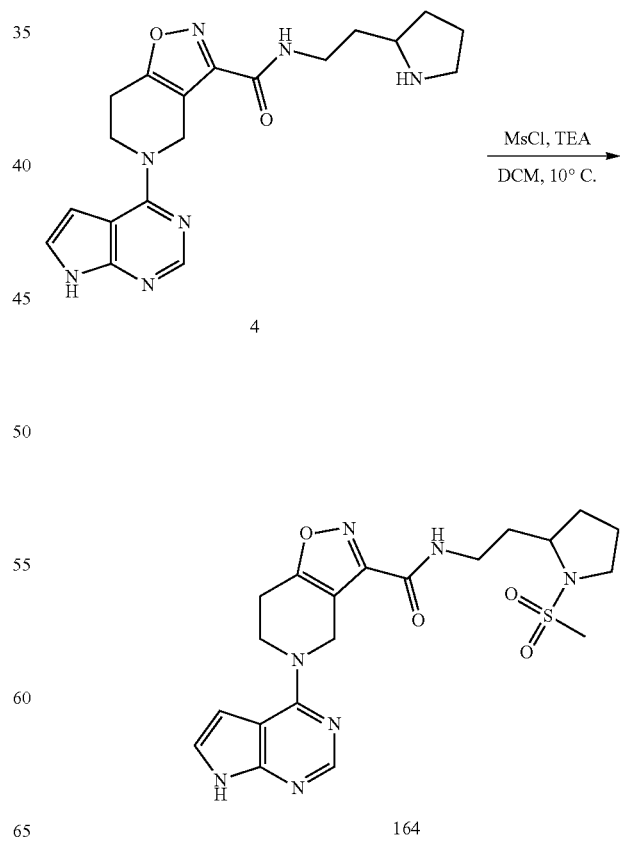

Preparation of Compound 3

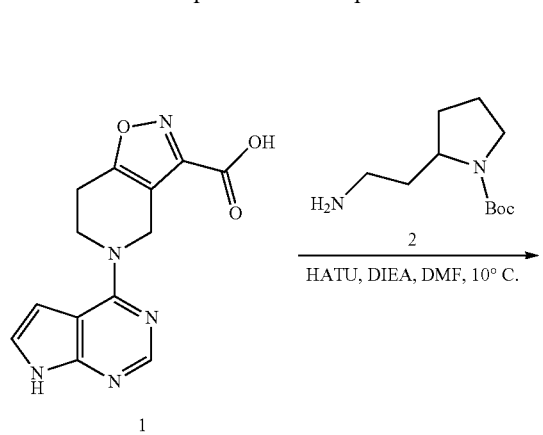

1

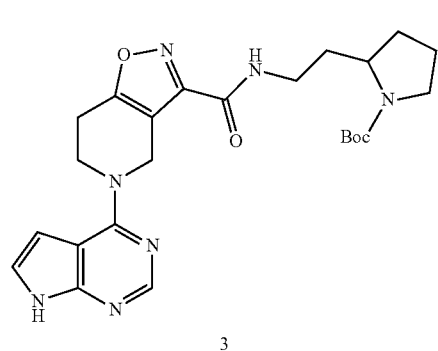

3

To a mixture of Compound 1 (150 mg, 525.84 umol, 1 eq) and Compound 2 (112.69 mg, 525.84 umol, 1 eq) in DMF (2 mL) was added HATU (799.76 mg, 2.10 mmol, 4 eq) and DIEA (339.81 mg, 2.63 mmol, 457.96 uL, 5 eq). The mixture was stirred at 10° C. for 16 hr. LCMS showed most of Compound 1 was consumed and desired mass was detected. The reaction mixture was diluted with water (50 mL), extracted with EtOAc (5 mL*3), dried over Na$_2$SO$_4$, filtered and concentrated. The residue was purified by prep-HPLC (column: Waters Xbridge 150*25 5 u; mobile phase: [water(10 mM NH$_4$HCO$_3$)-ACN]; B %: 50%-80%, 10 min) to give Compound 3 (102 mg, crude) as yellow solid.

LCMS: Rt=0.968 min, [M+H]$^+$=482.4

Preparation of Compound 4

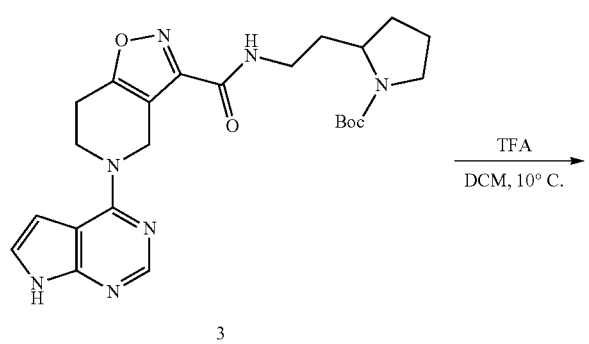

3

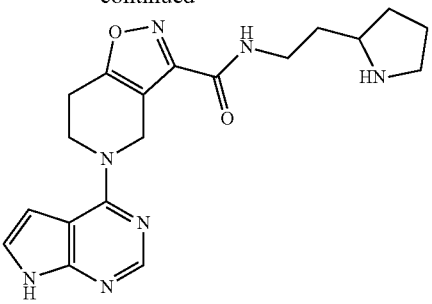

4

To a solution of Compound 3 (90 mg, 186.90 umol, 1 eq) in DCM (1 mL) was added TFA (770.00 mg, 6.75 mmol, 0.5 mL, 36.13 eq). The mixture was stirred at 10° C. for 0.5 hr. LCMS showed most of Compound 3 was consumed, and desired mass was detected. The reaction mixture was concentrated, neutralized with TEA (2 mL) at 0° C., the mixture was concentrated to give Compound 4 (82 mg, crude) as a yellow oil.

LCMS: Rt=1.143 min, [M+H]$^+$=382.3

Preparation of Compound 164

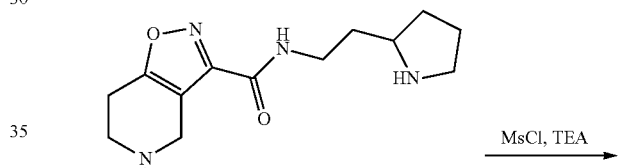

4

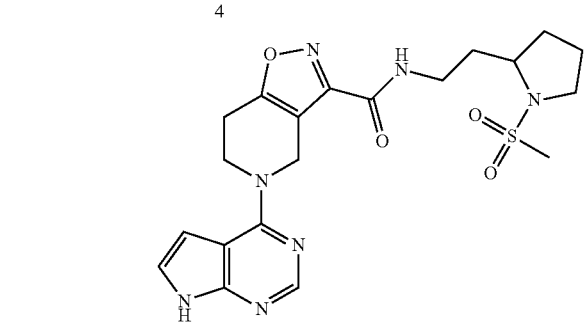

164

To a solution of Compound 4 (80 mg, 209.74 umol, 1 eq) in DCM (1.5 mL) was added TEA (42.45 mg, 419.47 umol, 58.39 uL, 2 eq) and MsCl (24.03 mg, 209.74 umol, 16.23 uL, 1 eq). The mixture was stirred at 10° C. for 1 hr. LCMS showed most of Compound 4 was consumed and desired mass was detected. The reaction mixture was diluted with water (20 mL), extracted with DCM (3 mL*3), dried over Na$_2$SO$_4$, filtered and concentrated. The residue was purified by prep-HPLC (column: Waters Xbridge 150*25 mm*5 um; mobile phase: [water(0.05% ammonia hydroxide v/v)-

ACN]; B %: 24%-54%, 10 min) to give Compound 164 (4.38 mg, 9.44 umol, 4.50% yield, 99% purity) as white solid.

¹H NMR (400 MHz, DMSO-d6) δ=11.80 (br. s, 1H), 8.74 (t, J=5.6 Hz, 1H), 8.21 (s, 1H), 7.27 (d, J=3.6 Hz, 1H), 6.65 (d, J=3.6 Hz, 1H), 4.98 (s, 2H), 4.22 (t, J=5.6 Hz, 2H), 3.71 (s, 1H), 3.30-3.20 (m, 4H), 3.03 (d, J=5.2 Hz, 2H), 2.89 (s, 3H), 2.08-1.95 (m, 1H), 1.92-1.78 (m, 3H), 1.73-1.59 (m, 2H)

LCMS: Rt=0.834 min, [M+H]⁺=460.3

Example 35: Synthesis of Compound 165

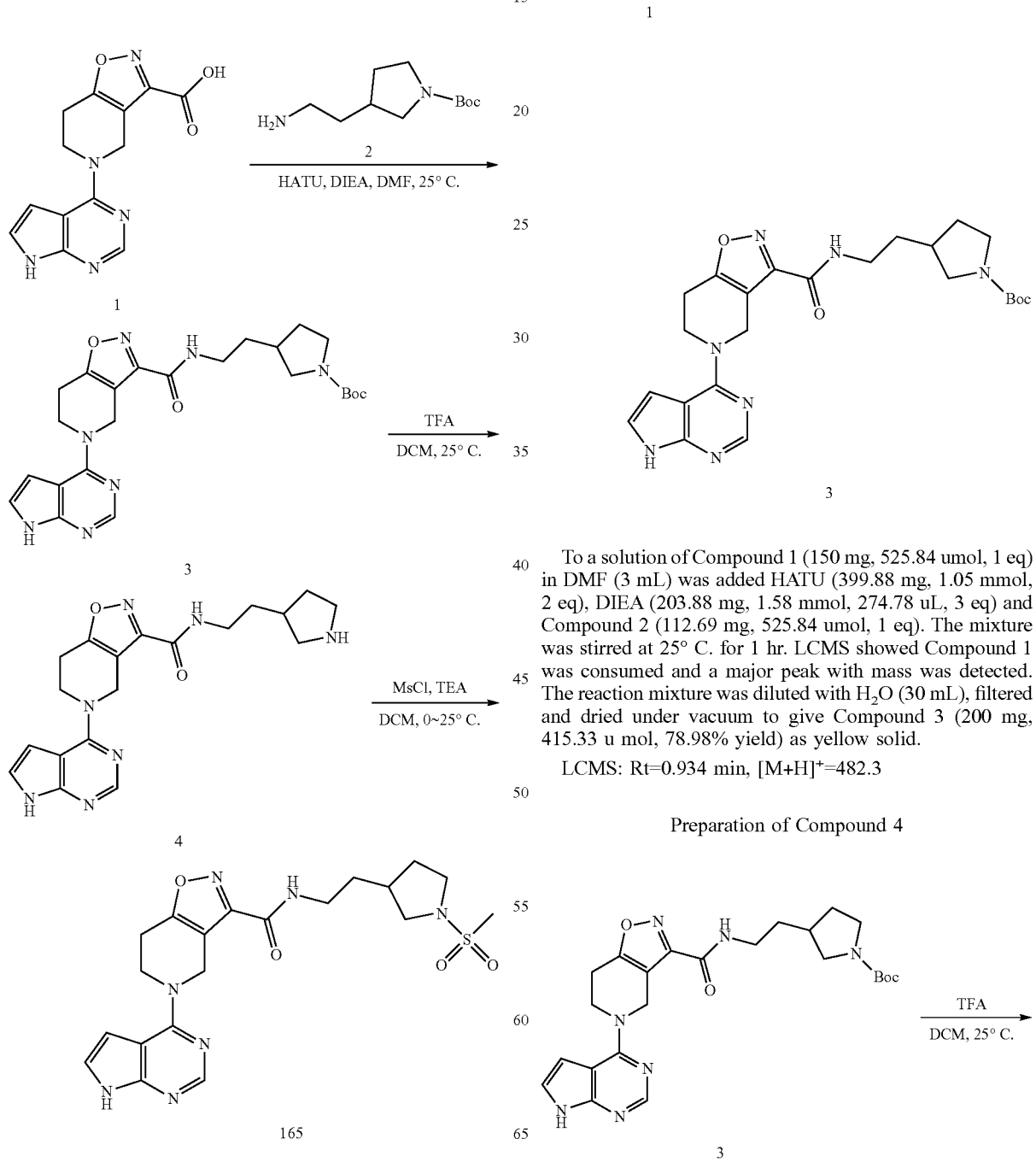

Preparation of Compound 3

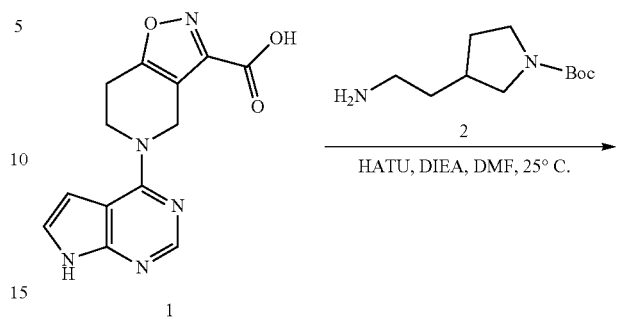

To a solution of Compound 1 (150 mg, 525.84 umol, 1 eq) in DMF (3 mL) was added HATU (399.88 mg, 1.05 mmol, 2 eq), DIEA (203.88 mg, 1.58 mmol, 274.78 uL, 3 eq) and Compound 2 (112.69 mg, 525.84 umol, 1 eq). The mixture was stirred at 25° C. for 1 hr. LCMS showed Compound 1 was consumed and a major peak with mass was detected. The reaction mixture was diluted with H₂O (30 mL), filtered and dried under vacuum to give Compound 3 (200 mg, 415.33 u mol, 78.98% yield) as yellow solid.

LCMS: Rt=0.934 min, [M+H]⁺=482.3

Preparation of Compound 4

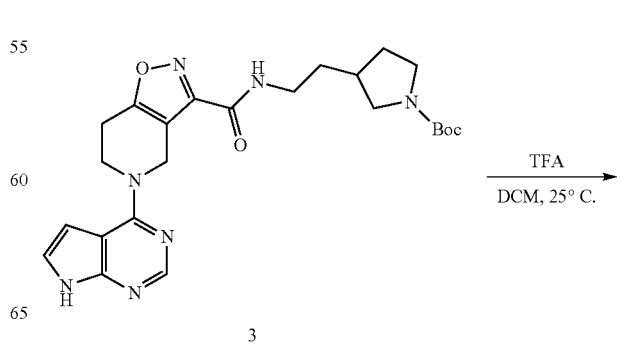

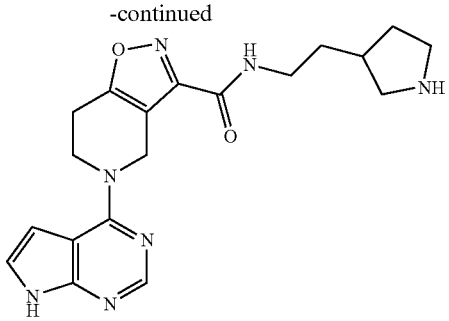

4

To a solution of Compound 3 (100 mg, 207.66 umol, 1 eq) in DCM (0.9 mL) was added TFA (462.00 mg, 4.05 mmol, 0.3 mL, 19.51 eq). The mixture was stirred at 25° C. for 0.5 hr. LCMS showed Compound 3 was consumed and a major peak with desired mass was detected. The reaction mixture was used into the next step directly as yellow solution, containing Compound 4 (102.89 mg, crude, TFA) in DCM (0.9 mL).

LCMS: Rt=1.282 min, [M+H]$^+$=382.3

Preparation of Compound 165

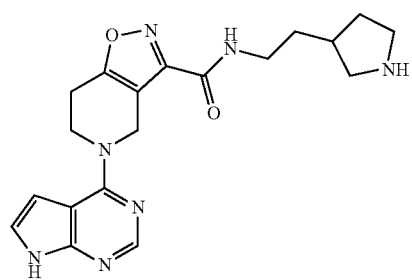

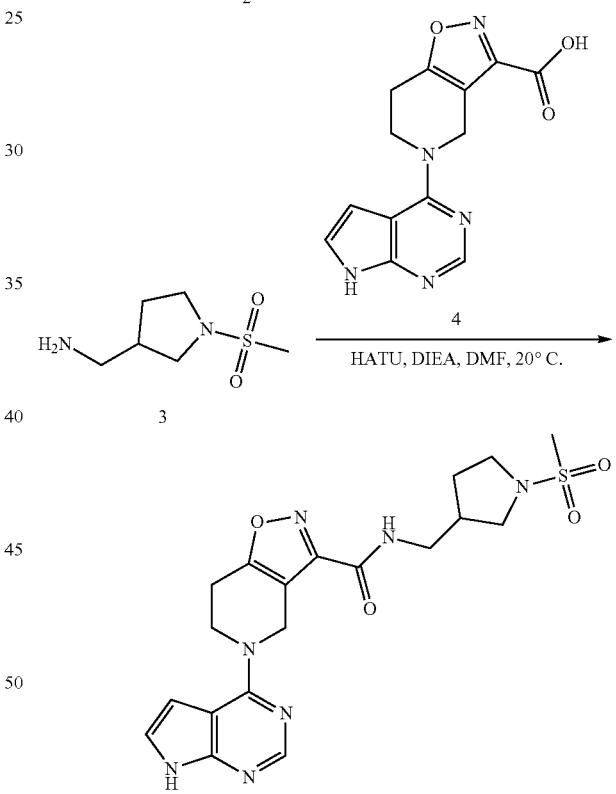

165

To a solution of Compound 4 (100 mg, 201.84 umol, 1 eq, TFA) in DCM (1 mL) was added TEA (61.27 mg, 605.51 umol, 84.28 uL, 3 eq) and MsCl (69.36 mg, 605.51 umol, 46.87 uL, 3 eq) at 0° C. The mixture was stirred at 25° C. for 1 hr. LCMS showed Compound 4 was consumed and a major peak with desired mass was detected. The reaction mixture was concentrated. The residue was purified by prep-HPLC (column: Waters Xbridge 150*25 mm*5 um; mobile phase: [water(10 mM NH$_4$HCO$_3$)-ACN]; B %: 23%-53%, 10 min) to give Compound 165 (23.23 mg, 50.45 u mol, 25.00% yield, 99.800% purity) as yellow solid.

$^1$H NMR (400 MHz, DMSO-d6)

δ=8.91 (br. d, J=2.9 Hz, 1H), 8.19 (s, 1H), 7.25 (br. d, J=1.9 Hz, 1H), 6.63 (br. d, J=1.0 Hz, 1H), 6.28-5.81 (m, 1H), 4.97 (s, 2H), 4.20 (br. t, J=5.3 Hz, 2H), 4.03-3.09 (m, 6H), 3.06-2.99 (m, 2H), 2.38-2.00 (m, 2H), 1.78-1.37 (m, 3H)

$^{13}$C NMR (101 MHz, DMSO-d6)

δ=169.16, 159.42, 159.40, 156.96, 154.83, 154.25, 152.43, 150.99, 122.55, 112.03, 102.94, 100.83, 52.78, 51.71, 47.47, 42.18, 41.88, 40.54, 39.77, 37.89, 37.78, 37.21, 34.30, 32.22, 31.94, 31.87, 29.19, 23.61

LCMS: Rt=0.908 min, [M+H+H$_2$O]$^+$=478.3

Example 36: Synthesis of Compound 166

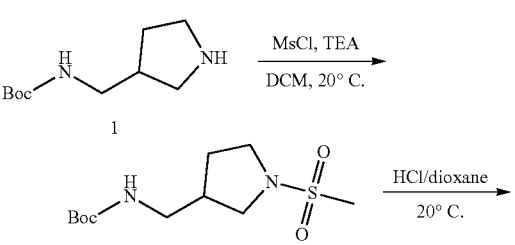

166

Preparation of Compound 2

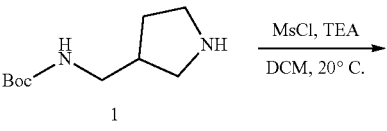

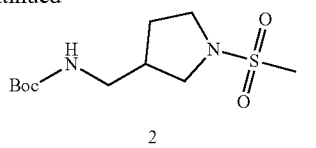

To a suspension of Compound 1 (500 mg, 2.5 mmol, 1 eq) in DCM (10 mL) was added TEA (758 mg, 7.5 mmol, 3 eq) and MsCl (570 mg, 5 mmol, 2 eq), the mixture was stirred at 20° C. for 12 hr. The mixture was diluted with water (10 mL), extracted with DCM (10 mL*2), washed with brine (10 mL), dried over Na$_2$SO$_4$, filtered and concentrated. The residue was purified by silica gel column chromatography (Petroleum ether/Ethyl acetate=20/1~1/1) to give Compound 2 (400 mg, 1.44 mmol, 57.55% yield) as off-white solid.

Preparation of Compound 3

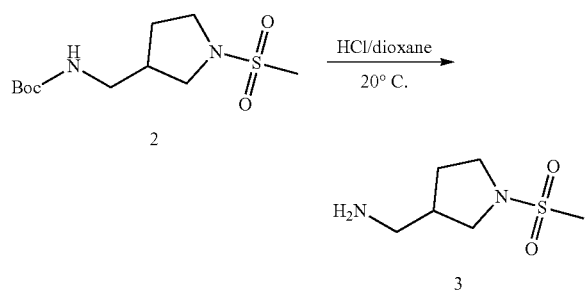

To a solution of Compound 2 (150 mg, 538.86 umol, 1 eq) in DCM (3 mL) was added TFA (1.5 mL), the mixture was stirred at 20° C. for 0.5 hr. LCMS showed Compound 2 was consumed completely and desired mass was detected. The mixture was concentrated to give Compound 3 (150 mg, crude, TFA) as brown oil.

LCMS: Rt=0.324 min, [M+H]$^+$=179.2

Preparation of Compound 166

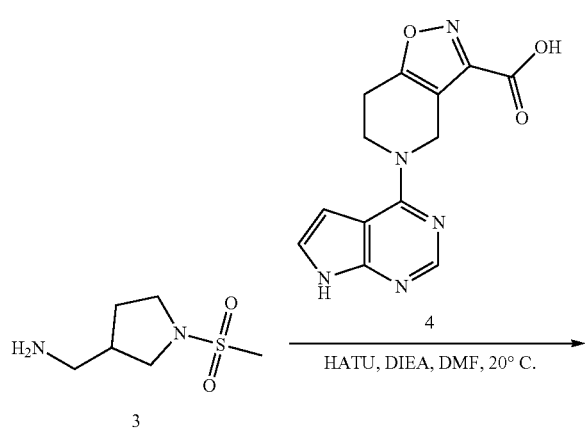

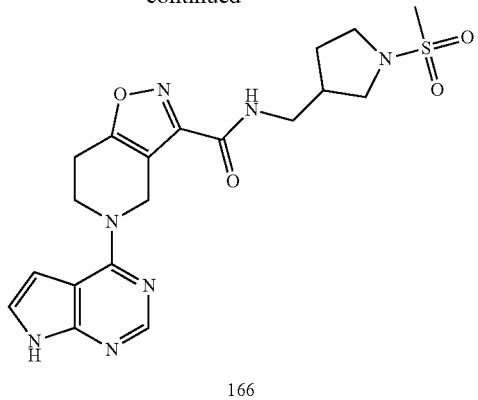

To a solution of Compound 4 (50 mg, 175.28 umol, 1 eq), HATU (199.94 mg, 525.84 umol, 3 eq) and DIEA (113.27 mg, 876.40 umol, 152.65 uL, 5 eq) in DMF (2 mL) was added Compound 3 (102.46 mg, 350.56 umol, 2 eq, TFA). The mixture was stirred at 20° C. for 0.5 hr. LCMS showed Compound 4 was consumed completely and desired mass was detected. The mixture was diluted with H$_2$O (20 mL), extracted with EtOAc (20 mL*2), washed with brine (20 mL), dried over Na$_2$SO$_4$, filtered and concentrated. The residue was purified by prep-HPLC (column: Welch Xtimate C18 150*25 mm*5 um; mobile phase: [water (0.05% ammonia hydroxide v/v)-ACN]; B %: 16%-46%, 10 min) to give Compound 166 (43.25 mg, 100% purity, 55.41% yield) as white solid.

$^1$H NMR (400 MHz, DMSO-d)

δ=11.78 (br. s, 1H), 9.00 (br. t, J=5.9 Hz, 1H), 8.22-8.14 (m, 1H), 7.26 (d, J=3.7 Hz, 1H), 6.63 (d, J=3.7 Hz, 1H), 4.97 (s, 2H), 4.21 (t, J=5.6 Hz, 2H), 3.36 (dd, J=7.3, 10.0 Hz, 2H), 3.30-3.17 (m, 3H), 3.05-2.97 (m, 3H), 2.90 (s, 3H), 2.07 (s, 1H), 2.03-1.92 (m, 1H), 1.72-1.61 (m, 1H)

$^{13}$C NMR (101 MHz, DMSO-d)

δ=167.10, 157.53, 154.83, 152.66, 150.35, 148.89, 120.46, 109.98, 98.73, 49.17, 45.24, 40.05, 39.74, 39.22, 36.80, 31.40, 27.17, 21.48, 42.09

LCMS: Rt=0.814 min, [M+H]$^+$=446.1

Example 37: Synthesis of Compound 167

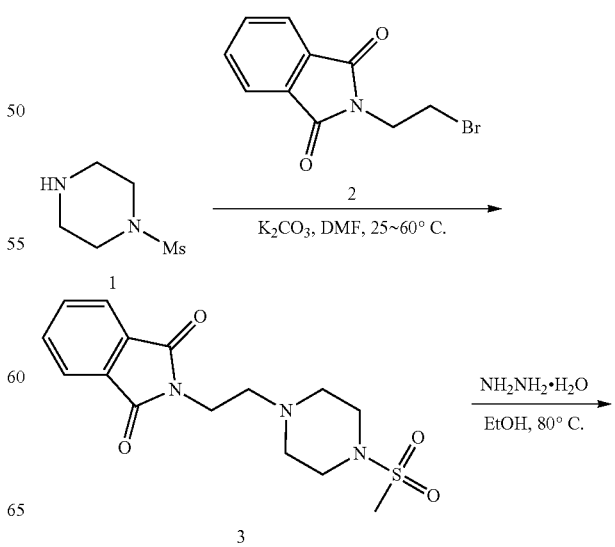

-continued

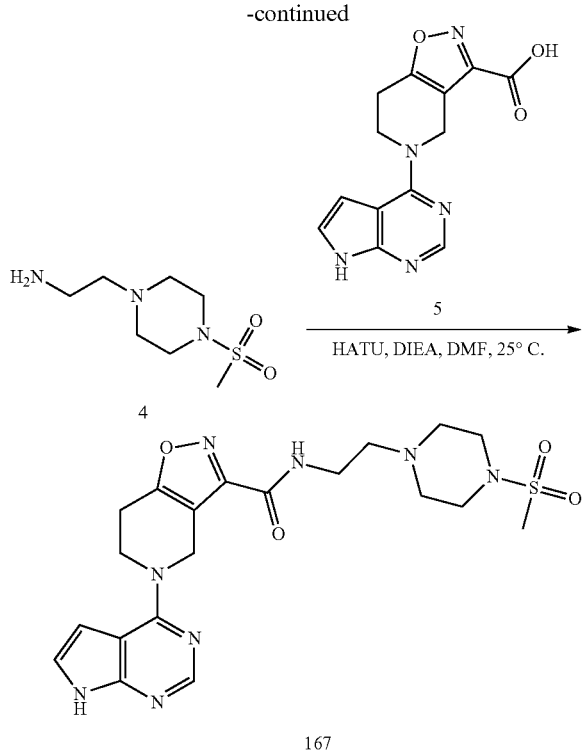

Preparation of Compound 3

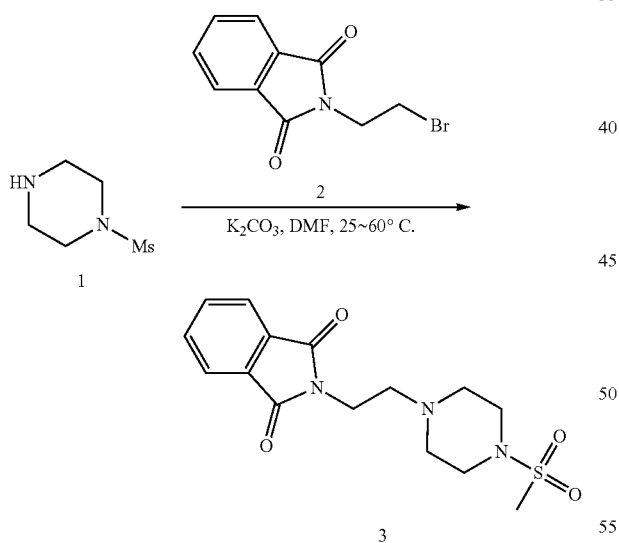

To a solution of Compound 1 (2 g, 12.18 mmol, 1 eq) and Compound 2 (4.64 g, 18.27 mmol, 1.5 eq) in DMF (20 mL) was added $K_2CO_3$ (3.37 g, 24.36 m mol, 2 eq). The mixture was stirred at 25° C. for 3 hr, then at 60° C. for 16 hr. LCMS showed a major peak with desired mass was detected. The reaction mixture was poured into water (100 mL), extracted with EtOAc (150 mL*3), washed with brine (50 mL*3), dried over $Na_2SO_4$, filtered and concentrated. The residue was purified by flash silica gel chromatography (ISCO®; 40 g SepaFlash® Silica Flash Column, Eluent of 0-20% Metha- nol/Dichloromethane @ 30 mL/min) to give Compound 3 (1.3 g, 3.85 m mol, 31.64% yield) as white solid.

$^1$H NMR (400 MHz, $CDCl_3$)

δ=7.95 (d, J=7.6 Hz, 1H), 7.88-7.83 (m, 1H), 7.78-7.70 (m, 1H), 7.58-7.41 (m, 2H), 4.48-4.32 (m, 2H), 3.20-3.12 (m, 2H), 2.82 (s, 3H), 2.75 (s, 2H), 2.70 (t, J=6.2 Hz, 1H), 2.66-2.61 (m, 2H)

LCMS: Rt=0.234 min, $[M+H]^+$=338.2

Preparation of Compound 4

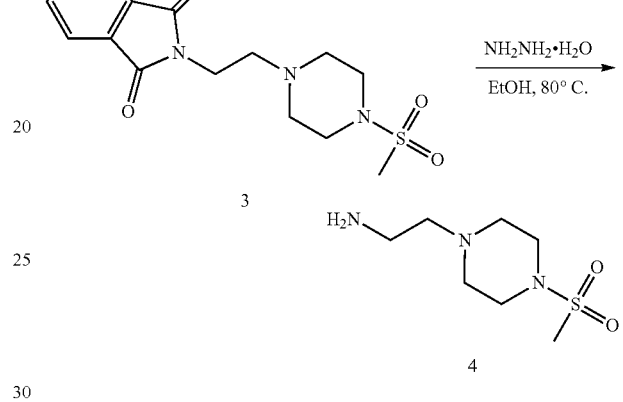

To a solution of Compound 3 (200 mg, 592.78 umol, 1 eq) in EtOH (3 mL) was added $NH_2NH_2·H_2O$ (296.75 mg, 5.93 mmol, 288.10 uL, 10 eq). The mixture was stirred at 80° C. for 3 hr. LCMS showed Compound 3 was consumed, and no desired mass was detected. The reaction mixture was filtered and concentrated to give a residue. 1 N HCl solution (1 mL) was added, the mixture was filtered and concentrated. The residue was purified by prep-HPLC (column: Shim-pack C18 150*25*10 um; mobile phase: [water(0.225% FA)-ACN]; B %: 0%-1%, 10 min) to give Compound 4 (120 mg, 473.71 umol, 79.91% yield, FA) as white solid.

$^1$H NMR (400 MHz, MeOD)

δ=4.84 (s, 4H), 3.63-3.45 (m, 4H), 3.38-3.32 (m, 2H), 3.00-2.94 (m, 2H), 2.70-2.62 (m, 3H)

LCMS: Rt=0.200 min, $[M+H]^+$=207.850

Preparation of Compound 167

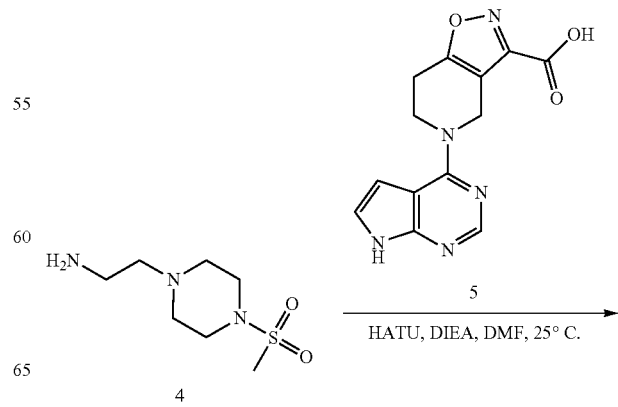

-continued

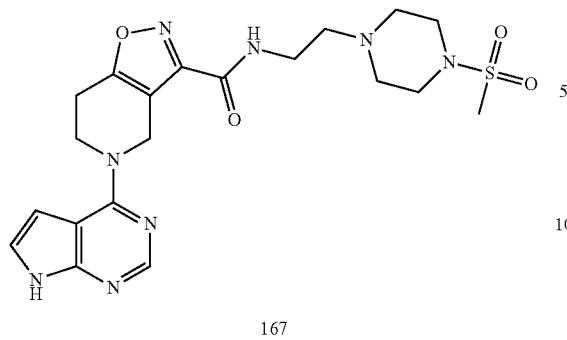

167

To a solution of Compound 5 (50 mg, 175.28 umol, 1 eq) in DMF (2 mL) was added HATU (133.29 mg, 350.56 umol, 2 eq), DIEA (67.96 mg, 525.84 umol, 91.59 uL, 3 eq) and Compound 4 (66.60 mg, 262.92 u mol, 1.5 eq, FA). The mixture was stirred at 25° C. for 1 hr. LCMS showed a major peak with desired mass was detected. The reaction mixture was diluted with H₂O (10 mL), filtered. The filter cake was purified by prep-HPLC (column: Welch Xtimate C18 150*25 mm*5 um; mobile phase: [water(0.05% ammonia hydroxide v/v)-ACN]; B %: 13%-43%, 10 min) to give Compound 167 (7.57 mg, 15.49 umol, 8.84% yield, 97.083% purity) as yellow solid.

$^1$H NMR (400 MHz, DMSO-d6)

δ=11.81 (br. s, 1H), 8.67 (br. t, J=5.6 Hz, 1H), 8.20 (s, 1H), 7.27 (d, J=3.5 Hz, 1H), 6.64 (d, J=3.7 Hz, 1H), 4.97 (s, 2H), 4.21 (br. t, J=5.5 Hz, 2H), 3.44-3.37 (m, 2H), 3.15-3.06 (m, 4H), 3.05-2.99 (m, 2H), 2.89-2.82 (m, 3H), 2.57-2.52 (m, 6H)

LCMS: Rt=0.831 min, [M+H]⁺=475.3

Example 38: Synthesis of Compound 168

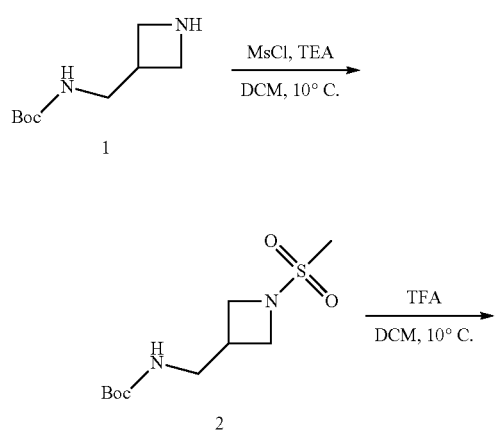

-continued

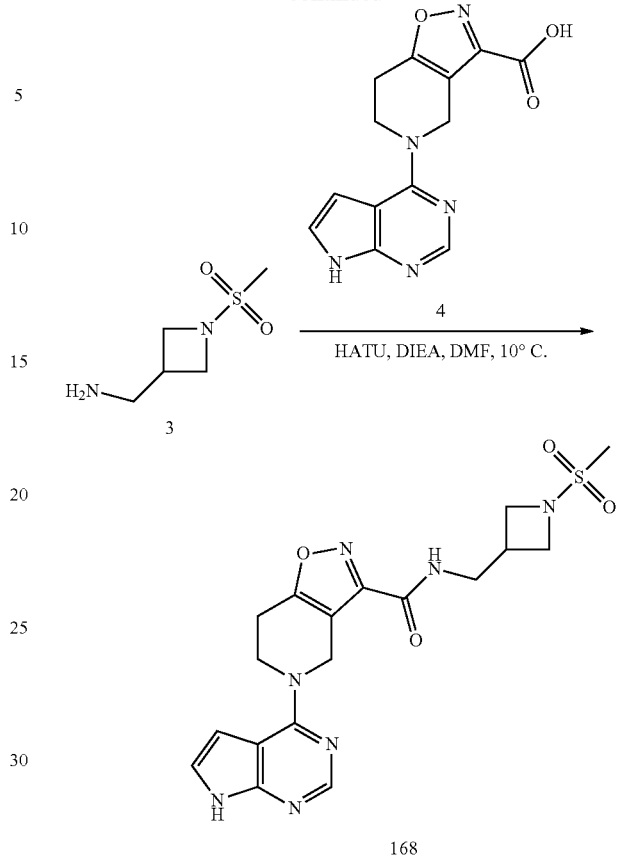

168

Preparation of Compound 2

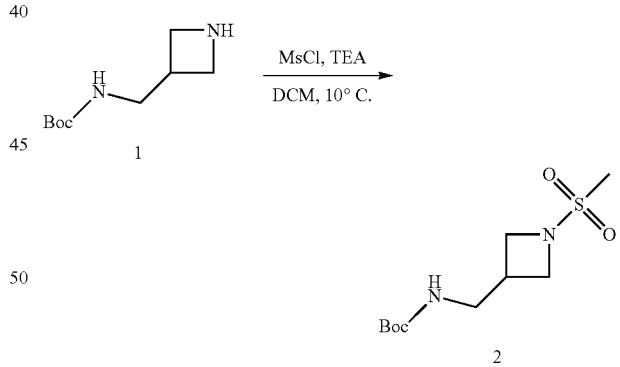

To a mixture of Compound 1 (2 g, 10.74 mmol, 1 eq) and TEA (2.17 g, 21.48 mmol, 2.99 mL, 2 eq) in DCM (20 mL) was added MsCl (1.85 g, 16.11 mmol, 1.25 mL, 1.5 eq) dropwise at 10° C. The mixture was stirred at 10° C. for 3 hr. TLC (PE/EA=1/1, Rf=0.5) indicated most of Compound 1 was consumed, and one new major spot was detected. The reaction mixture was quenched by water (100 mL) at 10° C., extracted with DCM (10 mL*3), dried over Na₂SO₄, filtered and concentrated. The residue was triturated with PE/EA (1:1, 10 mL*3), the filtrate was concentrated to give Compound 2 (1.8 g, 6.81 mmol, 63.41% yield) as white solid.

$^1$H NMR (400 MHz, MeOD)

δ=(t, J=8.2 Hz, 2H), 3.68-3.62 (m, 2H), 3.27 (d, J=6.4 Hz, 2H), 2.94 (s, 3H), 2.83-2.74 (m, 1H), 1.46 (s, 9H)

Preparation of Compound 3

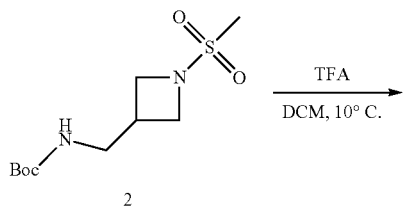

To a mixture of Compound 2 (150 mg, 567.45 umol, 1 eq) in DCM (2 mL) was added TFA (1.54 g, 13.51 mmol, 1 mL, 23.80 eq). The mixture was stirred at 10° C. for 1 hr. TLC (PE/EA=1/1, Rf=0.01) indicated Compound 2 was consumed completely and new spot was formed. The reaction mixture was concentrated to give Compound 3 (180 mg, crude, TFA) as yellow oil.

Preparation of Compound 168

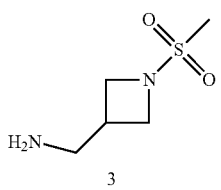

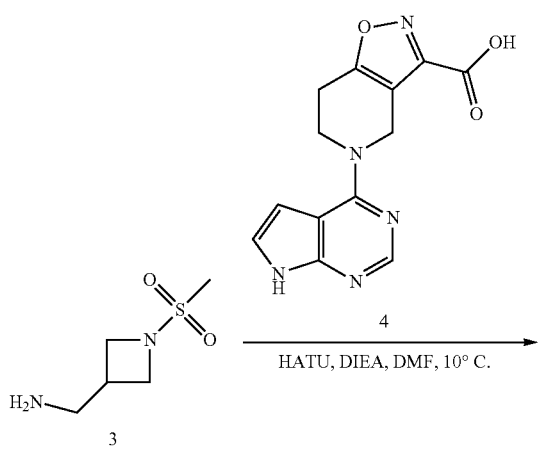

-continued

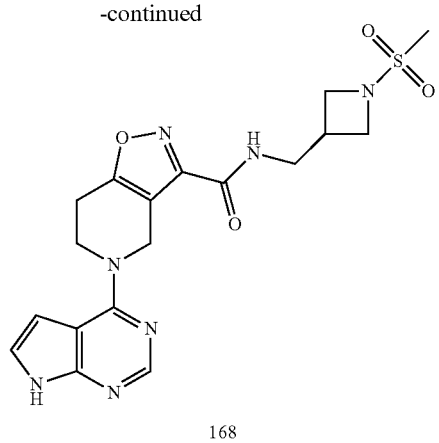
168

To a solution of Compound 3 (100 mg, 359.39 umol, 1 eq, TFA) and Compound 4 (102.52 mg, 359.39 umol, 1 eq) in DMF (2 mL) was added HATU (409.95 mg, 1.08 mmol, 3 eq) and DIEA (232.24 mg, 1.80 mmol, 313.00 uL, 5 eq). The mixture was stirred at 10° C. for 16 hr. LCMS showed most of Compound 4 was consumed and desired mass was detected. The reaction mixture was diluted with water (50 mL), extracted with EtOAc (5 mL*3), dried over Na$_2$SO$_4$, filtered and concentrated. The residue was purified by prep-HPLC (column: Welch Xtimate C18 150*25 mm*5 um; mobile phase: [water(0.05% ammonia hydroxide v/v)-ACN]; B %: 37%-67%, 10 min) to give Compound 168 (22.74 mg, 51.12 umol, 14.22% yield, 97% purity) as off-white solid.

$^1$H NMR (400 MHz, DMSO-d6)

δ=11.80 (s, 1H), 9.05 (t, J=5.6 Hz, 1H), 8.21 (s, 1H), 7.27 (d, J=3.6 Hz, 1H), 6.64 (d, J=3.6 Hz, 1H), 4.99 (s, 2H), 4.22 (t, J=5.6 Hz, 2H), 3.92 (t, J=8.4 Hz, 2H), 3.67-3.63 (m, 2H), 3.50 (t, J=6.4 Hz, 2H), 3.03 (t, J=5.2 Hz, 2H), 2.98 (s, 3H), 2.88-2.75 (m, 1H), 2.08 (s, 2H)

LCMS: Rt=0.774 min, [M+H]$^+$=432.1

Example 39: Synthesis of Compound 169

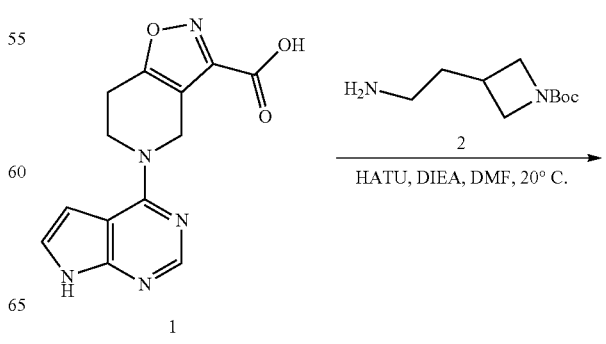

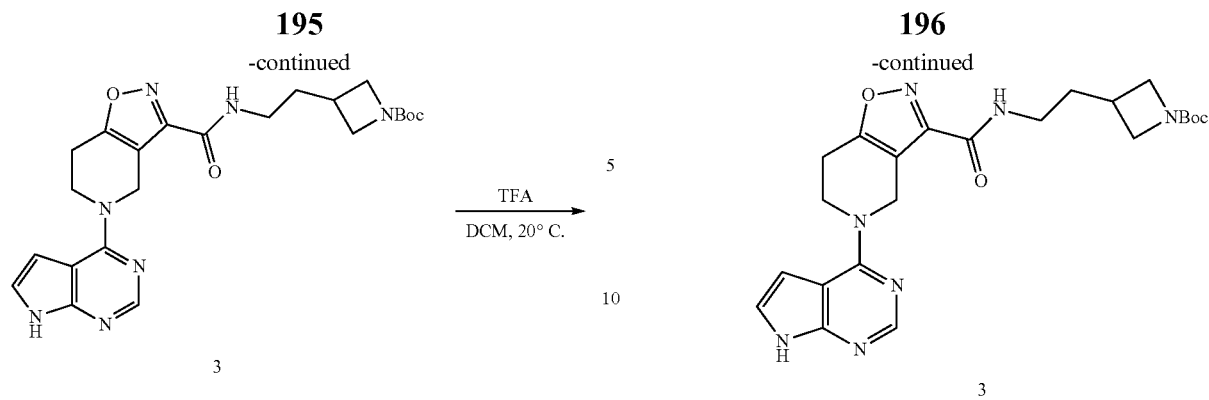

To a mixture of Compound 1 (400 mg, 1.40 mmol, 1 eq), Compound 2 (561.67 mg, 2.80 mmol, 2 eq) and HATU (2.13 g, 5.61 mmol, 4 eq) in DMF (3 mL) was added DIEA (1.09 g, 8.41 mmol, 1.47 mL, 6 eq). The mixture was stirred at 20° C. for 1 hr. LCMS showed Compound 1 was consumed completely and desired mass was detected. The mixture was diluted with water (20 mL), extracted with EtOAc (50 mL), dried over $Na_2SO_4$, filtered and concentrated to give Compound 3 (515 mg, crude) as a brown gum.

LCMS: Rt=0.929 min, $[M+H]^+$=468.4

Preparation of Compound 4

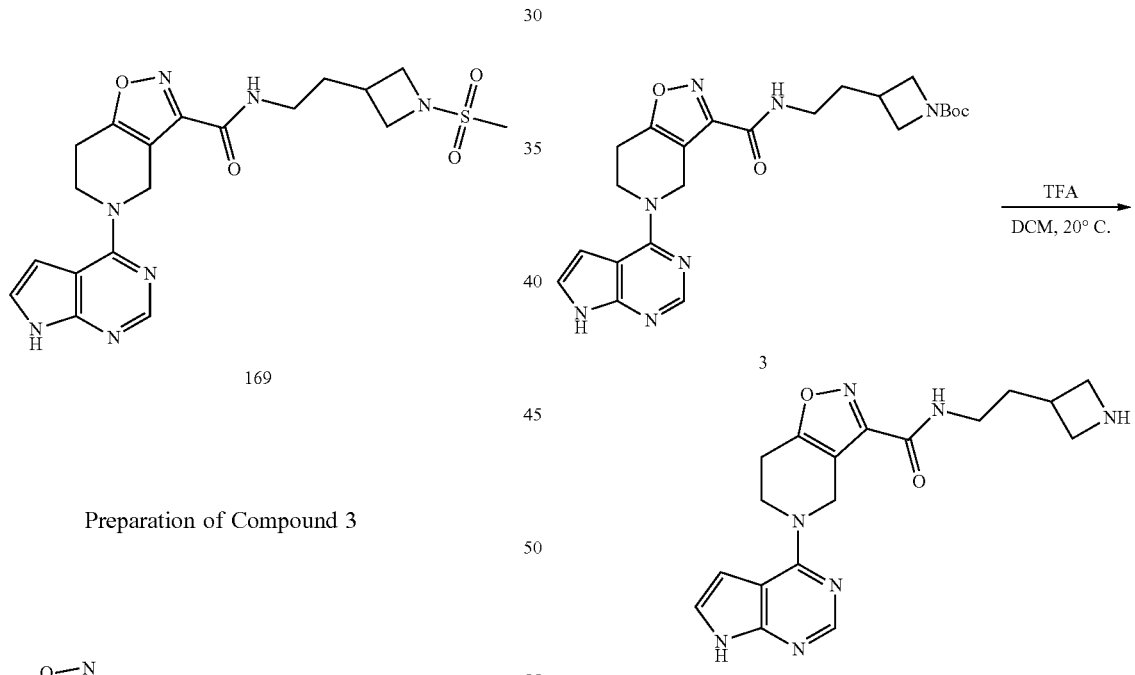

A solution of Compound 3 (510 mg, 1.09 mmol, 1 eq) and TFA (2.31 g, 20.26 mmol, 1.5 mL, 18.57 eq) in DCM (5 mL) was stirred at 20° C. for 2 hr. LCMS showed Compound 3 was consumed completely and desired mass was detected. The reaction mixture was concentrated, diluted with water (10 mL), neutralized with $NH_3$—$H_2O$ to pH=7-8, the final mixture was lyophilized to give Compound 4 (1.1 g, crude) as brown gum.

LCMS: Rt=1.071 min, $[M+H]^+$=368.3

Preparation of Compound 3

Preparation of Compound 169

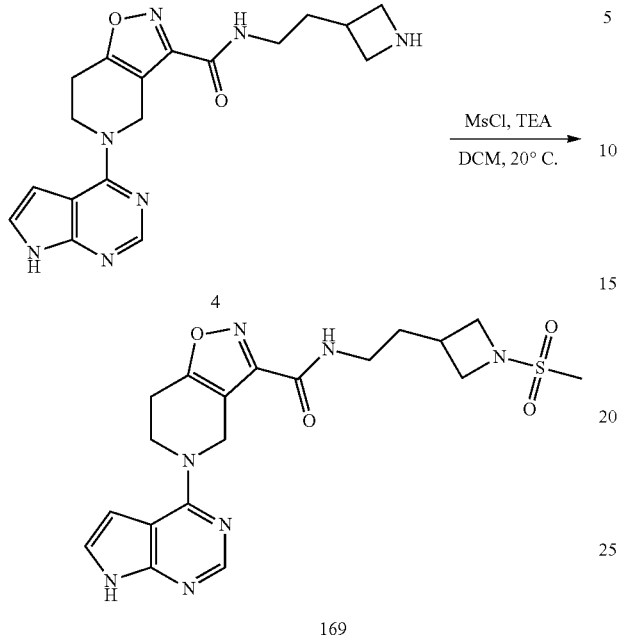

To a solution of Compound 4 (0.8 g, 2.18 mmol, 1 eq) and TEA (1.10 g, 10.89 mmol, 1.52 mL, 5 eq) in DCM (8.0 mL) was added MsCl (623.57 mg, 5.44 mmol, 421.33 uL, 2.5 eq) dropwise. After addition, the reaction mixture was stirred at 20° C. for 2 hr. LCMS showed Compound 4 was consumed completely and desired mass was detected. The reaction mixture was diluted with H$_2$O (20 mL), extracted with EtOAc (30 mL*2), washed with brine (30 mL), dried over Na$_2$SO$_4$, filtered and concentrated. The residue was purified by prep-HPLC (column: Waters Xbridge 150*25 mm*5 um; mobile phase: [water (0.05% ammonia hydroxide v/v)-ACN]; B %: 16%-44%, 10 min) to give Compound 169 (15.57 mg, 32.39 umol, 1.49% yield, 92.67% purity) as white solid.

$^1$H NMR (400 MHz, DMSO-d$_6$)

δ=11.80 (s, 1H), 8.82 (t, J=5.6 Hz, 1H), 8.24-8.16 (m, 1H), 7.33-7.23 (m, 1H), 6.64 (d, J=2.4 Hz, 1H), 4.98 (s, 2H), 4.21 (t, J=5.6 Hz, 2H), 3.91 (t, J=8.0 Hz, 2H), 3.56 (dd, J=6.4, 7.6 Hz, 2H), 3.25 (q, J=6.4 Hz, 2H), 3.02 (t, J=5.2 Hz, 2H), 2.97 (s, 3H), 2.65-2.56 (m, 1H), 1.82 (q, J=6.8 Hz, 2H).

$^{13}$C NMR (101 MHz, DMSO-d$_6$)

δ=168.78, 158.97, 156.92, 154.37, 152.03, 150.57, 122.14, 111.61, 102.51, 100.42, 55.35, 41.75, 40.13, 38.89, 32.87, 32.58, 25.99, 23.18.

LCMS: Rt=0.568 min, [M+H]$^+$=446.1.

Example 40: Synthesis of Compound 170

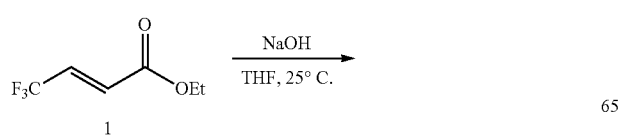

-continued

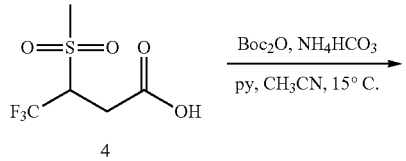

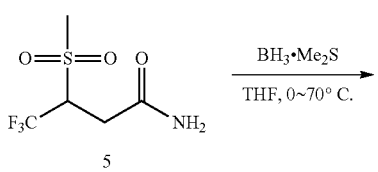

3 the compound was prepared according to ref: US2021/110702, 2012, A1

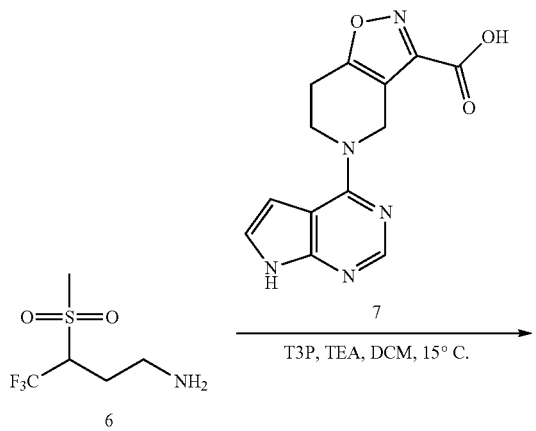

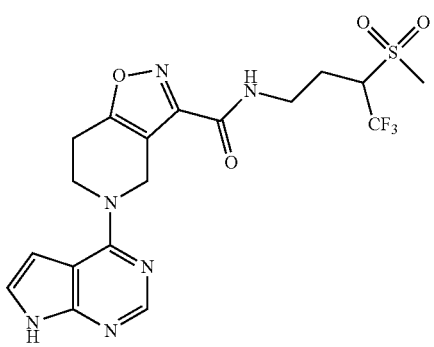

170

Preparation of Compound 2

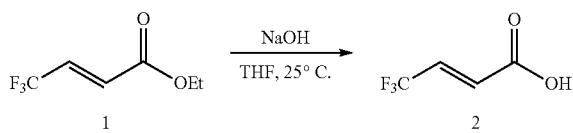 [SMILES: CCOC(=O)/C=C/C(F)(F)F ; "NaOH" ; O=C(O)/C=C/C(F)(F)F]

A mixture of Compound 1 (9.85 g, 58.59 mmol, 8.72 mL, 1 eq) and NaOH (1 M, 92.3 mL, 1.58 eq) in THF (24 mL) was stirred at 25° C. for 3 hr. TLC (PE/EA=20/1, $R_f$=0) showed Compound 1 was consumed completely and a new major spot was observed. The mixture was diluted with water (30 mL), adjusted with concentrated HCl solution to pH=1, extracted with EtOAc (30 mL*3), dried with MgSO$_4$, filtered and concentrated to afford Compound 2 (6.7 g, crude) as colorless crystal.

$^1$H NMR (400 MHz, CDCl$_3$)
δ=11.36 (s, 1H), 6.84-6.8-79 (m, 1H), 6.47-6.42 (m, 1H).

Preparation of Compound 3

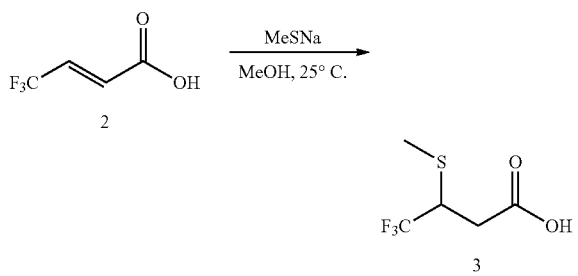

the compound was prepared according to ref: US2021/110702, 2012, A1

To a 100 mL round bottom flask was added Compound 2 (6.7 g, 47.84 mmol, 1 eq) and MeOH (20 mL), the solution was stirred with a water bath, then MeSNa (8.38 g, 119.59 mmol, 7.62 mL, 2.5 eq) was added in three portions. Vigorous bubbling was observed, the mixture was stirred at 25° C. for 16 h. TLC (PE/EA=3/1, $R_f$=0.3) showed Compound 2 was consumed completely and a new major spot was observed. The mixture was diluted with water (30 mL), adjusted with 2 N HCl solution to pH=3-4, extracted with chloroform (50 mL*5), dried over Na$_2$SO$_4$, filtered and concentrated to give Compound 3 (8.6 g, crude) as yellow oil.

$^1$H NMR (400 MHz, CDCl$_3$)
δ=11.11 (s, 1H), 3.55-3.53 (m, 1H), 2.99-2.94 (m, 1H), 2.69-2.66 (m, 1H), 2.30 (s, 3H).

Preparation of Compound 4

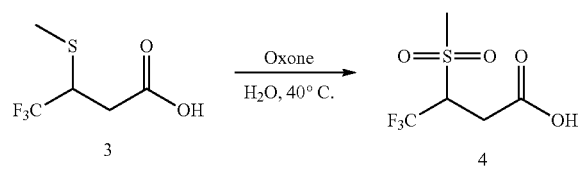

To a suspension of Compound 3 (4 g, 21.26 mmol, 1 eq) in H$_2$O (100 mL), Oxone (32.67 g, 53.14 mmol, 2.5 eq) was added. The mixture was stirred at 40° C. for 1.5 hr. TLC (PE/EA=3/1) showed Compound 3 was consumed completely and no obvious new spot was observed. The mixture was cooled to 25° C., extracted with EtOAc (100 mL*3), dried over Na$_2$SO$_4$, filtered and concentrated to give Compound 4 (3.7 g, crude) as white solid.

$^1$H NMR (400 MHz, DMSO-d$_6$)
δ=13.07 (s, 1H), 5.02-4.94 (m, 1H), 3.34 (s, 3H), 3.09-3.06 (dd, J=6.2, 17.6 Hz, 1H), 2.93-2.87 (dd, J=6.4, 17.6 Hz, 1H)

Preparation of Compound 5

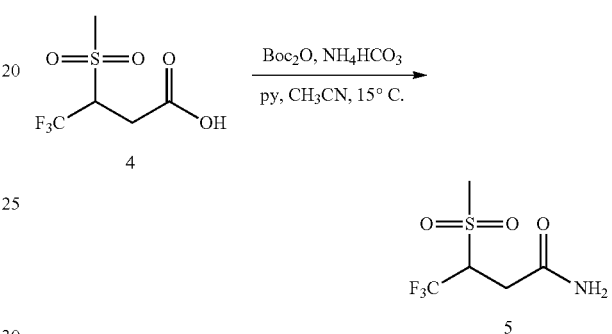

To a suspension of Compound 4 (1.23 g, 5.59 mmol, 1 eq) and Boc$_2$O (1.34 g, 6.15 mmol, 1.41 mL, 1.1 eq) in CH$_3$CN (12 mL) was added NH$_4$HCO$_3$ (463.74 mg, 5.87 mmol, 483.06 uL, 1.05 eq) and pyridine (464.00 mg, 5.87 mmol, 473.47 uL, 1.05 eq). The mixture was stirred at 15° C. for 2 hr. The mixture was diluted with water (30 mL), extracted with EtOAc (30 mL*3), dried with Na$_2$SO$_4$, filtered and concentrated. The residue was triturated with MTBE (10 mL) to give Compound 5 (0.6 g, crude) as white solid.

$^1$H NMR (400 MHz, DMSO-d$_6$)
δ=7.66 (s, 1H), 7.22 (s, 1H), 4.93-4.86 (m, 1H), 3.26 (s, 3H), 2.95-2.89 (dd, J=5.4, 16.8 Hz, 1H), 2.70-2.64 (dd, J=7.0, 16.8 Hz, 1H).
$^{19}$F NMR (400 MHz, DMSO-d$_6$)
δ=-64.52

Preparation of Compound 6

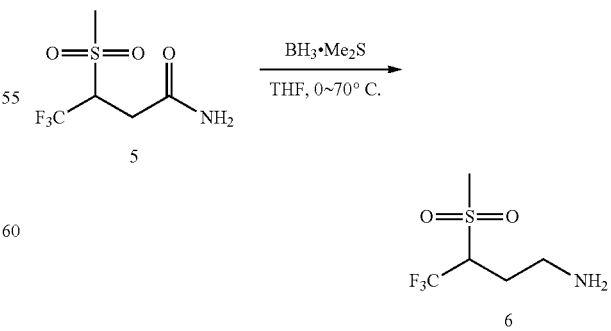

To a solution of Compound 5 (0.15 g, 684.36 umol, 1 eq) in THF (4.5 mL) was added BH$_3$·Me$_2$S (10 M, 205.31 uL, 3 eq) dropwise at 0° C. The mixture was heated at 70° C. for 2 hr. The mixture was quenched with MeOH (1 mL) at 0° C., concentrated to give Compound 6 (0.15 g, crude) as colorless oil.

Preparation of Compound 170

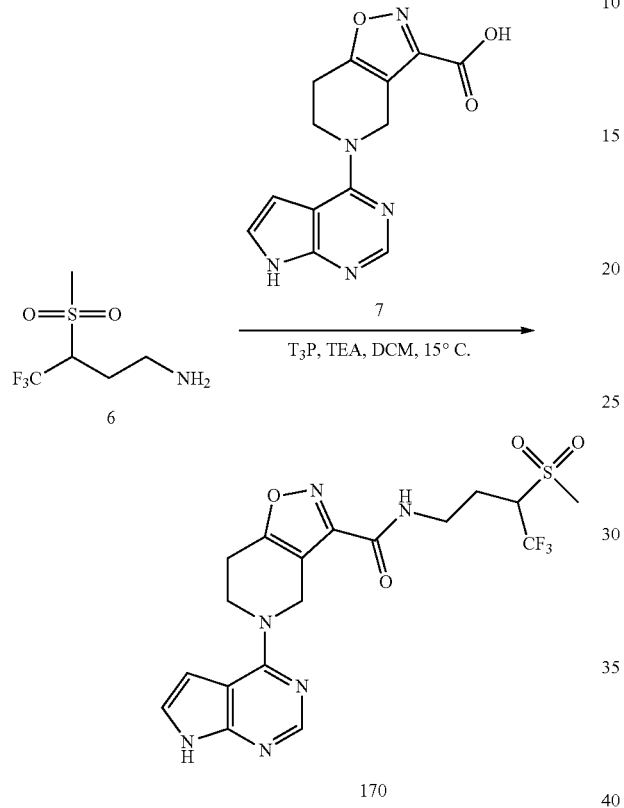

To a solution of Compound 7 (0.1 g, 350.56 umol, 1 eq) in DCM (2 mL) was added Compound 6 (143.87 mg, 701.12 umol, 2 eq), T3P (557.71 mg, 876.40 umol, 521.22 uL, 50% purity, 2.5 eq) and TEA (141.89 mg, 1.40 mmol, 195.18 uL, 4 eq). The mixture was stirred at 15° C. for 2 hr. LCMS showed desired MS was detected. The mixture was diluted with water (10 mL), extracted with EtOAc (10 mL*3), dried with Na$_2$SO$_4$, filtered and concentrated. The residue was purified by prep-HPLC (column: Phenomenex luna C18 250*50 mm*10 um; mobile phase: [water(0.075% TFA)-ACN]; B %: 12%-42%, 9 min) and prep-HPLC [column: Phenomenex Synergi C18 150*25*10 um; mobile phase: [water(0.225% FA)-ACN]; B %: 23%-43%, 9 min] to afford Compound 170 (8.98 mg, purity: 98.398%, 5.4% yield, FA salt) as white solid.

$^1$H NMR (400 MHz, DMSO-d$_6$)

δ=11.79 (s, 1H), 9.09-8.79 (t, J=5.8 Hz, 1H), 8.20 (s, 1H), 7.50-7.13 (m, 1H), 6.86-6.41 (m, 1H), 5.05-4.91 (m, 2H), 4.75-4.57 (m, 1H), 4.30-4.10 (t, J=5.8 Hz, 2H), 3.53-3.47 (m, 2H), 3.22 (s, 3H), 3.09-2.96 (m, 2H), 2.17-1.98 (m, 2H)

$^{19}$F NMR (400 MHz, DMSO-d$_6$)

δ=−64.1

LCMS: Rt=0.603 min, [M+H]$^+$=473.1

Example 41: Synthesis of Compound 186

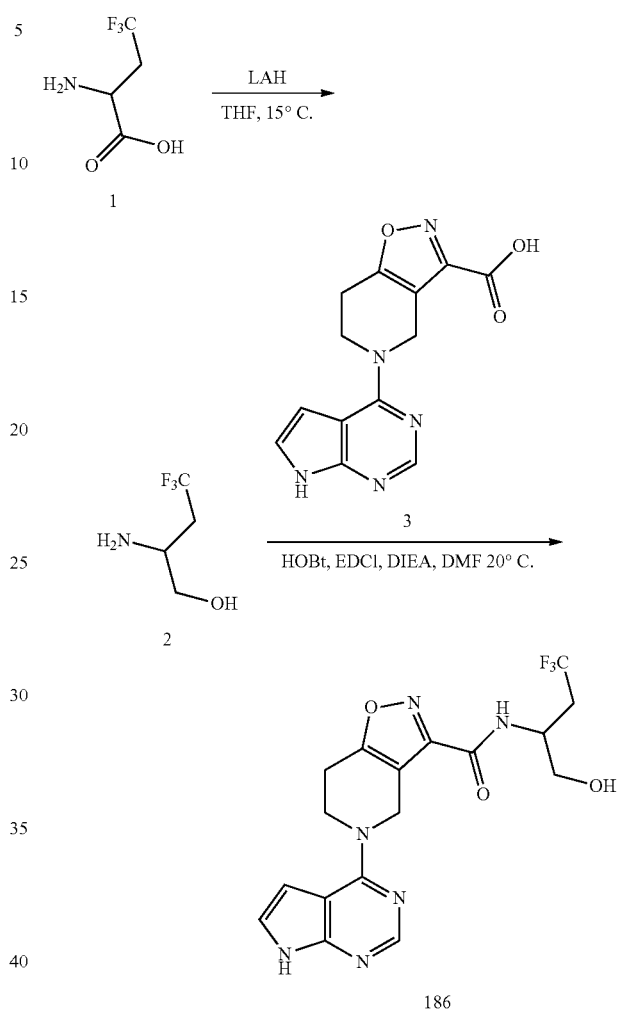

Preparation of Compound 2

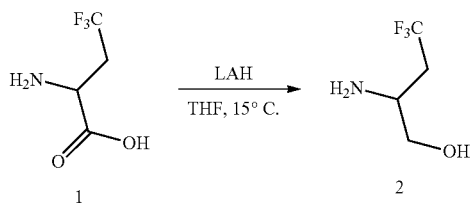 [SMILES: NC(CC(F)(F)F)C(=O)O ; "LAH" ; NC(CO)CC(F)(F)F]

To a solution of compound 1 (100 mg, 636.57 umol, 1 eq) in THF (2 mL) was added LAH (48.32 mg, 1.27 mmol, 2 eq). The mixture was stirred at 15'C for 1 hr. The mixture was treated sequentially with water (0.05 mL), 15% NaOH solution (0.05 mL) and water (0.15 ml), then filtered through celite and concentrated to give the compound 2 (100 mg, crude) as white solid. The H-NMR came from another batch.

$^1$H NMR (400 MHz, DMSO-d6)

δ=4.82 (br. t, J=4.8 Hz, 1H), 3.31 (br. t, J=5.0 Hz, 2H), 3.05-2.94 (m, 1H), 2.48-2.36 (m, 2H), 1.72-1.53 (m, 2H)

203
Preparation of Compound 186

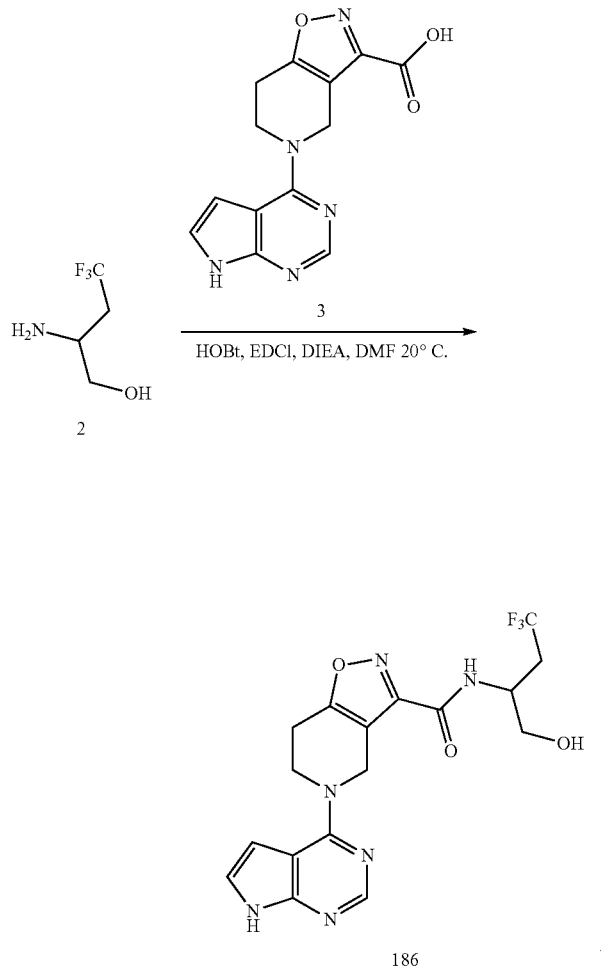

To a mixture of compound 2 (99.67 mg, 349.39 umol, 1 eq) and compound 3 (60 mg, 419.27 umol, 1.2 eq) in DMF (3 mL) was added DIEA (135.46 mg, 1.05 mmol, 182.57 uL, 3 eq), HOBt (47.21 mg, 349.39 umol, 1 eq) and EDCI (100.47 mg, 524.08 umol, 1.5 eq), the mixture was stirred at 20° C. for 8 hr. LCMS showed desired MS was detected. The reaction mixture was diluted with $H_2O$ (5 mL), extracted with EtOAc (5 mL*2), dried over $Na_2SO_4$, filtered and concentrated. The residue was purified by prep-TLC (Ethyl acetate/Methanol=10/1) to give compound 186 (30 mg, 69.45 umol, 19.88% yield, 95% purity) as white solid.

$^1$H NMR (400 MHz, MeOD)

δ=8.08 (s, 1H), 7.08 (d, J=3.6 Hz, 1H), 6.62 (d, J=3.8 Hz, 1H), 5.00-4.88 (m, 2H), 4.42-4.33 (m, 1H), 4.26-4.08 (m, 2H), 3.62-3.48 (m, 2H), 2.93 (t, J=5.6 Hz, 2H), 2.59-2.39 (m, 2H)

$^{13}$C NMR (101 MHz, MeOD)

δ=169.00, 159.71, 157.16, 154.03, 151.18, 150.19, 127.991, 127.06, 125.24, 121.59, 111.53, 103.18, 100.74, 62.69, 56.92, 46.04, 42.12, 41.87, 34.33, 34.05, 33.78, 33.49, 23.06, 16.96

LCMS: Rt=0.730 min, [M+H]$^+$=411.35

204
Example 42: Synthesis of Compound 187

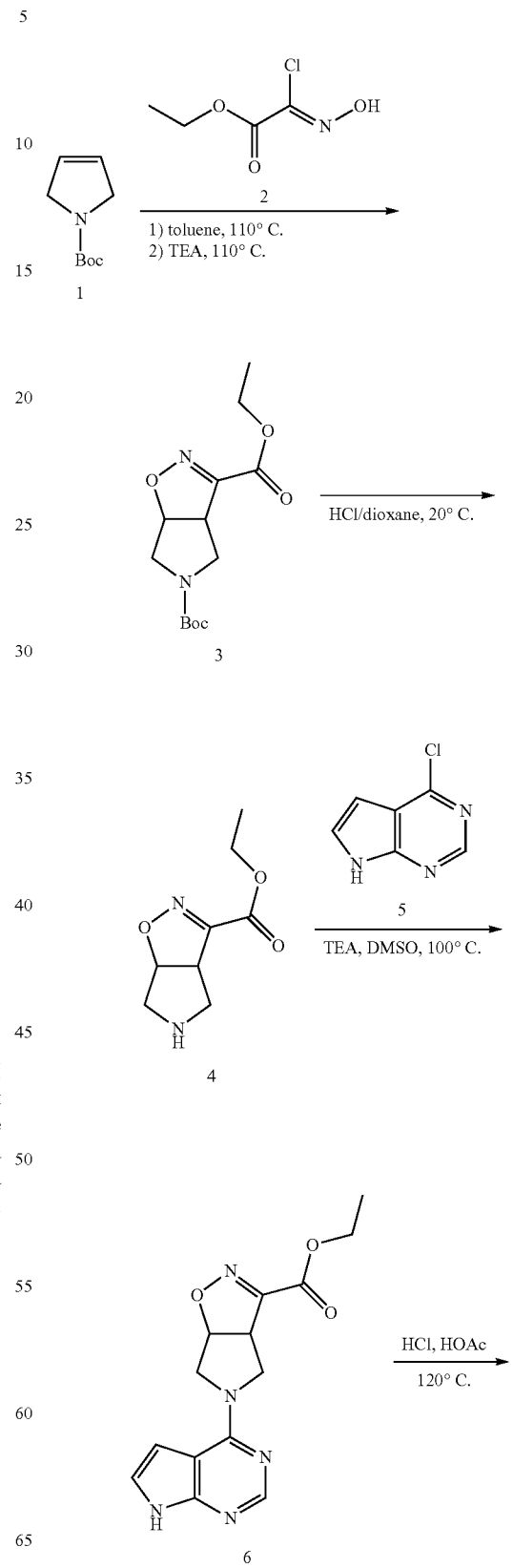

-continued

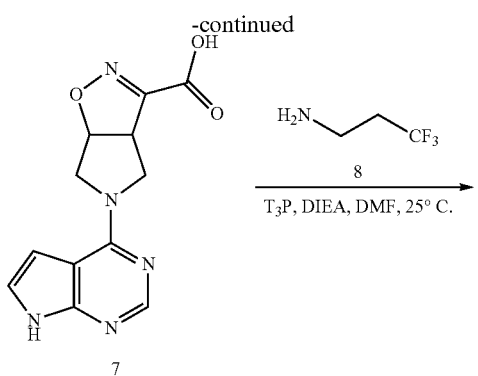

Preparation of Compound 4

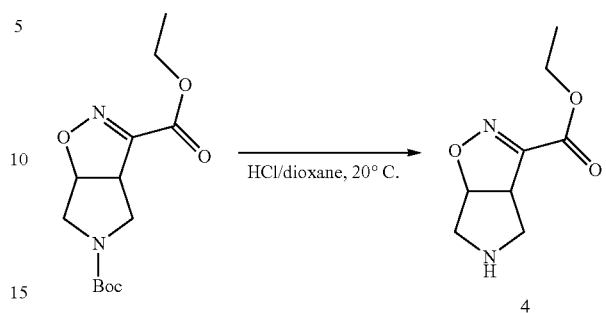

A mixture of compound 3 (500 mg, 1.76 mmol, 1 eq) in 4 N HCl/dioxane (5 mL) was stirred at 20° C. for 2 hr. TLC showed compound 3 was consumed. The mixture was concentrated to give compound 4 (388 mg, crude, HCl) as yellow solid.

$^1$H NMR (400 MHz, MeOD)

δ=5.60 (dd, J=5.0, 9.5 Hz, 1H), 4.48-4.42 (m, 1H), 4.41-4.33 (m, 2H), 3.88-3.75 (m, 2H), 3.60-3.51 (m, 2H), 1.38 (t, J=7.1 Hz, 3H)

Preparation of Compound 6

Preparation of Compound 3

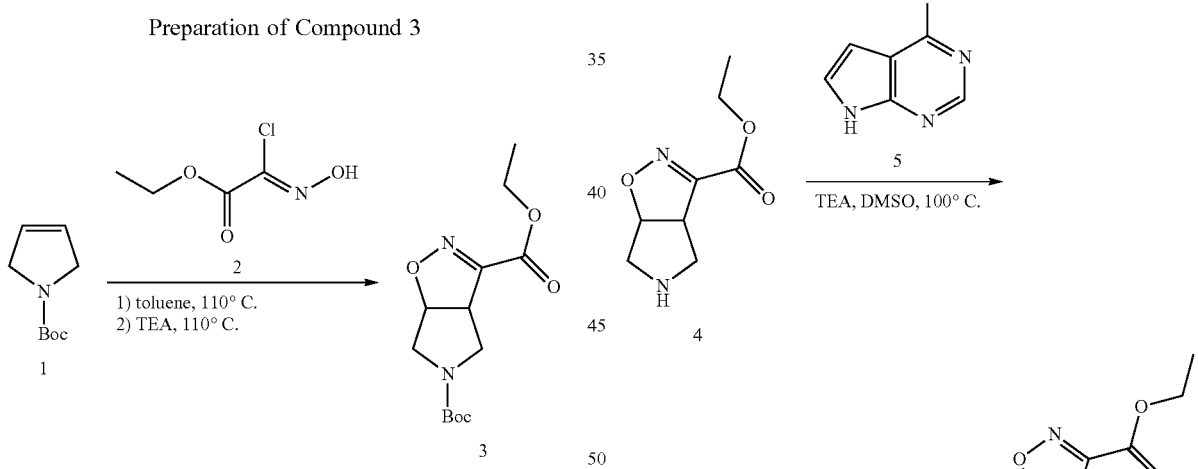

To a solution of compound 1 (2 g, 11.82 mmol, 1 eq) and compound 2 (1.79 g, 11.82 mmol, 1 eq) in toluene (50 nL) was added a solution of TEA (1.79 g, 17.73 mmol, 2.47 mL, 1.5 eq) in toluene (50 mL). at 130° C. over 6 hr. After addition, the mixture was stirred at 130° C. for 4 hr. LCMS showed desired MS was detected. The mixture was concentrated, purified by silica gel chromatography (Petroleum ether/Ethyl acetate=5/1) to give compound 3 (1.33 g, 4.68 mmol, 39.58% yield) as yellow oil.

$^1$H NMR (400 MHz, CDCl$_3$)

δ=5.34 (dd, J=4.6, 9.6 Hz, 1H), 4.37 (q, J=7.2 Hz, 2H), 4.12-3.75 (m, 3H), 3.57-3.43 (m, 2H), 1.45 (s, 9H), 1.39 (t, J=7.1 Hz, 3H)

LCMS: Rt=0.865 min, [M+Na]$^+$=307.0

Compound 4 (388 mg, 1.76 mmol, 1 eq, HCl) and compound 5 (270.04 mg, 1.76 mmol, 1 eq) were dissolved in TEA (711.73 mg, 7.03 mmol, 979.00 uL, 4 eq) and DMSO (5 mL). The reaction mixture was stirred at 100° C. for 16 hr. LCMS showed that the desired mass was detected. The reaction mixture was quenched with water (5 mL), extracted with ethyl acetate (10 mL*2) and washed with brine (5 mL). The crude product was triturated with PE/EA (1:1, 10 mL) at 25° C. for 30 min to give compound 6 (230 mg, 763.36 umol, 43.41% yield) as a brown solid.

¹H NMR (400 MHz, DMSO-d6)

δ=11.73 (br. s, 1H), 8.13 (s, 1H), 7.19 (dd, J=2.6, 3.4 Hz, 1H), 6.62-6.51 (m, 1H), 5.61-5.52 (m, 1H), 4.40-4.21 (m, 1H), 4.41-4.21 (m, 4H), 3.94-3.75 (m, 2H), 1.28 (t, J=7.1 Hz, 3H)

LCMS: Rt=0.217 min, [M+H]⁺=302.2

Preparation of Compound 7

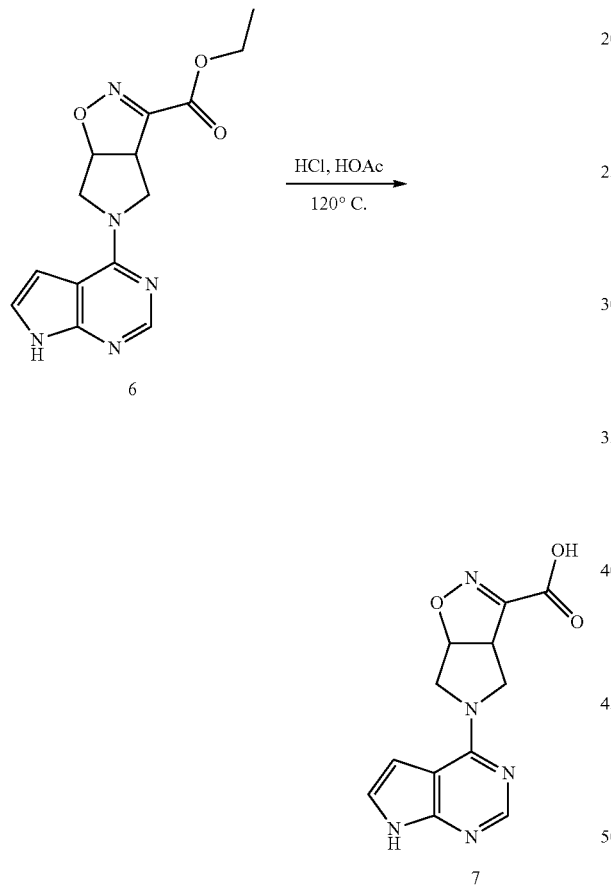

A suspension of compound 6 (50 mg, 165.95 umol, 1 eq) in concentrated HCl (1 mL) and AcOH (1 mL) was heated at 120° C. After 2 hours, TLC indicated compound 6 was consumed completely and only one new spot formed. LCMS showed that the mass of desired product was detected. The reaction mixture was concentrated to give compound 7 (40 mg, crude) as dark brown oil.

¹H NMR (400 MHz, DMSO-d6)

δ=12.90 (br. s, 1H), 8.49-8.30 (m, 1H), 7.60-7.45 (m, 1H), 7.12-6.88 (m, 1H), 4.53-4.31 (m, 3H), 4.29-3.96 (m, 4H), 2.54 (s, 2H)

LCMS: Rt=0.132 min, [M+H]⁺=274.1

Preparation of Compound 187

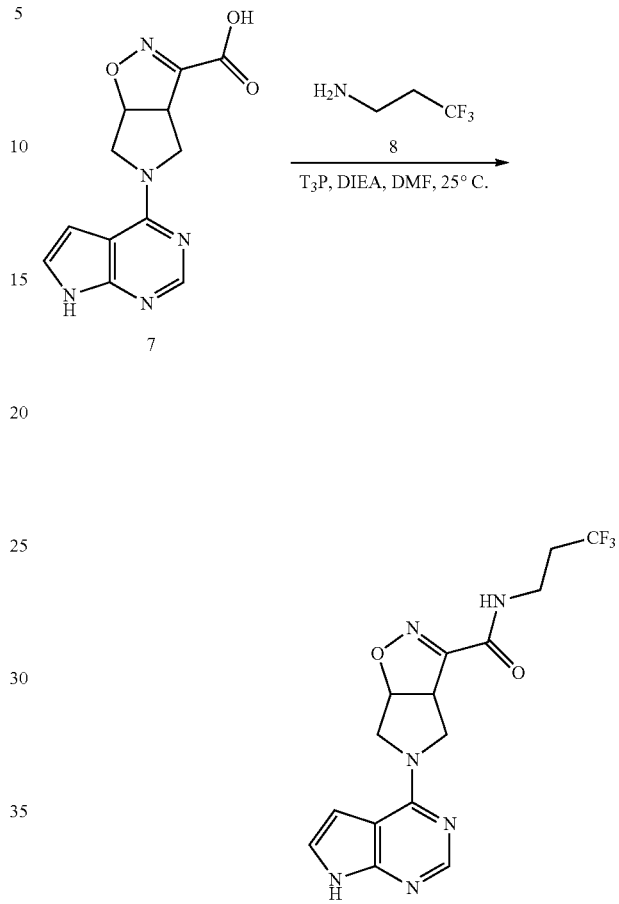

To a solution of compound 7 (130 mg, 475.76 umol, 1 eq) and compound 8 (85.38 mg, 570.91 umol, 1.2 eq, HCl) in DMF (6 mL) was added T3P (227.07 mg, 356.82 umol, 212.21 uL, 50% purity, 0.75 eq) and DIEA (184.47 mg, 1.43 mmol, 248.61 uL, 3 eq). The reaction mixture was stirred at 25° C. for 12 hr. LCMS showed that the mass of desire product was detected TLC showed that three new spots come out and the Rf value of product should be around 0.45. The reaction mixture was concentrated under reduced pressure to remove DMF. The residue was purified by prep-HPLC (column: Waters Xbridge C18 150*50 mm*10 um; mobile phase: [water(10 mM NH₄HCO₃)-ACN]; B %: 13%-43%, 10 min) to give compound 187 (12 mg, 32.09 umol, 6.74% yield, 98.49% purity) as pale yellow solid.

¹H NMR (400 MHz, MeOD)

δ=8.13 (br. s, 1H), 7.14 (d, J=3.5 Hz, 1H), 6.66 (d, J=3.7 Hz, 1H), 5.53 (dd, J=5.0, 9.5 Hz, 1H), 5.57-5.49 (m, 1H), 4.41 (br. s, 3H), 4.03-3.88 (m, 2H), 3.54 (br d, J=3.2 Hz, 2H), 2.46 (br d, J=10.9 Hz, 2H)

¹³C NMR (101 MHz, MeOD)

δ=161.86, 156.80, 155.96, 151.57, 129.33, 126.59, 123.02, 102.50, 88.06, 56.53, 52.63, 52.63, 51.87

LCMS: Rt=0.843 min, [M+H]⁺=369.2

Example 43: Synthesis of Compound 188

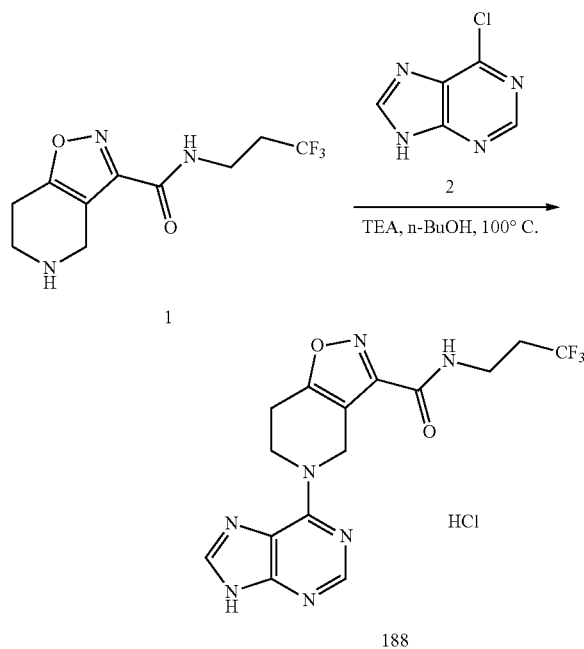

To a mixture of compound 1 (164 mg, 547.26 umol, 1 eq, HCl) in n-BuOH (3 mL) was added TEA (221.51 mg, 2.19 mmol, 304.69 uL, 4 eq) and compound 2 (76.12 mg, 492.53 umol, 0.9 eq), the mixture was stirred at 100° C. for 14 hr. LCMS showed a major peak with desired MS was detected. The mixture was concentrated. The residue was purified by prep-HPLC (column: Phenomenex Synergi C18 150*25*10 um; mobile phase: [water(0.05% HCl)-ACN]; B %: 21%-41%, 11 min) to give compound 188 (50 mg, 114.24 umol, 20.88% yield, 95.454% purity, HCl) as yellow solid.

$^1$H NMR (400 MHz, DMSO-d)

δ=9.00 (t, J=5.7 Hz, 1H), 8.36 (s, 1H), 8.29 (s, 1H), 5.55-5.06 (m, 2H), 4.83-4.43 (m, 2H), 3.52 (q, J=6.8 Hz, 2H), 3.05 (br. t, J=5.1 Hz, 2H), 2.66-2.54 (m, 2H)

$^{13}$C NMR (101 MHz, DMSO-d)

δ=169.14, 159.36, 154.60, 153.57, 150.96, 139.84, 131.32, 128.57, 125.81, 123.06, 119.15, 111.78, 33.09, 32.83, 32.75, 32.71, 32.56, 32.29, 23.59

LCMS: Rt=0.787 min, [M+H]$^+$=382.2

Example 44: Synthesis of Compound 189

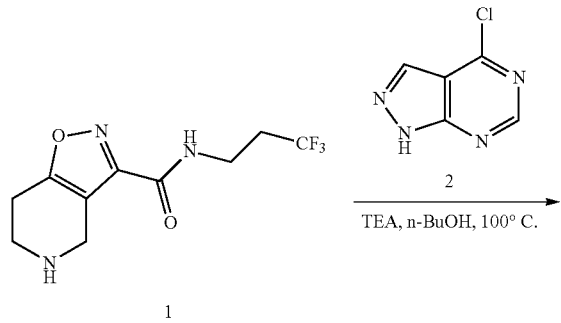

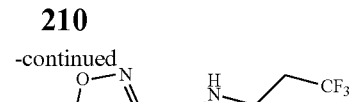

To a mixture of compound 1 (165 mg, 550.59 umol, 1 eq, HCl) in n-BuOH (3 mL) was added TEA (222.86 mg, 2.20 mmol, 306.54 uL, 4 eq) and compound 2 (76.59 mg, 495.53 umol, 0.9 eq), the mixture was stirred at 100° C. for 14 hr. LCMS showed a major peak with desired MS was detected. The mixture was concentrated. The residue was purified by prep-HPLC (column: Phenomenex Synergi C18 150*30 mm*4 um; mobile phase: [water(0.05% HCl)-ACN]; B %: 11%-41%, 10 min) to give compound 189 (100 mg, 228.57 umol, 41.51% yield, 95.489% purity, HCl) as yellow solid.

$^1$H NMR (400 MHz, MeOD)

δ=8.74 (br. s, 1H), 8.51 (s, 1H), 5.22 (br. s, 2H), 4.52 (br. s, 2H), 3.67 (t, J=7.1 Hz, 2H), 3.16 (br. t, J=5.1 Hz, 2H), 2.64-2.47 (m, 2H)

$^{13}$C NMR (101 MHz, MeOD)

δ=168.33, 160.01, 153.94, 151.53, 131.41, 130.56, 127.81, 125.07, 122.32, 110.29, 100.30, 42.75, 33.03, 32.75, 32.47, 32.45, 32.41, 32.38, 32.19, 22.61

LCMS: Rt=0.775 min, [M+H]$^+$=382.0

Example 45: Synthesis of Compound 190

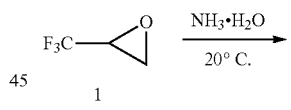

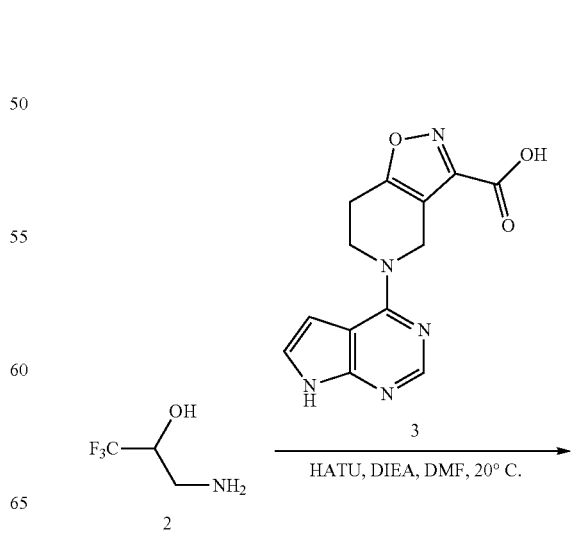

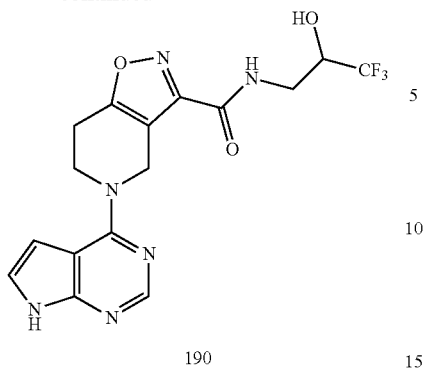

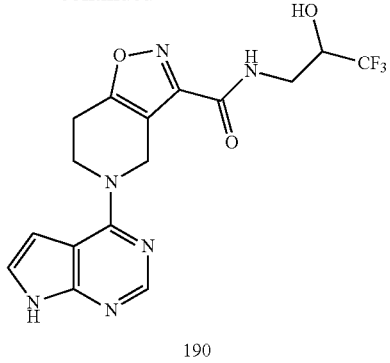

Preparation of Compound 2

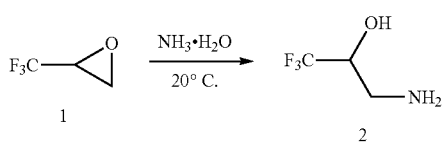

A mixture of compound 1 (1 g, 8.92 mmol, 1 eq) in concentrated NH₃·H₂O (20 mL) was stirred at 20° C. for 8 hr. The mixture was concentrated to give compound 2 (1.0 g, crude) as white solid.

¹H NMR (400 MHz, DMSO+D₂O)

δ=3.92-3.79 (m, 1H), 2.79-2.72 (m, 1H), 2.59 (dd, J=8.7, 13.6 Hz, 1H)

Preparation of Compound 190

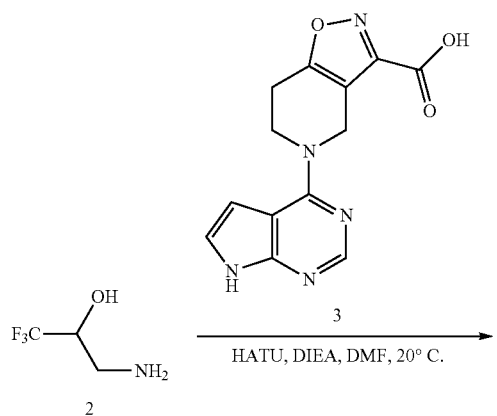

To a mixture of compound 2 (162.90 mg, 1.26 mmol, 1.2 eq) and compound 3 (300 mg, 1.05 mmol, 1 eq) in DMF (5 mL) was added DIEA (407.76 mg, 3.16 mmol, 549.54 uL, 3 eq) and HATU (599.82 mg, 1.58 mmol, 1.5 eq), the mixture was stirred at 20° C. for 8 hr. LCMS showed desired MS was detected. The mixture was diluted with water (5 mL), extracted with EtOAc (5 mL*2), dried over Na₂SO₄, filtered and concentrated. The residue was purified by prep-HPLC (column: Phenomenex Synergi C18 150*25*10 um; mobile phase: [water(0.225% FA)-ACN]; B %: 3%-42%, 12 min) to give Compound 190 (100 mg, 239.70 umol, 22.79% yield, 95% purity) as yellow solid.

¹H NMR (400 MHz, DMSO-d)

δ=11.82 (br s, 1H), 8.90 (t, J=5.8 Hz, 1H), 8.21 (s, 1H), 7.28 (dd, J=2.5, 3.5 Hz, 1H), 6.65 (dd, J=1.8, 3.6 Hz, 1H), 6.53 (d, J=6.5 Hz, 1H), 4.99 (s, 2H), 4.29-4.24 (m, 1H), 4.22 (br t, J=5.6 Hz, 2H), 3.57 (td, J=5.1, 13.5 Hz, 1H), 3.45-3.38 (m, 1H), 3.04 (br t, J=5.4 Hz, 2H)

¹³C NMR (101 MHz, DMSO-d)

δ=169.39, 159.73, 156.95, 154.55, 152.48, 151.01, 129.95, 127.13, 124.31, 122.59, 112.09, 102.95, 100.86, 67.84, 67.55, 67.27, 66.99, 42.17, 41.82, 23.63

LCMS: Rt=0.727 min, [M+H]⁺=397.2

Example 46: Synthesis of Compound 191

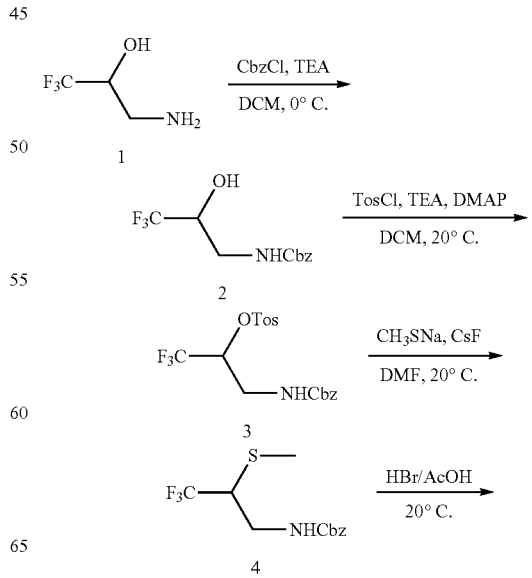

-continued

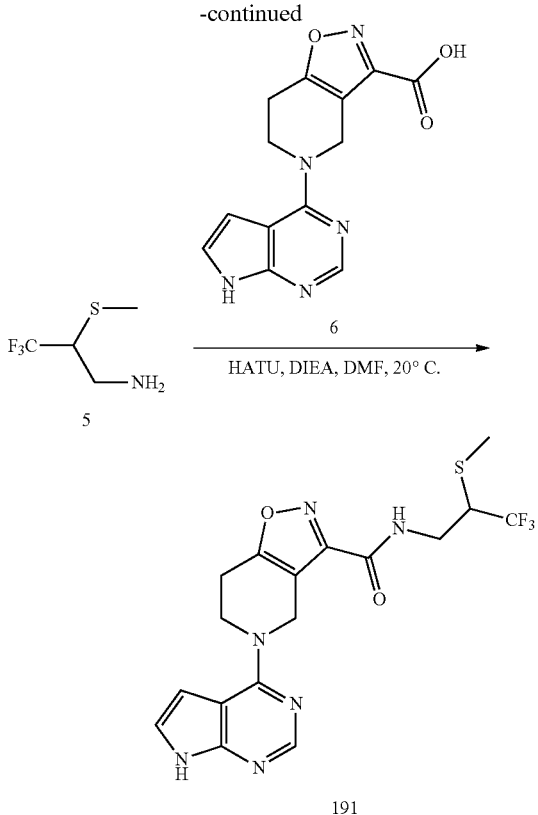

191

Preparation of Compound 2

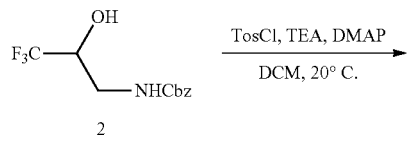

To a solution of compound 1 (2.8 g, 21.69 mmol, 1 eq) in DCM (30 mL) was added CbzCl (4.44 g, 26.03 mmol, 3.70 mL, 1.2 eq) and TEA (3.29 g, 32.54 mmol, 4.53 mL, 1.5 eq). The mixture was stirred at 0° C. for 1 hr. TLC showed compound 1 was consumed and some new spots formed. The reaction mixture was concentrated, diluted with EtOAc (100 mL), washed with water (50 mL) and brine (50 mL), dried over Na$_2$SO$_4$, filtered and concentrated. The residue was purified by silica gel column chromatography (Petroleum ether/Ethyl acetate=5/1~2/1) to give compound 2 (4.2 g, 15.96 mmol, 73.56% yield, 100% purity) as a white solid.
LCMS: Rt=0.837 min, [M+H]$^+$=264.1

Preparation of Compound 3

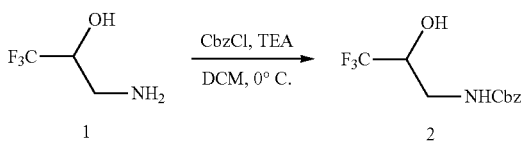 [SMILES: NCC(O)C(F)(F)F ; "CbzCl, TEA" ; O=C(NCC(O)C(F)(F)F)OCc1ccccc1]

-continued

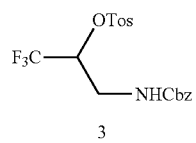

To a solution of compound 2 (1.88 g, 7.14 mmol, 1 eq) in DCM (20 mL) was added TEA (867.30 mg, 8.57 mmol, 1.19 mL, 1.2 eq), DMAP (87.26 mg, 714.25 umol, 0.1 eq) and TosCl (1.63 g, 8.57 mmol, 1.2 eq), the mixture was stirred at 20° C. for 12 hr. TLC showed compound 2 was consumed, and a new major spot was observed. The mixture was diluted with water (30 mL), extracted with EtOAc (30 mL*2), dried with Na$_2$SO$_4$, filtered and concentrated. The residue was triturated with PE/EA (20 mL, 3:1) to give compound 3 (2.8 g, 6.71 mmol, 93.92% yield) as yellow solid.

5 g of compound 3 was purified by silica gel chromatography (Petroleum ether/Ethyl acetate=10/1~2/1) to give compound 3 (4.8 g, 10.84 mmol, 90.53% yield, 94.298% purity) as white solid.

$^1$H NMR (400 MHz, CDCl$_3$)
δ=7.79 (br. d, J=8.2 Hz, 2H), 7.42-7.30 (m, 7H), 5.14 (s, 2H), 5.09-4.96 (m, 2H), 3.82 (ddd, J=2.8, 6.8, 15.1 Hz, 1H), 3.39 (ddd, J=5.6, 8.5, 14.5 Hz, 1H), 2.44 (s, 3H)
LCMS: Rt=0.952 min, [M+H]$^+$=374.1

Preparation of Compound 4

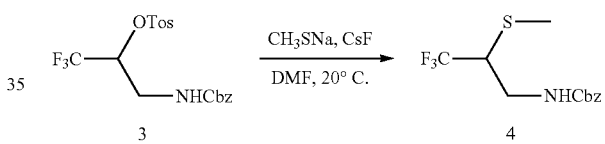

To a solution of compound 3 (3.5 g, 8.39 mmol, 1 eq) in DMF (35 mL) was added CsF (2.55 g, 16.77 mmol, 2 eq) and NaSMe (1.76 g, 25.16 mmol, 3 eq), the mixture was stirred at 20° C. for 1 hr. TLC showed compound 3 was consumed, and two new major spot was observed. The mixture was diluted with saturated NH$_4$Cl solution (150 mL), extracted with EtOAc (70 mL*2), washed with brine (100 mL), dried with Na$_2$SO$_4$, filtered and concentrated. The residue was purified by silica gel chromatography (Petroleum ether/Ethyl acetate=1/0~10:1) to give compound 4 (700 mg, 2.39 mmol, 28.46% yield) as white solid.

$^1$H NMR (400 MHz, CDCl$_3$)
δ=7.42-7.31 (m, 5H), 5.18 (s, 2H), 5.04 (br. dd, J=1.9, 8.0 Hz, 1H), 4.61-4.41 (m, 1H), 2.91 (br. dd, J=3.5, 14.4 Hz, 1H), 2.65 (dd, J=9.4, 14.3 Hz, 1H), 2.15 (s, 3H)

Preparation of Compound 5

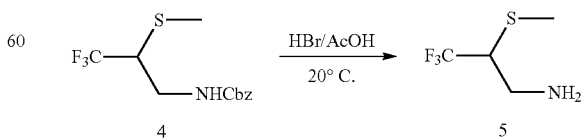

A mixture of compound 4 (150 mg, 511.41 umol, 1 eq) in 35% HBr/AcOH (5 mL) was stirred at 20° C. for 12 hr. TLC showed compound 4 was consumed, and a new major spot was observed. The mixture was concentrated to give compound 5 (120 mg, crude, HBr) as yellow solid.

$^1$H NMR (400 MHz, MeOD)

δ=4.40 (ddd, J=3.7, 7.0, 10.5 Hz, 1H), 3.17 (dd, J=3.9, 14.9 Hz, 1H), 2.84 (dd, J=10.3, 14.9 Hz, 1H), 2.23 (s, 3H)

Preparation of Compound 191

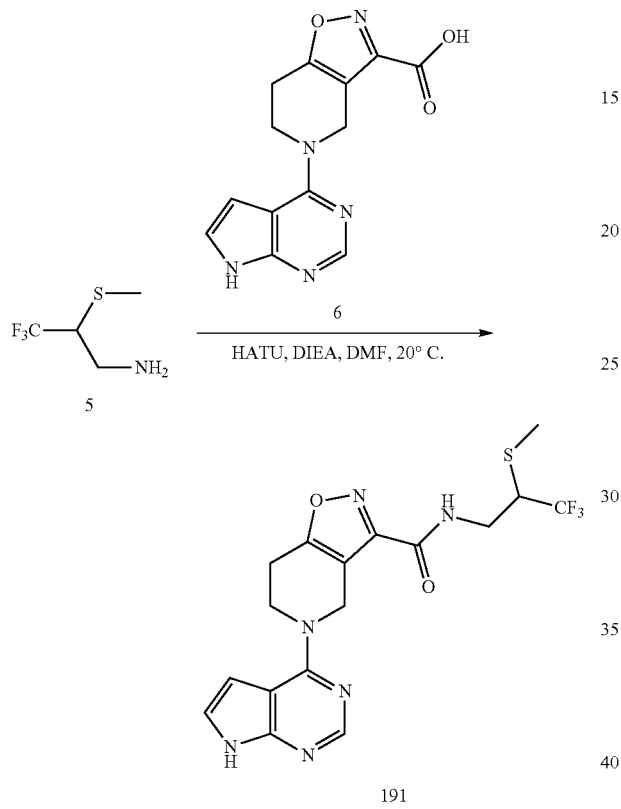

To a mixture of compound 6 (120 mg, 420.67 umol, 1 eq) and compound 5 (120 mg, 499.82 umol, 1.19 eq, HBr) in DMF (1.5 mL) was added HATU (191.94 mg, 504.81 umol, 1.2 eq) and DIEA (217.47 mg, 1.68 mmol, 293.09 uL, 4 eq). The mixture was stirred at 20° C. for 12 hr. LCMS showed a major peak with desired MS was detected. The mixture was diluted with water (20 mL), extracted with EtOAc (20 mL*2), washed with brine (50 mL), dried with Na$_2$SO$_4$, filtered and concentrated. The residue was purified by prep-HPLC (column: Shim-pack C18 150*25*10 um; mobile phase: [water(0.225% FA)-ACN]; B %: 19%-49%, 10 min) to give compound 191 (70 mg, 163.17 umol, 38.79% yield, 99.4% purity) as yellow solid.

$^1$H NMR (400 MHz, MeOD)

δ=8.23 (s, 1H), 7.23 (br. d, J=2.1 Hz, 1H), 6.77 (br. d, J=2.4 Hz, 1H), 5.11 (br. s, 2H), 4.97 (br. s, 1H), 4.33 (br. s, 2H), 3.10 (br. s, 2H), 3.04-2.84 (m, 2H), 2.18 (s, 3H)

$^{13}$C NMR (101 MHz, MeOD)

δ=169.18, 160.81, 157.01, 153.57, 150.80, 149.78, 133.92, 129.54, 126.18, 123.38, 121.78, 111.67, 103.15, 100.85, 50.34, 50.04, 49.74, 49.43, 42.13, 42.04, 31.10, 23.08, 14.19

LCMS: Rt=0.775 min, [M+H]$^+$=427.0

Example 47: Synthesis of Compounds 192 & 193

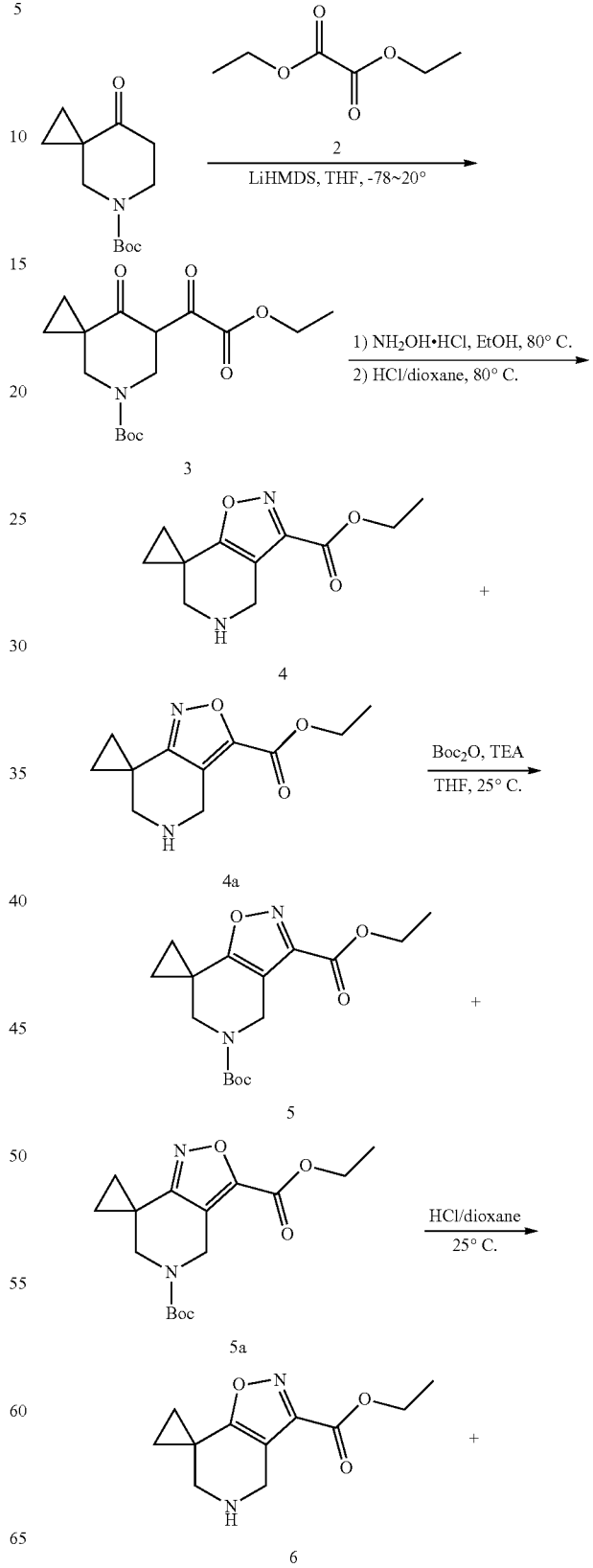

217
-continued
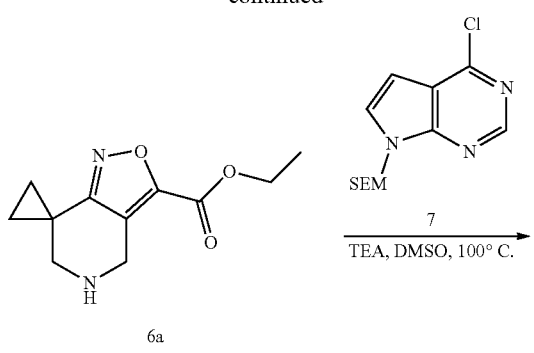
6a
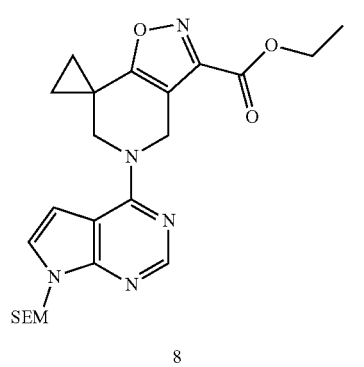
8
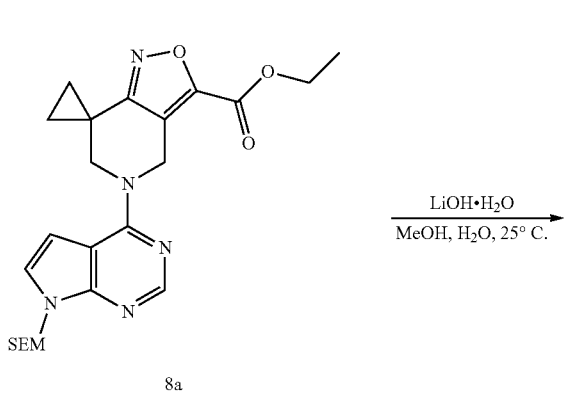
8a
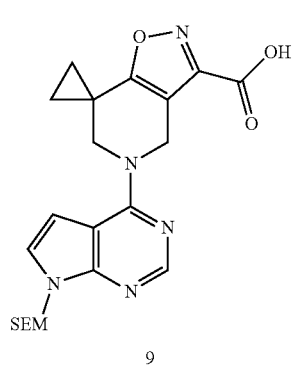
9
218
-continued
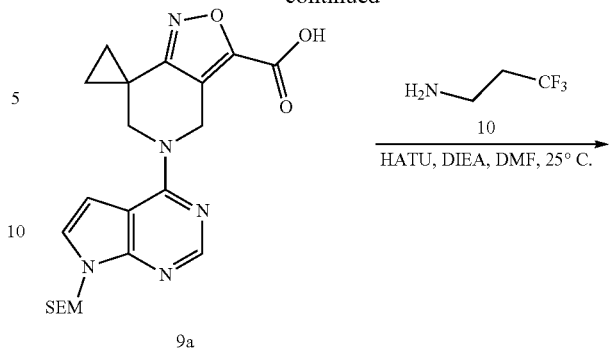
9a
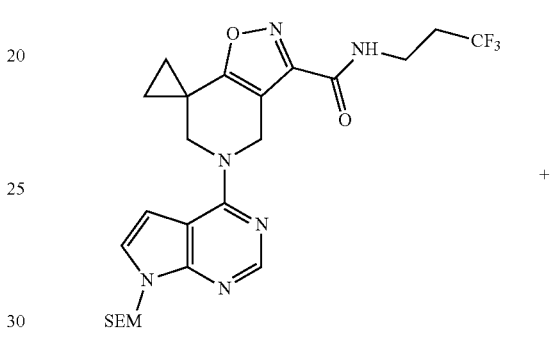
11
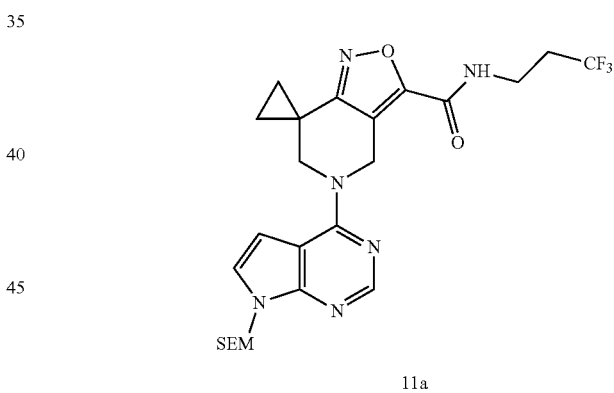
11a
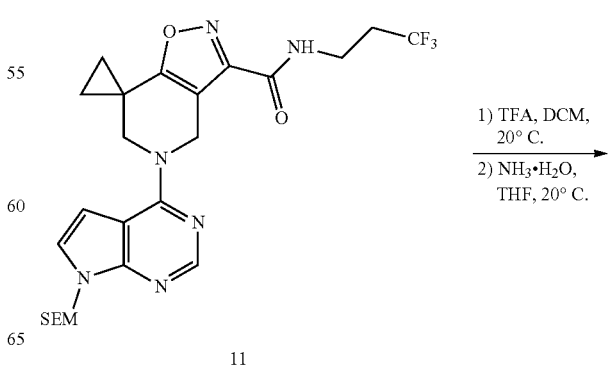
11

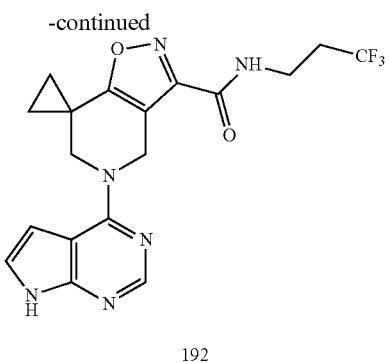

192

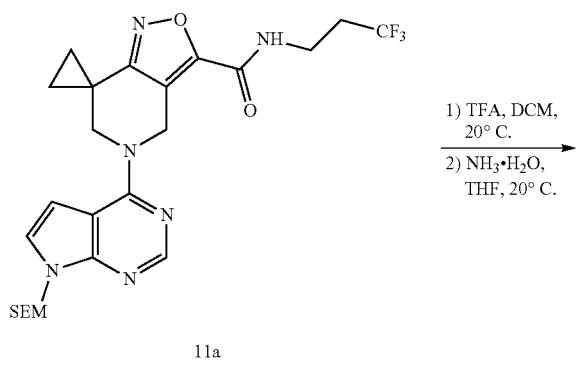

11a

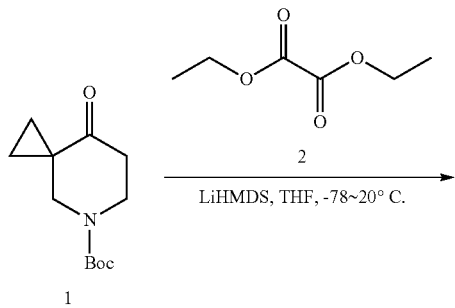

193

Preparation of Compound 3

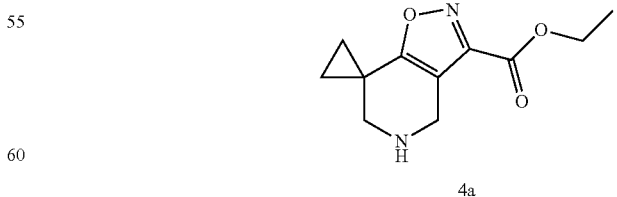

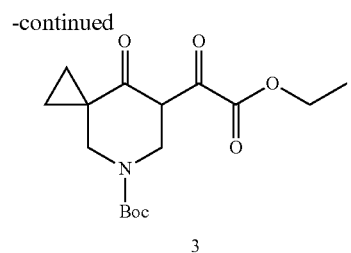

3

To a solution of compound 1 (650 mg, 2.89 mmol, 1 eq) in THF (6 mL) was added dropwise LiHMDS (1 M, 3.75 mL, 1.3 eq) at −78° C. under N$_2$. The mixture was stirred at −78° C. for 30 min. Then a solution of compound 2 (548.15 mg, 3.75 mmol, 512.29 uL, 1.3 eq) in THF (4 mL) was added to the above mixture at −78° C. The mixture was stirred at 20° C. for 12 hr. LCMS showed compound 1 was consumed and desired mass was detected. The reaction mixture was quenched with saturated NH$_4$Cl (20 mL), diluted with water (30 ml), extracted with EtOAc (50 mL*2). The combined organic layers were washed with brine (50 mL), dried over anhydrous Na$_2$SO$_4$, filtered and concentrated. The residue was purified by flash silica gel chromatography (0-15% Ethyl acetate/Petroleum ether) to give compound 3 (650 mg, 2.00 mmol, 69.24% yield) as yellow oil.

$^1$H NMR (400 MHz, CDCl$_3$)
δ=4.65 (s, 2H), 4.36 (q, J=7.1 Hz, 2H), 3.54 (s, 2H), 2.01 (br. s, 2H), 1.48 (br. s, 1H), 1.47 (s, 9H), 1.39 (br. t, J=7.0 Hz, 3H), 1.03 (br. s, 2H)
LCMS: Rt=0.963 min, [M-t-Bu+H]$^+$=270.0

Preparation of Compounds 4 and 4a

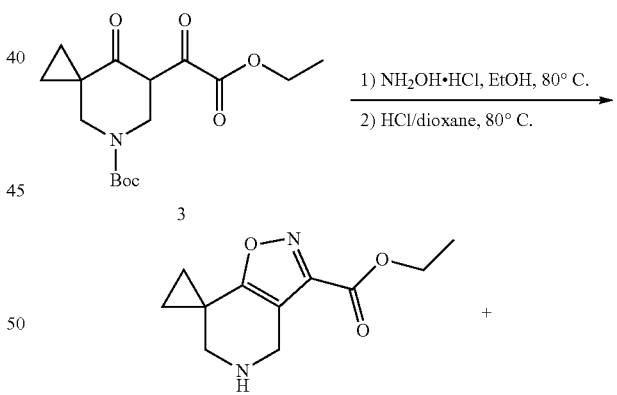

To a solution of compound 3 (650 mg, 2.00 mmol, 1 eq) in EtOH (7 mL) was added NH$_2$OH—HCl (208.24 mg, 3.00 mmol, 1.5 eq). The mixture was stirred at 80° C. for 12 hr. The reaction mixture was cooled down to 25° C. and HCl/dioxane (4 M, 3 mL, 6.01 eq) was then added. The mixture was stirred at 80° C. for another 12 hr. LCMS showed the reaction completed, one major peak with desired mass was detected. The reaction was concentrated to a mixture of compound 4 and 4a (520 mg, crude, HCl) as brown oil. The product was used directly for the next step without further purification.

LCMS: Rt=0.978 min, [M+H]⁺=223.2

Preparation of Compounds 5 and 5a

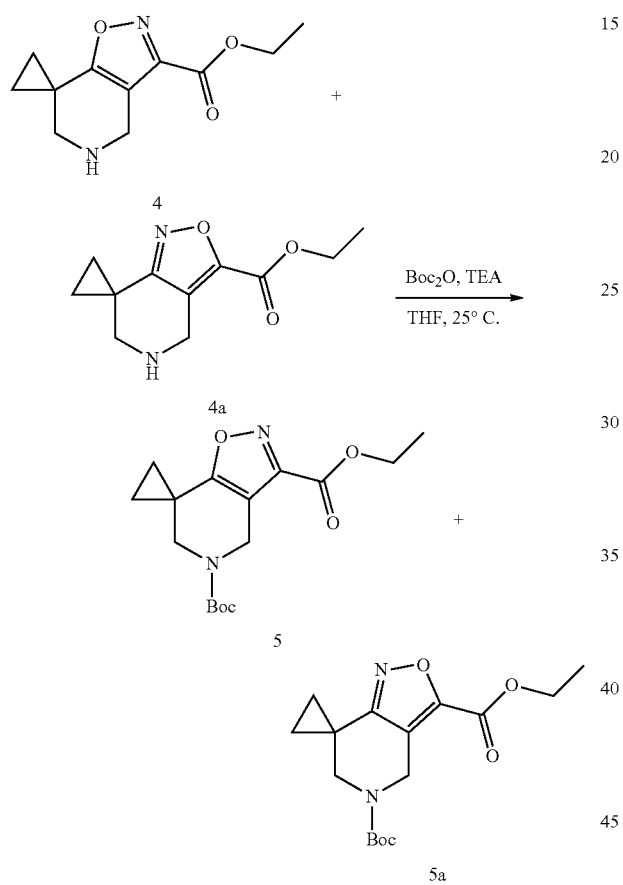

To a solution of compound 4 and 4a (520 mg, 2.02 mmol, 1 eq, HCl) in THF (6 mL) was added TEA (610.19 mg, 6.03 mmol, 839.32 uL, 3 eq) and Boc₂O (658.03 mg, 3.02 mmol, 692.66 uL, 1.5 eq). The mixture was stirred at 25° C. for 2 hr. TLC showed compound 4 and 4a were consumed and some new spots formed. The reaction mixture was diluted with EtOAc (10 mL) and washed with brine (10 mL), dried over anhydrous Na₂SO₄, filtered and concentrated. The residue was purified by flash silica gel chromatography (0-20% Ethyl acetate/Petroleum ether) to give a mixture of compound 5 and 5a (460 mg, 1.43 umol, 70.99% yield) as yellow oil.

¹H NMR (400 MHz, CDCl₃)

δ=4.85-4.57 (m, 2H), 4.50-4.38 (m, 2H), 3.64-3.47 (m, 2H), 1.49 (s, 9H), 1.42 (dt, J=2.3, 7.1 Hz, 3H), 1.38-1.32 (m, 2H), 1.09 (br. s, 2H)

LCMS: Rt=0.970 min, [M+H]⁺=323.0

Preparation of Compounds 6 and 6a

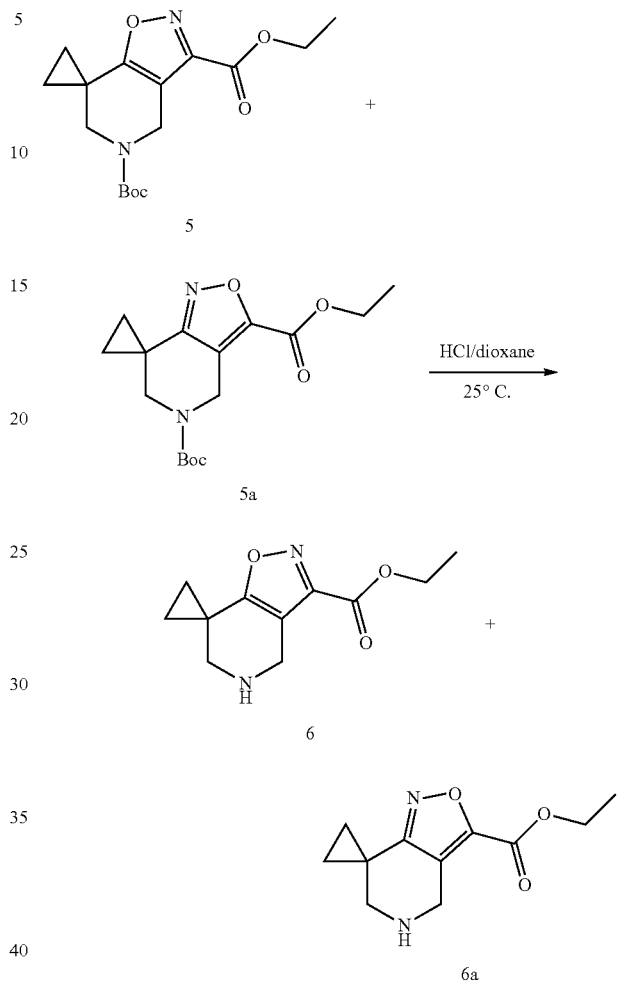

A mixture of compound 5 and 5a (360 mg, 1.12 mmol, 1 eq) was dissolved in HCl/dioxane (4 M, 3.60 mL, 12.89 eq) and stirred at 25° C. for 2 hr. LCMS showed compound 6 and compound 6a was consumed and one major peak with desired mass was detected. The reaction mixture was concentrated under reduced pressure to give a mixture of compound 6 and 6a (290 mg, crude, HCl) as a yellow solid.

LCMS: Rt=0.798 min, [M+H]⁺=223.2

Preparation of Compounds 8 and 8a

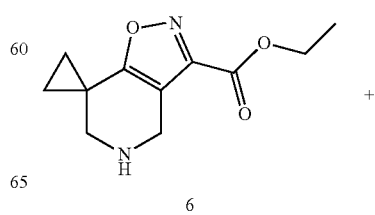

224

Preparation of Compounds 9 and 9a

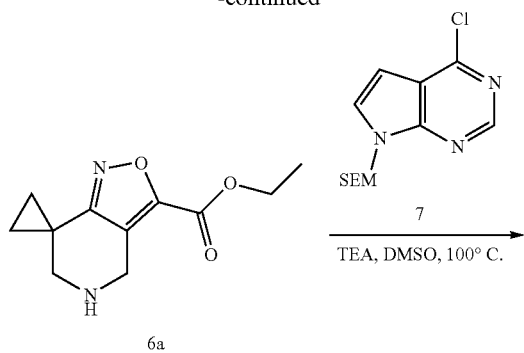
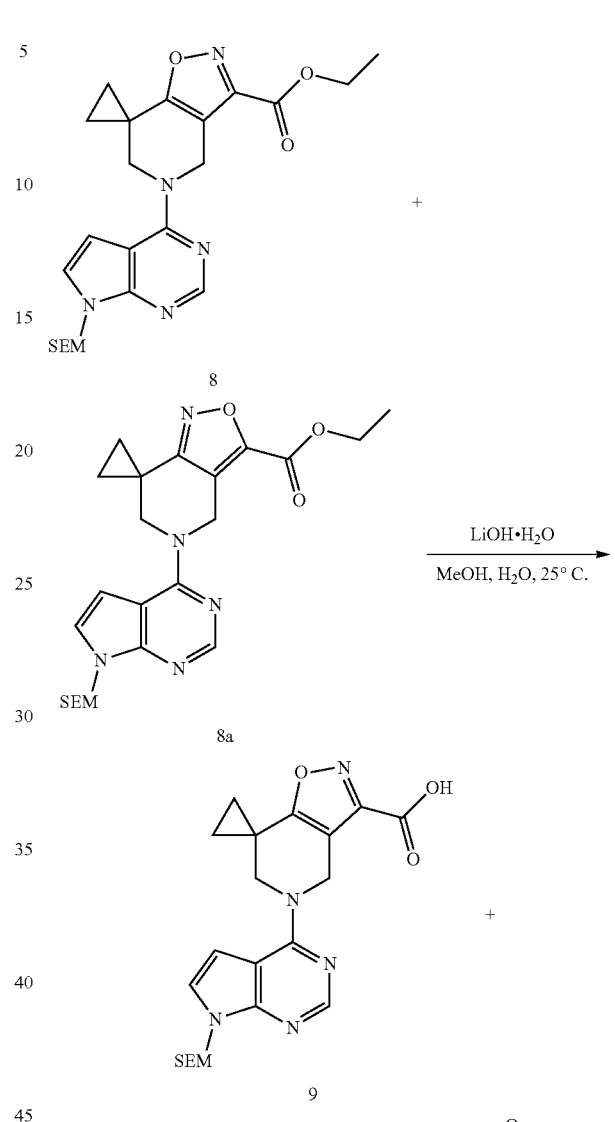

To a solution of compound 6 and 6a (370 mg, 1.43 mmol, 1 eq, HCl) in DMSO (4 mL) was added TEA (434.17 mg, 4.29 mmol, 597.21 uL, 3 eq) and compound 7 (405.94 mg, 1.43 mmol, 1 eq). The mixture was stirred at 100° C. for 12 hr. LCMS showed compound 6 and 6a were consumed and desired mass was detected. The reaction mixture was diluted with water (30 mL), extracted with EtOAc (30 mL*2). The combined organic layers were washed with brine (30 mL*2), dried over anhydrous $Na_2SO_4$, filtered and concentrated. The residue was purified by flash silica gel chromatography (0-20%, Ethyl acetate/Petroleum ether) to give a mixture of compound 8 and 8a (420 mg, 894.36 umol, 62.53% yield) as yellow oil.

$^1$H NMR (400 MHz, $CDCl_3$)

δ=8.39-8.33 (m, 1H), 7.19-7.12 (m, 1H), 6.73-6.61 (m, 1H), 5.60 (s, 2H), 5.37-5.15 (m, 2H), 4.55-4.46 (m, 2H), 4.22-4.11 (m, 2H), 3.57-3.50 (m, 2H), 1.51-1.45 (m, 3H), 1.45-1.36 (m, 2H), 1.29-1.25 (m, 2H), 0.95-0.87 (m, 2H), −0.05 (s, 9H)

LCMS: Rt=1.025 min, [M+H]$^+$=470.0

To a solution of compound 8 and 8a (100 mg, 212.94 umol, 1 eq) in MeOH (1 mL) was added 1M LiOH (1 M, 425.89 uL, 2 eq) aqueous solution. The mixture was stirred at 25° C. for 0.5 hr. LCMS showed compound 8 and 8a were consumed and desired mass was detected. The reaction mixture was diluted with water (5 mL) and adjusted to pH=3 with 1 N HCl aqueous solution. The precipitate was collected by filtration and dried under reduced pressure to give a mixture of compound 9 and 9a (84 mg, crude) as a yellow solid.

¹H NMR (400 MHz, DMSO-d6)

δ=8.32-8.23 (m, 1H), 7.50-7.38 (m, 1H), 6.81-6.71 (m, 1H), 5.57-5.50 (m, 2H), 5.26-4.54 (m, 2H), 4.30-4.13 (m, 1H), 4.06-3.91 (m, 1H), 3.54-3.45 (m, 2H), 1.20-1.01 (m, 3H), 0.82 (dt, J=3.6, 8.0 Hz, 2H), −0.09 (d, J=3.6 Hz, 9H)

LCMS: Rt=0.744 min, [M+H]⁺=441.9

Preparation of Compounds 11 and 11a

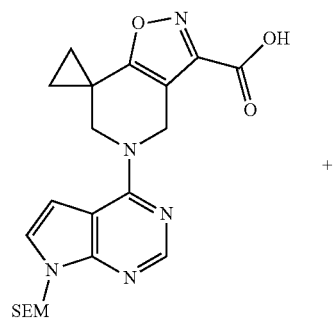

9

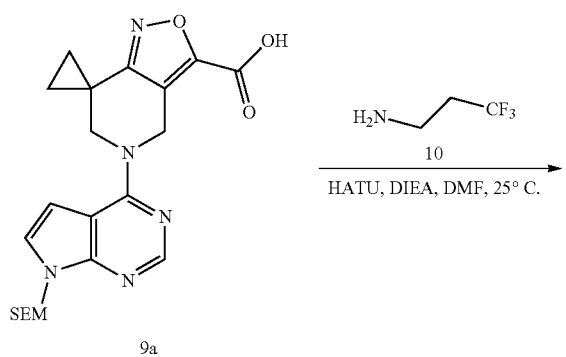

9a

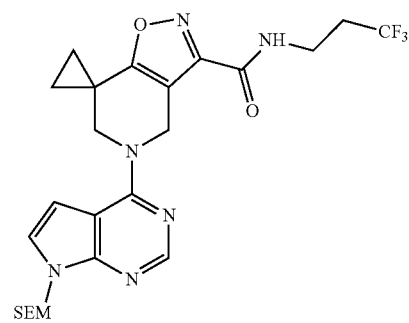

11

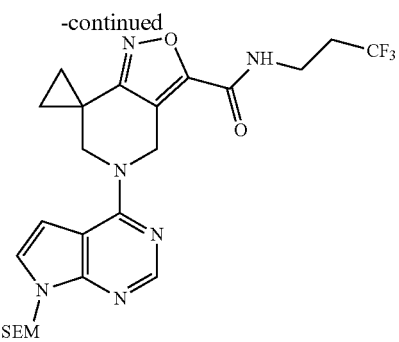

11a

To a mixture of compound 9 and 9a (84 mg, 190.24 umol, 1 eq) in DMF (1 mL) was added HATU (108.50 mg, 285.36 umol, 1.5 eq), DIEA (73.76 mg, 570.72 umol, 99.41 uL, 3 eq) and compound 10 (31.29 mg, 209.26 umol, 1.1 eq, HCl). The mixture was stirred at 25° C. for 12 hr. LCMS showed compound 9 and 9a were consumed and desired mass was detected. The reaction mixture was diluted with water (10 ml), extracted with EtOAc (10 mL*3). The organic layer was washed with brine (10 mL*2), dried over anhydrous Na₂SO₄, filtered and concentrated. The residue was purified by prep-TLC (SiO₂, Petroleum ether/Ethyl acetate=3/1) to give compound 11 (65 mg, 118.71 umol, 62.40% yield, 98% purity) as colorless oil and compound 11a (20 mg, 34.66 umol, 18.22% yield, 93% purity) as colorless oil.

Compound 11

¹H NMR (400 MHz, CDCl₃)

δ=8.34 (s, 1H), 7.14 (d, J=3.8 Hz, 1H), 7.13-7.08 (m, 1H), 6.75 (d, J=3.8 Hz, 1H), 5.59 (s, 2H), 5.23 (s, 2H), 4.19 (s, 2H), 3.73 (q, J=6.6 Hz, 2H), 3.55-3.49 (m, 2H), 2.49 (tq, J=6.7, 10.6 Hz, 2H), 1.41-1.36 (m, 2H), 1.30-1.23 (m, 3H), 0.94-0.87 (m, 2H), −0.06 (s, 9H)

LCMS: Rt=0.973 min, [M+H]⁺=537.1

Compound 11a

¹H NMR (400 MHz, CDCl₃)

δ=8.35 (s, 1H), 7.14 (d, J=3.8 Hz, 1H), 6.80 (br. t, J=6.0 Hz, 1H), 6.72 (d, J=3.8 Hz, 1H), 5.59 (s, 2H), 5.36 (s, 2H), 4.13 (s, 2H), 3.75 (q, J=6.6 Hz, 2H), 3.56-3.49 (m, 2H), 2.50 (tq, J=6.6, 10.6 Hz, 2H), 1.37-1.32 (m, 2H), 1.31-1.24 (m, 3H), 0.94-0.87 (m, 2H), −0.05 (s, 9H)

Preparation of Compound 192

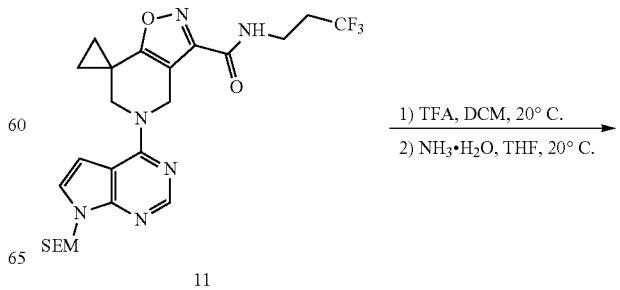

11

227

-continued

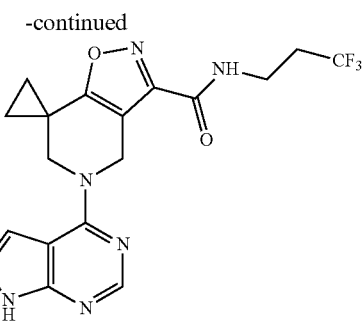

192

To a solution of compound 11 (50 mg, 93.18 umol, 1 eq) in DCM (0.5 mL) was added TFA (770.00 mg, 6.75 mmol, 0.5 mL, 72.48 eq). The mixture was stirred at 20° C. for 2 hr. After the compound 11 was consumed completely, the reaction mixture was concentrated. The residue was dissolved in THF (0.5 mL) and added $NH_3$—$H_2O$ (455.00 mg, 3.25 mmol, 0.5 mL, 25% purity, 34.83 eq). The mixture was stirred at 20° C. for another 1 hr. LCMS showed one major peak with desired mass was detected. The reaction mixture was concentrated and dissolved in DMSO (1 mL) and MeOH (1 mL). The mixture was purified by prep-HPLC (column: Phenomenex Synergi C18 150*25*10 um; mobile phase: [water(0.225% FA)-ACN]; B %: 30%-60%, 10 min) to give compound 192 (16 mg, 39.33 umol, 42.22% yield, 99.9% purity) as a white solid.

$^1$H NMR (400 MHz, DMSO-d6)

δ=11.81 (br. s, 1H), 8.96 (t, J=5.7 Hz, 1H), 8.19 (s, 1H), 7.31-7.22 (m, 1H), 6.61 (d, J=2.1 Hz, 1H), 5.10 (s, 2H), 4.13 (s, 2H), 3.52 (q, J=6.7 Hz, 2H), 2.64-2.53 (m, 2H), 1.25 (s, 4H)

$^{13}$C NMR (101 MHz, DMSO-d6)

δ=171.79, 159.43, 156.82, 154.67, 152.58, 150.92, 131.32, 128.56, 125.81, 123.06, 122.55, 112.23, 102.80, 101.02, 49.52, 42.01, 33.10, 32.83, 32.77, 32.73, 32.58, 32.29, 18.84, 13.38

LCMS: Rt=0.810 min, [M+H]$^+$=407.0

Preparation of Compound 193

228

-continued

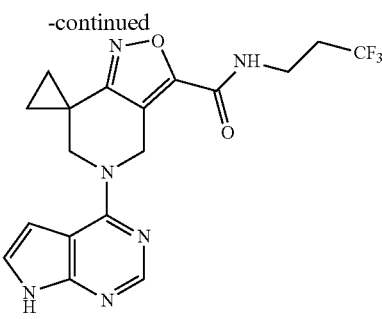

193

To a solution of compound 11a (50 mg, 93.18 umol, 1 eq) in DCM (1 mL) was added TFA (1.54 g, 13.51 mmol, 1.00 mL, 144.96 eq). The mixture was stirred at 20° C. for 2 hr. After the compound 11a was consumed completely, the reaction mixture was concentrated. The residue was dissolved in THF (1 mL) and added $NH_3$—$H_2O$ (455.00 mg, 3.25 mmol, 500.00 uL, 25% purity, 34.83 eq). The mixture was stirred at 20° C. for another 1 hr. LCMS showed one major peak with desired mass was detected. The reaction mixture was concentrated and dissolved in DMSO (1 mL) and MeOH (1 mL). The mixture was purified by prep-HPLC (column: Shim-pack C18 150*25*10 um; mobile phase: [water(0.225% FA)-ACN]; B %: 22%-42%, 10 min) to give compound 193 (20 mg, 47.89 umol, 51.40% yield, 97.3% purity) as a white solid.

$^1$H NMR (400 MHz, DMSO-d6)

δ=11.84 (br. s, 1H), 9.15 (t, J=5.6 Hz, 1H), 8.19 (s, 1H), 7.31-7.21 (m, 1H), 6.61 (d, J=2.4 Hz, 1H), 5.25 (s, 2H), 4.08 (s, 2H), 3.52 (q, J=6.8 Hz, 2H), 2.65-2.53 (m, 2H), 1.28-1.20 (m, 2H), 1.17-1.11 (m, 2H)

$^{13}$C NMR (101 MHz, DMSO-d6)

δ=165.70, 156.67, 155.25, 152.57, 150.93, 131.30, 128.55, 125.80, 123.04, 122.59, 117.75, 102.72, 100.92, 49.65, 41.70, 33.05, 32.78, 32.70, 32.67, 32.51, 32.24, 16.93, 15.72

LCMS: Rt=0.772 min, [M+H]$^+$=407.0

Example 48: Synthesis of Compound 180

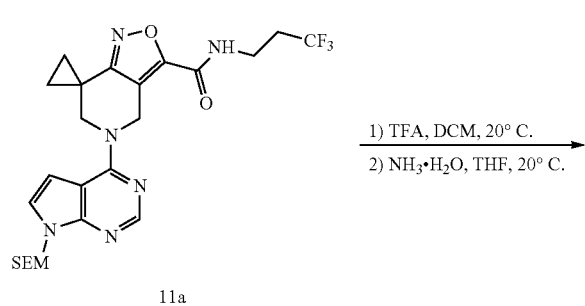

11a

1) TFA, DCM, 20° C.
2) NH$_3$·H$_2$O, THF, 20° C.

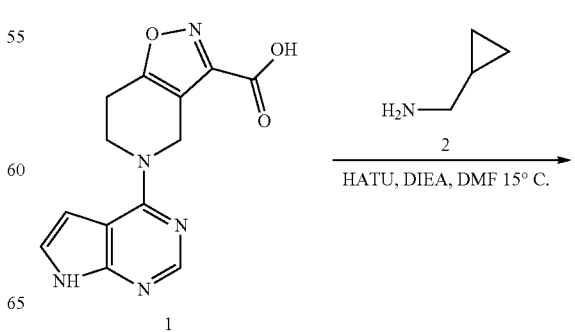

1

2

HATU, DIEA, DMF 15° C.

229

-continued

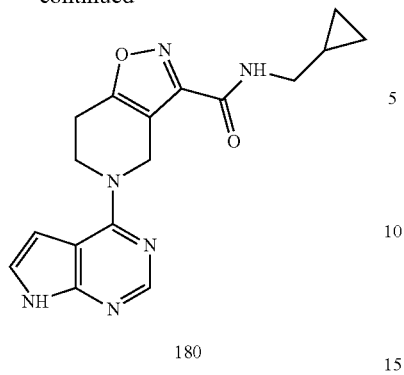

180

To a mixture of compound 1 (100 mg, 350.56 umol, 1 eq) and compound 2 (29.92 mg, 420.67 umol, 1.2 eq) n DMF (2 mL) was added HATU (199.94 mg, 525.84 umol, 1.5 eq) and DIEA (135.92 mg, 1.05 mmol, 183.18 uL, 3 eq), which was stirred at 15° C. for 10 hr. LCMS showed compound 1 was consumed completely and desired MS was detected. The mixture was filtered. The residue was purified by prep-HPLC (column: Phenomenex Synergi C18 150*25*10 um; mobile phase: [water(0.225% FA)-ACN]; B %: 10%-40%, 10 min) to give compound 180 (40 mg, 118.22 umol, 33.72% yield) as a yellow solid.

$^1$H NMR (400 MHz, MeOD)

δ=8.21 (s, 1H), 7.21 (d, J=3.6 Hz, 1H), 6.77 (d, J=3.6 Hz, 1H), 5.10 (s, 2H), 4.32 (t, J=5.7 Hz, 2H), 3.27 (d, J=7.0 Hz, 2H), 3.07 (br. t, J=5.6 Hz, 2H), 1.19-1.07 (m, 1H), 0.59-0.53 (m, 2H), 0.36-0.28 (m, 2H)

$^{13}$C NMR (101 MHz, MeOD)

δ=167.83, 159.01, 156.08, 153.23, 150.03, 149.03, 147.74, 120.55, 110.36, 99.70, 42.48, 41.12, 40.82, 21.97, 9.14, 1.42

LCMS: Rt=0.755 min, [M+H]$^+$=339.0

Example 49: Synthesis of Compound 1%

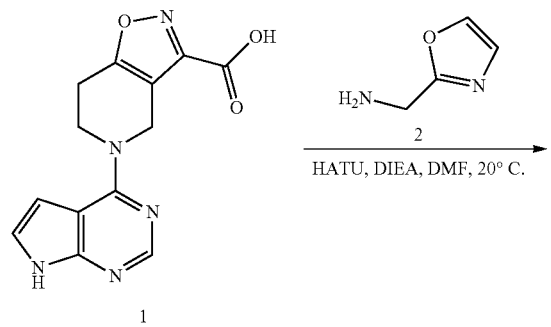

230

-continued

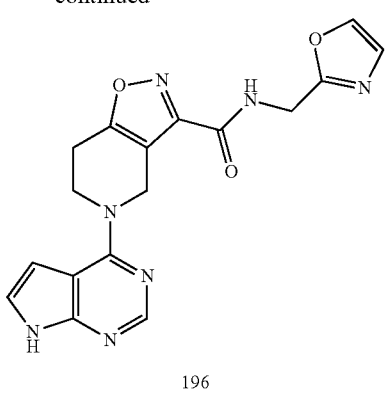

196

To a mixture of compound 1 (100 mg, 350.56 umol, 1 eq) and compound 2 (56.61 mg, 420.67 umol, 1.2 eq, HCl) in DMF (2 mL) was added DIEA (135.92 mg, 1.05 mmol, 183.18 uL, 3 eq) and HATU (199.94 mg, 525.84 umol, 1.5 eq), the mixture was stirred at 20° C. for 8 hr. LCMS showed desired MS was detected. The reaction mixture was diluted with water (5 mL), extracted with EtOAc (5 mL*2), dried over Na$_2$SO$_4$, filtered and concentrated. The residue was purified by prep-HPLC (column: Boston Green ODS 150*30 mm*5 um; mobile phase: [water(0.225% FA)-ACN]; B %: 10%-40%, 10 min) to give compound 1% (30 mg, 78.01 umol, 22.25% yield, 95% purity) as yellow solid.

$^1$H NMR (400 MHz, DMSO-d)

δ=12.42 (br. s, 1H), 9.52 (t, J=5.9 Hz, 1H), 8.38 (s, 1H), 8.07 (d, J=0.8 Hz, 1H), 7.47-7.43 (m, 1H), 7.18 (d, J=0.8 Hz, 1H), 6.83 (br. d, J=1.9 Hz, 1H), 5.05 (s, 2H), 4.58 (d, J=6.0 Hz, 2H), 4.28 (br. t, J=5.6 Hz, 2H), 3.12 (br. t, J=5.1 Hz, 2H)

$^{13}$C NMR (101 MHz, DMSO-d)

δ=169.09, 160.95, 159.61, 154.38, 140.31, 127.53, 124.09, 111.48, 102.75, 102.64, 43.35, 42.86, 36.58, 23.63.

LCMS: Rt=0.700 min, [M+H]$^+$=366.2

Example 50: Synthesis of Compound 145

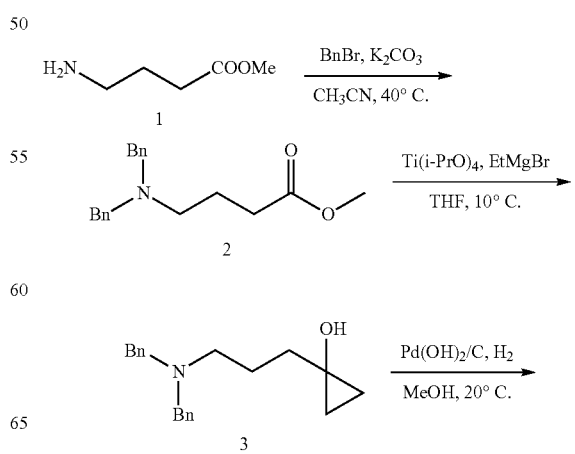

-continued

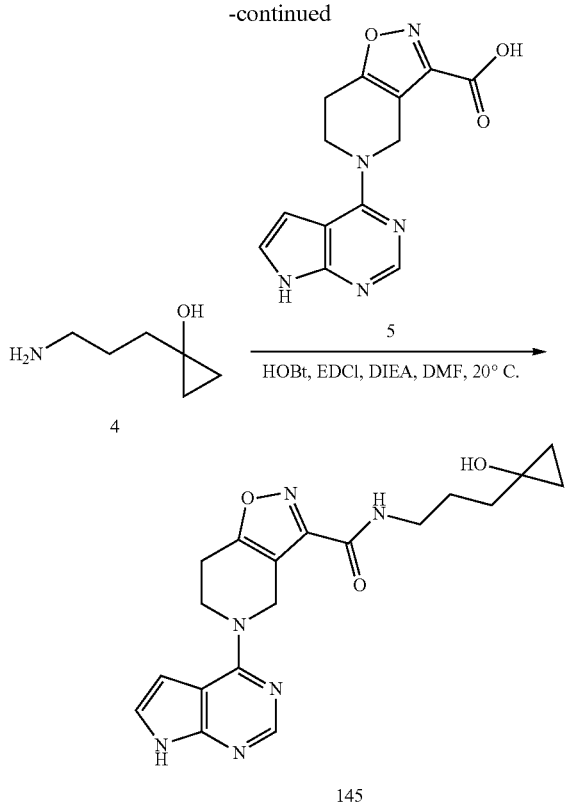

Preparation of Compound 2

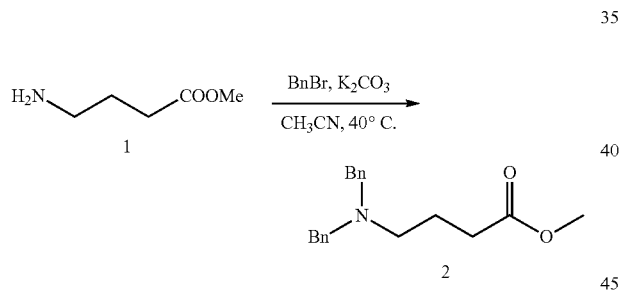

To a mixture of compound 1 (2 g, 17.07 mmol, 1 eq) and K₂CO₃ (5.90 g, 42.68 mmol, 2.5 eq) in CH₃CN (15 mL) was added BnBr (6.13 g, 35.85 mmol, 4.26 mL, 2.1 eq), the mixture was stirred at 40° C. for 11 hr. TLC showed compound 1 was consumed completely and a new spot was detected. The mixture was diluted with water (100 mL), extracted with EtOAc (200 mL), washed with brine (80 mL), dried with Na₂SO₄, filtered and concentrated. The residue was purified by silica gel column chromatography Petroleum ether/Ethyl acetate=1/0~10/1) to give compound 2 (3.3 g, 11.10 mmol, 65.00% yield) as a white oil.

Preparation of Compound 3

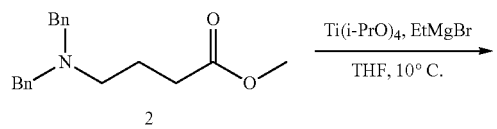

-continued

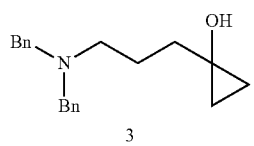

To a solution of compound 2 (3.3 g, 11.10 mmol, 1 eq) and Ti(i-PrO)₄ (1.58 g, 5.55 mmol, 1.64 mL, 0.5 eq) in THF (10 mL) was added EtMgBr (3 M, 11.10 mL, 3 eq) dropwise for 0.5 hr at 10° C., the mixture was stirred 10° C. for 0.5 hr. LCMS showed compound 2 was consumed completely and desired MS was detected. The mixture was quenched with saturated NH₄Cl solution (50 mL) and saturated NaHCO₃ solution (50 mL), extracted with EtOAc (100 mL), washed with brine (50 mL), dried with Na₂SO₄, filtered and concentrated. The residue was purified by silica gel column chromatography (Petroleum ether/Ethyl acetate=10/1~5/1) to give compound 3 (3 g, 10.16 mmol, 91.52% yield) as white oil.

LCMS: Rt=0.758 min, [M+H]⁺=296.3

Preparation of Compound 4

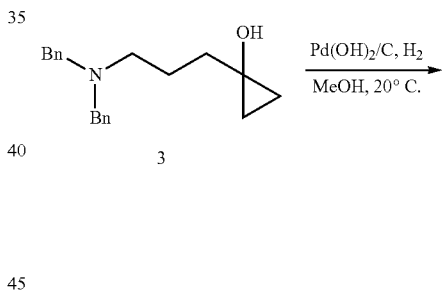

A mixture of compound 3 (600 mg, 2.03 mmol, 1 eq) and Pd(OH)₂/C (285.23 mg) in MeOH (2 mL) was stirred at 15° C. under H₂ balloon for 10 hr at 15 psi. TLC showed compound 3 was consumed completely and a new spot was detected. The mixture was filtered and concentrated to give compound 4 (160 mg, crude) as yellow oil.

¹H NMR (400 MHz, MeOD)

δ=2.72 (t, J=7.1 Hz, 2H), 1.72 (quin, J=7.3 Hz, 2H), 1.62-1.54 (m, 2H), 0.72-0.60 (m, 2H), 0.50-0.37 (m, 2H)

Preparation of Compound 145

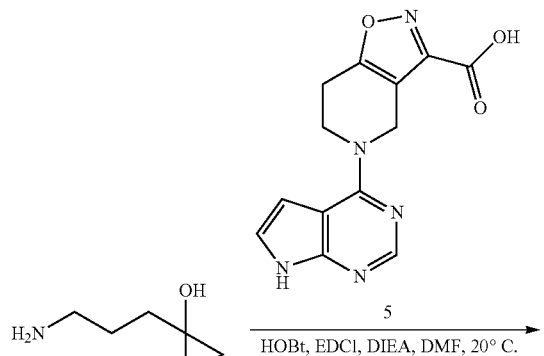

Example 51 Synthesis of Compound 197

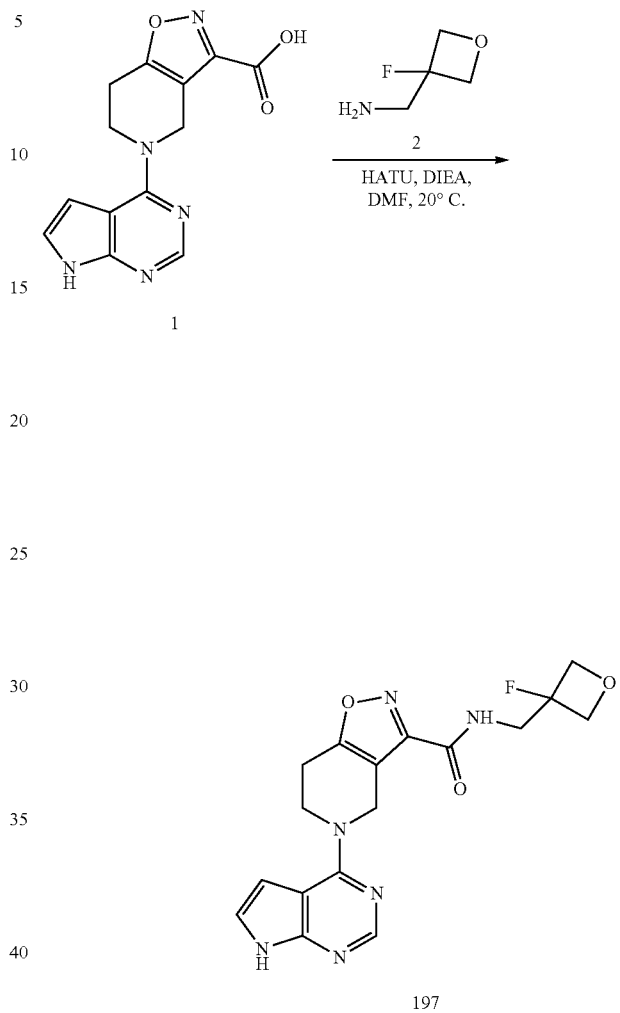

To a solution of compound 4 (70 mg, 607.78 umol, 1.2 eq) and compound 5 (144.48 mg, 506.48 umol, 1 eq) in DMF (1 mL) was added HOBt (82.13 mg, 607.78 umol, 1.2 eq), EDCI (145.64 mg, 759.73 umol, 1.5 eq) and DIEA (261.84 mg, 2.03 mmol, 352.88 uL, 4 eq), the mixture was stirred at 20° C. for 1 hr. LCMS showed compound 4 was consumed completely and desired MS was detected. The mixture was filtered, the residue was purified by prep-HPLC (column: Phenomenex luna C18 150*40 mm*15 um; mobile phase: [water(0.225% FA)-ACN]; B %: 1%-30%, 8.5 min) to give compound 145 (30 mg, 78.45 umol, 15.49% yield, 100% purity) as yellow solid.

$^1$H NMR (400 MHz, MeOD)

δ=8.08 (s, 1H), 7.08 (d, J=3.7 Hz, 1H), 6.63 (d, J=3.7 Hz, 1H), 4.96 (s, 2H), 4.18 (t, J=5.6 Hz, 2H), 3.34 (t, J=7.2 Hz, 2H), 2.94 (br t, J=5.4 Hz, 2H), 1.75 (quin, J=7.5 Hz, 2H), 1.56-1.44 (m, 2H), 0.61-0.51 (m, 2H), 0.40-0.31 (m, 2H)

$^1$C NMR (101 MHz, MeOD)

δ=168.89, 160.14, 157.16, 154.29, 151.17, 150.20, 121.58, 111.43, 103.17, 100.75, 53.83, 42.17, 41.85, 39.01, 35.28, 25.66, 23.04, 12.23

LCMS: Rt=0.729 min, [M+H]$^+$=383.2

To a solution of compound 1 (100 mg, 350.56 umol, 1 eq) and compound 2 (55.27 mg, 525.84 umol, 1.5 eq) in DMF (3 mL) was added HATU (199.94 mg, 525.84 umol, 1.5 eq) and DIEA (90.61 mg, 701.12 umol, 122.12 uL, 2 eq), the mixture was stirred at 20° C. for 2 hr. LCMS showed compound 1 was consumed completely and desired MS was detected. The mixture was purified by prep-HPLC (column: Phenomenex Synergi C18 150*25*10 um; mobile phase: [water(0.225% FA)-ACN]; B %: 1%-31%, 10 min) to give compound 197 (30 mg, 79.76 umol, 22.75% yield, 99% purity) as yellow solid.

$^1$H NMR (400 MHz, DMSO-d)

δ=11.82 (br. s, 1H), 9.19 (t, J=6.1 Hz, 1H), 8.20 (s, 1H), 7.27 (dd, J=2.5, 3.4 Hz, 1H), 6.64 (dd, J=1.6, 3.4 Hz, 1H), 4.98 (s, 2H), 4.76-4.55 (m, 4H), 4.21 (t, J=5.6 Hz, 2H), 3.80 (dd, J=6.1, 19.4 Hz, 2H), 3.03 (br. t, J=5.3 Hz, 2H)

$^{13}$CNMR (400 MHz, DMSO-d6)

δ=167.25, 158.17, 154.86, 152.46, 150.39, 148.90, 120.15, 110.04, 100.87, 98.73, 93.80, 91.72, 76.63, 76.40, 40.11, 39.70

LCMS: Rt=0.684 min, [M+H]$^+$=373.2

Example 52: Synthesis of Compound 198

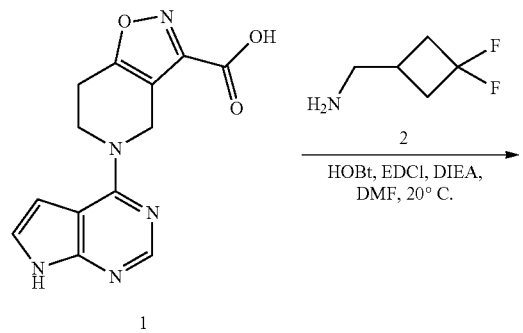

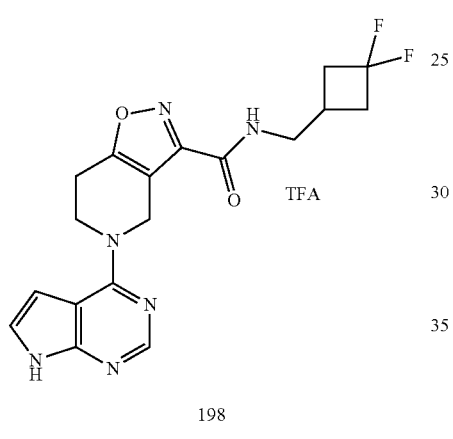

To a solution of compound 1 (100 mg, 350.56 umol, 1 eq) in DMF (2.5 mL) was added HOBt (56.84 mg, 420.67 umol, 1.2 eq), EDCI (100.80 mg, 525.84 umol, 1.5 eq), DIEA (181.23 mg, 1.40 mmol, 244.25 uL, 4 eq) and compound 2 (66.29 mg, 420.67 umol, 1.2 eq, HCl). The mixture was stirred at 20° C. for 12 hr. LCMS showed desired MS was detected. The mixture was diluted with water (30 mL), extracted with EtOAc (20 mL*2), washed with brine (50 mL), dried with Na$_2$SO$_4$, filtered and concentrated. The residue was purified by prep-HPLC (column: Phenomenex Luna C18 150*25 mm*10 um; mobile phase: [water(0.1% TFA)-ACN]; B %: 19%-39%, 10 min) to give compound 198 (35 mg, 69.41 umol, 19.80% yield, 99.63% purity, TFA) as yellow solid.

$^1$H NMR (400 MHz, MeOD)

δ=8.40 (s, 1H), 7.43 (d, J=3.7 Hz, 1H), 7.03 (d, J=3.8 Hz, 1H), 5.21 (s, 2H), 4.43 (t, J=5.7 Hz, 2H), 3.58-3.49 (m, 2H), 3.19 (t, J=5.7 Hz, 2H), 2.77-2.59 (m, 2H), 2.54-2.29 (m, 3H)

$^{13}$C NMR (101 MHz, MeOD)

δ=168.21, 160.19, 158.17, 157.33, 156.52, 155.92, 154.97, 154.08, 143.55, 123.73, 110.44, 103.18, 102.78, 43.35, 43.32, 42.91, 42.88, 38.16, 37.93, 37.71, 22.91, 22.82, 22.76, 22.71, 22.64

LCMS: Rt=0.778 min, [M+H]$^+$=389.1

Example 53: Synthesis of Compound 199

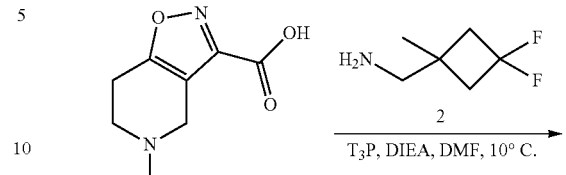

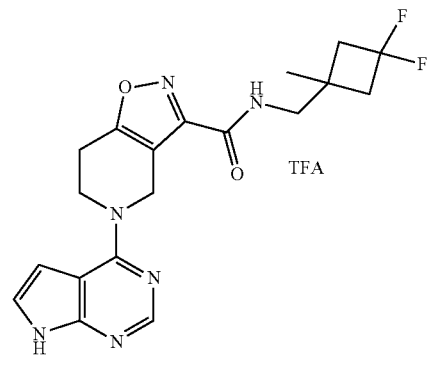

To a mixture of compound 1 (138.52 mg, 485.58 umol, 1 eq) and compound 2 (100 mg, 582.70 umol, 1.2 eq, HCl) in DMF (1.5 mL) was added DIEA (251.03 mg, 1.94 mmol, 338.31 uL, 4 eq) and T3P (252.96 mg, 795.01 umol, 236.41 uL, 50% purity, 0.75 eq), the mixture was stirred at 10° C. for 14 hr. LCMS showed compound 1 was consumed, and desired MS was detected. The mixture was diluted with water (30 mL), extracted with EtOAc (30 mL*3), washed with brine (30 mL*2), dried over Na$_2$SO$_4$, filtered and concentrated. The residue was purified by prep-HPLC (column: Phenomenex Luna C18 150*25 mm*10 um; mobile phase: [water(0.1% TFA)-ACN]; B %: 19%-49%, 10 min) to give compound 199 (35 mg, 65.81 umol, 13.55% yield, 97.1% purity, TFA) as white solid.

$^1$H NMR (400 MHz, MeOD)

δ=8.41 (s, 1H), 7.45 (d, J=3.8 Hz, 1H), 7.06 (d, J=3.8 Hz, 1H), 5.21 (s, 2H), 4.44 (t, J=5.8 Hz, 2H), 3.54-3.45 (m, 2H), 3.21 (br t, J=5.7 Hz, 2H), 3.02 (br. s, 1H), 2.72-2.57 (m, 2H), 2.37-2.20 (m, 2H), 1.30 (s, 3H)

$^{13}$C NMR (101 MHz, MeOD)

δ=168.16, 160.45, 154.10, 142.60, 124.05, 122.10, 121.75, 119.00, 116.23, 113.65, 110.31, 103.55, 102.70, 43.81, 43.59, 43.52, 43.37, 28.81, 28.69, 28.61, 23.44, 22.90.

LCMS: Rt=0.799 min, [M+H]$^+$=403.1

Example 54: Synthesis of Compound 200

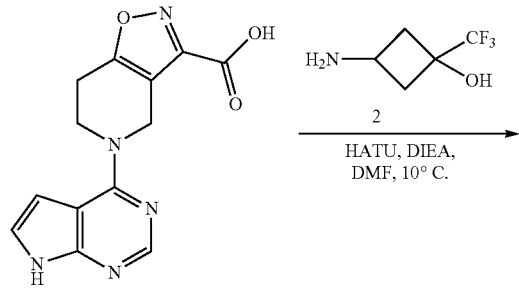

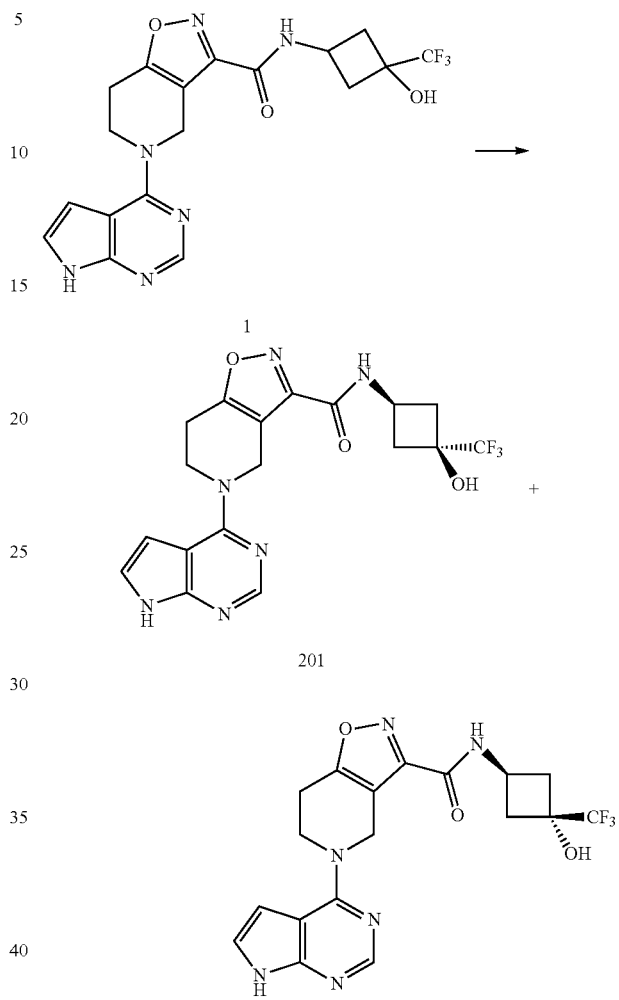

To a mixture of compound 1 (153.25 mg, 537.23 umol, 1 eq) and compound 2 (100 mg, 644.67 umol, 1.2 eq) in DMF (1.5 mL) was added DIEA (277.72 mg, 2.15 mmol, 374.29 uL, 4 eq) and HATU (306.40 mg, 805.84 umol, 1.5 eq), the mixture was stirred at 10° C. for 14 hr. LCMS showed compound 1 was consumed, and desired MS was detected. The mixture was diluted with water (35 mL), extracted with EtOAc (40 mL*3), washed with brine (40 mL*2), dried over $Na_2SO_4$, filtered and concentrated. The residue was purified by prep-HPLC (column: Phenomenex Synergi C18 150*25*10 um; mobile phase: [water(0.225% FA)-ACN]; B %: 10%-40%, 10 min) to give COMPOUND 200 (53 mg, 125.23 umol, 23.31% yield, 99.8% purity) as off-white solid.

$^1$H NMR (400 MHz, MeOD)

δ=8.20 (s, 1H), 7.20 (d, J=3.6 Hz, 1H), 6.74 (dd, J=2.1, 3.6 Hz, 1H), 5.06 (s, 2H), 4.76 (s, 1H), 4.30 (t, J=5.6 Hz, 2H), 3.33 (td, J=1.6, 3.3 Hz, 2H), 2.99-2.87 (m, 1H), 2.62-2.52 (m, 1H), 2.51-2.46 (m, 1H), 2.45-2.35 (m, 1H)

$^{13}$C NMR (101 MHz, MeOD)

δ=168.96, 168.92, 159.84, 159.69, 157.15, 154.01, 151.15, 150.17, 121.62, 111.53, 103.17, 100.74, 42.11, 41.88, 38.97, 38.30, 36.32, 35.94, 23.04

LCMS: Rt=0.741 min, [M+H]$^+$=423.0

Example 55: Synthesis of Compounds 201 & 202

Compound 1 (100 mg, 236.76 umol, 1 eq) was separated by SFC (column: DAICEL CHIRALPAK IG (250 mm*30 mm, 10 um); mobile phase: [0.1% $NH_3H_2O$ MEOH]; B %: 50%-50%, 3.1 min) to give Compound 201 (Rt=1.686 min, 24.95 mg, 58.48 umol, 24.70% yield, 99% purity) obtained as a white solid and Compound 202 (Rt=2.226 min, 39.84 mg, 91.50 umol, 38.64% yield, 97% purity) as a white solid.

Compound 201:

$^1$H NMR (400 MHz, MeOD-d4)

δ=8.19 (s, 1H), 7.19 (d, J=3.6 Hz, 1H), 6.73 (d, J=3.6 Hz, 1H), 5.05 (s, 2H), 4.34-4.24 (m, 3H), 3.05 (t, J=5.6 Hz, 2H), 2.97-2.89 (m, 2H), 2.45-2.34 (m, 2H)

LCMS: Rt=0.760 min, [M+H]$^+$=423.1 Compound 202:

$^1$H NMR (400 MHz, MeOD-d4)

δ=8.19 (s, 1H), 7.19 (d, J=3.6 Hz, 1H), 6.74 (d, J=3.6 Hz, 1H), 5.06 (s, 2H), 4.74 (t, J=8.3 Hz, 1H), 4.60 (s, 1H), 4.29 (t, J=5.6 Hz, 2H), 3.05 (br t, J=5.5 Hz, 2H), 2.60-2.50 (m, 2H), 2.49-2.39 (m, 2H)

LCMS: Rt=0.768 min, [M+H]$^+$=423.1

Example 56: Synthesis of Compound 194

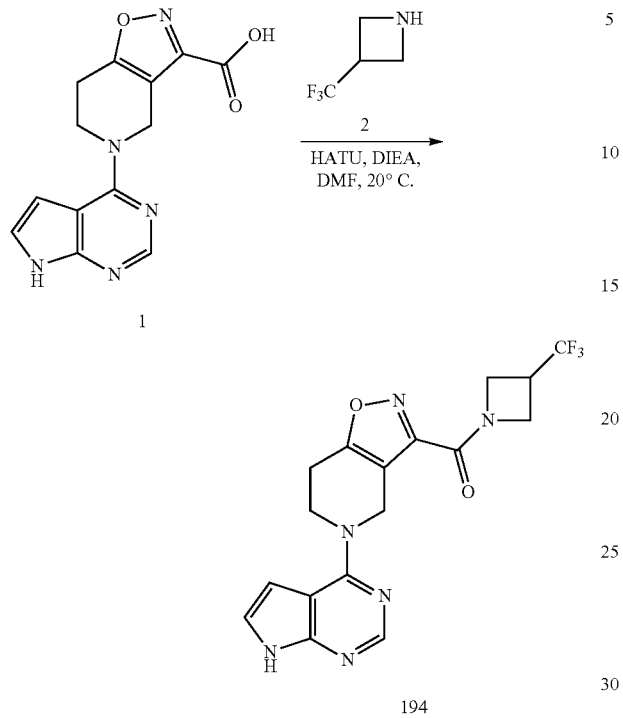

To a solution of compound 1 (100 mg, 350.56 umol, 1 eq) and compound 2 (84.95 mg, 525.84 umol, 1.5 eq, HCl) in DMF (2 mL) was added HATU (199.94 mg, 525.84 umol, 1.5 eq) and DIEA (90.61 mg, 701.12 umol, 122.12 uL, 2 eq), the mixture was stirred at 20° C. for 2 hr. LCMS showed compound 1 was consumed completely and desired MS was detected. The mixture was filtered, the filter cake was purified by prep-HPLC (column: Phenomenex Synergi C18 150*25*10 um; mobile phase: [water(0.225% FA)-ACN]; B %: 25%-55%, 9 min) to give compound 194 (40 mg, 96.55 umol, 27.54% yield, 94.7% purity) as yellow solid.

$^1$H NMR (400 MHz, DMSO-d)

δ=12.53 (br. s, 1H), 8.43 (s, 1H), 7.49 (br. s, 1H), 6.87 (br. s, 1H), 5.05 (s, 2H), 4.74 (t, J=9.6 Hz, 1H), 4.45 (dd, J=5.4, 10.5 Hz, 1H), 4.37 (t, J=9.8 Hz, 1H), 4.29 (br. t, J=5.7 Hz, 2H), 4.10 (br. dd, J=5.4, 10.8 Hz, 1H), 3.79-3.70 (m, 1H), 3.14 (br. t, J=5.3 Hz, 2H)

$^{13}$C NMR (101 MHz, DMSO-d)

δ=169.85, 169.35, 159.57, 158.19, 157.58, 127.50, 124.06, 116.97, 49.08, 48.75, 48.42, 47.76, 47.66, 36.27, 24.18, 23.47

LCMS: Rt=0.789 min, [M+H]$^+$=393.2

Example 57: Synthesis of Compound 182

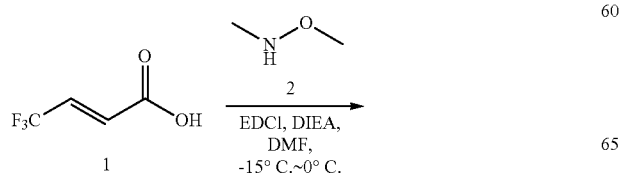

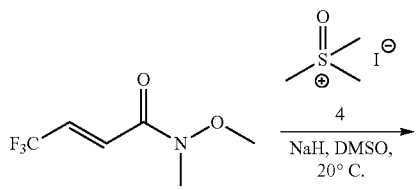

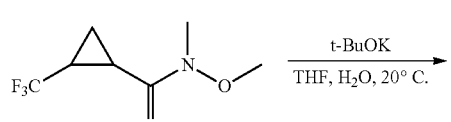

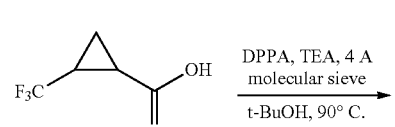

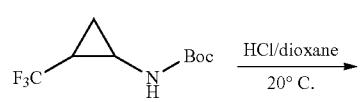

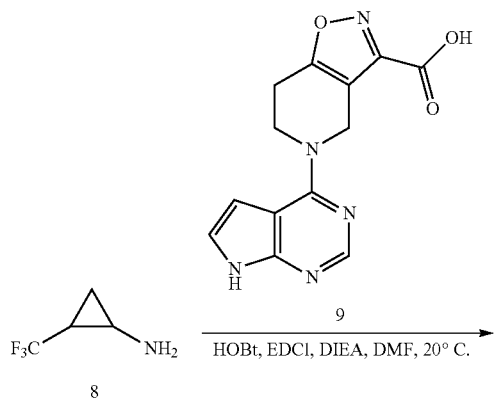

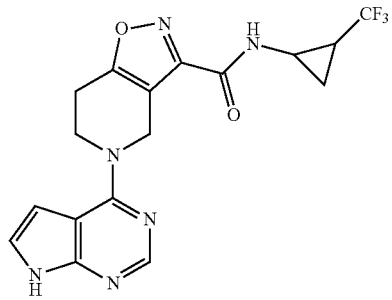

Preparation of Compound 3

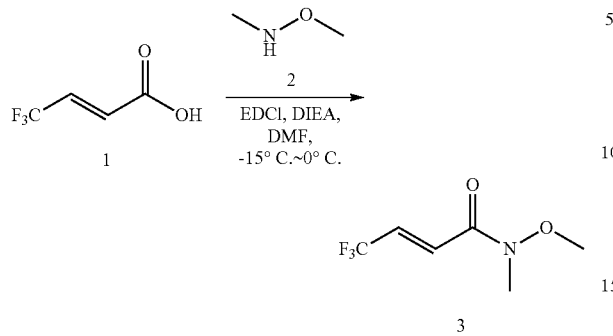

To a solution of compound 1 (1.3 g, 9.28 mmol, 1 eq) in DCM (10 mL) was added a solution of compound 2 (1.13 g, 11.60 mmol, 1.25 eq, HCl) and DIEA (1.92 g, 14.85 mmol, 2.59 mL, 1.6 eq) in DCM (10 mL) at −15° C., then EDCI (2.14 g, 11.14 mmol, 1.2 eq) was added. The mixture was stirred at 0° C. for 3 hr. TLC showed compound 1 was consumed, and a new major spot was observed. The mixture diluted with water (50 mL), extracted with DCM (30 mL*2), washed with brine (50 mL*2), dried with $Na_2SO_4$, filtered and concentrated at 25° C. to give compound 3 (1.4 g, crude) as colorless oil.

$^1$H NMR (400 MHz, $CDCl_3$)

δ=7.09 (br. d, J=15.9 Hz, 1H), 6.89-6.77 (m, 1H), 3.75 (s, 3H), 3.30 (s, 3H)

Preparation of Compound 5

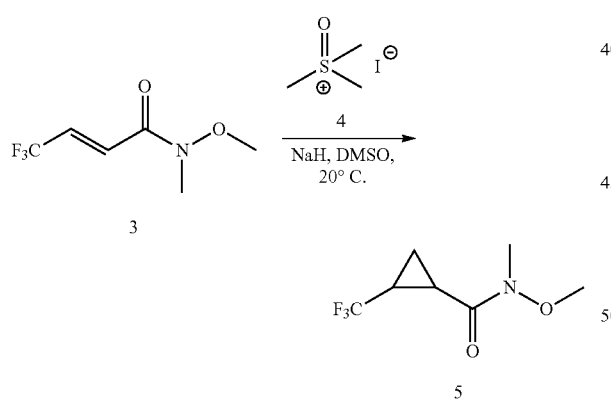

To a solution of compound 4 (3.36 g, 15.29 mmol, 2 eq) in DMSO (10 mL) was added NaH (611.59 mg, 15.29 mmol, 60% purity, 2 eq), the mixture was stirred at 20° C. for 1 hr, then a solution of compound 3 (1.4 g, 7.64 mmol, 176.99 uL, 1 eq) in DMSO (10 mL) was added. The mixture was stirred at 20° C. under $N_2$ for 11 hr. TLC showed a major spot was observed. The mixture was quenched with sat. $NH_4Cl$ solution (50 mL), extracted with DCM (40 mL*2), washed with brine (50 mL*5), dried with $Na_2SO_4$, filtered and concentrated at 25° C. to give compound 5 (1.3 g, crude) as yellow oil.

$^1$H NMR (400 MHz, $CDCl_3$)

δ=3.78 (s, 3H), 3.24 (s, 3H), 2.64-2.51 (m, 1H), 2.22-2.03 (m, 1H), 1.41-1.35 (m, 1H), 1.24-1.20 (m, 1H)

Preparation of Compound 6

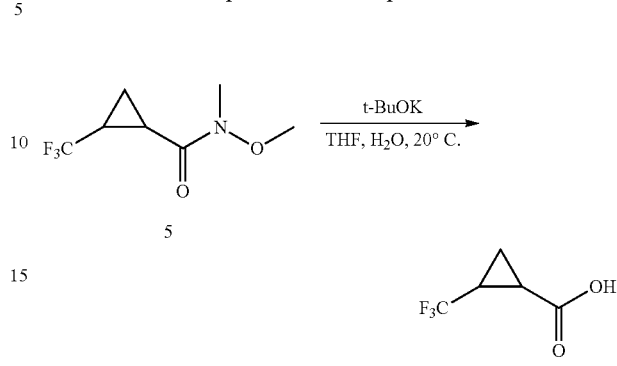

To a solution of compound 5 (1.3 g, 6.59 mmol, 1 eq) in THF (15 mL) was added t-BuOK (3.70 g, 32.97 mmol, 5 eq) and $H_2O$ (237.58 mg, 13.19 mmol, 237.58 uL, 2 eq). The mixture was stirred at 20° C. under $N_2$ for 4 hr. TLC showed a major spot was observed. The mixture was poured into ice/water (40 mL), adjusted with 1 N HCl solution to pH=1, extracted with EtOAc (30 mL*2), washed with brine (50 mL*3), dried with $Na_2SO_4$, filtered and concentrated at 40° C. to give compound 6 (800 mg, crude) as yellow oil.

$^1$H NMR (400 MHz, $CDCl_3$)

δ=2.28-2.20 (m, 1H), 2.06-2.01 (m, 1H), 1.48-1.41 (m, 1H), 1.40-1.33 (m, 1H)

Preparation of Compound 7

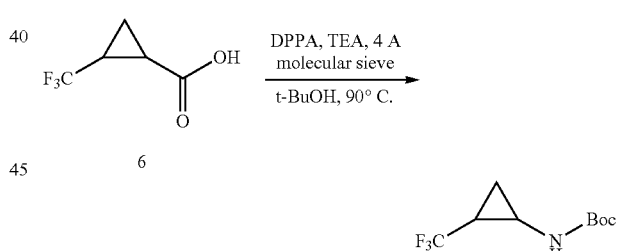

To a solution of compound 6 (300 mg, 1.95 mmol, 1 eq) and 4 Å molecular sieve (600 mg) in t-BuOH (6 mL) was added TEA (197.01 mg, 1.95 mmol, 270.99 uL, 1 eq) and DPPA (535.80 mg, 1.95 mmol, 421.89 uL, 1 eq). The mixture was stirred at 90° C. under $N_2$ for 12 hr. TLC showed several new spots were observed. The mixture was concentrated, diluted with EtOAc (30 mL), filtered, diluted with water (30 mL), extracted with EtOAc (20 mL*2), washed with 10% citric acid solution (30 mL), saturated $NaHCO_3$ solution (30 mL) and brine (30 mL), dried with $Na_2SO_4$, filtered and concentrated to give compound 7 (340 mg, crude) as yellow oil.

$^1$H NMR (400 MHz, $CDCl_3$)

δ=4.77-4.29 (m, 1H), 2.90-2.68 (m, 1H), 1.69-1.56 (M, 1H), 1.39 (s, 9H), 1.15-1.09 (m, 1H), 1.06-0.90 (m, 1H)

Preparation of Compound 8

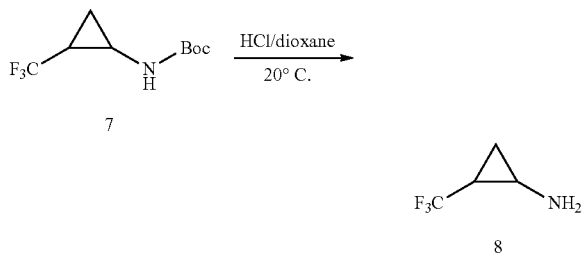

A mixture of compound 7 (200 mg, 888.07 umol, 1 eq) in HCl/dioxane (4 mL, 4 N) was stirred at 20° C. for 2 hr. TLC showed compound 7 was consumed. The mixture was concentrated to give compound 8 (150 mg, crude, HCl) as white oil.

Preparation of Compound 182

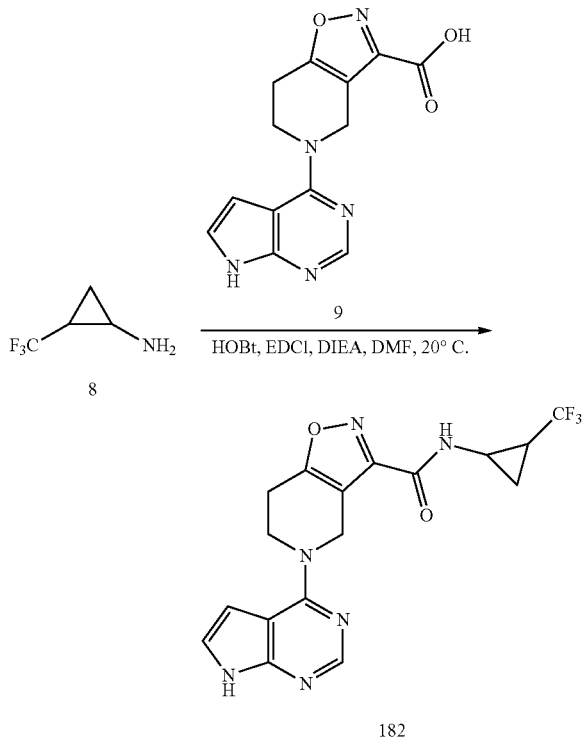

To a solution of compound 9 (150 mg, 525.84 umol, 1 eq) in DMF (2.5 mL) was added HOBt (85.26 mg, 631.01 umol, 1.2 eq), EDCI (151.21 mg, 788.76 umol, 1.5 eq), DIEA (271.84 mg, 2.10 mmol, 366.37 uL, 4 eq) and compound 8 (127.43 mg, 788.76 umol, 41.34 uL, 1.5 eq, HCl). The mixture was stirred at 20° C. for 12 hr. LCMS showed desired MS was detected. The mixture was diluted with water (20 mL), extracted with EtOAc (15 mL*2), washed with brine (50 mL), dried with $Na_2SO_4$, filtered and concentrated. The residue was purified by prep-HPLC (column: Shim-pack C18 150*25*10 um; mobile phase: [water (0.225% FA)-ACN]; B %: 18%-40%, 11 min) to give compound 182 (35 mg, 88.41 umol, 16.81% yield, 99.102% purity) as off-white solid.

$^1$H NMR (400 MHz, DMSO-d)

δ=11.81 (br. s, 1H), 9.19 (d, J=4.8 Hz, 1H), 8.21 (s, 1H), 7.28 (dd, J=2.3, 3.3 Hz, 1H), 6.65 (d, J=2.1 Hz, 1H), 5.10-4.89 (m, 2H), 4.27-4.13 (m, 2H), 3.33-3.24 (m, 1H), 3.03 (br. t, J=5.4 Hz, 2H), 2.26-2.12 (m, 1H), 1.43-1.28 (m, 1H), 1.23 (td, J=6.2, 8.3 Hz, 1H)

$^{13}$C NMR (101 MHz, DMSO-d)

δ=167.23, 158.41, 154.83, 152.23, 148.87, 128.23, 125.34, 122.84, 120.47, 120.16, 110.00, 100.82, 98.75, 40.06, 39.69, 24.00, 23.97, 23.93, 21.50, 18.66, 18.30, 17.94, 17.59, 6.96

LCMS: Rt=0.779 min, [M+H]$^+$=393.1

Example 58: Synthesis of Compound 179

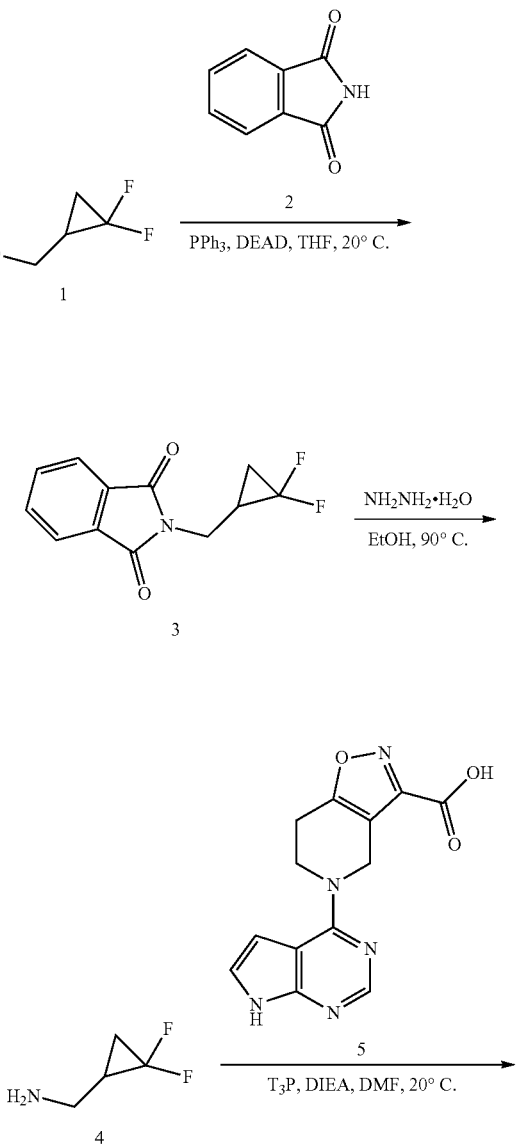

-continued

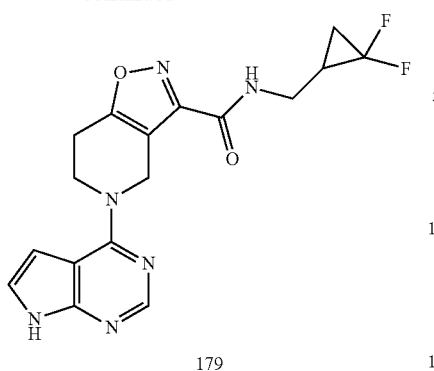

179

Preparation of Compound 3

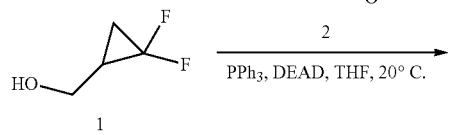

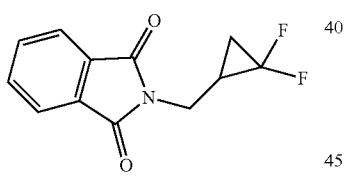

2

To a solution of compound 1 (500 mg, 4.63 mmol, 1 eq), compound 2 (816.74 mg, 5.55 mmol, 1.2 eq) and PPh₃ (1.82 g, 6.94 mmol, 1.5 eq) in THF (50 mL) was added DEAD (966.75 mg, 5.55 mmol, 1.01 mL, 1.2 eq), the mixture was stirred at 20° C. for 10 hr. LCMS showed compound 1 was consumed completely and desired MS was detected. The mixture was diluted with water (20 mL), extracted with EtOAc (50 mL), washed with brine (50 mL), dried with Na₂SO₄, filtered and concentrated. The residue was purified by silica gel column chromatography (Petroleum ether/Ethyl acetate=20/1~10/1) to give compound 3 (700 mg, 2.95 mmol, 63.79% yield) as white oil.

¹H NMR (400 MHz, DMSO-d)

δ=7.99-7.78 (m, 4H), 3.80-3.70 (m, 1H), 3.65-3.55 (m, 1H), 2.18-2.03 (m, 1H), 1.68-1.60 (m, 1H), 1.40-1.30 (m, 1H)

Preparation of Compound 4

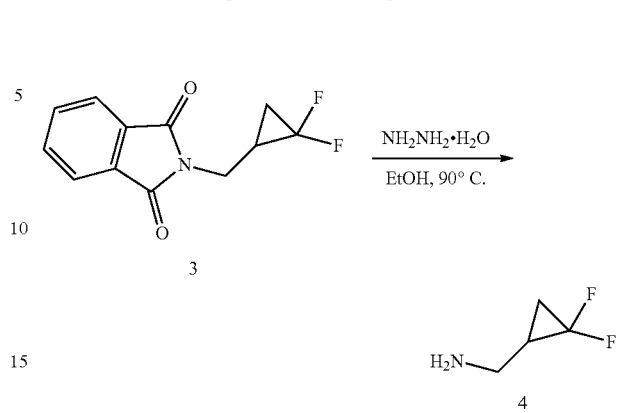

To a mixture of compound 3 (100 mg, 421.58 umol, 1 eq) in EtOH (2 mL) was added NH₂NH₂·H₂O (29.79 mg, 505.90 umol, 28.93 uL, 85% purity, 1.2 eq), the mixture was stirred at 90° C. for 1 hr. TLC showed part of compound 3 was remained, and a new spot was observed. The mixture was cooled to room temperature, filtered to remove the white solid. The filtrate was diluted with HCl (1 mL, 1 N) and concentrated to give compound 3 (45 mg, crude, HCl) as white solid. ¹H NMR (400 MHz, MeOD)

δ=3.22 (td, J=1.7, 3.3 Hz, 1H), 3.11-2.90 (m, 2H), 1.97-1.86 (m, 1H), 1.62 (ddt, J=5.1, 8.1, 11.6 Hz, 1H), 1.38-1.28 (m, 1H)

Preparation of Compound 179

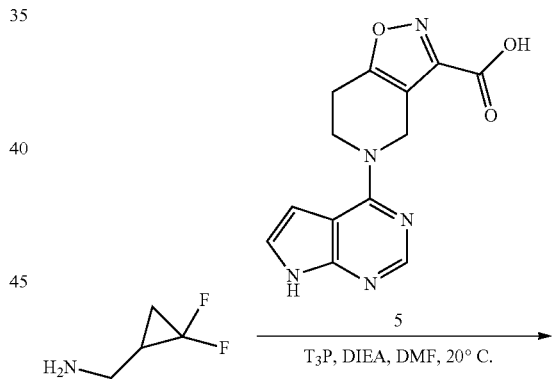

179

To a mixture of compound 4 (20 mg, 139.31 umol, 0.75 eq. HCl) and compound 5 (53.27 mg, 186.74 umol, 1 eq) in DMF (1 mL) was added DIEA (72.40 mg, 560.21 umol, 97.58 uL, 3 eq) and T3P (178.25 mg, 280.11 umol, 166.59 uL, 50% purity, 1.5 eq), the mixture was stirred at 20° C. for 8 hr. LCMS showed a major peak with desired mass was detected. The mixture was diluted with water (20 mL), extracted with EtOAc (50 mL), washed with brine (50 mL), dried with $Na_2SO_4$, filtered and concentrated. The filter cake was purified by prep-HPLC (column: Phenomenex Synergi C18 150*25*10 um; mobile phase: [water(0.225% FA)-ACN]; B %: 23%-53%, 9 min) to give compound 179 (12 mg, 30.35 umol, 16.25% yield, 94.669% purity) as white solid.

$^1$H NMR (400 MHz, $CDCl_3$)

δ=9.81-9.61 (m, 1H), 8.35 (s, 1H), 7.12 (d, J=3.6 Hz, 1H), 7.01 (br. t, J=5.3 Hz, 1H), 6.73 (d, J=3.8 Hz, 1H), 5.17 (s, 2H), 4.34 (t, J=5.3 Hz, 2H), 3.84-3.75 (m, 1H), 3.45-3.35 (m, 1H), 3.07 (br. t, J=5.6 Hz, 2H), 2.03-1.89 (m, 1H), 1.53 (ddt, J=4.5, 7.7, 11.7 Hz, 1H), 1.24-1.15 (m, 1H)

LCMS: Rt=0.746 min, $[M+H]^+$=375.0

Example 59: Synthesis of Compound 178

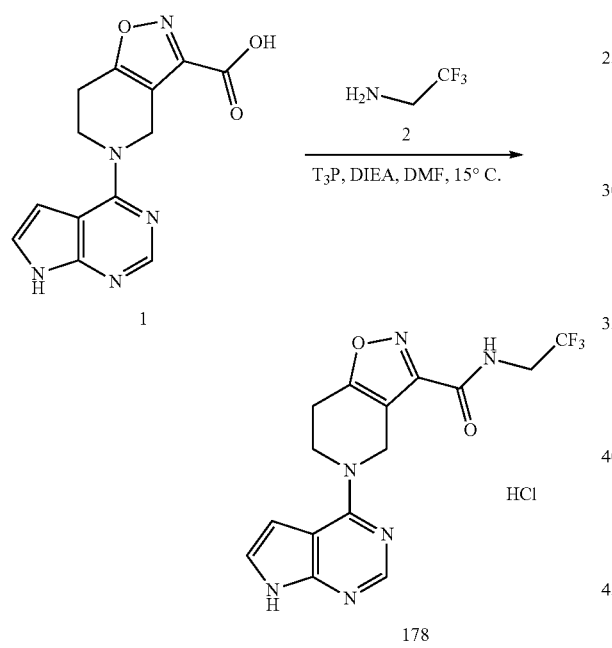

To a solution of compound 1 (100 mg, 350.56 umol, 1 eq) in DMF (2 mL) was added T3P (167.31 mg, 525.84 umol, 156.37 uL, 1.5 eq), DIEA (135.92 mg, 1.05 mmol, 183.18 uL, 3 eq) and compound 2 (52.09 mg, 525.84 umol, 41.34 uL, 1.5 eq). The mixture was stirred at 15° C. for 12 hr. LCMS showed desired MS was detected. The mixture was diluted with water (30 mL), extracted with EtOAc (20 mL*2), washed with brine (50 mL), dried with $Na_2SO_4$, filtered and concentrated. The residue was purified by prep-HPLC (column: Phenomenex Synergi C18 150*25*10 um; mobile phase: [water(0.05% HCl)-ACN]; B %: 16%-36%, 12 min) to give compound 178 (34 mg, 84.25 umol, 24.03% yield, 99.801% purity, HCl) as yellow solid.

$^1$H NMR (400 MHz, DMSO-d6)

δ=12.71 (br. s, 1H), 9.55 (t, J=6.4 Hz, 1H), 8.43 (s, 1H), 7.56-7.44 (m, 1H), 6.88 (br. d, J=1.9 Hz, 1H), 5.10 (s, 2H), 4.33 (br. t, J=5.6 Hz, 2H), 4.12-4.05 (m, 2H), 3.16 (br. t, J=5.1 Hz, 2H)

$^{13}$C NMR (101 MHz, DMSO-d6)

δ=169.17, 160.07, 154.08, 145.60, 129.17, 128.43, 126.39, 124.65, 123.61, 111.38, 103.16, 102.70, 49.06, 43.75, 43.16, 23.64, LCMS: Rt=0.751 min, $[M+H]^+$=367.0

Example 60: Synthesis of Compound 134

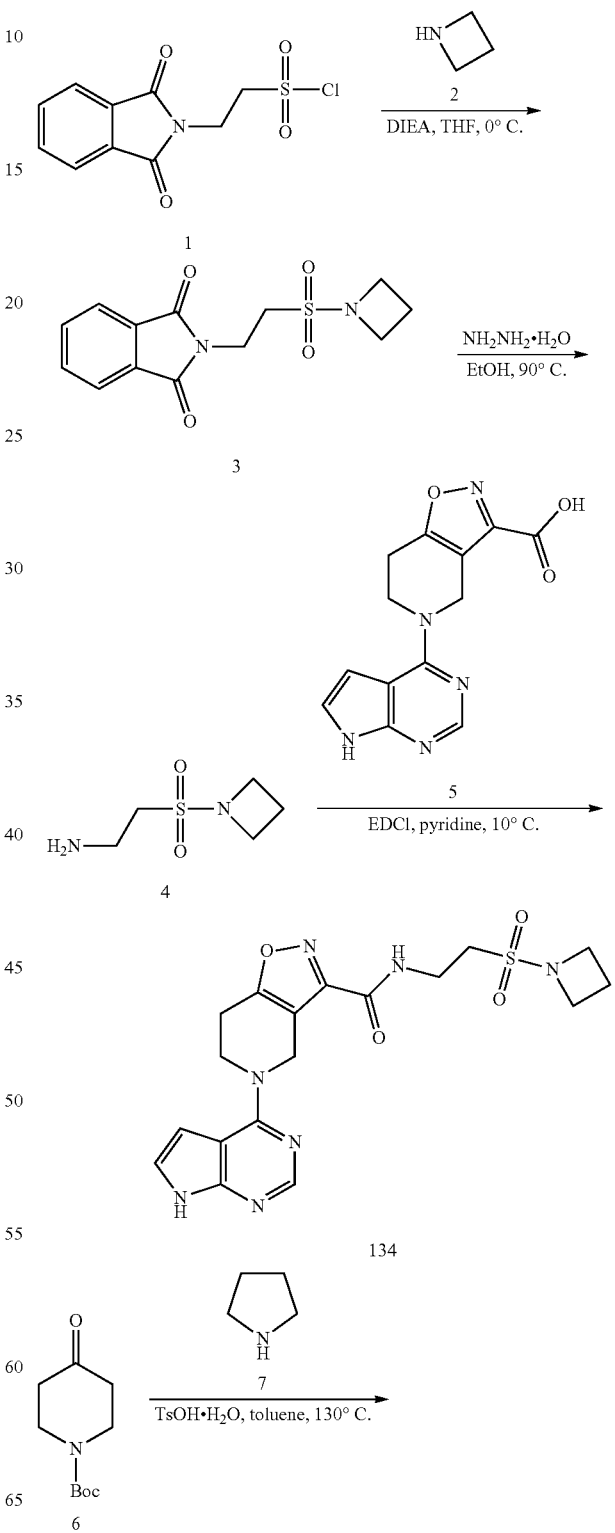

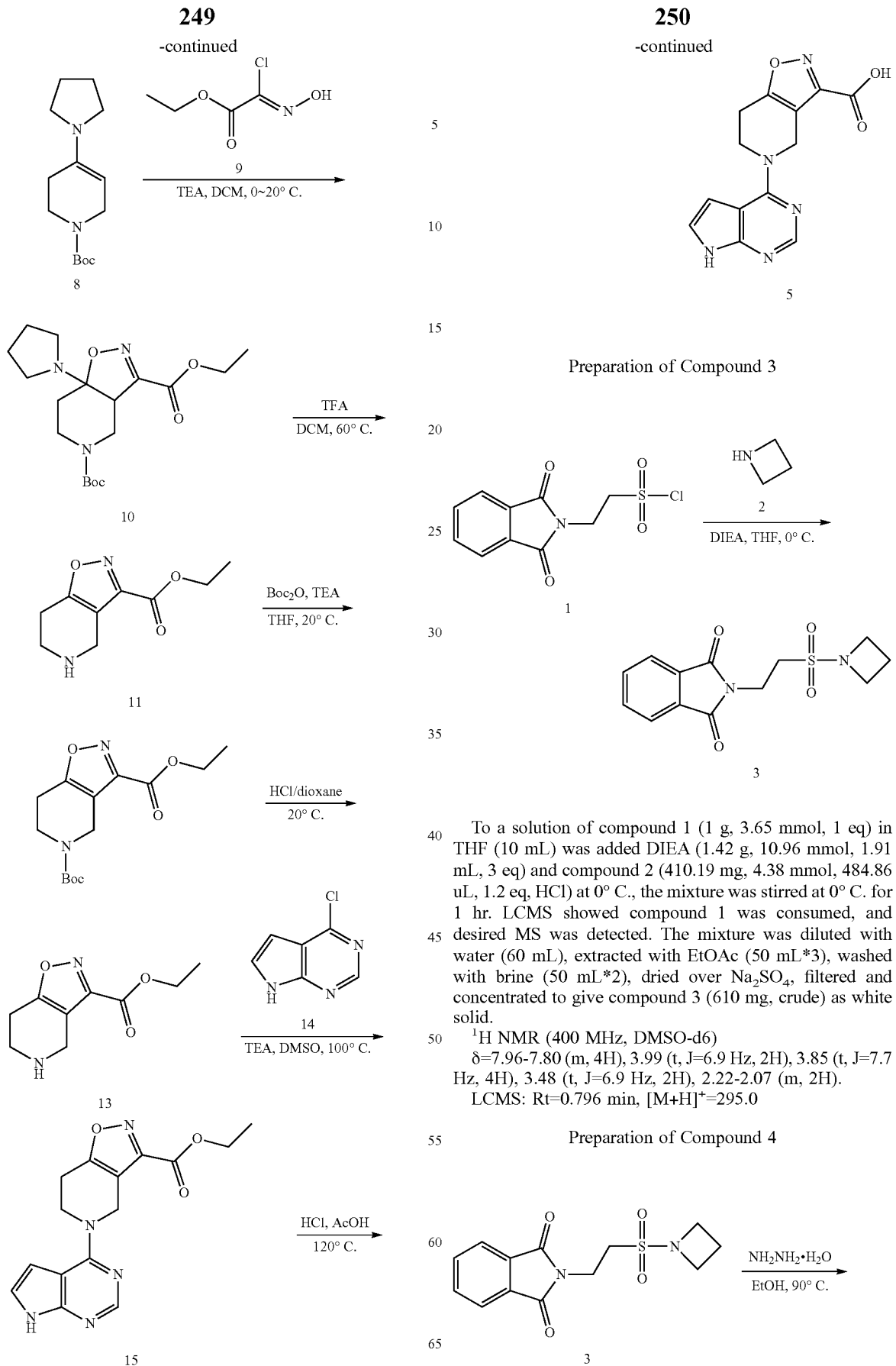

Preparation of Compound 3

To a solution of compound 1 (1 g, 3.65 mmol, 1 eq) in THF (10 mL) was added DIEA (1.42 g, 10.96 mmol, 1.91 mL, 3 eq) and compound 2 (410.19 mg, 4.38 mmol, 484.86 uL, 1.2 eq, HCl) at 0° C., the mixture was stirred at 0° C. for 1 hr. LCMS showed compound 1 was consumed, and desired MS was detected. The mixture was diluted with water (60 mL), extracted with EtOAc (50 mL*3), washed with brine (50 mL*2), dried over $Na_2SO_4$, filtered and concentrated to give compound 3 (610 mg, crude) as white solid.

$^1$H NMR (400 MHz, DMSO-d6)

δ=7.96-7.80 (m, 4H), 3.99 (t, J=6.9 Hz, 2H), 3.85 (t, J=7.7 Hz, 4H), 3.48 (t, J=6.9 Hz, 2H), 2.22-2.07 (m, 2H).

LCMS: Rt=0.796 min, [M+H]$^+$=295.0

Preparation of Compound 4

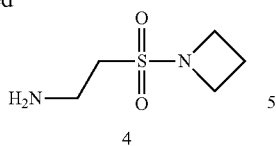

4

To a solution of compound 3 (130 mg, 441.69 umol, 1 eq) in EtOH (3 mL) was added NH$_2$NH$_2$·H$_2$O (31.22 mg, 530.03 umol, 30.31 uL, 85% purity, 1.2 eq), the mixture was stirred at 90° C. for 12 hr. TLC showed compound 3 was consumed, and white precipitate was formed. The reaction mixture was filtered and concentrated to give compound 4 (100 mg, crude) as yellow solid.

$^1$H NMR (400 MHz, DMSO-d)

δ=8.13 (dd, J=3.3, 6.0 Hz, 1H), 7.94 (dd, J=3.3, 5.9 Hz, 1H), 3.90 (t, J=7.7 Hz, 4H), 3.30-3.15 (m, 2H), 3.05-2.91 (m, 2H), 2.23 (t, J=7.7 Hz, 2H).

Preparation of Compound 8

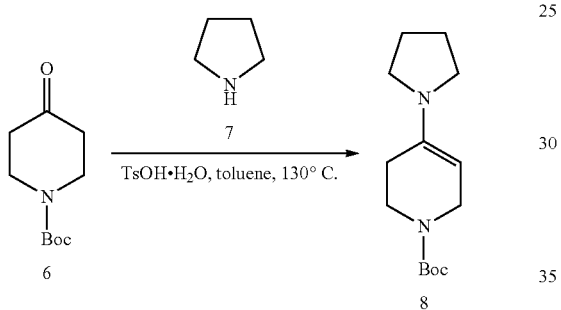

To a suspension of compound 6 (50 g, 250.95 mmol, 1 eq) in toluene (300 mL) was added TsOH·H$_2$O (238.67 mg, 1.25 mmol, 0.005 eq) and compound 7 (26.77 g, 376.42 mmol, 31.42 mL, 1.5 eq). The mixture was stirred at 130° C. with a Dean-starks apparatus for 12 hr. TLC showed most of compound 6 was consumed. The mixture was concentrated to give compound 8 (63 g, crude) as brown oil.

$^1$H NMR (400 MHz, CDCl$_3$)

δ=3.65 (t, J=6.2 Hz, 4H), 2.83 (br. t, J=6.4 Hz, 4H), 2.37 (t, J=6.2 Hz, 4H), 1.64 (td, J=3.3, 6.4 Hz, 4H), 1.43 (s, 9H)

Preparation of Compound 10

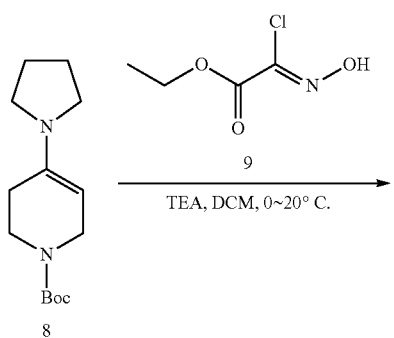

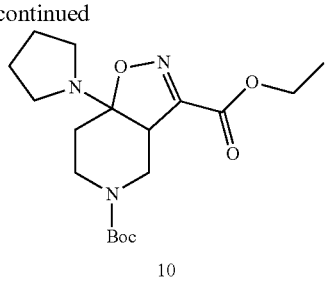

10

To a suspension of compound 9 (56.75 g, 374.48 mmol, 1.5 eq) in DCM (500 mL) was added compound 8 (63 g, 249.65 mmol, 1 eq) and TEA (75.79 g, 748.96 mmol, 104.25 mL, 3 eq) dropwise at 0° C. After addition, the mixture was stirred at 0° C. for 2 hr, then at 20° C. for 10 hr. LCMS showed a major peak with desired MS was detected. The mixture was quenched with 10% citric acid solution (200 mL), diluted with water (300 mL), extracted with DCM (300 mL*2), washed with saturated NaHCO$_3$ solution (500 mL), dried with Na$_2$SO$_4$, filtered and concentrated. The residue was purified by silica gel column chromatography (Petroleum ether/Ethyl acetate=10/1~1:2) to give compound 10 (80 g, 217.72 mmol, 86.96% yield) as yellow oil.

$^1$H NMR (400 MHz, CDCl$_3$)

δ=4.46-4.20 (m, 3H), 3.52-3.23 (m, 4H), 2.97-2.81 (m, 2H), 2.78-2.64 (m, 2H), 2.47-2.11 (m, 2H), 1.87-1.77 (m, 4H), 1.42 (s, 9H), 1.40-1.31 (m, 3H)

LCMS: Rt=0.841 min, [M+H]$^+$=368.1

Preparation of Compound 11

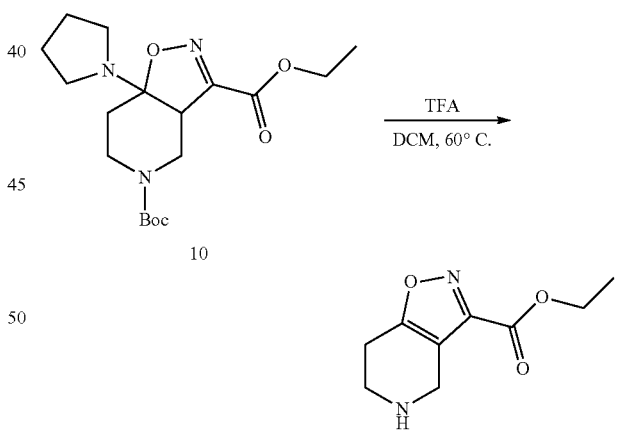

A mixture of compound 10 (79.6 g, 216.63 mmol, 1 eq) in TFA (200 mL) and DCM (400 mL) was stirred at 60° C. for 12 hr. LCMS showed compound 10 was consumed, desired MS was detected. The mixture was concentrated, diluted with water (2.5 L), neutralized with solid NaHCO$_3$ to pH=7, extracted with DCM/IPA (3:1, 2 L*3), dried with Na$_2$SO$_4$, filtered and concentrated to give compound 11 (46.5 g, crude) as brown oil.

LCMS: Rt=0.137 min, [M+H]$^+$=197.0

Preparation of Compound 12

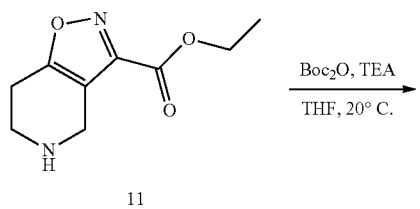

To a solution of compound 11 (46.5 g, 237.00 mmol, 1 eq) in THF (500 mL) was added Boc$_2$O (51.72 g, 237.00 mmol, 54.45 mL, 1 eq) and TEA (47.96 g, 474.00 mmol, 65.98 mL, 2 eq), the mixture was stirred at 20° C. for 1 hr. TLC showed a major new spot was observed. The mixture was concentrated, the residue was purified by silica gel chromatography (Petroleum ether/Ethyl acetate=10/1~3/1) to give compound 12 (50 g, 168.74 mmol, 71.20% yield) as light yellow oil.

$^1$H NMR (400 MHz, CDCl$_3$)

δ=4.56 (br. s, 2H), 4.45 (q, J=7.1 Hz, 2H), 3.77 (br. s, 2H), 2.87 (br. t, J=5.3 Hz, 2H), 1.50 (s, 9H), 1.43 (t, J=7.2 Hz, 3H)

Preparation of Compound 13

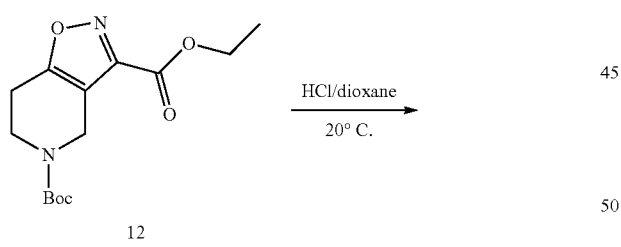

A mixture of compound 12 (20 g, 67.49 mmol, 1 eq) in 4 N HCl/dioxane (200 mL) was stirred at 20° C. for 0.5 hr. LCMS showed most of compound 12 was consumed, and desired MS was detected. The mixture was concentrated to give compound 13 (15.7 g, crude, HCl) as a yellow oil.

LCMS: Rt=0.133 min, [M+H]$^+$=197.1

Preparation of Compound 15

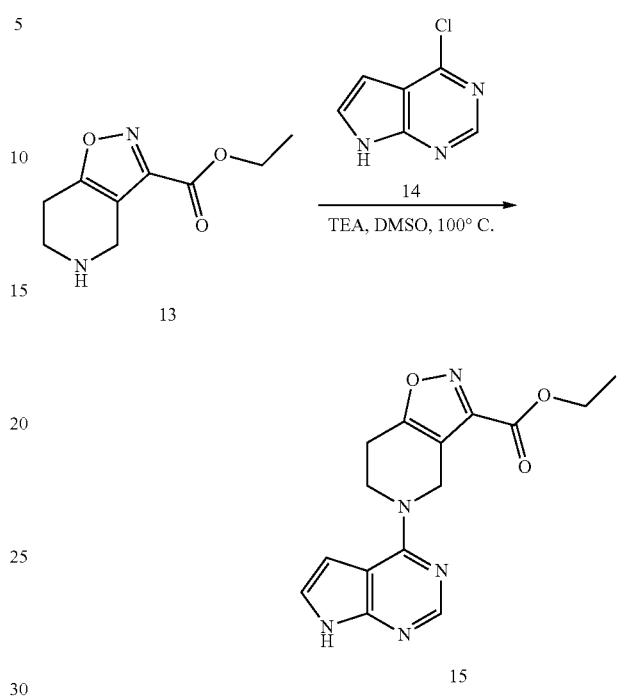

To a solution of compound 13 (15.7 g, 67.48 mmol, 1 eq, HCl) in DMSO (130 mL) was added compound 14 (10.36 g, 67.48 mmol, 1 eq) and TEA (27.31 g, 269.92 mmol, 37.57 mL, 4 eq), the mixture was stirred at 100° C. for 14 hr. LCMS showed most of compound 13 was consumed, and desired MS was detected. The mixture was poured into ice/water (2.5 L), filtered and dried under vacuum to give compound 15 (15 g, crude) as brown solid.

$^1$H NMR (400 MHz, DMSO-d)

δ=11.89 (br s, 1H), 8.27 (s, 1H), 7.34 (dd, J=2.5, 3.4 Hz, 1H), 6.70 (dd, J=1.6, 3.5 Hz, 1H), 5.03 (s, 2H), 4.46 (q, J=7.1 Hz, 2H), 4.27 (t, J=5.6 Hz, 2H), 3.10 (br t, J=5.5 Hz, 2H), 1.42 (t, J=7.1 Hz, 3H)

LCMS: Rt=0.865 min, [M+H]$^+$=314.1

Preparation of Compound 5

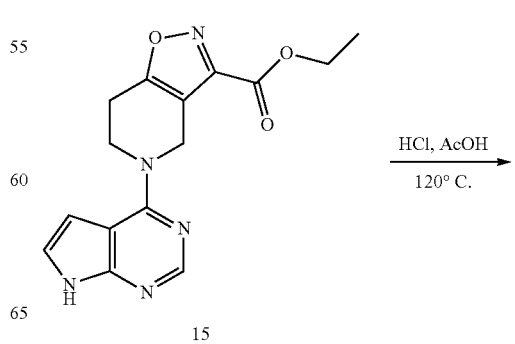

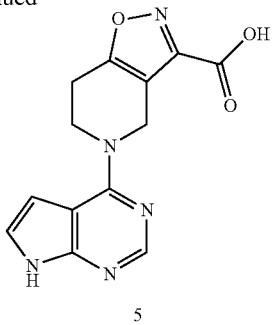

A mixture of compound 15 (5 g, 15.96 mmol, 1 eq) in 6 N HCl (30 mL) and AcOH (30 mL) was stirred at 120° C. for 12 hr. LCMS showed compound 15 was consumed, and a major peak with desired MS was detected. The mixture was concentrated to give compound 5 (5 g, crude) as brown solid.

$^1$H NMR (400 MHz, DMSO-d)

δ=12.62 (br. s, 1H), 8.43 (s, 1H), 7.49 (br. s, 1H), 6.87 (br. s, 1H), 5.06 (s, 2H), 4.31 (br. t, J=5.5 Hz, 2H), 3.20-3.07 (m, 2H)

LCMS: Rt=0.709 min, [M+H]$^+$=285.9

Preparation of Compound 134

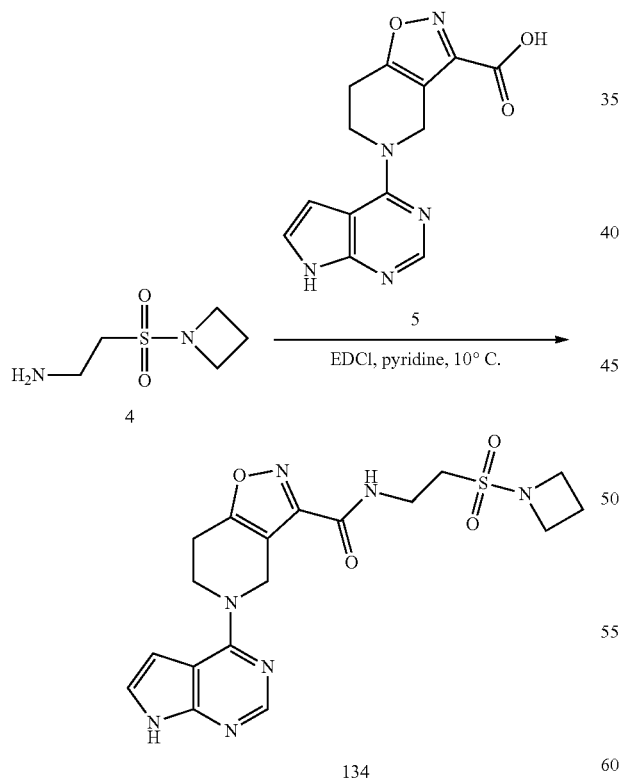

To a mixture of compound 5 (130.27 mg, 456.69 umol, 1 eq) in pyridine (5 mL) was added EDCI (131.32 mg, 685.03 umol, 1.5 eq) and compound 4 (90 mg, 548.03 umol, 1.2 eq), the mixture was stirred at 10° C. for 15 hr. LCMS showed compound 5 was consumed, and desired MS was detected.

The mixture was concentrated and purified by prep-HPLC (column: Waters Xbridge 150*25 mm*5 um; mobile phase: [water(10 mM NH$_4$HCO$_3$)-ACN]; B %: 13%-43%, 10 min) to give compound 134 (17.8 mg, 40.43 umol, 8.85% yield, 98% purity) as yellow solid.

$^1$H NMR (400 MHz, DMSO-d6)

δ=11.97-11.59 (m, 1H), 9.12-8.71 (m, 1H), 8.21 (s, 1H), 7.27 (d, J=3.5 Hz, 1H), 6.73-6.42 (m, 1H), 5.00 (s, 2H), 4.22 (br t, J=5.6 Hz, 2H), 3.89 (t, J=7.7 Hz, 4H), 3.71-3.59 (m, 2H), 3.40 (t, J=7.2 Hz, 2H), 3.13-2.98 (m, 2H), 2.26-2.12 (m, 2H)

$^{13}$C NMR (101 MHz, DMSO-d6)

δ=169.43, 159.46, 156.95, 154.52, 152.48, 151.00, 122.60, 112.10, 102.95, 100.88, 50.47, 46.36, 42.20, 41.83, 33.90, 23.65, 15.12

LCMS: Rt=0.722 min, [M+H]$^+$=432.0

Example 61: Synthesis of Compound 140

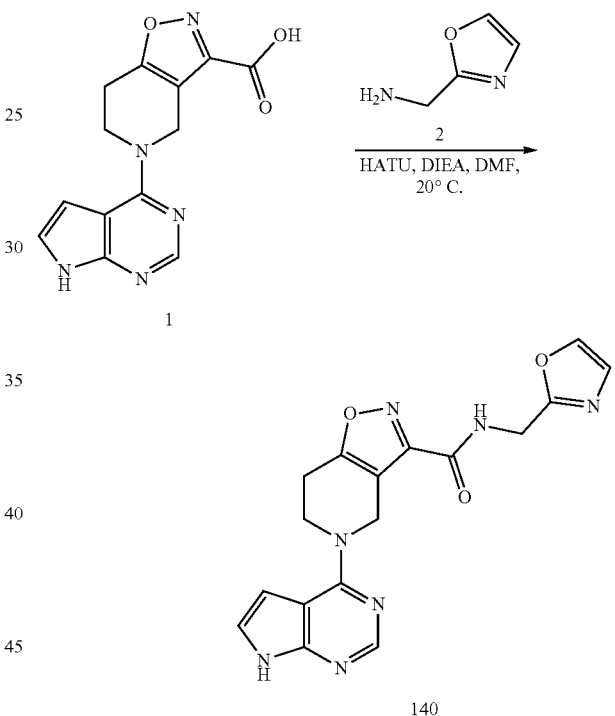

To a mixture of compound 1 (100 mg, 350.56 umol, 1 eq) and compound 2 (56.61 mg, 420.67 umol, 1.2 eq, HCQ) in DMF (2 mL) was added DIEA (135.92 mg, 1.05 mmol, 183.18 uL, 3 eq) and HATU (199.94 mg, 525.84 umol, 1.5 eq), the mixture was stirred at 20° C. for 8 hr. LCMS showed desired MS was detected. The reaction mixture was diluted with water (5 mL), extracted with EtOAc (5 mL*2), dried over Na$_2$SO$_4$, filtered and concentrated. The residue was purified by prep-HPLC (column: Boston Green ODS 150*30 mm*5 um; mobile phase: [water(0.225% FA)-ACN]; B %: 10%-40%, 10 min) to give compound 140 (30 mg, 78.01 umol, 22.25% yield, 95% purity) as yellow solid.

$^1$H NMR (400 MHz, DMSO-d)

δ=12.42 (br. s, 1H), 9.52 (t, J=5.9 Hz, 1H), 8.38 (s, 1H), 8.07 (d, J=0.8 Hz, 1H), 7.47-7.43 (m, 1H), 7.18 (d, J=0.8 Hz, 1H), 6.83 (br. d, J=1.9 Hz, 1H), 5.05 (s, 2H), 4.58 (d, J=6.0 Hz, 2H), 4.28 (br. t, J=5.6 Hz, 2H), 3.12 (br. t, J=5.1 Hz, 2H)

$^{13}$C NMR (101 MHz, DMSO-d)

δ=169.09, 160.95, 159.61, 154.38, 140.31, 127.53, 124.09, 111.48, 102.75, 102.64, 43.35, 42.86, 36.58, 23.63.
LCMS: Rt=0.700 min, [M+H]$^+$=366.2
Example 62: Synthesis of Compound 143
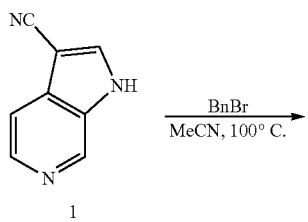
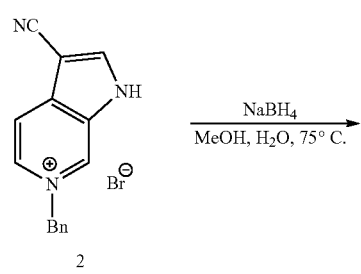
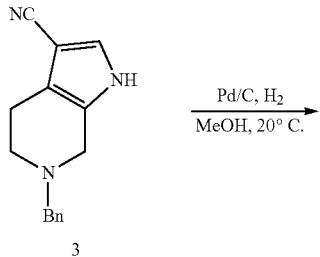
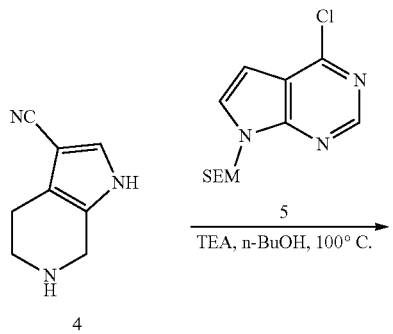
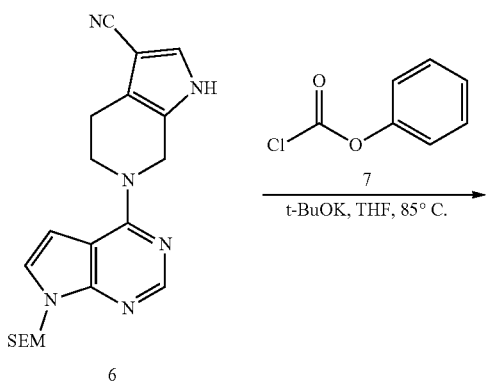
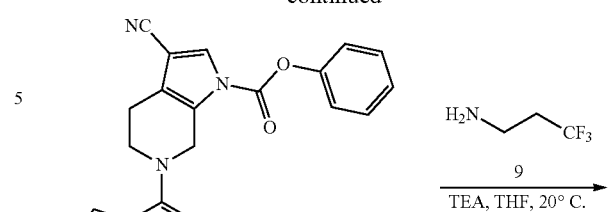
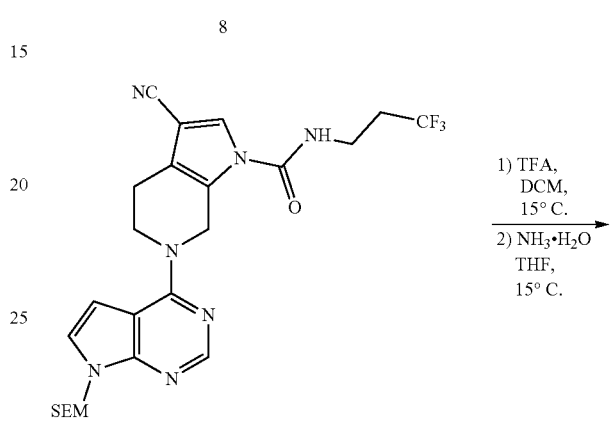
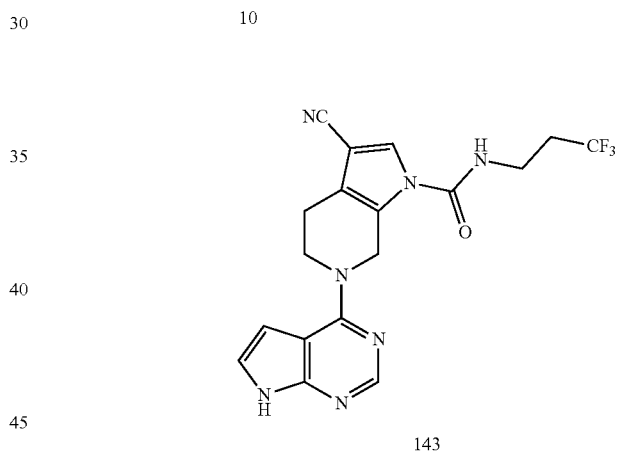
Preparation of Compound 2
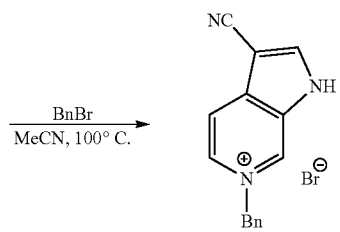

To a solution of compound 1 (900 mg, 6.29 mmol, 1 eq) in MeCN (5 mL) was added BnBr (1.08 g, 6.29 mmol, 746.75 uL, 1 eq). The mixture was warmed to 100° C., stirred for 14 hr under $N_2$ atmosphere. LCMS showed most of compound 1 was consumed, and desired MS was detected. The mixture was concentrated, triturated with EtOAc (50 mL), filtered to give compound 2 (2.05 g, crude) as brown solid.

$^1$H NMR (400 MHz, MeOD)

δ=9.57 (s, 1H), 8.85 (s, 1H), 8.69-8.64 (m, 1H), 8.30-8.25 (m, 1H), 7.48-7.41 (m, 5H), 5.96 (s, 2H)

LCMS: Rt=0.258 min, [M+H]$^+$=234.0

Preparation of Compound 3

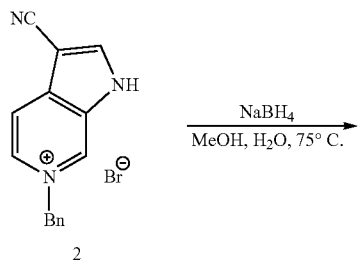

To a solution of compound 2 (1.93 g, 6.24 mmol, 1 eq) in MeOH (5 mL) and $H_2O$ (5 mL) was slowly added $NaBH_4$ (1.18 g, 31.22 mmol, 5 eq). Then the mixture was warmed to 75° C., stirred for 14 hr. LCMS showed most of compound 2 was consumed, and desired MS was detected. The mixture was diluted with water (45 mL), extracted with EtOAc (40 mL*2), washed with brine (40 mL*2), dried with $Na_2SO_4$, filtered and concentrated. The residue was purified by silica gel column chromatography (Petroleum ether/Ethyl acetate=10/1~1/1) to give compound 3 (820 mg, 3.46 mmol, 55.42% yield) as colorless oil.

$^1$H NMR (400 MHz, CDCl$_3$)

δ=8.34-8.11 (m, 1H), 7.41-7.31 (m, 5H), 7.12 (d, J=3.0 Hz, 1H), 3.74 (s, 2H), 3.47 (s, 2H), 2.87-2.79 (m, 2H), 2.75-2.67 (m, 2H)

LCMS: Rt=0.265 min, [M+H]$^+$=238.2

Preparation of Compound 4

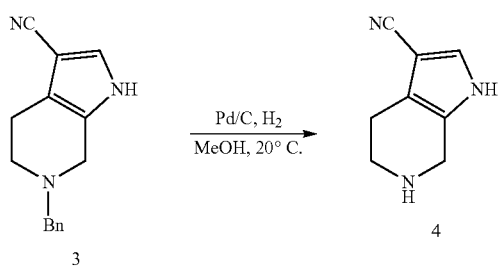 [SMILES: N#Cc1c[nH]c2c1CCN(Cc1ccccc1)C2 ; "Pd/C, H2" ; N#Cc1c[nH]c2c1CCNC2]

To a solution of compound 3 (540 mg, 2.28 mmol, 1 eq) in MeOH (10 mL) was added Pd/C (120 mg, 10% purity). The mixture was stirred at 10° C. for 14 hr under $H_2$ balloon at 15 psi. LCMS showed most of compound 3 was consumed, and desired MS was detected. The mixture was filtered and concentrated under reduced pressure to give compound 4 (320 mg, crude) as yellow solid.

$^1$H NMR (400 MHz, MeOD)

δ=7.13 (s, 1H), 3.67 (s, 2H), 2.92 (t, J=5.8 Hz, 2H), 2.53-2.46 (m, 2H)

LCMS: Rt=0.376 min, [M+H]$^+$=148.2

Preparation of Compound 6

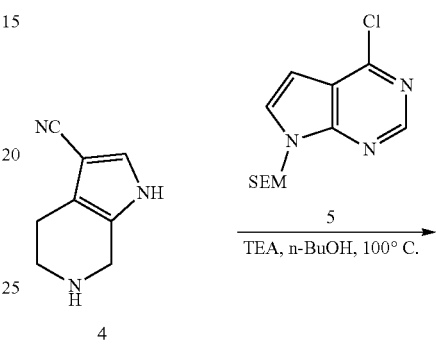

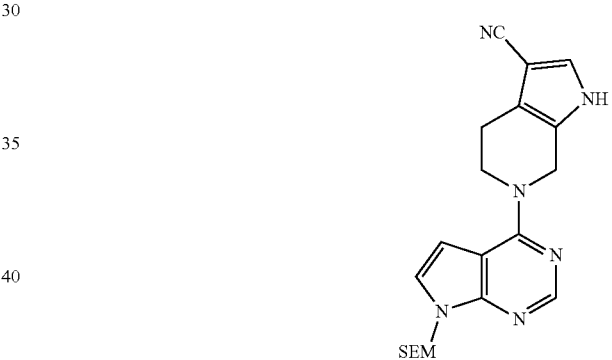

To a mixture of compound 4 (210 mg, 1.43 mmol, 1 eq) and compound 5 (404.98 mg, 1.43 mmol, 1 eq) in n-BuOH (5 mL) was added TEA (433.15 mg, 4.28 mmol, 595.81 uL, 3 eq), the mixture was stirred at 100° C. for 14 hr. LCMS showed a little compound 5 was remained, and 85% of desired MS was detected. The mixture was concentrated. The mixture was diluted with water (25 mL), extracted with EtOAc (30 mL*3), washed with brine (30 mL*2), dried over $Na_2SO_4$, filtered and concentrated. The residue was purified by silica gel column chromatography (Petroleum ether/Ethyl acetate=10/1~1/2) to give compound 6 (400 mg, 1.01 mmol, 71.05% yield) as yellow oil.

$^1$H NMR (400 MHz, CDCl$_3$)

δ=8.81-8.66 (m, 1H), 8.42 (s, 1H), 7.27 (d, J=2.9 Hz, 1H), 7.21 (d, J=3.7 Hz, 1H), 6.66 (d, J=3.8 Hz, 1H), 5.65 (s, 2H), 5.02 (s, 2H), 4.24 (t, J=5.6 Hz, 2H), 3.65-3.48 (m, 2H), 2.96 (br t, J=5.6 Hz, 2H), 1.05-0.83 (m, 2H), 0.03-0.07 (m, 9H)

LCMS: Rt=0.872 min, [M+H]$^+$=395.2

Preparation of Compound 8

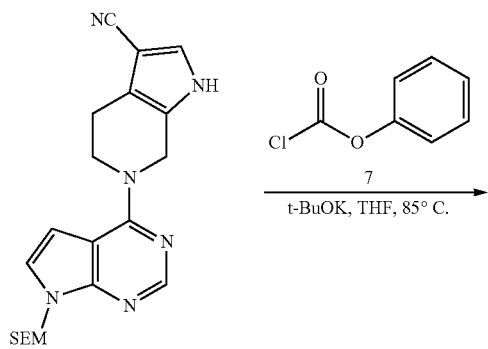

Preparation of Compound 10

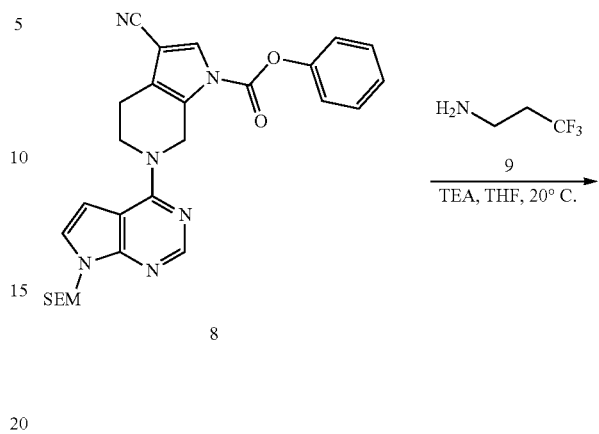

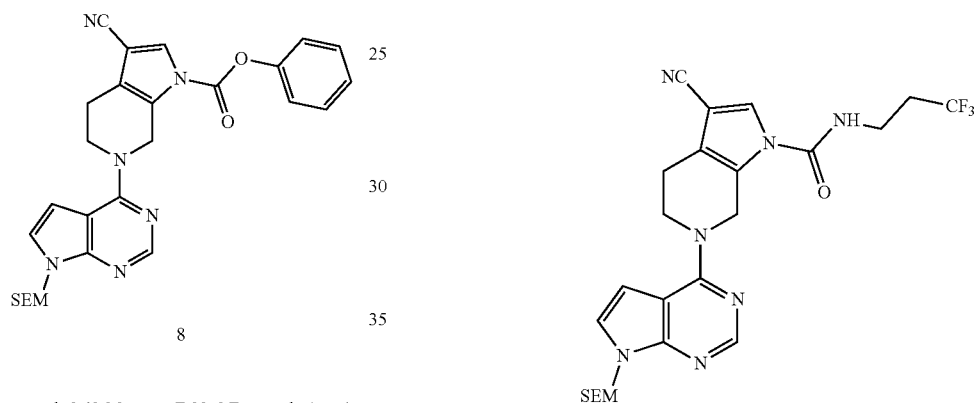

To a solution of compound 6 (300 mg, 760.37 umol, 1 eq) in THF (20 mL) was added t-BuOK (103.57 mg, 923.00 umol, 1.21 eq) and compound 7 (492.86 mg, 3.15 mmol, 394.29 uL, 4.14 eq), the mixture was stirred at 85° C. for 14 hr under $N_2$ atmosphere. LCMS showed most of compound 6 was consumed, and desired MS was detected. The mixture was concentrated, diluted with water (35 mL), extracted with EtOAc (30 mL*3), dried over $Na_2SO_4$, filtered and concentrated. The residue was purified by silica gel column chromatography (Petroleum ether/Ethyl acetate=10/1~1/2) to give compound 8 (100 mg, 194.31 umol, 25.55% yield) as yellow oil.

$^1$H NMR (400 MHz, CDCl$_3$)

δ=8.44 (s, 1H), 7.95 (s, 1H), 7.55 (d, J=8.3 Hz, 2H), 7.48-7.39 (m, 1H), 7.36-7.32 (m, 2H), 7.17 (d, J=3.8 Hz, 1H), 6.76-6.63 (m, 1H), 5.64 (s, 2H), 5.36 (s, 2H), 4.31 (s, 2H), 3.58 (dd, J=7.6, 8.7 Hz, 2H), 2.98-2.87 (m, 2H), 1.00-0.93 (m, 2H), 0.03-0.05 (m, 9H)

The H-NMR was came from a small batch.

LCMS: Rt=1.021 min, [M+H]$^+$=515.3

To a solution of compound 8 (100 mg, 194.31 umol, 1 eq) in THF (3 mL) was added TEA (58.99 mg, 582.92 umol, 81.14 uL, 3 eq) and compound 9 (43.59 mg, 291.46 umol, 1.5 eq, HCl), the mixture was stirred at 15° C. for 14 hr. LCMS showed most of compound 8 was consumed, and desired MS was detected. The mixture was diluted with water (35 mL), extracted with EtOAc (30 mL*3), washed with brine (30 mL*2), dried over $Na_2SO_4$, filtered and concentrated. The residue was purified by prep-TLC (Petroleum ether/Ethyl acetate=2/1) to give compound 10 (50 mg, 93.70 umol, 48.22% yield) as a yellow oil.

$^1$H NMR (400 MHz, CDCl$_3$)

δ=8.42 (s, 1H), 7.52 (s, 1H), 7.20 (d, J=3.7 Hz, 1H), 6.74 (d, J=3.8 Hz, 1H), 6.43 (s, 1H), 5.64 (s, 2H), 5.30 (s, 2H), 4.26 (t, J=5.6 Hz, 2H), 3.76 (q, J=6.3 Hz, 2H), 3.61-3.53 (m, 2H), 2.89 (br. t, J=5.5 Hz, 2H), 2.57 (tq, J=6.5, 10.6 Hz, 2H), 0.96 (dd, J=7.7, 8.8 Hz, 2H), 0.07-0.08 (m, 9H)

LCMS: Rt=0.962 min, [M+H]$^+$=534.2

Preparation of Compound 143

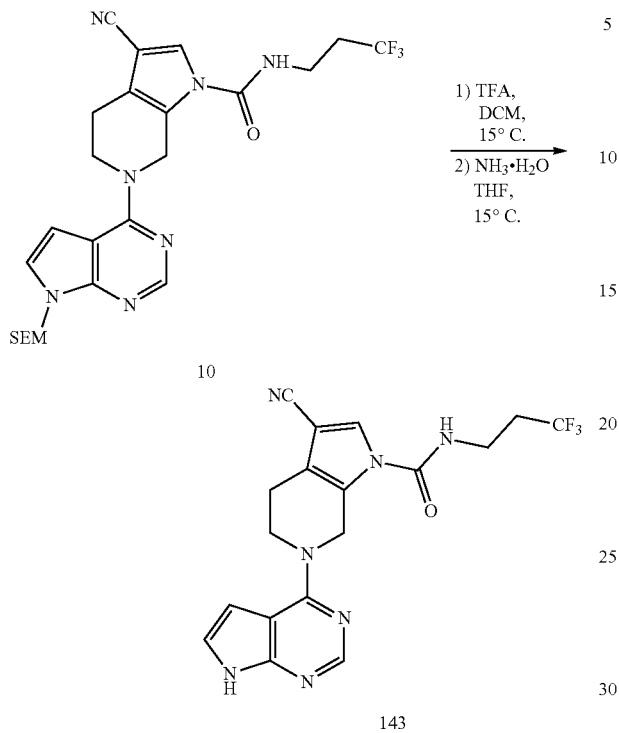

A solution of compound 10 (100 mg, 196.61 umol, 1 eq) in TFA (1 mL) and DCM (1 mL) was stirred at 15° C. for 0.5 hr. The mixture was concentrated, dissolved in THF (1 mL), concentrated $NH_3$—$H_2O$ (1 mL) was added, the mixture was stirred at 15° C. for 1 hr. LCMS showed compound 10 was consumed, and a major peak with desired MS was detected. The mixture diluted with water (30 mL), extracted with EtOAc (30 mL*2), washed with brine (30 mL*2), dried with $Na_2SO_4$, filtered and concentrated. The residue was purified by prep-HPLC (column: Shim-pack C18 150*25*10 um; mobile phase: [water(0.225% FA)-ACN]; B %: 18%/6-40%, 11 min) to give compound 143 (8 mg, 19.30 umol, 20.60% yield, 97.3% purity) as off-white solid.

$^1$H NMR (400 MHz, DMSO-d6)
δ=11.88-11.55 (m, 1H), 8.73 (s, 1H), 8.18 (s, 1H), 8.02 (s, 1H), 7.26 (dd, J=2.5, 3.5 Hz, 1H), 6.63 (dd, J=1.8, 3.6 Hz, 1H), 5.17 (s, 2H), 4.13 (t, J=5.6 Hz, 2H), 3.62-3.43 (m, 2H), 2.75-2.65 (m, 2H), 2.64-2.54 (m, 2H)
LCMS: Rt=0.796 min, [M+H]$^+$=404.0

Example 63: Synthesis of Compound 144

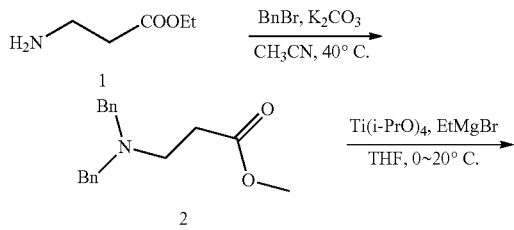

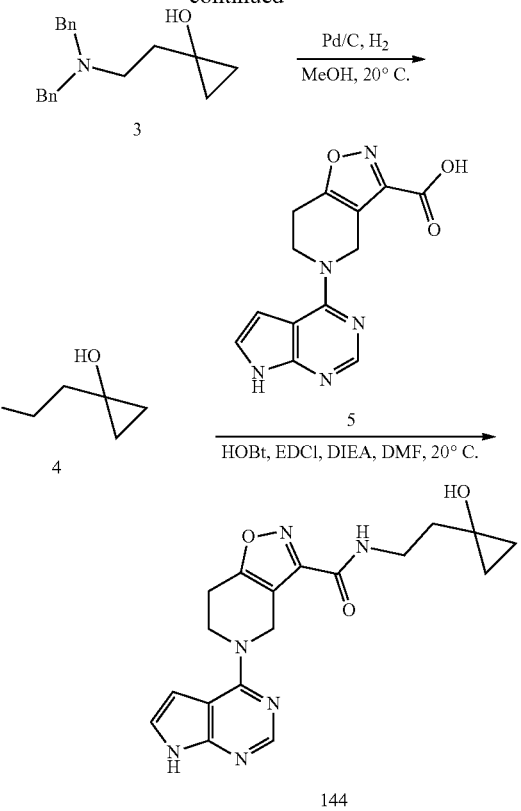

reference compound
(ref: WO2006/28545, 2006, A2)
used different strategy

Preparation of Compound 2

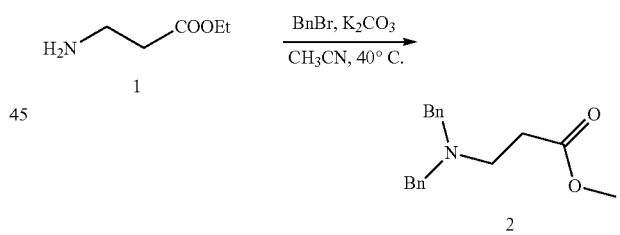

To a mixture of compound 1 (5 g, 42.68 mmol, 1 eq) and $K_2CO_3$ (14.75 g, 106.70 mmol, 2.5 eq) in $CH_3CN$ (60 mL) was added BnBr (15.33 g, 89.63 mmol, 10.65 mL, 2.1 eq), the mixture was stirred at 40° C. for 10 hr. TLC showed compound 1 was consumed completely and a new spot was detected. LCMS showed desired MS was detected. The mixture was diluted with water (50 mL), extracted with EtOAc (100 mL), washed with brine (80 mL), dried with $Na_2SO_4$, filtered and concentrated. The residue was purified by silica gel column chromatography (Petroleum ether/Ethyl acetate=1/0~10/1) to give compound 2 (7.5 g, 25.22 mmol, 59.09% yield) as white oil.

$^1$H NMR (400 MHz, CDCl$_3$)
δ=7.40-6.89 (m, 11H), 4.01 (q, J=7.2 Hz, 2H), 2.74 (t, J=7.2 Hz, 2H), 2.42 (t, J=7.2 Hz, 2H), 1.48 (s, 1H), 1.13 (t, J=7.2 Hz, 3H)
LCMS: Rt=0.702 min, [M+H]$^+$=298.3

Preparation of Compound 3

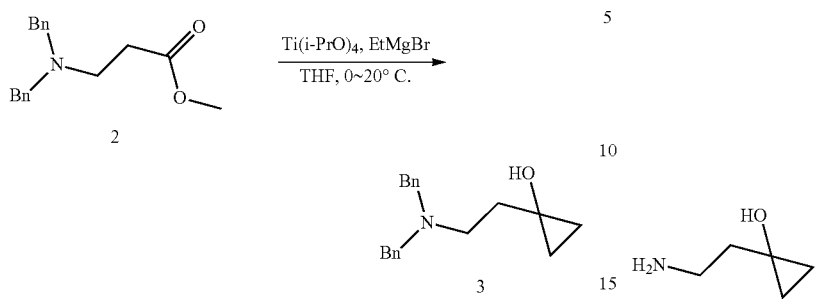

To a solution of compound 2 (500 mg, 1.68 mmol, 1 eq) in THF (10 mL) was added Ti(i-PrO)$_4$ (238.92 mg, 840.65 umol, 248.10 uL, 0.5 eq) at 0° C., then EtMgBr (3 M, 1.68 mL, 3 eq) was added to the mixture at 20° C., the mixture was stirred at 20° C. for 0.5 hr. LCMS showed compound 2 was consumed completely and desired MS was detected. The mixture was diluted with saturated NH$_4$Cl solution (50 mL) and saturated NaHCO$_3$ solution (50 mL), extracted with EtOAc (100 mL), washed with brine (50 mL), dried with Na$_2$SO$_4$, filtered and concentrated. The residue was purified by silica gel column chromatography (Petroleum ether/Ethyl acetate=10/1~5/1) to give compound 3 (445 mg, 1.58 mmol, 94.06% yield) as yellow oil $^1$H NMR (400 MHz, CDCl$_3$)

δ=7.28 (d, J=2.1 Hz, 4H), 7.27-7.15 (m, 6H), 3.56 (s, 4H), 2.77-2.65 (m, 2H), 1.74-1.63 (m, 2H), 0.52-0.42 (m, 2H), 0.22-0.05 (m, 2H)

LCMS: Rt=0.742 min, [M+H]$^+$=282.1

Preparation of Compound 4

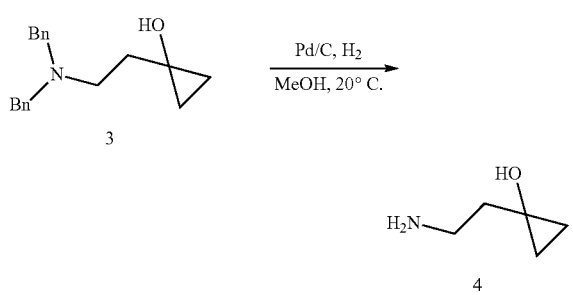

reference compound
(ref: WO2006/28545, 2006, A2)
used different strategy

A mixture of compound 3 (500 mg, 1.78 mmol, 1 eq) and Pd/C (20 mg, 10% purity) in MeOH (5 mL) was stirred at 20° C. under H$_2$ balloon for 10 hr. The mixture was filtered and concentrated to give compound 4 (70 mg, crude) as a white oil.

$^1$H NMR (400 MHz, MeOD)

δ=2.93 (t, J=7.2 Hz, 2H), 1.71 (t, J=7.1 Hz, 2H), 0.72-0.61 (m, 2H), 0.51-0.42 (m, 2H)

Preparation of Compound 140

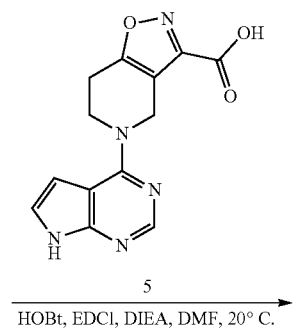

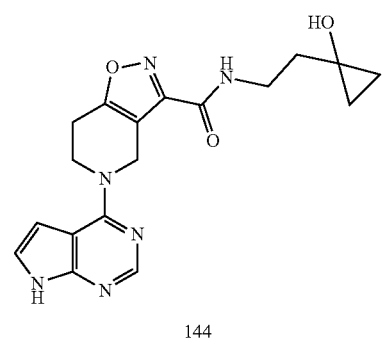

To a solution of compound 5 (117.51 mg, 411.94 umol, 1 eq) and compound 4 (50 mg, 494.33 umol, 1.2 eq) in DMF (1 mL) was added HOBt (66.80 mg, 494.33 umol, 1.2 eq), EDCI (118.46 mg, 617.92 umol, 1.5 eq) and DIEA (212.96 mg, 1.65 mmol, 287.01 uL, 4 eq), the mixture was stirred at 20° C. for 1 hr. LCMS showed compound 5 was consumed completely and desired MS was detected. The mixture was filtered, purified by prep-HPLC (column: Phenomenex Synergi C18 150*25*10 um; mobile phase: [water(0.225% FA)-ACN]; B %: 1%-31%, 11 min). Compound 144 (22 mg, 58.53 umol, 14.21% yield, 98% purity) was obtained as a yellow solid.

$^1$H NMR (400 MHz, CDCl$_3$)

δ=8.21 (s, 1H), 7.20 (d, J=3.6 Hz, 1H), 6.75 (d, J=3.6 Hz, 1H), 5.09 (s, 2H), 4.31 (t, J=5.6 Hz, 2H), 3.65 (t, J=7.0 Hz, 2H), 3.06 (br. t, J=5.5 Hz, 2H), 1.84 (t, J=7.0 Hz, 2H), 0.77-0.63 (m, 2H), 0.55-0.45 (m, 2H)

$^1$C NMR (101 MHz, CDCl$_3$)

δ=168.99, 160.28, 157.16, 154.22, 151.15, 150.19, 121.61, 111.43, 103.17, 100.75, 52.47, 42.16, 41.86, 37.12, 36.47, 23.04, 11.90

LCMS: Rt=0.702 min, [M+H]$^+$=369.0

Example 64: Synthesis of Compound 147

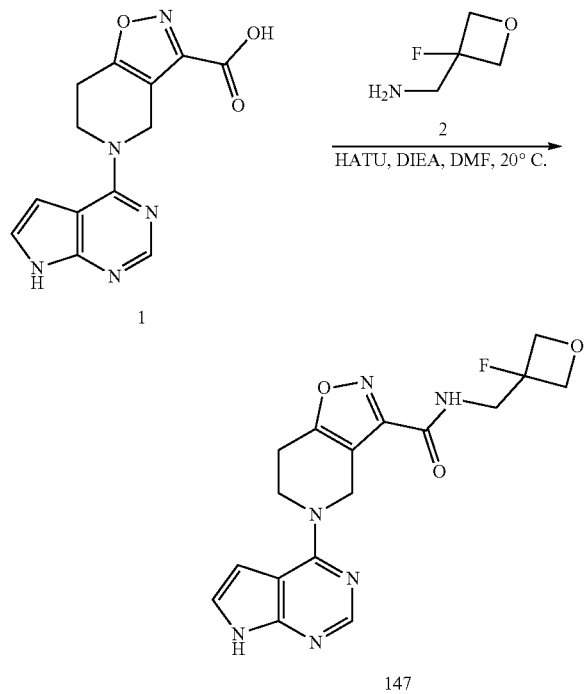

To a solution of compound 1 (100 mg, 350.56 umol, 1 eq) and compound 2 (55.27 mg, 525.84 umol, 1.5 eq) in DMF (3 mL) was added HATU (199.94 mg, 525.84 umol, 1.5 eq) and DIEA (90.61 mg, 701.12 umol, 122.12 uL, 2 eq), the mixture was stirred at 20° C. for 2 hr. LCMS showed compound 1 was consumed completely and desired MS was detected. The mixture was purified by prep-HPLC (column: Phenomenex Synergi C18 150*25*10 um; mobile phase: [water(0.225% FA)-ACN]; B %: 1%-31%, 10 min) to give compound 147 (30 mg, 79.76 umol, 22.75% yield, 99% purity) as yellow solid.

$^1$H NMR (400 MHz, DMSO-d)

δ=11.82 (br. s, 1H), 9.19 (t, J=6.1 Hz, 1H), 8.20 (s, 1H), 7.27 (dd, J=2.5, 3.4 Hz, 1H), 6.64 (dd, J=1.6, 3.4 Hz, 1H), 4.98 (s, 2H), 4.76-4.55 (m, 4H), 4.21 (t, J=5.6 Hz, 2H), 3.80 (dd, J=6.1, 19.4 Hz, 2H), 3.03 (br. t, J=5.3 Hz, 2H)

$^{13}$CNMR (400 MHz, DMSO-d6)

δ=167.25, 158.17, 154.86, 152.46, 150.39, 148.90, 120.15, 110.04, 100.87, 98.73, 93.80, 91.72, 76.63, 76.40, 40.11, 39.70

LCMS: Rt=0.684 min, [M+H]$^+$=373.2

Example 65: Inhibition of JAK1-3 and TYK2 Kinases

Exemplary compounds were assayed to determine potency in inhibiting activity of JAK1-3 and TYK2 kinases by determining IC$_{50}$ values.

Materials and Methods

The sources of test materials and equipment are as follows: JAK1 (Invitrogen, Cat. No PV4775), JAK2 (Invitrogen, Cat. No PV4210), JAK3 (Invitrogen, Cat. No PV4080), TYK2 (Invitrogen, Cat. No PR8440C), ATP (Sigma, Cat. No. A7699-1G), DMSO (Sigma, Cat. No. D2650), DTT (Sigma, Cat. No. 43815), 384 wells_compound plate (Greiner, Cat. No. 781280), 384 wells_assay plate (Perkin Elmer, Cat. No. 6007299), LANCE Ultra ULight™-JAK-1 peptide (Perkin Elmer, Cat. No. TRF0121), LANCET™ Eu-W1024 Anti-phosphotyrosine (PT66) (Perkin Elmer, Cat. No. AD0069), LANCET™ Detection Buffer(Perkin Elmer, Cat. No. CR97-100).

Final Compound Concentrations

The concentrations of test compounds varied from 100 μM to 1.7 nM with 3-fold dilution, 11 points, in duplicates while the concentrations of the reference compound, Tofacitinib, varied from 1 μM to 0.017 nM with 3-fold dilution, 11 points, in duplicates.

Enzyme Reaction

The assay buffer contained 50 mM HEPES (pH 7.5), 0.01% Brij-35, 10 mM MgCl$_2$, 1 mM EDTA, 2 mM DTT. Incubations were carried out at 23° C.

Prior to the assay, enzyme, peptide substrate and serially diluted test compounds were pre-incubated together in assay buffer (5 μL) for 15 minutes (peptide substrate concentration: 50 nM; JAK enzyme concentrations: 2 nM JAK1; 30 μM JAK2; 80 μM JAK3 and 4 nM TYK2). And the assay was initiated by the addition of 5 μL assay buffer containing 2× final ATP concentration (these are the 2×ATP concentrations: 76 μM JAK1; 24 μM JAK2; 8 μM JAK3 and 30 μM TYK2). Following the 90-minute incubation, antibody conjugated with Eu is dissolved in detection buffer to add into wells and then incubated for 60 minutes. The 10 μL detection buffer contains EDTA to stop the enzymatic reaction. The plate is analyzed by Perkin Elmer Envision on TR-FRET mode. The high ratio of 665/615 represents no inhibition of kinase reaction while the low ratio of 665/615 represents complete inhibition of kinase reaction.

Curves are fit by XLFIT5 as inhibition rate % vs. log [compound concentration] using 4 parameters logistic model 205.

The IC$_{50}$ for each compound tested was determined and is summarized in Table 2 below. In the table, "A" indicates an IC$_{50}$ of less than 100 nM, "B" indicates an IC$_{50}$ range from 100 nM to 500 nM; "C" indicates an IC$_{50}$ range from 500 nM to 2 μM; and "D" indicates an IC$_{50}$ greater than 2 μM. Also, "na" indicates data is not available.

TABLE 2

Efficacy of exemplary compounds of the invention for binding to Jak receptors

| Compound No. | Jak1 | Jak2 | Jak3 | tyk |
|---|---|---|---|---|
| | | IC50 (nM) | | |
| 101 | D | D | C | D |
| 102 | C | B | A | D |
| 103 | B | B | A | D |
| 104 | B | B | A | D |
| 105 | B | B | A | D |
| 106 | D | D | B | D |
| 107 | A | B | A | C |
| 108 | D | D | B | D |
| 109 | A | B | A | C |
| 110 | A | A | A | B |
| 111 | B | C | A | D |
| 112 | B | C | A | D |
| 113 | B | B | A | C |
| 114 | B | C | A | C |
| 115 | C | D | B | D |
| 116 | B | D | B | D |
| 117 | B | C | A | D |
| 118 | C | D | B | D |
| 119 | na | C | C | na |
| 120 | na | B | C | na |
| 121 | D | D | D | D |

TABLE 2-continued

Efficacy of exemplary compounds of the invention for binding to Jak receptors

| Compound No. | Jak1 | Jak2 | Jak3 | tyk |
|---|---|---|---|---|
| | | IC50 (nM) | | |
| 122 | D | D | D | D |
| 123 | D | D | D | D |
| 124 | C | D | C | D |
| 125 | B | C | B | D |
| 126 | B | C | B | D |
| 127 | B | C | B | D |
| 128 | C | C | C | D |
| 130 | A | B | A | B |
| 131 | B | B | A | B |
| 132 | B | C | C | D |
| 134 | C | C | B | D |
| 135 | B | B | B | D |
| 136 | C | D | B | D |
| 138 | B | B | A | C |
| 139 | D | D | D | D |
| 140 | C | C | B | D |
| 141 | A | A | A | B |
| 143 | B | B | A | C |
| 144 | B | B | A | D |
| 145 | B | C | B | D |
| 146 | B | C | B | D |
| 147 | B | B | B | D |
| 148 | B | C | B | D |
| 149 | C | C | B | D |
| 150 | B | B | A | D |
| 150-1 | C | C | B | D |
| 150-2 | B | B | A | D |
| 151 | A | A | A | C |
| 152 | D | D | D | D |
| 153 | C | C | B | D |
| 154 | B | B | A | D |
| 155 | C | C | C | D |
| 156 | B | B | B | D |
| 157 | A | B | A | D |
| 158 | B | B | A | D |
| 159 | C | D | B | D |
| 160 | C | D | C | D |
| 161 | C | D | C | D |
| 162 | D | D | C | D |
| 163 | B | B | A | D |
| 164 | C | D | B | D |
| 165 | D | D | D | D |
| 166 | C | C | B | D |
| 167 | B | C | B | D |
| 168 | C | C | B | D |
| 169 | C | C | B | D |
| 170 | B | B | B | D |
| 178 | A | A | A | C |
| 179 | B | B | A | D |
| 180 | B | B | A | D |
| 182 | A | B | A | C |
| 186 | A | A | A | B |
| 187 | B | C | B | D |
| 188 | B | C | B | D |
| 189 | B | D | B | D |
| 190 | A | A | A | B |
| 191 | B | B | B | D |
| 192 | A | B | A | D |
| 193 | B | B | A | C |
| 194 | A | A | A | B |
| 198 | A | B | A | D |
| 199 | A | B | A | C |
| 201 | A | B | A | D |
| 202 | A | A | A | C |

Example 66: Inhibition in Hut-78 Cells

Exemplary compounds were assayed to determine potency in inhibiting Hut-78 cells by determining $IC_{50}$ values.

Hut-78 cells were cultures in IMDM+20% FBS medium. Cells were maintained in log phase before the assay. Cell pellets were collected and resuspended in serum-free and phenol-free RPMI 1640 medium. 40,000 cells/well (10 μL) were seeded in each well of a 384-well plate and incubated with and without compound for 2 hours at 37° C. and 5% CO2. IL-2 was added (2 μL, final concentration 100 ng/mL) and the mixture was incubated for 10 min. Cells were lysed by adding 4 μL labeled antibodies and the mixture was incubated overnight. The plate was read using the HTRF protocol on an Envision plate reader. The data was analyzed using XL-fit software (Supplier: ID business solutions Ltd.; Software version: XL fit 5.0). Inhibition %=(Max−Sample value)/(Max−Min)*100.

The $IC_{50}$ for each compound tested was determined and is summarized in Table 3 below. In the table, "A" indicates an $IC_{50}$ of less than 0.5 μM, "B" indicates an $IC_{50}$ range from 0.5 μM to 1 μM; and "C" indicates an $IC_{50}$ range from 1 μM to 10 μM. Also, "na" indicates data is not available.

TABLE 3

Efficacy of exemplary compounds of the invention for inhibition of Hut-78 cells

| Compound No. | Hut-78 cells IC50 (μM) |
|---|---|
| 109 | C |
| 110 | B |
| 178 | B |
| 102 | C |
| 103 | C |
| 104 | B |
| 105 | B |
| 201 | A |
| 202 | A |
| 198 | A |
| 199 | A |
| 194 | A |
| 182 | A |
| 179 | C |
| 186 | A |
| 143 | C |
| 192 | B |
| 193 | B |
| 190 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A compound of formula I, formula II, formula III, or formula IV:

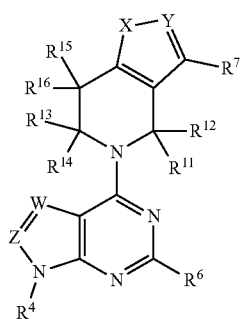

(I)

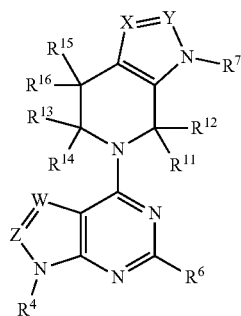

(II)

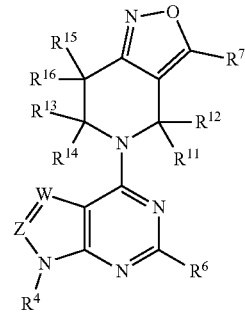

(III)

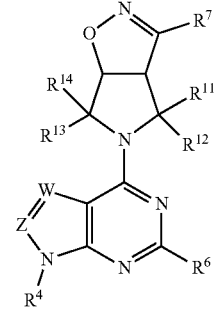

(IV)

or a pharmaceutically acceptable salt thereof, wherein
For formula I: X is $NR^1$, $C(R^8)R^1$, O, S, S(O), or $S(O)_2$;
For formula II: X is N or $CR^1$; and
For formula I, formula II, formula III, and formula (IV):
W is N or $CR^5$;
Y is N or $CR^2$;
Z is N or $CR^3$;
wherein W and Z are not both N;
$R^1$ is selected from the group consisting of cyano, hydroxyl, $NR^aR^b$, $C_{1-6}$alkoxy, and -A-$L^1$-$R^9$;
$R^2$, $R^3$, $R^4$, and $R^6$ are each independently selected from the group consisting of hydrogen, deuterium, halogen, cyano, hydroxyl, —$NR^aR^b$, $C_{1-6}$alkyl, $C_{2-6}$alkenyl, $C_{2-6}$alkynyl, $C_{1-6}$haloalkyl, and $C_{1-6}$alkoxy;
$R^5$ is selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, -heterocyclyl-$C_{1-6}$alkyl, halogen, cyano, hydroxyl, $C_{1-6}$alkoxy, $C_{1-6}$haloalkoxy, amino, carboxy, aminocarbonyl, —$C_{1-6}$alkyl-aminocarbonylamino, $C_{1-6}$alkylaminocarbonyl, —S(O)—$R^8$, —$S(O)_2$—$R^8$, —$NR^8$—$S(O)_2$—$R^8$, —$S(O)_2$—$NR^aR^b$, —$NR^8$—$S(O)_2$—$NR^aR^b$, —$C_{1-6}$alkyl-aryl, —$C_{1-6}$alkyl-heteroaryl, —$C_{1-6}$alkyl-heterocycle, and —$C_{1-6}$alkyl-cycloalkyl, wherein said alkyl, aryl, and heteroaryl is optionally substituted with one or substituents independently selected from the group consisting of halo, hydroxyl, methoxy, amino, cyano, alkylamino, dialkylamino, $CF_3$, aminocarbonyl, —$C_{1-6}$alkyl-aminocarbonylamino, and $C_{3-6}$cycloalkyl;

$R^7$ is B-$L^2$-$R^{10}$, or $R^7$ is aryl or heteroaryl, wherein the aryl or heteroaryl is optionally substituted with one to four $R^{17}$;

each $R^8$ is independently selected from the group consisting of hydrogen, $C_{1-6}$alkyl, $C_{1-6}$haloalkyl, hydroxy, $C_{1-6}$alkoxy, and —O—$C_{1-6}$haloalkyl;

$R^9$ is selected from the group consisting of hydrogen, cycloalkyl, heterocycloalkyl, aryl, and heteroaryl, wherein any non-hydrogen $R^9$ is optionally substituted with one to four $R^{17}$;

$R^{10}$ is selected from the group consisting of hydrogen, cyano, hydroxyl, $C_{1-6}$haloalkyl, $C_{1-6}$alkoxy, —O—$C_{1-6}$ haloalkyl, cycloalkyl, heterocycloalkyl, aryl, heteroaryl, —C(O)-heterocycloalkyl, and —S(O)$_2$-heterocycloalkyl, wherein any $R_{10}$ other than hydrogen, cyano, and hydroxyl is optionally substituted with one to four $R^{17}$;

$R^{11}$, $R^{12}$, $R^{13}$, $R^{14}$, $R^{15}$, and $R^{16}$ are each independently selected from the group consisting of hydrogen, $C_{1-6}$alkyl, $C_{2-6}$alkenyl, $C_{2-6}$alkynyl, $C_{1-6}$haloalkyl, aryl, heteroaryl, cycloalkyl, heterocyclyl, -aryl-$C_{1-6}$alkyl, -heteroaryl-$C_{1-6}$alkyl, halogen, cyano, hydroxyl, $C_{1-6}$alkoxy, amino, carboxy, aminocarbonyl, —$C_{1-6}$alkyl-aryl, —$C_{1-6}$alkyl-heteroaryl, —$C_{1-6}$alkyl-heterocycle, and $C_{1-6}$alkyl-cycloalkyl, wherein said alkyl is optionally substituted with one or more substituents independently selected from the group consisting of halo, hydroxyl, methoxy, alkylamino, dialkylamino, $CF_3$, and $C_{3-6}$cycloalkyl; or $R^{11}$ and $R^{12}$, $R^{13}$ and $R^{14}$, or $R^{15}$ and $R^{16}$ can be taken together including the atom to which they are attached to form a 3-6-membered spiro-fused ring optionally substituted by 1-3 substituents independently selected from the group consisting of halogen, $C_{1-6}$alkyl, and $C_{1-6}$haloalkyl;

$R^{17}$ is, independently for each occurrence, selected from the group consisting of halogen, cyano, hydroxyl, —N$R^aR^b$, $C_{1-6}$alkyl, $C_{2-6}$alkenyl, $C_{2-6}$alkynyl, $C_{1-6}$haloalkyl, $C_{1-6}$alkoxy, $CF_3$, —SH, —S—$C_{1-6}$alkyl, —COOH, —$CO_2$—$C_{1-6}$alkyl, —$C_{1-6}$alkyl-CN, —C(O) N$R^aR^b$, —C(O)—$C_{1-6}$alkyl-N$R^aR^b$, —C(O)—N$R^a$—S(O)$_2$—$C_{1-6}$alkyl, —S(O)$_2$—$C_{1-6}$alkyl, —S(O)$_2$ —N$R^aR^b$, —S(O)$_2$—$C_{1-6}$alkyl-N$R^aR^b$;

A is selected from the group consisting of —C(O)—, —S(O)—, and —S(O)$_2$—, or A is absent;

B is selected from the group consisting of —C(O)—, —S(O)$_2$—N$R^8$—, —CH$_2$—N$R^8$—, and —C(O)N$R^8$—;

$L^1$ is selected from the group consisting of a bond, $C_{1-6}$alkylene, $C_{1-6}$heteroalkylene, $C_{2-6}$alkenylene, and $C_{2-6}$alkynylene, wherein $L^1$ is optionally substituted with one to four $R^{17}$ groups;

$L^2$ is selected from the group consisting of a bond, $C_{1-6}$alkylene, $C_{2-6}$alkenylene, and $C_{2-6}$alkynylene, wherein any $CH_2$ group of $C_{1-6}$alkylene can be replaced with a moeity selected from the group consisting of —O—, —N$R^a$—, and —S(O)$_2$—, and one $CH_2$ group of $C_{1-6}$alkylene can be replaced with a moiety selected from the group consisting of cycloalkylene, heterocycloalkylene, arylene, and heteroarylene, and wherein $L^2$ is optionally substituted with one to four $R^{17}$ groups; or when B is —S(O)$_2$—N$R_8$—, —CH$_2$—N$R^8$—, or —C(O)N$R^8$—, $R^8$ and $L^2$ can be taken together including the nitrogen atom to which they are attached to form a 3-7-membered heterocycloalkyl optionally substituted with one to four $R^{17}$ groups; and each of $R^a$ and $R^b$ are, independently for each occurrence, selected from the group consisting of hydrogen, $C_{1-6}$alkyl, and $C_{1-6}$haloalkyl, or $R^a$ and $R^b$ are taken together, including the nitrogen to which they are attached, to form a heterocycloalkyl ring.

2. The compound of claim 1, wherein the compound is of formula I or formula II.

3. The compound of claim 1, wherein W is $CR^5$.

4. The compound of claim 1, wherein X is $NR^1$ or O.

5. The compound of claim 1, wherein Y is N.

6. The compound of claim 1, wherein Z is $CR^3$.

7. The compound of claim 1, wherein $R^{11}$, $R^{12}$, $R^{13}$, $R^{14}$, $R^{15}$, and $R^{16}$ are each hydrogen.

8. The compound of claim 1, wherein $R^3$, $R^4$, $R^5$, and $R^6$ are each hydrogen.

9. The compound of claim 1, wherein $R^1$ is -$L^1$-$R^9$.

10. The compound of claim 9, wherein $R^9$ is aryl or heteroaryl.

11. The compound of claim 1, wherein $L^1$ is $C_{1-6}$alkylene optionally substituted with one to four substituents.

12. The compound of claim 1, wherein $R^1$ is $C_{1-6}$alkyl or hydrogen.

13. The compound of claim 1, wherein $R^7$ is B-$L^2$-$R^{10}$.

14. The compound of claim 1, wherein B is —C(O)NH—.

15. The compound of claim 1, wherein $L^2$ is $C_{1-6}$alkylene substituted with one $R^{17}$ at a terminal carbon position.

16. The compound of claim 1, wherein $R^7$ is —C(O)N$R^8$—$C_{3-7}$cycloalkyl-$R^{17}$.

17. The compound of claim 1, wherein $R^{17}$ is selected from the group consisting of $C_{1-6}$haloalkyl, —$CO_2$—$C_{1-6}$alkyl, —$C_{1-6}$alkyl-CN, —C(O)N$R^aR^b$, and —C(O)—N$R^a$—S(O)$_2$—$C_{1-6}$alkyl.

18. A pharmaceutical composition comprising a compound of claim 1 and a pharmaceutically acceptable carrier.

19. A method of treating a disease which can be treated with a JAK3 inhibitor, the method comprising administering a pharmaceutically effective amount of a compound or composition of claim 1 to a patient in need thereof.

20. A method of treating a disease, the method comprising administering a pharmaceutically effective amount of a compound of claim 1 to a patient in need thereof, wherein the disease is selected from the group consisting of rheumatoid arthritis, myositis, vasculitis, pemphigus, bullous pemphigoid, inflammatory bowel disease including Crohn's disease and ulcerative colitis, celiac diseases, proctitis, eosinophilic gastroenteritis, or mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis nodosa, dry eye syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation, including Cogan's syndrome, ankylosing spondylitis, Wegener's granulomatosis, autoimmune alopecia, Type I or juvenile onset diabetes, and complications from diabetes, or thyroiditis, chronic pulmonary obstructive disorder, acute respiratory disease, cachexia, cancer, including alimentary/gastrointestinal tract cancer, colon cancer, liver cancer, skin cancer including mast cell tumor and squamous cell carcinoma, breast and mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma including oral and metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, or angiogenic-associated disorders including solid tumors, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotropic Lateral Sclerosis, Huntington's disease, cerebral ischemia, fronto-temporal lobe dementia, and with neuropsychiatric disorders including schizophrenia, bipolar disorder, treatment resistant depression, Post Traumatic Stress Disorder, anxiety, and auto-antibodies mediated encephalopathies, Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization.

\* \* \* \* \*